United States Patent
Wall et al.

(10) Patent No.: US 12,264,195 B2
(45) Date of Patent: *Apr. 1, 2025

(54) MODIFIED IMMUNOGLOBULINS FOR TARGETING AMYLOID DEPOSITS

(71) Applicants: Attralus, Inc., Burlingame, CA (US); UNIVERSITY OF TENNESSEE RESEARCH FOUNDATION, Knoxville, TN (US)

(72) Inventors: Jonathan S. Wall, Knoxville, TN (US); James S. Foster, Knoxville, TN (US); Spencer Guthrie, San Francisco, CA (US)

(73) Assignees: Attralus, Inc, Burlingame, CA (US); University of Tennessee Research Foundation, Knoxville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/660,162

(22) Filed: May 9, 2024

(65) Prior Publication Data

US 2024/0294621 A1 Sep. 5, 2024

Related U.S. Application Data

(60) Division of application No. 18/181,489, filed on Mar. 9, 2023, now Pat. No. 12,030,934, which is a continuation of application No. 17/776,827, filed as application No. PCT/US2020/060596 on Nov. 13, 2020, now abandoned.

(60) Provisional application No. 63/074,912, filed on Sep. 4, 2020, provisional application No. 62/936,002, filed on Nov. 15, 2019.

(51) Int. Cl.
| | |
|---|---|
| *C07K 16/18* | (2006.01) |
| *A61K 47/68* | (2017.01) |
| *A61P 25/28* | (2006.01) |
| *C12N 15/85* | (2006.01) |
| *A61K 39/00* | (2006.01) |

(52) U.S. Cl.
CPC .......... *C07K 16/18* (2013.01); *A61K 47/6843* (2017.08); *A61P 25/28* (2018.01); *C12N 15/85* (2013.01); *A61K 2039/505* (2013.01); *C07K 2317/24* (2013.01); *C07K 2317/52* (2013.01); *C07K 2317/55* (2013.01); *C07K 2317/565* (2013.01); *C07K 2317/622* (2013.01); *C07K 2317/92* (2013.01); *C07K 2317/94* (2013.01); *C07K 2319/00* (2013.01); *C07K 2319/01* (2013.01)

(58) Field of Classification Search
None
See application file for complete search history.

(56) References Cited

U.S. PATENT DOCUMENTS

| | | |
|---|---|---|
| 5,648,237 A | 7/1997 | Carter |
| 5,789,199 A | 8/1998 | Joly |
| 5,840,523 A | 11/1998 | Simmons |
| 5,959,177 A | 9/1999 | Hein |
| 6,040,498 A | 3/2000 | Stomp |
| 6,180,370 B1 | 1/2001 | Queen et al. |
| 6,417,429 B1 | 7/2002 | Hein |
| 6,420,548 B1 | 7/2002 | Vezina |
| 7,125,978 B1 | 10/2006 | Vezina |
| 8,105,594 B2 | 1/2012 | Solomon et al. |
| 8,808,666 B2 | 8/2014 | Wall et al. |
| 9,683,017 B2 | 6/2017 | Wall et al. |
| 10,046,050 B2 | 8/2018 | Wall et al. |
| 10,213,506 B2 | 2/2019 | Wall et al. |
| 10,308,685 B2 | 6/2019 | Wall et al. |
| RE47,838 E | 2/2020 | Wall et al. |
| 11,530,257 B2 | 12/2022 | Jones et al. |
| 12,030,934 B2 | 7/2024 | Wall |
| 12,139,529 B2 | 11/2024 | Wall |
| 12,157,765 B2 | 12/2024 | Wall |
| 2010/0322932 A1 | 12/2010 | Solomon et al. |
| 2011/0300141 A1 | 12/2011 | Chakravarthy |
| 2014/0079691 A1 | 3/2014 | Mcconnell et al. |
| 2016/0016999 A1 | 1/2016 | Wall et al. |
| 2019/0038745 A1 | 2/2019 | Lentzsch |
| 2019/0070285 A1 | 3/2019 | Martin et al. |
| 2019/0083616 A1 | 3/2019 | Wall et al. |
| 2019/0352383 A1 | 11/2019 | Chakravarthy et al. |
| 2020/0002410 A1 | 1/2020 | Lentzsch et al. |
| 2022/0411489 A1 | 12/2022 | Wall et al. |

(Continued)

FOREIGN PATENT DOCUMENTS

| | | |
|---|---|---|
| JP | 2012246299 A | 12/2012 |
| WO | 199515982 A2 | 6/1995 |

(Continued)

OTHER PUBLICATIONS

Kipriyanov et al., Mol Biotechnol. Jan. 2004;26(1):39-60. doi: 10.1385/MB:26:1:39. PMID: 14734823.*
Ailles, L. et al. (Oct. 1993). "Induction Of Perlecan Gene Expression Precedes Amyloid Formation During Experimental Murine AA Amyloidogenesis," Laboratory Investigation 69(4):443-448.
Almagro, J.C. et al. (Jan. 1, 2008). "Humanization of Antibodies," Frontiers in Bioscience 13:1619-1633.
Altschul, S.F. et al. (Oct. 5, 1990). "Basic Local Alignment Search Tool," J. Mol. Biol. 215(3):403-410.

(Continued)

*Primary Examiner* — Michael Szperka
(74) *Attorney, Agent, or Firm* — Morrison & Foerster LLP

(57) ABSTRACT

Provided herein are modified immunoglobulins comprising an amyloid reactive peptide joined to an antibody, as well as humanized antibodies that bind to human amyloid fibrils and antibody-peptide fusion proteins. Also provided herein are methods of treating amyloid-based diseases by administering a modified immunoglobulin, humanized antibody, or antibody-peptide fusion protein.

24 Claims, 30 Drawing Sheets

Specification includes a Sequence Listing.

(56) References Cited

U.S. PATENT DOCUMENTS

| | | |
|---|---|---|
| 2023/0265178 A1 | 8/2023 | Wall et al. |
| 2023/0416347 A1 | 12/2023 | Wall |
| 2024/0294620 A1 | 9/2024 | Wall |

FOREIGN PATENT DOCUMENTS

| | | | |
|---|---|---|---|
| WO | 199960024 A1 | 11/1999 | |
| WO | WO-9960024 A1 * | 11/1999 | ............... A61P 1/04 |
| WO | 2003074567 A2 | 9/2003 | |
| WO | 2005000193 A2 | 1/2005 | |
| WO | 2008091954 A2 | 7/2008 | |
| WO | 2016032949 A1 | 3/2016 | |
| WO | WO-2017146880 A1 * | 8/2017 | ......... A61K 38/1716 |
| WO | 2019006062 A1 | 1/2019 | |
| WO | 2019241216 A1 | 12/2019 | |
| WO | 2021097360 A1 | 5/2021 | |
| WO | 2022246433 A1 | 11/2022 | |

OTHER PUBLICATIONS

Ancsin, J.B. (2003, e-pub. Jul. 6, 2009). "Amyloidogenesis: Historical And Modern Observations Point To Heparan Sulfate Proteoglycans As A Major Culprit," Amyloid 10(2):67-79.

Attwood, T.K. (Oct. 20, 2000). "The Babel Of Bioinformatics," Science 290(5491):471-473, 7 pages.

Bitter, G.A. et al. (1987). "Expression and Secretion Vectors For Yeast," Methods in Enzymol. 153:516-544.

Bowie, J.U. et al. (Jul. 12, 1991). "A Method To Identify Protein Sequences That Fold Into A Known Three-Dimensional Structure," Science 253(5016):164-170.

Buck, F.S. et al. (Jul. 1989). "Ethnic Distribution Of Amyloidosis: An Autopsy Study," Modern Pathology 2(4):372-377.

Charlton, K.A. (2004). "Expression and Isolation of Recombinant Antibody Fragments in E. coli," Methods Mol Biol 248:245-254.

Comenzo, R.L. et al. (Jun. 15, 2002). "Autologous Stem Cell Transplantation For Primary Systemic Amyloidosis," Blood, The Journal of the American Society of Hematology 99(12):4276-4282.

Corpet, F. (Nov. 25, 1988). "Multiple Sequence Alignment With Hierarchical Clustering," Nucleic Acids Res. 16(22):10881-10890.

De Lorenzi, E. et al. (2004). "Pharmaceutical Strategies Against Amyloidosis: Old And New Drugs In Targeting A "Protein Misfolding Disease"," Current Medicinal Chemistry 11(8):1065-1084.

Edwards, B.M. et al. (Nov. 14, 2003). "The Remarkable Flexibility of the Human Antibody Repertoire; Isolation of Over One Thousand Different Antibodies to a Single Protein, BLyS," J. Mol. Biol. 334(1):103-118.

Foster, J.S. et al. (Oct. 2, 2023). "Development And Characterization Of A Prototypic Pan-Amyloid Clearing Agent—A Novel Murine Peptide-Immunoglobulin Fusion," Frontiers in Immunology 14(1275372):1-14.

Foster, J.S. et al. (Sep. 4, 2017). "A Peptide-Fc Opsonin With Pan-Amyloid Reactivity," Frontiers in Immunology 8(1082):1-14.

Gertz, M.A. et al. (Jul. 7, 2020). "Systemic Amyloidosis Recognition, Prognosis, And Therapy: A Systematic Review," JAMA 324(1):79-89.

Goel, M. et al. (2004). "Plasticity within the Antigen-Combining Site May Manifest as Molecular Mimicry in the Humoral Immune Response," J. Immunol. 173(12):7358-7367.

Graham, F.L. et al. (1977). "Characteristics of a Human Cell Line Transformed by DNA from Human Adenovirus Type 5," J. Gen Virol. 36:59-72.

Higgins, D.G. et al. (1988). "CLUSTAL: A Package For Performing Multiple Sequence Alignment On A Microcomputer," Gene 73(1):237-244.

Higgins, D.G. et al. (1989). "Fast and Sensitive Multiple Sequence Alignments on a Microcomputer," CABIOS Communications 5(2):151-153.

Huang, X. et al. (Apr. 1992). "Parallelization of a Local Similarity Algorithm," Comput. Appl. Biosci. 8(2):155-165.

Jaikaran, E.T.A.S. et al. (2001). "Islet Amyloid And Type 2 Diabetes: From Molecular Misfolding To Islet Pathophysiology," Biochimica et Biophysica Acta 1537(3):179-203.

Janeway, C.A. et al. (1997). Immunobiology, 3rd edition Garland Press, pp. 3.1-3.11, 14 pages.

Kanyavuz, A. et al. (Jun. 2019, e-pub. Feb. 4, 2019). "Breaking the Law: Unconventional Strategies For Antibody Diversification," Nat. Rev. Immunol 19(6):355-368.

Kisilevsky, R. (1994). "Proteoglycans And Other Basement Membrane Proteins In Amyloidosis," Molecular Neurobiology 9(1):23-24.

Kisilevsky, R. (Nov. 1990). "Heparan Salfate Proteoglycans In Amyloidogenesis: An Epiphenomenom, A Unique Factor, Or The Tip Of A More Fundamental Process?," Laboratory Investigation 63(5):589-591.

Lescar, J. et al. (Jul. 30, 1995). "Crystal Structure of a Cross-Reaction Complex Between Fab F9.13.7 and Guinea Fowl Lysozyme," The Journal of Biological Chemistry 276(30):18067-18076.

Li, J.P. et al. (May 3, 2005). "In Vivo Fragmentation Of Heparan Sulfate By Heparanase Overexpression Renders Mice Resistant To Amyloid Protein A Amyloidosis," PNAS 102(18):6473-6477.

Lin, C.Y. et al. (May 2007). "Toxic Human Islet Amyloid Polypeptide (h-IAPP) Oligomers Are Intracellular, And Vaccination To Induce Anti-Toxic Oligomer Antibodies Does Not Prevent h-IAPP-Induced β-Cell Apoptosis In h-IAPP Transgenic Mice," Diabetes 56:1324-1332.

Lloyd, C. et al. (2009, e-pub. Oct. 29, 2008). "Modelling the Human Immune Response: Performance of a 1011 Human Antibody Repertoire Against a Broad Panel of Therapeutically Relevant Antigens," Protein Engineering, Design & Selection 22(3):159-168.

Lofberg, H. et al. (1987). "The Prevalence Of Renal Amyloidosis Of The AA-Type In A Series Of 1,158 Consecutive Autopsies," Acta Path. Microbiol. Immunol. Scand. Sect. A 95:297-302.

Mather, J.P. et al. (1980). "Establishment and Characterization Of Two Distinct Mouse Testicular Epithelial Cell Lines," Biology of Reproduction 23:243-252.

Mather, J.P. et al. (1982). "Culture of Testicular Cells in Hormone-Supplemented Serum-Free Medium," Annals New York Academy of Sciences pp. 44-68.

Merlini, G. (2004). "Systemic Amyloidosis: Are We Moving Ahead?," Neth J Med 62(4):104-105, 2 pages.

Merlini, G. et al. (2004). "The Systemic Amyloidoses: Clearer Understanding Of The Molecular Mechanisms Offers Hope For More Effective Therapies," Journal Of Internal Medicine 255:159-178.

Merlini, G. et al. (Aug. 7, 2003). "Molecular Mechanisms Of Amyloidosis," New England Journal of Medicine 349:583-596.

Mucchiano, G.I. et al. (2001, e-pub. Nov. 16, 2000). "Apolipoprotein A-1-Derived Amyloid In Atherosclerotic Plaques Of The Human Aorta," The Journal of Pathology 193(2):270-275.

Needleman, S. B. et al. (Mar. 1970). "A General Method Applicable to the Search for Similarities in the Amino Acid sequence of Two Proteins," J. Mol. Biol. 48:443-453.

Pearson, W.R. (1994). "Using The FASTA Program To Search Protein And DNA Sequence Databases," Methods Mol Biol. 25:365-389.

Pearson, W.R. et al. (Apr. 1988). "Improved Tools For Biological Sequence Comparison," Proc. Natl. Acad. Sci. USA 85(8):2444-2448.

Pras, M. et al. (1968). "The Characterization Of Soluble Amyloid Prepared In Water," The Journal of Clinical Investigation 47:924-933.

Rocken, C. (2002, e-pub. Jan. 4, 2002). "Pathology, Diagnosis And Pathogenesis Of AA Amyloidosis," Virchows Arch 440(2):111-122.

Rocken, C. et al. (2006, e-pub. Oct. 26, 2006). "Cathepsin Protease Activity Modulates Amyloid Load In Extracerebral Amyloidosis," The Journal of Pathology 210(4):478-487.

Rocken, C. et al. (Mar. 2001). "A Putative Role For Cathepsin K In Degradation Of AA and AL Amyloidosis," Am. J. Pathol. 158(3):1029-1038.

Rudikoff, S. et al. (Mar. 1982). "Single Amino Acid Substitution Altering Antigen-Binding Specificity," Proc. Natl. Acad. Sci. USA 79:1979-1983.

(56) References Cited

OTHER PUBLICATIONS

Skolnick, J. et al. (Jan. 2000). "From Genes To Protein Structure and Function: Novel Applications of Computational Approaches In The Genomic Era," Trends in Biotechnology 18:34-39.
Smith, T.F. et al. (1981). "Comparison of Biosequences," Advances in Appl. Math. 2:482-489.
Snow, A.D. et al. (Jan. 1987). "Sulfated Glycosaminoglycans: A Common Constituent Of All Amyloids?," Laboratory Investigation 56(1):120-123.
Solomon, A. et al. (Nov. 2006). "Amyloid Contained In The Knee Joint Meniscus Is Formed From Apolipoprotein A-I," Arthritis & Rheumatism 54(11):3545-3550.
Stryer, L. (1995). Biochemistry, Fourth Edition, W.H. Freeman and Company: New York, 18-23, 8 pages.
Sunde, M. et al. (1997). "Common Core Structure Of Amyloid Fibrils By Synchrotron X-Ray Diffraction," Journal of Molecular Biology 273(3):729-739.
Thornton, J.M. et al. (Nov. 14, 1991). "Prediction Of Progress At Last," Nature 354(6349):105-106.
Urlaub, G. et al. (Jul. 1980). "Isolation of Chinese Hamster Cell Mutants Deficient in Dihydrofolate Reductase Activity," Proc. Natl. Acad. Sci. USA 77(7):4216-4220.
Vollmer, E. et al. (1991). "Distribution Patterns Of Apolipoproteins A1, A2, And B In The Wall Of Atherosclerotic Vessels," Virchows Archiv A 419(2):79-88.
Wall, J. et al. (1999, e-pub. Sep. 30, 1999). "Thermodynamic Instability Of Human λ6 Light Chains: Correlation With Fibrillogenicity," Biochemistry 38:14101-14108.
Wall, J.S. et al. (Jun. 4, 2013). "A Binding-Site Barrier Affects Imaging Efficiency Of High Affinity Amyloid-Reactive Peptide Radiotracers In Vivo," PloS One 8(6):e66181, 1-10.
Westermark, P. et al. (Jun. 30, 2009). "Fibrils From Designed Non-Amyloid-Related Synthetic Peptides Induce AA-Amyloidosis During Inflammation In An Animal Model," PLoS One 4(6):e6041, 7 pages.
Westermark, P. et al. (Nov. 1995). "Apolipoprotein A1-Derived Amyloid In Human Aortic Atherosclerotic Plaques," The American Journal of Pathology 147(5):1186-1192.
Westermark, P. et al. (Sep. 2007). "A Primer Of Amyloid Nomenclature," Amyloid 14(3):179-183.
Wikipedia (Oct. 2, 2023). "Amyloid—Proteins Forming Amyloids In Diseases," 18 pages as retrieved on Dec. 1, 2023 from https://en.wikipedia.org/w/index.php?title=Amyloid&oldid=1178199603.
Yazaki, P.J. et al. (2003). "Expression of Recombinant Antibodies in Mammalian Cell Lines," Methods in Molecular Biology 248:255-268.
Beierle, S.P. et al. (2016). "A Novel Murine Model Of Light Chain Associated (AL) Amyloidosis For Validating Peptide Amyloid Imaging Agents—A SPECT/CT And Microautoradiography Study," 2016 World Molecular Imaging Congress, New York, NY, Sep. 7-10, 2016, Control ID 2500594:1 page.
Edwards, C.V. et al. (2017, e-pub. Apr. 22, 2017). "Interim Analysis Of The Phase 1a/b Study Of Chimeric Fibril-Reactive Monoclonal Antibody 11-1F4 In Patients With AL Amyloidosis," Amyloid 24(S1):58-59.
Foster, J.S. et al. (2020). "Collagen Addition To Synthetic Amyloid Fibrils Presents A "Don't Eat Me" Signal That Prevents Macrophage Phagocytosis," International Symposium on Amyloidosis, Tarragona, Spain, Sep. 14-18, 2020 (virtual), PM030:110, 1 page.
Heidel, R.E. et al. (2020). "Validation Of A Novel Model For The Comparative Analysis Of Amyloid-Reactive Biologicals Using A Single Mouse," International Symposium on Amyloidosis, Tarragona, Spain, Sep. 14-18, 2020 (virtual), PM001:80, 1 page.
Kennel, S.J. et al. (2020). "Amyloid Binding And Opsonization Properties Of A Novel Peptope-Antibody Complex," International Symposium on Amyloidosis, Tarragona, Spain, Sep. 14-18, 2020 (virtual), PM031:111, 1 page.
Lee, S. et al. (2013). "Dual Isotope SPECT Imaging Of I-123 And I-125," IEEE Medical Imaging Conference, Seoul, South Korea, Oct. 27-Nov. 2, 2013, 4 pages.

Martin, E.B. et al. (2014). "Characterization Of A Novel Peptide, P43, Optimized For Renal And Pancreatic Amyloid Detection," XIVth International Symposium on Amyloidosis, Indianapolis, IN, Apr. 28-May 1, 2014, OP-28:47, 1 page.
Martin, E.B. et al. (2014). "Characterization Of Peptide 125I-p5R+14 As An Optimized Radiotracer For The In Vivo Detection Of ApoA2c Amyloidosis," XIVth International Symposium on Amyloidosis, Indianapolis, IN, Apr. 28-May 1, 2014, PA-26:127, 1 page.
Martin, E.B. et al. (2014). "Detection Of Cardiac Amyloidosis By SPECT/CT Imaging Using Both 125I-Serum Amyloid P-Component And The Novel 125I-p5R+14 Peptide," XIVth International Symposium on Amyloidosis, Indianapolis, IN, Apr. 28-May 1, 2014, OP-22:40-41.
Martin, E.B. et al. (2017). "Recruitment Of Human Light Chain Proteins By Synthetic Fibrils Is Dependent On Disease State And May Be Used To Predict Amyloidogenic Propensity," Amyloid 24(S1):24-25.
Martin, E.B. et al. (Nov. 2020). "Looking For Amyloid In All The Right Places," Journal of Cardiac Failure 26(11):917-918.
Martin, E.B. et al. (Sep. 20, 2013). "Characterization Of Peptide 125I-p5R+14 As An Optimized Radiotracer For The In Vivo Detection Of ApoA2c Amyloidosis," World Molecular Imaging Congress, Savannah, GA, Sep. 18-21, 2013, Poster Session 3, Presentation No. P333:S839-S840.
Martin, E.B. et al. (Sep. 7, 2012). "Ex Vivo Identification And In Vivo Validation Of A Novel Visceral Amyloid Imaging Peptide," World Molecular Imaging Congress, Dublin, Ireland, Sep. 5-8, 2012, Poster Session 3, Presentation No. P481:S1517, 1 page.
Morgan, G.J. et al. (2020). "The Process Of Amyloid Formation Due To Monoclonal Immunoglobulins," Hematology/Oncology Clinics of North America 34(6):1041-1054.
Osborne, D. et al. (Sep. 5, 2012). "I-131 Rodent Imaging On The Inveon SPECT Platform Using A Novel Blended Collimator Acquisition Method," World Molecular Imaging Congress, Dublin, Ireland, Sep. 5-8, 2012, Poster Session 1, Presentation No. P154:S1190, 1 page.
Ramirez-Alvarado, M. et al. (Feb. 12, 2017). "82-Symp. From Native To Amyloid In The Test Tube And In Cells: A Journey Of Misbehaving Antibodies," Biophys J. 112(3):15a, 1 page.
Stuckey, A. et al. (2020). "Dynamic Biodistribution Of 124I-p5+14 In Patients With AL Amyloidosis," International Symposium on Amyloidosis, Tarragona, Spain, Sep. 14-18, 2020 (virtual), PT046:272, 1 page.
Stuckey, A. et al. (May 1, 2017). "Preclinical SPECT/CT Imaging, In A Mouse, Of A Novel Bifunctional Pre-Targeting Peptide For Systemic Amyloidosis Immunotherapy," Journal of Nuclear Medicine 58 (Suppl 1):1112, 2 pages.
Stuckey, A. et al. (May 1, 2018). "Preliminary Pharmacokinetic Study Of A Bispecific Peptide For Pretargeting Immunotherapy Of Amyloidosis Using PreClinical SPECT/CT," Journal of Nuclear Medicine 59(Suppl 1):1834, 2 pages.
Stuckey, A. et al. (May 1, 2019). "Characterization Of A Novel Â Sheet-Structured Peptide For Pretargeting Immunotherapy Of Amyloidosis," Journal of Nuclear Medicine 60(Suppl 1):3021, 2 pages.
U.S. Appl. No. 18/907,295, filed Oct. 4, 2024, for Jonathan S. Wall, et al. (U.S. Patent Application is not submitted herewith pursuant to the waiver of 37 C.F.R. § 1.98(a)(2)(iii) issued by the Office on Sep. 21, 2004.).
Wall, J. et al. (2022). "Preclinical Characterization Of AT-02, A Pan-Amyloid-Binding Immunoglobulin-Peptide Fusion Protein Capable Of Enhancing Phagocytosis And Facilitating Reduction of Amyloid," International Society of Amyloidosis, Heidelberg, Germany, Sep. 4-8, 2022, OP037: 14 pages.
Wall, J. et al. (2024). "Characterization Of A Novel Beta-Sheet Peptide-Fc Fusion For Targeting Systemic Amyloid Deposits," International Society of Amyloidosis XIX International Meeting, Rochester, MN, May 2024 254:S102, 1 page.
Wall, J. et al. (2024). "Characterization Of The Peptide-Antibody Fusion, AT-02—Studies To Support Its Use As An Immunotherapy

(56) References Cited

OTHER PUBLICATIONS

In Patients With Amyloidosis," Poster, presented at International Society of Amyloidosis XIX International Meeting, Rochester, MN, May 2024, 1 page.
Wall, J. et al. (Jan. 1, 2024). "The Peptide Fusion Immunoglobulin, AT-02, Exhibits Highly Potent Pan-Amyloid Reactivity And Immunomodulation," Journal of Cardiac Failure 30(1):217, 1 page.
Wall, J. et al. (May 1, 2020). "Characterization And In Vivo Target Engagement Studies Of A Novel, Preformed, Amyloid-Reactive Peptope-Antibody Complex," Journal of Nuclear Medicine 61(Suppl 1) 324:2 pages.
Wall, J.S. et al. (2014). "Heparin-Binding Peptides, Basic Fibroblast Growth Factor And p5R, Bind To Different Targets In Amyloid-Laden Mice And Controls," XIVth International Symposium on Amyloidosis, Indianapolis, IN, Apr. 28-May 1, 2014, PA-46:144-145.
Wall, J.S. et al. (2014). "High Affinity Amyloid-Reactive Peptide, p5R, Binds Non-Uniformly To Large Amyloid Deposits Due To A Binding Site Barrier Effect," XIVth International Symposium on Amyloidosis, Indianapolis, IN, Apr. 28-May 1, 2014, OP-23:41-42.
Wall, J.S. et al. (2014). "Soluble, Recombinant, Receptor For Advanced Glycation End-Products (RAGE) Binds AA Amyloid In Vivo," XIVth International Symposium on Amyloidosis, Indianapolis, IN, Apr. 28-May 1, 2014, OP-2:21, 1 page.
Wall, J.S. et al. (2014). "Specific Accumulation Of Radiolabeled Peptide p5 In Cerebral Vascular And Parenchymal Aβ Amyloid In Mice," XIVth International Symposium on Amyloidosis, Indianapolis, IN, Apr. 28-May 1, 2014, PA-45:143-144.
Wall, J.S. et al. (2016). "A Bifunctional Peptide, "Peptope", For Pre-Targeting Immunotherapy Of Systemic Amyloidosis Evaluated By Using Microautoradiography And SPECT/CT Imaging In A Mouse Model," 2016 World Molecular Imaging Congress, New York, NY, Sep. 7-10, 2016, Control ID 2500429:1 page.
Wall, J.S. et al. (2017, e-pub. Aug. 21, 2017). "Pretargeting Immunotherapy: A Novel Treatment Approach For Systemic Amyloidosis," Pharmaceutical Patent Analyst 6(5):215-223.
Wall, J.S. et al. (2018, e-pub. Oct. 30, 2018). "Bifunctional Amyloid-Reactive Peptide Promotes Binding Of Antibody 11-1F4 To Diverse Amyloid Types And Enhances Therapeutic Efficacy," PNAS 115(46):E10839-E10848.
Wall, J.S. et al. (2020). "Synthesis And Evaluation Of A Novel Peptide-Immunoglobulin Fusion For Targeting And Phagocytosis Of Amyloid," International Symposium on Amyloidosis, Tarragona, Spain, Sep. 14-18, 2020 (virtual), PM053:133, 1 page.
Wall, J.S. et al. (2023). "Characterization Of AT-02, A Pan-Amyloid-Binding Peptide Fusion Immunoglobulin With High Binding Potency, Complement Activation, And Immune Cell Stimulation," European Heart Journal 44(Suppl 2):1 page.
Wall, J.S. et al. (Dec. 26, 2012). "AL Amyloid Imaging And Therapy With A Monoclonal Antibody To A Cryptic Epitope On Amyloid Fibrils," PloS One 7(12):e52686, 10 pages.
Wall, J.S. et al. (May 7, 2012). "Amyloid-Reactive Peptides Bind MelA+ Melanocytes And Extracellular Melanin In Human, Canine And Murine Melanoma Tumors," XIIIth International Symposium on Amyloidosis, Groningen, Netherlands, May 6-10, 2012, PA62:123-124.
Wall, J.S. et al. (Sep. 18, 2013). "Evaluation Of SPECT Detection Of Cardiac Amyloidosis In Mice By Using 125I-p5R+14 Peptide Or 125I-SAP," World Molecular Imaging Congress, Savannah, GA, Sep. 18-21, 2013, Poster Session 1, Presentation No. P071:S418-S419.
Wall, J.S. et al. (Sep. 19, 2013). "Preliminary Evaluation Of [18F]SFB- And [18F]FBAM-Labeled Amyloidophilic Peptides In Mice With Visceral Amyloidosis," World Molecular Imaging Congress, Savannah, GA, Sep. 18-21, 2013, Poster Session 2, Presentation No. P163:S572-S573.
Wall, J.S. et al. (Sep. 7, 2012). "Arginine-Rich Peptide p5R Provides Enhanced Binding To Visceral Amyloid Deposits In Vitro And In Vivo," World Molecular Imaging Congress, Dublin, Ireland, Sep. 5-8, 2012, Poster Session 3, Presentation No. P493:S1529, 1 page.
Wall, J.S. et al. (Sep. 7, 2012). "Heparin-Binding Peptides bFGF And p5R Bind To Different Targets In Amyloid-Laden Mice And Controls," World Molecular Imaging Congress, Dublin, Ireland, Sep. 5-8, 2012, Poster Session 3, Presentation No. P492:S1528, 1 page.
Wall, J.S. et al. (Sep. 8, 2012). "Heparin-Reactive Peptide p5R Preferentially Binds A Subset Of MelA+ Melanocytes And Extracellular Melanin—A Novel Biomarker In Metastatic Melanoma Tumors," World Molecular Imaging Congress, Dublin, Ireland, Sep. 5-8, 2012, Scientific Session 25: Preclinical In Vivo—Oncology, Presentation No. SS176:S1970, 1 page.
Wang, Z. et al. (2021). "Computational Investigation Of The Binding Of A Designed Peptide To λ Light Chain Amyloid Fibril," Physical Chemistry Chemical Physics 23:20634-20644.
Wells, K. et al. (May 2012). "Radioimmunoimaging Of Amyloid Deposits In AL Amyloidosis," Journal of Nuclear Medicine 53(Suppl 1):537, 3 pages.

\* cited by examiner

FIG. 1

C-terminal —PTQTMVVDVT PTVQKAQKAQ AKQAKQAQKA QKAQAKQAKQAKS YGGGQAQAGA QGAQA- $^{125}$I-mIgp5 in AA mice at 24 h pi (autoradiography)

>11-1F4- VH
QVQLKESGPGLVAPSQSLSITCTVSGFSLSSYGVSWVRQPPGKGLEWLGVIWGDGSTNYHPNLMS
RLSISKDISKSQVLFKLNSLQTDDTATYYCVTLDYWGQGTSVTVSS

>11-1F4- VL
DVVMTQTPLSLPVSLGDQASISCRSSQSLVHRNGNTYLHWYLQKPGQSPKLLIYKVSNRFSGVPD
RFSGSGSGTDFTLKISRVEAEDLGLYFCFQTTYVPNTFGGGTKLEIK

FIG. 12

MODIFIED IMMUNOGLOBULINS FOR TARGETING AMYLOID DEPOSITS

CROSS-REFERENCE TO RELATED APPLICATIONS

This application is a divisional of U.S. patent application Ser. No. 18/181,489, filed on Mar. 9, 2023, which is a continuation of U.S. patent application Ser. No. 17/776,827, which adopts the international filing date of Nov. 13, 2020, which is a U.S. national phase application under 35 U.S.C. § 371 of International Application No. PCT/US2020/060596, filed on Nov. 13, 2020, which claims priority to U.S. Provisional Application No. 62/936,002, filed on Nov. 15, 2019, and U.S. Provisional Application No. 63/074,912, filed Sep. 4, 2020, the contents of which are each incorporated herein by reference in their entirety.

REFERENCE TO AN ELECTRONIC SEQUENCE LISTING

The contents of the electronic sequence listing (165992000111SEQLIST.xml; Size: 107,930 bytes; and Date of Creation: Mar. 15, 2024) is herein incorporated by reference in its entirety.

FIELD OF THE INVENTION

This application relates to modified immunoglobulins for targeting amyloid deposits, humanized antibodies that bind to human amyloid fibrils, and antibody-peptide fusion proteins, and methods of using the same.

BACKGROUND

Amyloidosis is a fatal protein-folding disorder characterized by the aggregation and deposition of proteinaceous fibrils and heparan sulfate proteoglycan in vital organs and tissues (Merlini, G. et al. (2003) *N. Engl. J. Med.* 349, 583-596; Merlini, G. et al. (2004) *J. Intern. Med.* 255, 159-178; De Lorenzi, E. et al. (2004) *Curr. Med. Chem.* 11, 1065-1084; Merlini, G. (2004) *Neth. J. Med.* 62, 104-105). The unrelenting accumulation of amyloid invariably leads to organ dysfunction and severe morbidity or death. The deposits can be cerebral, as in patients with Alzheimer's, Huntington's or prion diseases, or peripheral such as seen in patients with light chain (AL) amyloidosis and type 2 diabetes. Further sub-grouping into localized or systemic indicates whether the precursor protein is produced locally (at the site of deposition) or circulates in the blood stream and deposits at distant anatomic sites, respectively (Westermark, P. et al. (2007) *Amyloid.* 14, 179-183). Amyloid can affect any organ or tissue but the kidneys, pancreas, liver, spleen, nervous tissue and heart constitute the major sites of deposition in patients with familial or sporadic forms of peripheral amyloid disease. Alzheimer's disease currently affects more than 4 million Americans and this figure is estimated to increase to more than 16 million by the year 2050. It is by far the most common form of amyloidosis and poses the greatest socioeconomic impact. In contrast, the peripheral (or systemic) amyloidosis are orphan disorders but account for more than 5,000 new patients annually in the USA alone.

Of these, the major peripheral amyloidosis is light chain-associated (AL) amyloidosis, a sporadic monoclonal plasma cell dyscrasia resulting in the deposition of fibrils composed of immunoglobulin light chain proteins. AL accounts for approximately two thirds of all peripheral amyloid cases and has a calculated incidence of ~1.4 per 100,000 persons per year in the USA, which is comparable to that of acute lymphocytic and chronic myeloid leukemia (Group, U. S. C. S. W. (2007) United States Cancer Statistics: 1999-2003 Incidence and Mortality Web-Based Report, U.S. Department of Health and Human Services Centers for Disease Control and Prevention National Cancer Institute, Atlanta). Although AL is one fifth as common as the related plasma cell dyscrasia multiple myeloma it is arguably more devastating with a median survival of only 13.2 months due partly to the rapidly progressive nature of the organ destruction, the lack of effective anti-amyloid therapeutics and the inability to effectively diagnose the disease before organ failure occurs. Fewer than 5% of all AL patients survive 10 years or more from the time of diagnosis (Comenzo, R. L. et al. (2002) *Blood* 99, 4276-4282). Moreover, in patients with cardiac AL amyloidosis the median survival is less than 5 months.

ATTR is a form of systemic amyloidosis. 25% of patients with ATTR amyloidosis dies within 24 months of diagnosis. (Gertz and Dispenzieri JAMA 324(1)79-89 (2002).) Current therapies do not prevent organ damage. ATTR amyloidosis is caused by transtheryretin (TTR) fibrils. Transthyretin is a protein made by the liver that helps carry thyroid hormone and vitamin A in the blood. Normally, TTR is a tetramer made up of 4 single-chain monomers. In hereditary ATTR amyloidosis, TTR gene mutations are thought to destabilize the protein and cause tetramer dissociation into monomers, which aggregate into amyloid fibrils. In wild-type ATTR amyloidosis, the normal TTR protein becomes unstable, misfolds, and forms amyloid fibrils.

These amyloid fibrils then accumulate in multiple organs throughout the body For example, The wrist, in a narrow pathway called the carpal tunnel. This can cause carpal tunnel syndrome, which causes your hand and ARM TO BECOME NUMB AND TINGLE. The spinal canal, which can cause narrowing of the spinal column (spinal stenosis). The heart, which can cause heart failure and/or an irregular heart rhythm called atrial fibrillation.

Another prevalent form of peripheral amyloidosis in the U.S. is inflammation-associated (AA) amyloidosis, which is associated with chronic inflammatory disorders such as arthritis, tuberculosis and Familial Mediterranean Fever. The incidence of AA is greatest in certain regions of Europe and the frequency varies among ethnic groups (Buck, F. S. et al. (1989) *Mod. Pathol.* 2, 372-377). In areas where Familial Mediterranean Fever is prevalent and goes untreated, the incidence of AA can be 100%. In Europe the incidence, based on autopsy studies performed in the Denmark, is estimated to be 0.86% (Lofberg, H. et al. (1987) *Acta pathologica, microbiologica, et immunologica Scandinavica* 95, 297-302); however, in patients with rheumatoid or psoriatic arthritis the occurrence of AA can be as high as 26%. Such a high prevalence may warrant a screening program to detect the disease earlier. Deposition of amyloid is associated with a sustained increase in the plasma concentration of serum amyloid protein A (sAA), the precursor of the amyloid fibrils (Rocken, C. et al. (2002) *Virchows Arch.* 440, 111-122). AA differs from AL in the type of precursor protein that is deposited but both share common mechanistic features associated with fibril formation and deposition (Rocken, C. et al. (2006) *J. Pathol.* 210, 478-487; Rocken, C. et al. (2001) *Am. J. Pathol.* 158, 1029-1038).

In addition to the disorders in which the etiopathology of amyloid is well established, fibrillar deposits with the structural and tinctorial properties of amyloid have been identified in other syndromes although their relevance to the disease state has yet to be established. In type 2 diabetes for example, islet amyloid precursor protein (IAPP) deposits as amyloid in the Islets of Langerhans (Jaikaran, E. T. et al. (2001) *Biochim. Biophys. Acta* 1537, 179-203). The aggregation of IAPP results in oligomeric structures that are toxic to pancreatic cells (Lin, C. Y. et al. (2007) *Diabetes* 56, 1324-1332). Thus, it is suggested that the formation of IAPP amyloid in type 1 diabetic patients contributes to β cell destruction and ushers in the transition to insulin dependence (Jaikaran, E. T. et al. (2001) *Biochim. Biophys. Acta* 1537, 179-203). In another example, plaques containing amyloid fibrils composed of apolipoprotein A-I have been identified in over half of patients with atherosclerotic carotid arteries (Westermark, P. et al. (1995) *Am. J. Pathol.* 147, 1186-1192; Mucchiano, G. I. et al. (2001) *J. Pathol.* 193, 270-275). The deposition of these fibrils was more common in older patients but apoA-I is undoubtedly present early in plaque development (Vollmer, E. et al. (1991) *Virchows Arch. A. Pathol. Anat. Histopathol.* 419, 79-88). As a final example, Apo-A-I amyloid was also recently identified in knee joint menisci obtained from patients having knee replacement surgery and may contribute to the physical deterioration of the joint (Solomon, A. et al. (2006) *Arthritis Rheum.* 54, 3545-3550).

In total, more than 29 proteins have been chemically or serologically identified as constituents of fibrils in amyloid deposits. It is the nature of these proteins that differentiate the diseases, determine the treatment, and establish the prognosis. Although amyloid fibrils are associated with a clinically heterogeneous group of diseases and can form from structurally distinct and functionally diverse precursor proteins, the deposits themselves share a number of remarkably similar characteristics including fibril structure, fibril epitopes and accrual of similar accessory molecules including heparan sulfate proteoglycans (HSPGs). Amyloid is a heterogeneous complex that includes, in addition to fibrils, glycosaminoglycans (GAGs) and in particular the perlecan HSPG (Ancsin, J. B. (2003) *Amyloid* 10, 67-79; Ailles, L. et al. (1993) *Lab. Invest.* 69, 443-448; Kisilevsky, R. (1994) *Mol. Neurobiol.* 9, 23-24; Kisilevsky, R. (1990) *Lab. Invest.* 63, 589-591; Snow, A. D. et al. (1987) *Lab. Invest.* 56, 120-123; Li, J. P. et al. (2005) *Proc. Natl. Acad. Sci. USA* 102, 6473-6477). A partial list of amyloid and amyloid related disorders is provided in FIG. 1.

To date, the most effective therapeutic intervention for removing amyloid deposits, which may promote recovery of organ function and lead to an improved prognosis, involves the use of amyloid-reactive antibodies as a means of immunotherapy. Several immunotherapies (antibodies) have been developed for amyloid-related diseases, including monoclonal antibody 11-1F4 for the treatment of AL amyloidosis, NEOD001 for patients with AL amyloidosis, GSK2398852 (anti-SAP monoclonal antibody) for amyloidosis, Solanezumab for Alzheimer's disease, intravenous IgG (IVIG) for Alzheimer's disease, and Bapineuzumab for Alzheimer's disease. Each of these approaches has limitations or did not meet primary outcomes in late stage clinical trials (Phase 2/3).

SUMMARY OF THE INVENTION

Provided herein are modified immunoglobulins and antibody-peptide fusion proteins comprising an amyloid reactive peptide linked to an antibody or functional thereof that binds to human amyloid fibrils. The modified immunoglobulins and antibody-peptide fusion proteins provided herein unexpectedly show higher affinity to human amyloid fibrils by virtue of binding of the antibody and the amyloid reactive peptide to human amyloid fibrils. In some embodiments, the peptide provides enhanced activity of the antibody to clear amyloid deposits. In particular, the antibody Fc recruits macrophages that are able phagocytose and clear amyloid fibrils and deposits, for example by opsonization and the amyloid-reactive peptide is able to bind diverse amyloid fibrils and heparan sulfate glycosaminoglycans. Surprisingly, humanized anti-amyloid antibodies conjugated to a N-terminal amyloid-reactive peptide provide significantly better opsonization than a chimeric antibody that binds to amyloid fibers. Moreover, certain humanized antibodies, such as VH9/VL4, bind to amyloid fibrils with higher affinity than either a murine or chimeric antibody.

Also provided herein are methods of detecting and treating amyloidosis or using the modified immunoglobulins provided herein.

Further provided herein are nucleic acids encoding the modified immunoglobulins. In some embodiments, provided herein is a host cell comprising nucleic acid encoding a modified immunoglobulin. In some embodiments, the host cell is a CHO cell.

In one aspect, the present invention provides a modified immunoglobulin, comprising: an amyloid reactive peptide; and an Ig antibody or functional fragment thereof that binds to a human amyloid fibrils, wherein the Ig antibody or functional fragment thereof comprises a heavy chain and a light chain, wherein the peptide and the Ig antibody or functional fragment thereof are joined together at the N-terminal end of the Ig light chain and/or the N- and/or C-terminal end of the Ig heavy chain.

In some embodiments, the amyloid reactive peptide comprises an amino acid sequence having at least 85% sequence identity to any one of the amino acid sequences set forth as SEQ ID NOS:1-14.

In some embodiments, the amyloid-reactive peptide and the Ig antibody or functional fragment thereof are joined together at the N-terminal end of the Ig light chain.

In some embodiments, the modified immunoglobulin comprises a spacer sequence between the amyloid-reactive peptide and the Ig antibody or functional fragment thereof.

In some embodiments, the modified immunoglobulin comprises at least two amyloid-reactive peptides and wherein the amyloid-reactive peptides are the same peptide or different peptides.

In some embodiments, the Ig antibody or functional fragment thereof comprises a light chain variable region (VL) and a heavy chain variable region (VH), wherein the VL comprises a CDRL1 set forth in SEQ ID NO:20, a CDRL2 set forth in SEQ ID NO: 21, and a CDRL3 set forth in SEQ ID NO: 22; and wherein the VH comprises a CDRH1 set forth in SEQ ID NO: 17, a CDRH2 set forth in SEQ ID NO: 18, a CDRH3 set forth in the amino acid sequence LDY.

In some embodiments, the Ig antibody or functional fragment thereof is a chimeric antibody or functional fragment thereof.

In some embodiments, in the Ig antibody or functional fragment thereof comprises a light chain variable region (VL) and a heavy chain variable region (VH), wherein a) the VL comprises a CDR-L1 comprising the amino acid sequence set forth in SEQ ID NO:64-70, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in SEQ ID NO:18, and a CDR-H3 comprising the amino acid sequence LDY; or b) the VL comprises a CDR-L1 comprising the amino acid sequence set forth in SEQ ID NO: 20; a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in SEQ ID NO: 71-81; and a CDR-H3 comprising the amino acid sequence LDY.

In some embodiments, the Ig antibody or functional fragment thereof comprises human framework sequences.

In some embodiments, the Ig antibody comprises a human Fc region.

In some embodiments, the modified immunoglobulin comprises at least two amyloid reactive peptides, wherein peptides are the same peptide or different peptides.

In some embodiments, the modified immunoglobulin binds to rVλ6Wil, Aβ, Aβ(1-40), IAAP, ALκ4, Alλ1, or ATTR fibrils.

In another aspect, provided herein is an antibody-peptide fusion protein comprising an antibody that binds human amyloid fibrils fused to an amyloid-reactive peptide, wherein the antibody comprises a light chain variable region (VL), and a heavy chain variable region (VH).

In some embodiments, the VL comprises a CDR-L1 comprising the amino acid sequence set forth in SEQ ID NO:20, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in SEQ ID NO:18, and a CDR-H3 comprising the amino acid sequence LDY.

In some embodiments, the antibody is a chimeric antibody.

In some embodiments, a) the VL comprises a CDR-L1 comprising the amino acid sequence set forth in SEQ ID NO:64-70, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in SEQ ID NO:18, and a CDR-H3 comprising the amino acid sequence LDY; or b) the VL comprises a CDR-L1 comprising the amino acid sequence set forth in SEQ ID NO: 20; a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in SEQ ID NO: 71-81; and a CDR-H3 comprising the amino acid sequence LDY; or c) the VL comprises a CDR-L1 comprising the amino acid sequence set forth in SEQ ID NO:64-70, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in SEQ ID NO: 71-81; and a CDR-H3 comprising the amino acid sequence LDY.

In some embodiments, the VL comprises a CDR-L1 comprising the amino acid sequence set forth in SEQ ID NO:64, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in SEQ ID NO:73, and a CDR-H3 comprising the amino acid sequence LDY.

In some embodiments, the VL comprises Leu at position 46 and Phe at position 87, and the VH comprises Leu at position 48, Ser at position 96, Val at position 78, Leu at position 79, Phe at position 80, and Thr at position 94.

In some embodiments, the VL comprises an amino acid sequence set forth in SEQ ID NO:36, and the VH comprises an amino acid sequence set forth in SEQ ID NO:55.

In some embodiments, the VL comprises one or more amino acid residues selected from the group consisting of: Tyr at position 36; Leu at position 37; Leu at position 46; Leu at position 85; and Phe at position 87. In some embodiments, the VH comprises one or more amino acid residues selected from the group consisting of: Val at position 37; Leu at position 48; Leu at position 67; Ser at position 68; Lys at position 71; Ser at position 76; Val at position 78; Leu at position 79; Phe at position 80; Thr at position 89; Val at position 93; and Thr at position 94 wherein the amino acid positions are numbered according to the numbering system of Kabat.

In some embodiments, the VL comprises Tyr at position 36, Leu at position 37, Leu at position 46, Leu at position 85, and Phe at position 87, and the VH comprises Val at position 37, Leu at position 48, Leu at position 67, Ser at position 68, Lys at position 71, Thr at position 89, Val at position 93, and Thr at position 94.

In some embodiments, the VL comprises Leu at position 46 and Phe at position 87, and the VH comprises Leu at position 48, Ser at position 96, Val at position 78, Leu at position 79, Phe at position 80, and Thr at position 94.

In some embodiments, the VL comprises an amino acid sequence set forth in the group consisting of SEQ ID NOs:32-42

In some embodiments, the VH comprises an amino acid sequence set forth in the group consisting of SEQ ID NOs:43-63.

In some embodiments, the VL comprises an amino acid sequence set forth in SEQ ID NO:34, and the VH comprises an amino acid sequence set forth in SEQ ID NO:48.

In some embodiments, the VL comprises an amino acid sequence set forth in SEQ ID NO:35, and the VH comprises an amino acid sequence set forth in SEQ ID NO:51.

In some embodiments, the amyloid-reactive peptide comprises the amino acid sequence set forth in SEQ ID NO:1-14.

In some embodiments, the amyloid reactive peptide is fused to the N-terminus of the VL or VH.

In some embodiments, the amyloid reactive peptide is fused to the N-terminus of the VL or VH by a spacer. In some embodiments, the spacer is a peptide spacer. In some embodiments, the spacer comprises the amino acid sequence GGGYS (SEQ ID NO:27).

In some embodiments, the antibody-peptide fusion protein binds to rVλ6Wil, Aβ, Aβ(1-40), IAAP, ALκ4, Alλ1, or ATTR fibrils.

In another aspect, provided herein is a pharmaceutical composition comprising a modified immunoglobulin or an antibody-peptide fusion protein.

In another aspect, provided herein is nucleic acid(s) encoding a modified immunoglobulin an the antibody-peptide fusion protein. In another aspect, provided herein is a vector comprising the nucleic acid(s). In another aspect, provided herein is a host cell comprising the vector.

In another aspect, the present invention provides a method of making a modified immunoglobulin or an antibody-peptide fusion protein comprising culturing a host cell under conditions suitable for expression of the vector encoding the modified immunoglobulin or antibody-peptide fusion protein and recovering the modified immunoglobulin or antibody-peptide fusion protein.

In another aspect, the present invention provides a method of treating a subject having an amyloid related disorder, comprising administering to the subject an effective amount of a modified immunoglobulin or an antibody-peptide fusion protein.

In some embodiments, the amyloid related disorder is amyloidosis.

In some embodiments, the amyloid related disorder is selected from the group consisting of AL, AH, Aβ2M, ATTR, transthyretin, AA, AApoAI, AApoAII, AGel, ALys, ALEct2, AFib, ACys, ACal, AMed, AIAPP, APro, AIns, APrP, or Aβ amyloidosis In some embodiments, the subject is a human.

In another aspect, the present invention provides a method of targeting an amyloid deposit for clearance, comprising contacting an amyloid deposit with a modified immunoglobulin or an antibody-peptide fusion protein provided herein. In some embodiments, the amyloid deposit is removed. In some embodiments, the amyloid deposit is opsonized by the modified immunoglobulin or the antibody-peptide fusion protein.

In another aspect, provided herein is a method of targeting an amyloid deposit for clearance, comprising contacting an amyloid deposit with a modified immunoglobulin an antibody-peptide fusion protein.

In some embodiments, targeting the amyloid deposit for clearance results in clearance of the amyloid deposit.

In some embodiments, clearance results from opsonization of the amyloid deposit.

In some embodiments, the half-life of the amyloid reactive peptide in the modified immunoglobulin or antibody-peptide fusion protein is increased by about 10%, 20%, 30%, 40%, 50%, 60%, 70%, 80% or more as compared to the amyloid-reactive peptide alone.

In another aspect, provided herein is a method for generating a modified immunoglobulin, comprising: providing a first expression vector and a second expression vector, wherein the first expression vector comprises a first nucleic acid sequence encoding an Ig antibody light chain or functional fragment thereof; wherein the second expression vector comprises a second nucleic acid sequence encoding an Ig antibody heavy chain or functional fragment thereof; and wherein the first expression vector and/or the second expression vector comprise a third nucleic acid sequence that encodes a first peptide, the third nucleic acid sequence being located adjacent to the first nucleic acid sequence and/or the second nucleic acid sequence; and inserting the first and second expression vectors into a cell, wherein expression of the first and second expression vectors in the cell results in an immunoglobulin that is joined to the first peptide.

In some embodiments, the first expression vector and/or the second expression vector comprise a fourth nucleic acid sequence that encodes a second peptide, the fourth nucleic acid sequence being located adjacent to the first nucleic acid sequence and/or the second nucleic acid sequence.

In some embodiments, expression of the first and second expression vectors in the cell results in an immunoglobulin that is joined to the first peptide and the second peptide.

In some embodiments, a spacer nucleic acid sequence is located between the third nucleic acid sequence and the first nucleic acid sequence and/or the second first nucleic acid sequence.

In another aspect, the present invention provides a method of treating a subject suffering from, or suspected to be suffering from, an amyloid-based disease, comprising: i) administering the modified immunoglobulin or the antibody-peptide fusion protein to the subject, wherein the modified immunoglobulin or antibody-peptide fusion comprises a detectable label; and ii) determining whether a signal associated with the detectable label can be detected from the subject; and b) if the signal is detected, administering to the subject an amyloidosis treatment.

In some embodiments, if a signal is not detected, the method further comprises monitoring the subject for a later development of an amyloid deposit.

In some embodiments, the method further comprising determining the intensity of the signal and comparing the signal to a threshold value, above which the subject is determined to possess an amyloid deposit.

In some embodiments, the amyloidosis treatment comprises administering a modified immunoglobulin or an antibody-peptide fusion protein to the subject.

In some embodiments, administration of the modified immunoglobulin or the antibody-peptide fusion protein results in clearance of the amyloid deposit in the subject.

In another aspect, the present invention provides a method of identifying an amyloid deposit in a subject, comprising administering the modified immunoglobulin or antibody-peptide fusion protein to the subject, wherein the modified immunoglobulin or antibody-peptide fusion comprises a detectable label and detecting a signal from the modified immunoglobulin or antibody peptide fusion protein.

In some embodiments, the subject is determined to be amyloid free or suffering from monoclonal gammopathy of unknown significance (MGUS), multiple myeloma (MM), or one or more related plasma cell diseases.

In another aspect, the present invention provides a method of detecting a ligand, comprising: detectably labeling a modified immunoglobulin or an antibody-peptide fusion of any one of paragraphs, wherein the peptide of the modified immunoglobulin or antibody-peptide fusion protein has binding affinity to the ligand; contacting the ligand with the modified immunoglobulin or antibody-peptide fusion protein; and, determining a signal from the detectable label, thereby detecting the ligand.

In some embodiments, the modified immunoglobin or antibody peptide fusion protein is conjugated to a detectable label.

In some embodiments, the modified immunoglobulin or antibody-peptide fusion protein comprises a spacer that is N-terminal to the amyloid reactive peptide.

In some embodiments, the amyloid reactive peptide is joined to the N terminus of the VH of the antibody.

In one aspect, provided herein is a humanized antibody that binds to human amyloid fibrils, wherein the humanized antibody comprises a light chain variable region (VL) and a heavy chain variable region (VH), wherein the VL comprises a CDR-L1 comprising the amino acid sequence set forth in SEQ ID NO:20, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in SEQ ID NO:18, and a CDR-H3 comprising the amino acid sequence LDY, wherein the VL comprises one or more amino acid residues selected from the group consisting of: Tyr at position 36; Leu at position 37; Leu at position 46; Leu at position 85; and Phe at position 87; wherein the VH comprises one or more amino acid residues selected from the group consisting of: Val at position 37; Leu at position 48; Leu at position 67; Ser at position 68; Lys at position 71; Ser at position 76; Val at position 78; Leu at position 79; Phe at position 80; Thr at position 89; Val at position 93; and Thr at position 94; wherein the amino acid positions are numbered according to the numbering system of Kabat.

In some embodiments, the VL comprises Tyr at position 36, Leu at position 37, Leu at position 46, Leu at position 85, and Phe at position 87, and the VH comprises Val at position 37, Leu at position 48, Leu at position 67, Ser at position 68, Lys at position 71, Thr at position 89, Val at position 93, and Thr at position 94.

In some embodiments, the VL comprises Leu at position 46 and Phe at position 87, and the VH comprises Leu at position 48, Leu at position 67, Ser at position 68, Lys at position 71, Thr at position 89, Val at position 93, and Thr at position 94.

In some embodiments, the VL comprises an amino acid sequence set forth in the group consisting of SEQ ID NOs:33-42.

In some embodiments, the VH comprises an amino acid sequence set forth in the group consisting of SEQ ID NOs:44-63.

In some embodiments, the VL comprises an amino acid sequence set forth in SEQ ID NO:34, and the VH comprises an amino acid sequence set forth in SEQ ID NO:48.

In some embodiments, the VL comprises an amino acid sequence set forth in SEQ ID NO:35, and the VH comprises an amino acid sequence set forth in SEQ ID NO:51.

In another aspect, provided herein is a humanized antibody that binds to human amyloid fibrils, wherein the humanized antibody comprises a light chain variable region (VL) and a heavy chain variable region (VH), wherein a) the VL comprises a CDR-L1 comprising the amino acid sequence set forth in SEQ ID NO:64-70, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in SEQ ID NO:18, and a CDR-H3 comprising the amino acid sequence LDY; or b) the VL comprises a CDR-L1 comprising the amino acid sequence set forth in SEQ ID NO: 20; a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in SEQ ID NO: 71-81; and a CDR-H3 comprising the amino acid sequence LDY; or c) the VL comprises a CDR-L1 comprising the amino acid sequence set forth in SEQ ID NO:64-70, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in SEQ ID NO: 71-81; and a CDR-H3 comprising the amino acid sequence LDY.

In some embodiments, VL comprises one or more amino acid residues selected from the group consisting of: Tyr at position 36; Leu at position 37; Leu at position 46; Leu at position 85; and Phe at position 87; wherein the VH comprises one or more amino acid residues selected from the group consisting of: Val at position 37; Leu at position 48; Leu at position 67; Ser at position 68; Lys at position 71; Ser at position 76; Val at position 78; Leu at position 79; Phe at position 80; Thr at position 89; Val at position 93; and Thr at position 94; wherein the amino acid positions are numbered according to the numbering system of Kabat.

In some embodiments, the antibody is a full-length antibody, a Fab fragment, or a scFv.

In some embodiments, the antibody comprises an Fc region.

In some embodiments, the Fc region is of an IgG1, IgG2, IgG3, or IgG4 isotype.

In some embodiments, the humanized antibody or antibody-peptide fusion protein is conjugated to a detectable label.

In some embodiments, the humanized antibody binds to rVλ6Wil fibrils, Per125 wtATTR extract, KEN hATTR extract, SHI ALλ liver extract, and/or TAL ALκ liver extract.

In some embodiments, the humanized antibody binds to rVλ6Wil, Aβ, Aβ(1-40), IAAP, ALκ4, Alλ1, or ATTR fibrils.

In another aspect, provided herein is a pharmaceutical composition comprising the humanized antibody. In another aspect, the present invention provides nucleic acid(s) encoding the humanized antibody]. In another aspect, provided herein is a vector comprising the nucleic acid(s). In another aspect, provided herein is a host cell comprising the vector.

In another aspect, the present invention provides a method of making a humanized antibody comprising culturing the host cell as described herein under conditions suitable for expression of the vector encoding the humanized antibody and recovering the humanized antibody.

In another aspect, the present invention provides a method of treating a subject having an amyloid related disorder, comprising administering to the subject an effective amount of the humanized antibody. In some embodiments, the amyloid related disorder is amyloidosis. In some embodiments, the amyloid related disorder is selected from the group consisting of AL, AH, Aβ2M, ATTR, transthyretin, AA, AApoAI, AApoAII, AGel, ALys, ALEct2, AFib, ACys, ACal, AMed, AIAPP, APro, AIns, APrP, or Aβ amyloidosis. In some embodiments, the subject is a human.

In another aspect, the present invention provides a method of treating a subject suffering from, or suspected to be suffering from, an amyloid-based disease, comprising: determining whether the subject has an amyloid deposit by: detectably labeling the humanized antibody, administering the humanized antibody to the subject, determining whether a signal associated with the detectable label can be detected from the subject; and, if the signal is detected, administering to the subject an amyloidosis treatment.

In some embodiments, if a signal is not detected, the method further comprises monitoring the subject for a later development of an amyloid deposit.

In some embodiments, the method further comprises determining the intensity of the signal and comparing the signal to a threshold value, above which the subject is determined to possess an amyloid deposit. In some embodiments, the amyloidosis treatment comprises administering the humanized antibody to the subject.

In another aspect, the present invention provides a method of identifying an amyloid deposit in a subject, comprising detectably labeling the humanized antibody, administering the humanized antibody to the subject, and detecting a signal from the humanized antibody.

In some embodiments, the subject is determined to be amyloid free or suffering from monoclonal gammopathy of unknown significance (MGUS), multiple myeloma (MM), or one or more related plasma cell diseases.

BRIEF DESCRIPTION OF THE DRAWINGS

Figure 1:
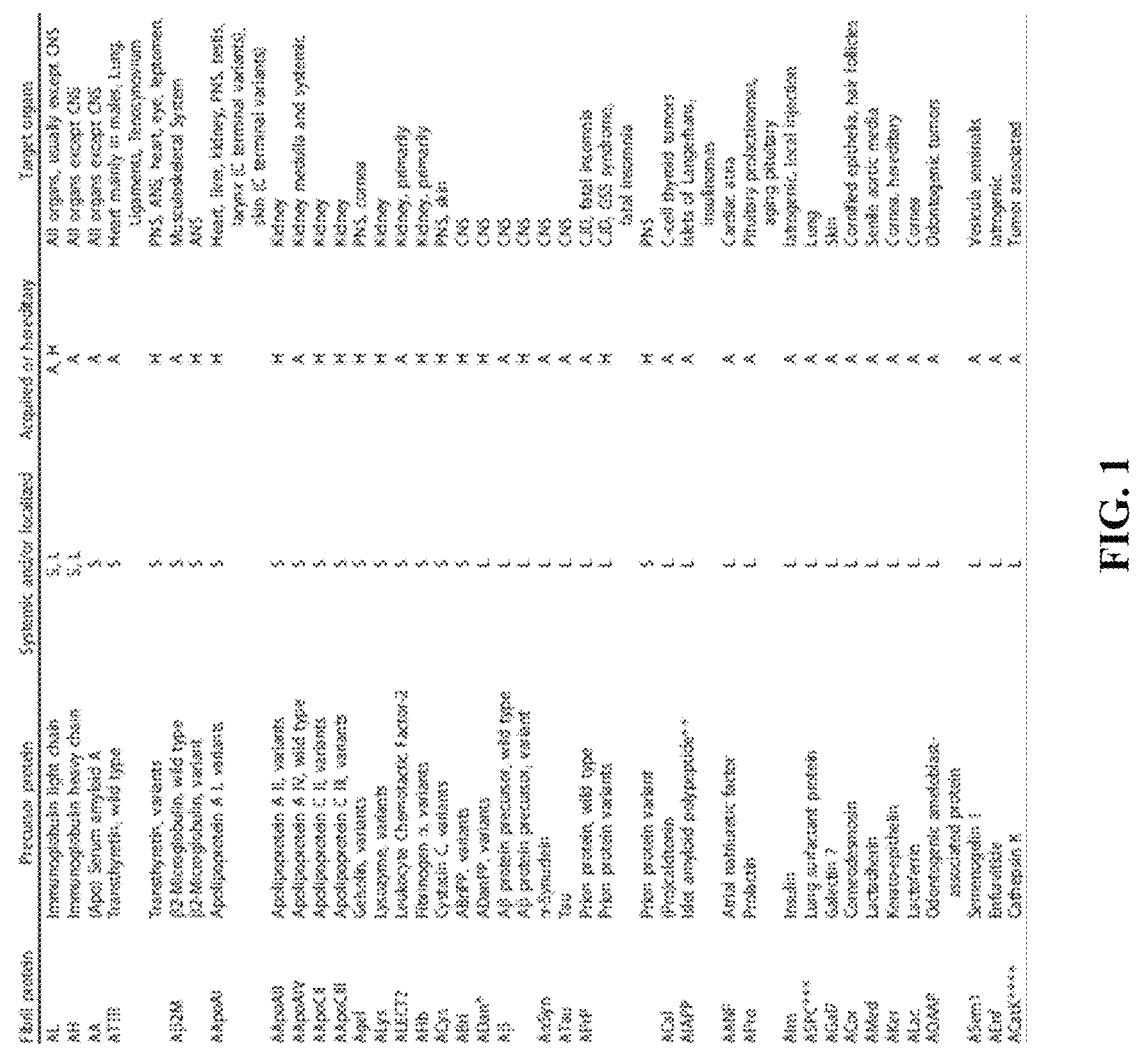

FIG. 1 shows a partial list of amyloid and amyloid-related disorders.

In FIG. 11B, the amino acid sequences are depicted from C- to N-terminus.

FIG. 12 provides annotated VH (top, SEQ ID NO: 15) and VL (bottom, SEQ ID NO: 16) amino acid sequences of the parental murine antibody m11-1F4. CDRs are shown in boxes, canonical framework region residues are underlined, and VH-VL interface residues are shown in bold and italic.

FIG. 13G shows data from an EuLISA measuring binding of VH6/VL3-p5R to Per125 wtATTR (gray circles, see label), Sno ATTR extract (dark gray circles), or Ken ATTR extract (light gray circles), and c11-1F4 binding to Sno ATTR extract (black squares). The log-transformed molar concentration of monoclonal antibody (−log(M)) is shown on the x-axis, and the level of binding (femtomoles europium) is shown on the y-axis.

Figure 14:
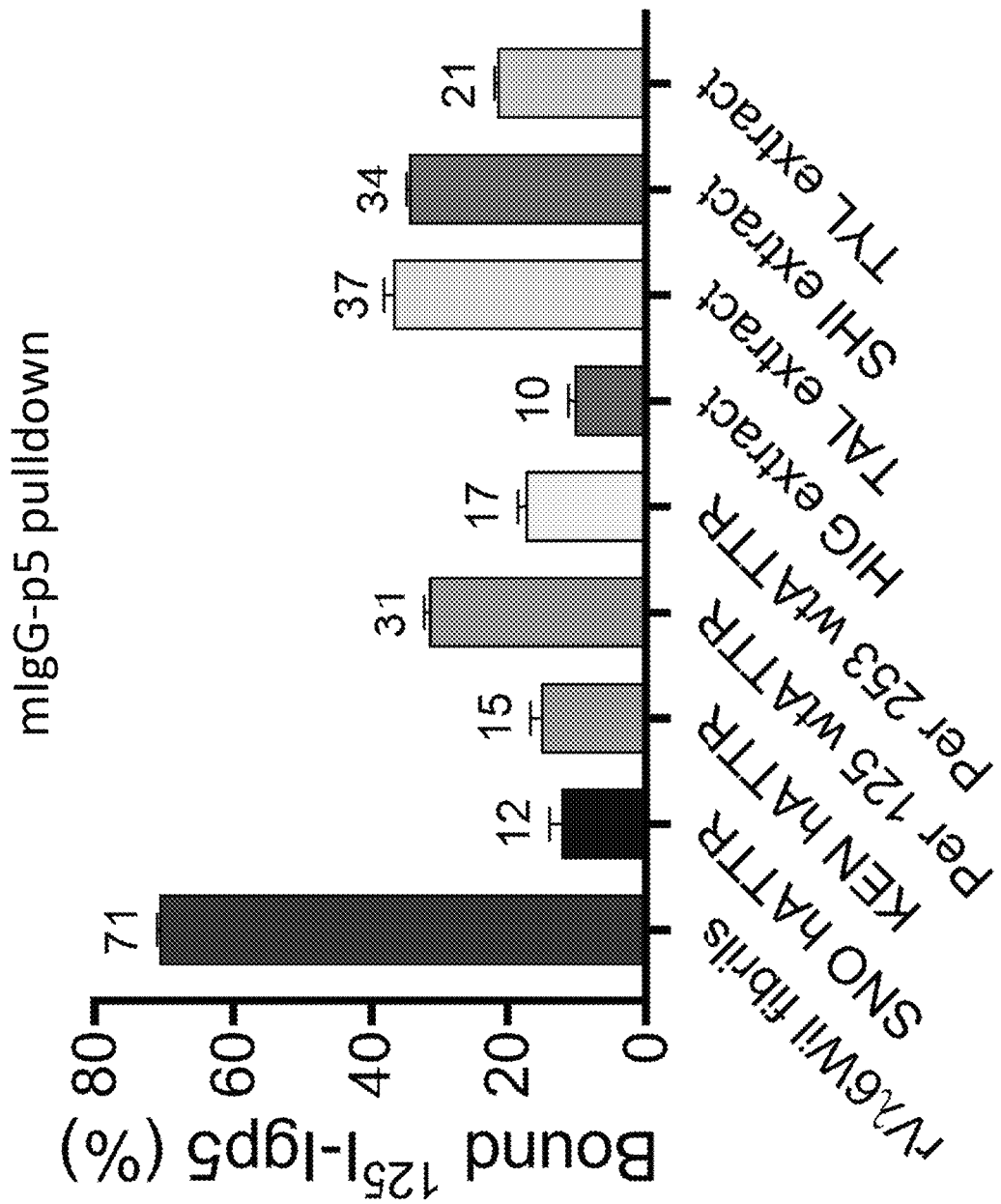

FIG. 14 shows the results of $^{125}$I-mIgp5 binding to rVλ6Wil amyloid-like fibrils and human amyloid extracts, obtained from tissues in a pulldown assay. The y-axis shows the percentage of bound $^{125}$I-mIgG-p5, and the percentage bound for each sample is indicated above the bars of the histograms. The x-axis shows the type of amyloid extract tested including, from left to right, rVλ6Wil fibrils (71% binding), SNO hereditary (h) ATTR (12% binding), KEN hATTR (15% binding), Per 125 wtATTR (31% binding), Per253 wild type (wt) ATTR (17% binding), ALκ HIG extract (10% binding), ALκ TAL extract (37% binding), ALλ SHI extract (34% binding), and ALλ TYL (21% binding) extract. The error bars represent the standard deviation.

Figure 15A:
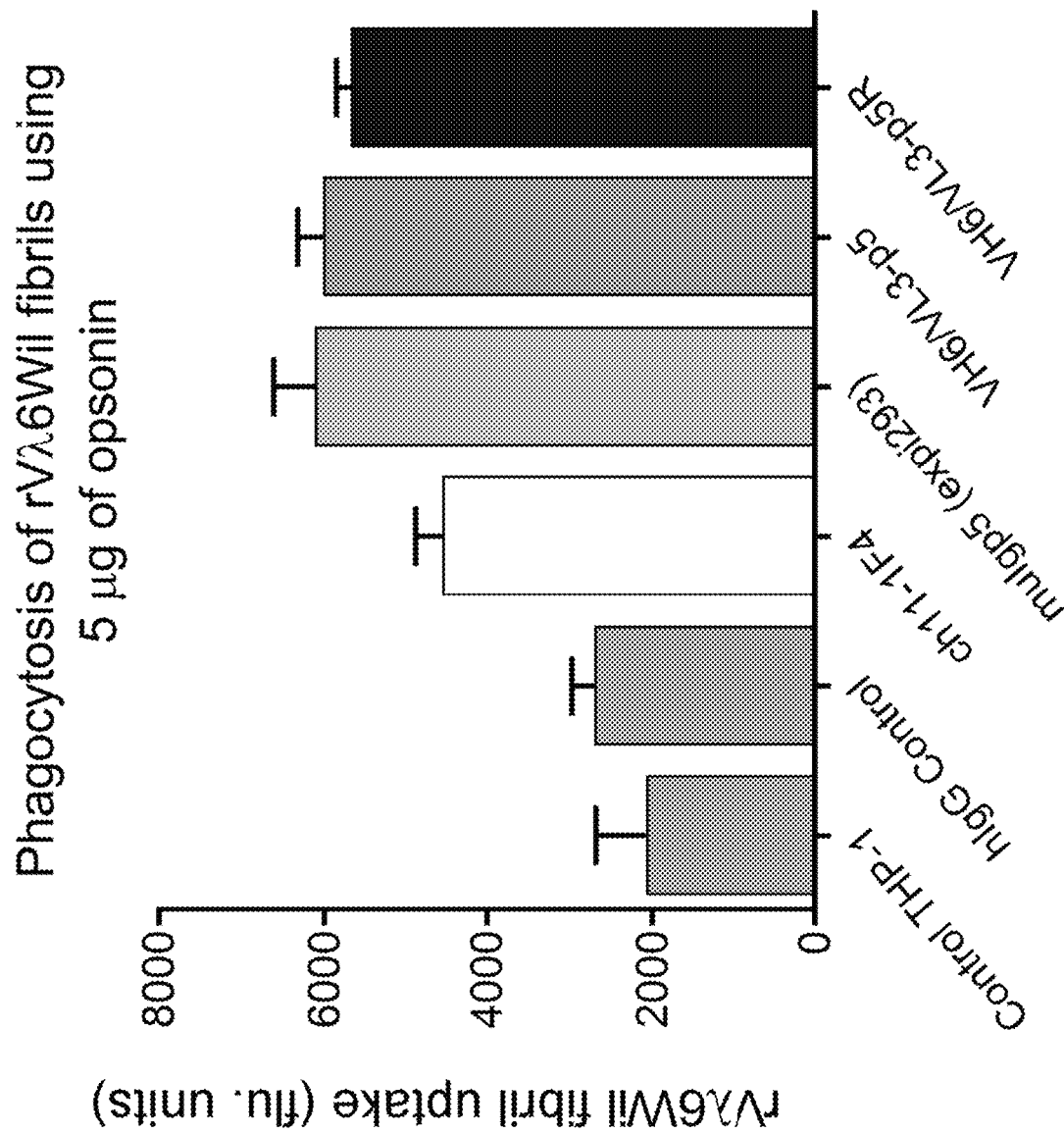
Figure 15B:
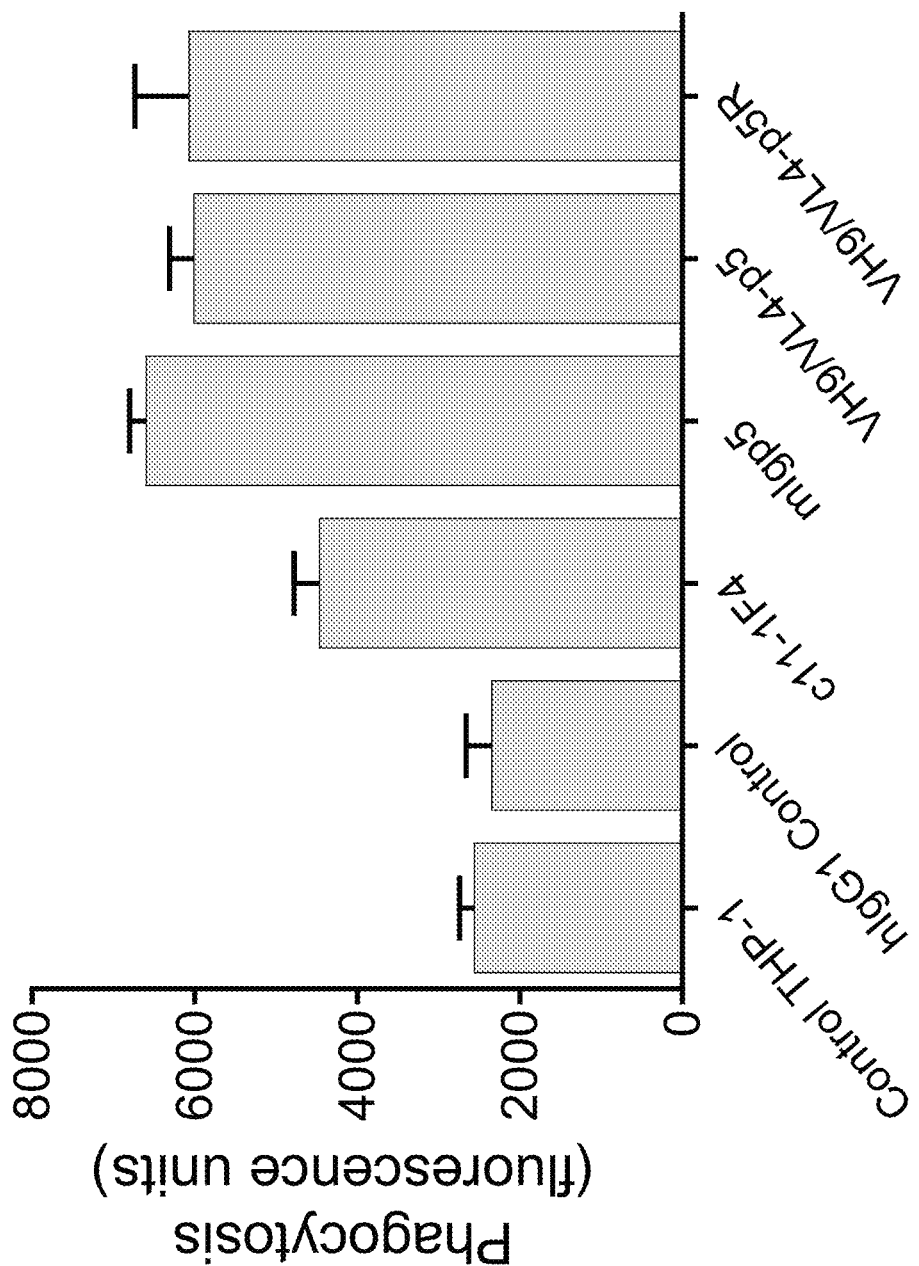
Figure 15C:
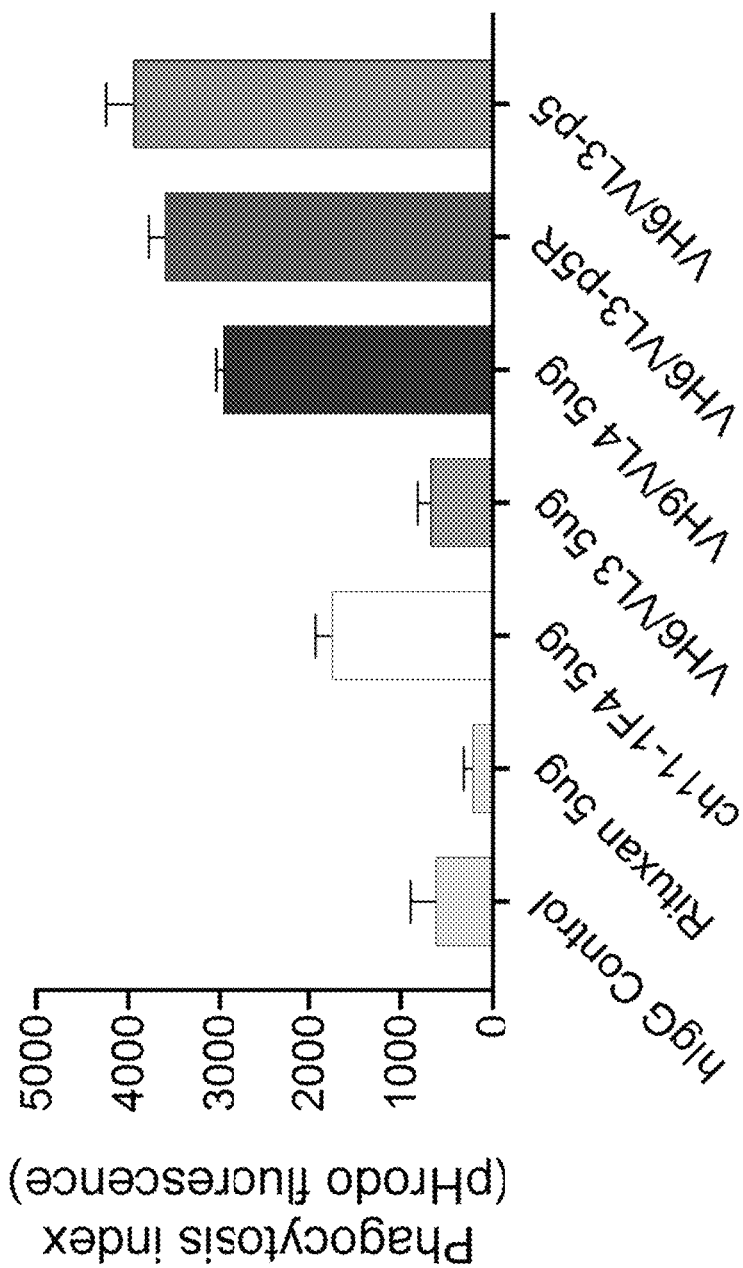

FIG. 15A shows pHrodo red-labeled rVλ6Wil fibril uptake by human THP-1 macrophages alone, or in the presence of human (h) IgG control, ch11-1F4, muIgp5 (produced in the expiHEK293 cell line), VH6/VL3-p5, or VH6/VL3-p5R, as indicated from left to right on the x-axis. The y-axis shows the level of rVλ6Wil fibril uptake (measured in fluorescent units), and the error bars represent the standard deviation. FIG. 15B shows phagocytosis of pHrodo red-labeled rVλ6Wil fibrils by macrophages in the presence of a THP-1 alone or with, hIgG control, c11-1F4, mIgp5, VH9/VL4-p5, or VH9/VL4-p5R, as indicated from left to right on the x-axis. The y-axis shows the level of phagocytosis (fluorescent units), and the error bars represent the standard deviation. FIG. 15C shows phagocytosis of pHrodo red-labeled rVλ6Wil fibrils by macrophages in the presence of a hIgG control, 5 μg Rituxan (a chimeric mAb as a negative control), 5 μg c11-1F4, 5 μg VH6/VL3, 5 μg VH9/VL4, VH6/VL3-p5R, or VH6/VL3-p5, as indicated from left to right on the x-axis. The y-axis shows the level of phagocytosis (pHrodo fluorescence), and the error bars represent the standard deviation.

Figure 16:
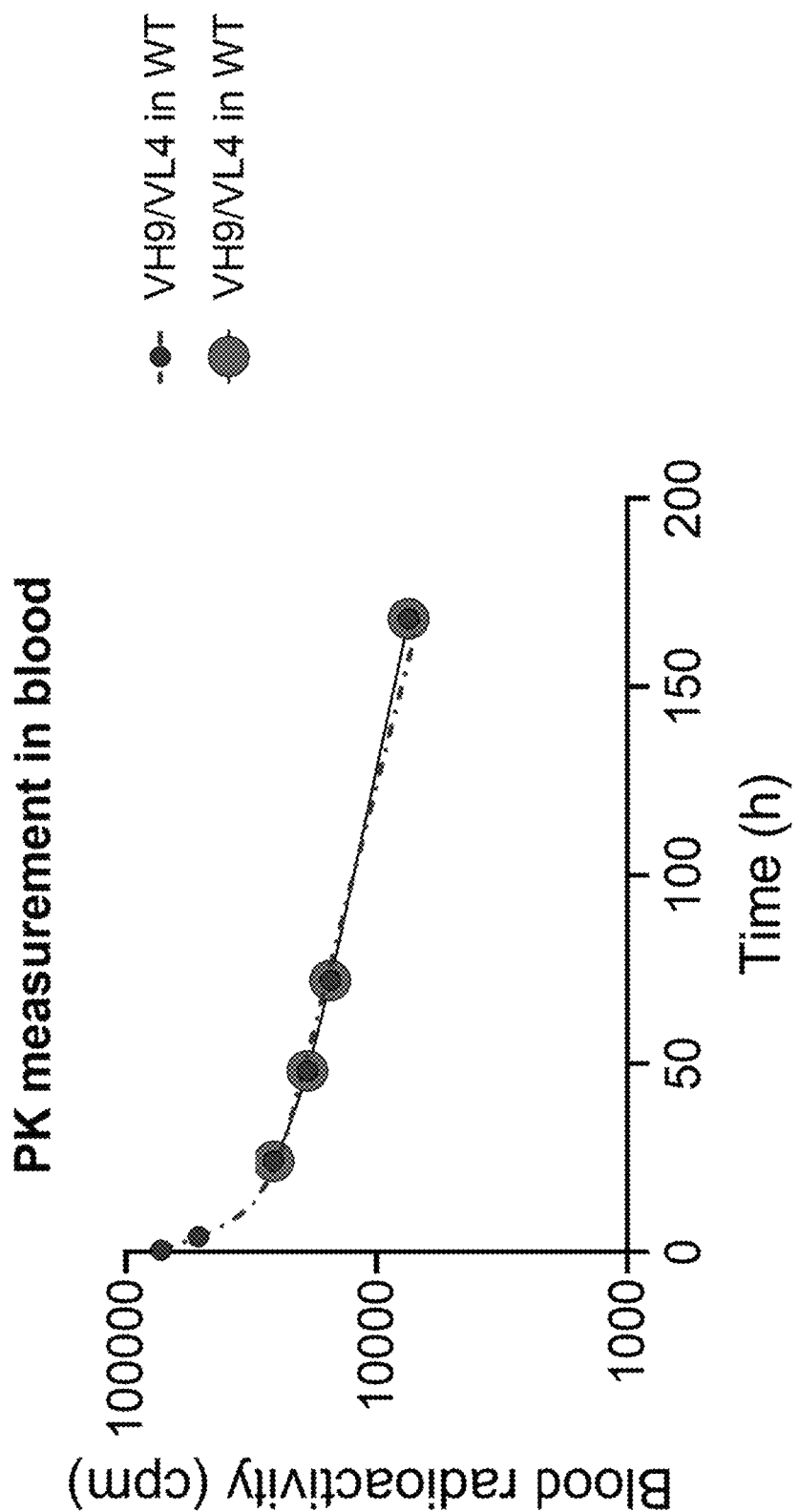

FIG. 16 shows a pharmacokinetic (PK) analysis of $^{125}$I-labeled VH9/VL4 antibody administered intravenously to wild-type ("WT") mice. The x-axis shows the time following administration in hours, and the y-axis shows the level of blood radioactivity in counts per minute ("cpm"). The fit to the curves uses a double exponential decay equation.

Figure 17A:
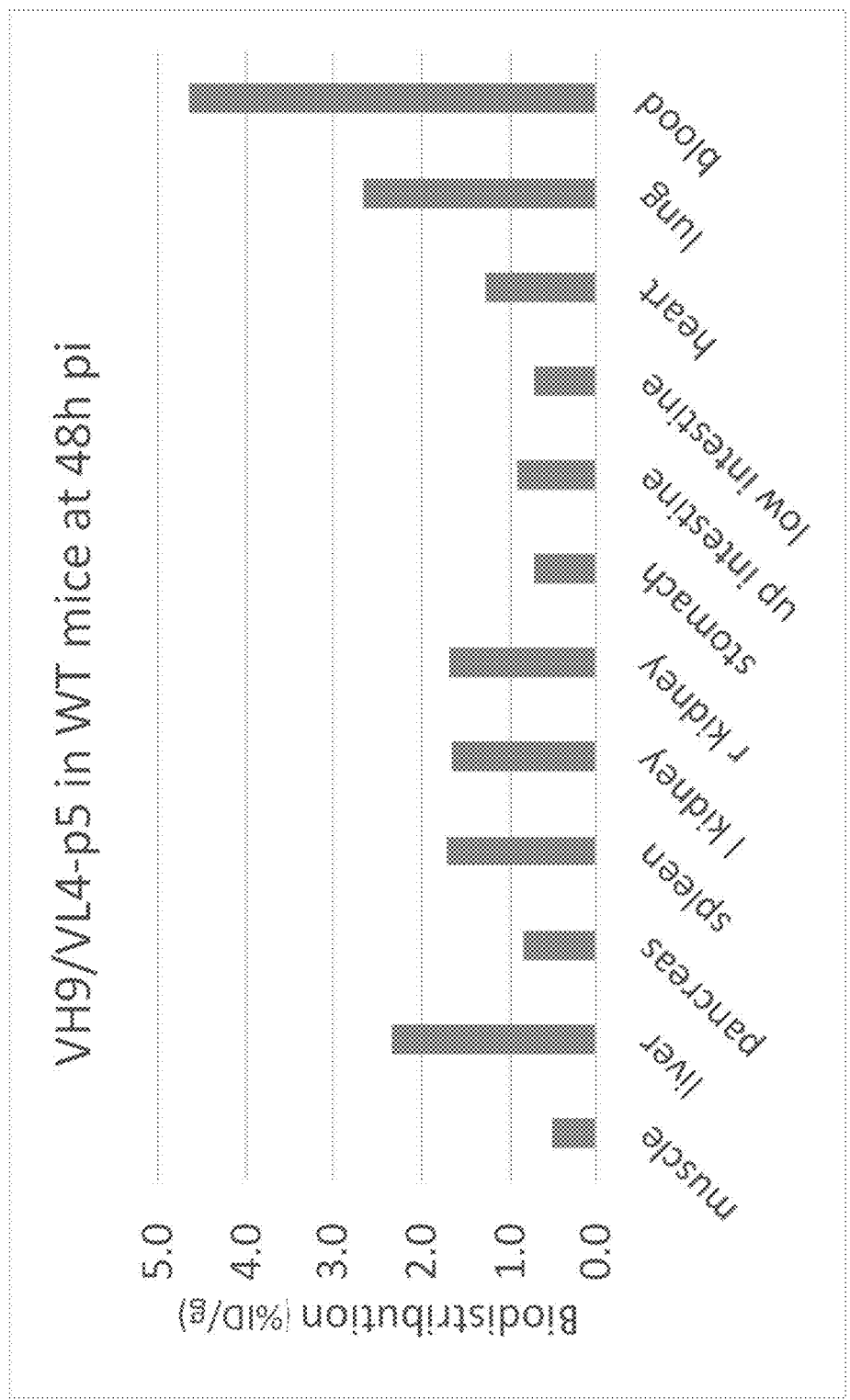
Figure 17B:
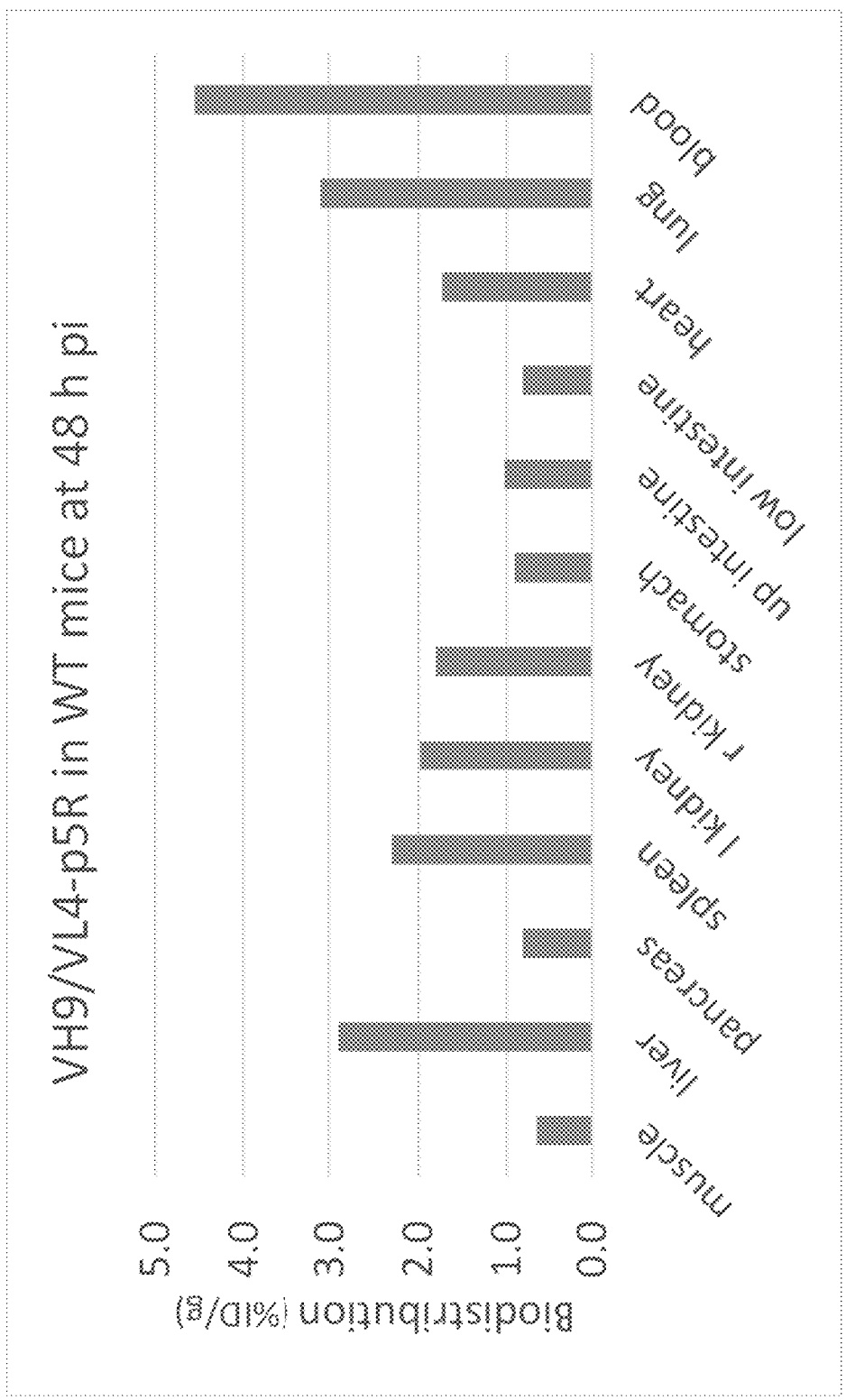

FIG. 17A shows the biodistribution of $^{125}$I-VH9/VL4-p5 in WT, amyloid free mice. FIG. 17B shows the biodistribution of $^{125}$I-VH9/VL4-p5R in WT, amyloid free mice. In both FIGS. 17A and 17B, the x-axis indicates the organ sampled including, from left to right, muscle, liver, pancreas, spleen, left kidney, right kidney, stomach, upper intestine, lower intestine, heart, lung, and blood; the y-axis indicates the level of biodistribution as a percentage of injected dose per gram tissue.

Figure 18:
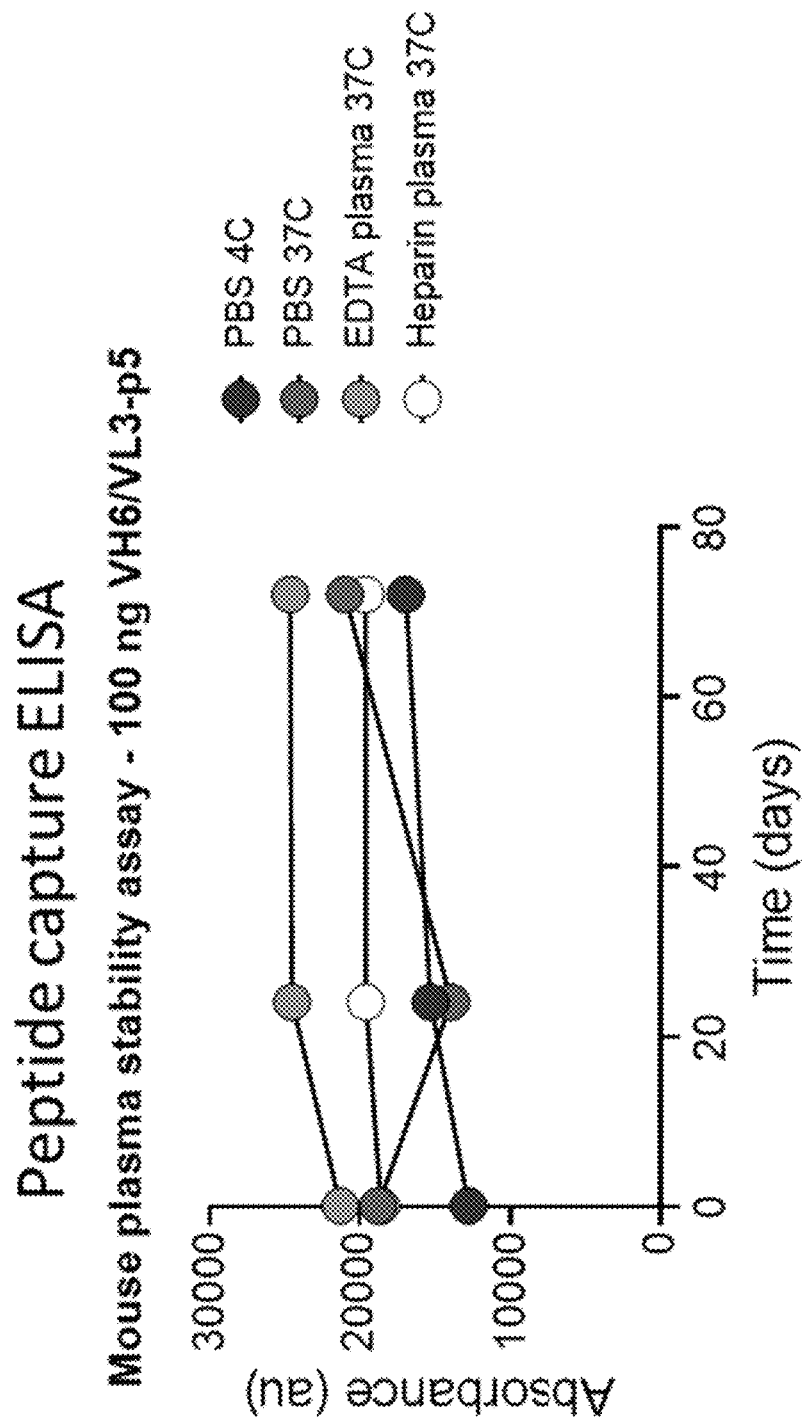

FIG. 18 shows data from a peptide capture ELISA measuring the stability of VH6/VL3-p5 in mouse plasma. 100 nM of VH6/VL3-p5 was added to either PBS at 4° C. (darkest gray), PBS at 37° C. (medium dark gray circles), EDTA anti-coagulated plasma at 37° C. (medium light gray circles), or heparin anticoagulated plasma at 37° C. (lightest gray circles). The x-axis indicates the time post administration in days, and the y-axis indicates antibody binding to ligand in absorbance units ("au").

DETAILED DESCRIPTION

Provided herein are modified immunoglobulins that bind amyloids. In some embodiments, the modified immunoglobulins are peptide-Ig fusion.

I. Definitions

Unless otherwise noted, technical terms are used according to conventional usage. Definitions of common terms in molecular biology may be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710) and other similar references. As used herein, the singular forms "a," "an," and "the," refer to both the singular as well as plural, unless the context clearly indicates otherwise. The abbreviation, "e.g." is derived from the Latin exempli gratia, and is used herein to indicate a non-limiting example. Thus, the abbreviation "e.g." is synonymous with the term "for example." As used herein, the term "comprises" means "includes."

Ranges can be expressed herein as from "about" one particular value, and/or to "about" another particular value. When such a range is expressed, another aspect includes from the one particular value of the range and/or to the other particular value of the range. It will be further understood that the endpoints of each of the ranges are significant both in relation to the other endpoint, and independently of the other endpoint. Similarly, when values are expressed as approximations, by use of the antecedent "about," it will be understood that the particular value forms another aspect. In certain example embodiments, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about. Further, terms used herein such as "example," "exemplary," or "exemplified," are not meant to show preference, but rather to explain that the aspect discussed thereafter is merely one example of the aspect presented.

It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. In case of conflict, the present specification, including explanations of terms, will control. In addition, the materials, methods, and examples are illustrative only and not intended to be limiting.

To facilitate review of the various embodiments of this disclosure, the following explanations of specific terms are provided:

Administration: The introduction of a composition into a subject by a chosen route. For example, if the chosen route is intravenous, the composition is administered by introducing the composition into a vein of the subject. In some examples a peptides are administered to a subject.

The terms amyloids, amyloid deposits, amyloid fibrils, and amyloid fibers refer to insoluble fibrous protein aggregates sharing specific structural traits. The protein aggregates have a tertiary structure, for example, that is formed by aggregation of any of several different proteins and that consists of an ordered arrangement of p sheets stacked perpendicular to a fiber axis. See Sunde et al., J. Mol. Biol. (1997) 273:729-39. Abnormal accumulation of amyloids in organs may lead to amyloidosis. Although they are diverse in their occurrence, all amyloids have common morphologic properties in that they stain with specific dyes such as Congo red and have a characteristic red-green birefringent appearance in polarized light after staining. Amyloids also share common ultrastructural features and common x-ray diffraction and infrared spectra.

Amyloidosis refers to a pathological condition or disease characterized by the presence of amyloids, such as the presence of amyloid deposits. "Amyloid diseases" or "amyloidosis" are diseases associated with the formation, deposition, accumulation or persistence of amyloid fibrils. Such diseases include, but are not limited to, Alzheimer's disease, Down's syndrome, hereditary cerebral hemorrhage with amyloidosis of the Dutch type, and cerebral beta-amyloid angiopathy. Other amyloid diseases such as systemic AA amyloidosis, AL amyloidosis, ATTR amyloidosis, ALect2 amyloidosis, and IAPP amyloidosis of type II diabetes are also amyloid diseases.

Amyloidogenic refers to producing or tending to produce amyloid deposits. For example, certain soluble monomeric proteins can undergo extensive conformational changes leading to their aggregation into well-ordered, unbranching, 8- to 10-nm wide fibrils, which culminate in the formation of amyloid aggregates. More than thirty proteins, for example, have been found to form amyloid deposits (or amyloids) in man. Not all proteins within the class of diverse proteins, such as immunoglobulin light chains, are capable of forming amyloid, i.e., some proteins are non-amyloidogenic, meaning that they do not tend to form amyloids. Other proteins of the class, however, can form amyloid deposits and are thus amyloidogenic. Furthermore, within the class of light chain protein, some may be deemed more "amyloidogenic" than others based upon the ease with which they form amyloid fibrils. Certain light chain proteins are deemed non-amyloidogenic or less amyloidogenic because of their inability to readily form amyloid fibrils in patients or in vitro.

Animal: Living multi-cellular vertebrate organisms, a category that includes, for example, mammals and birds. The term mammal includes both human and non-human mammals. Similarly, the term "subject" includes both human and veterinary subjects. In some examples a subject is a subject, such as a subject suffering from an amyloid disease.

Clearance: The terms "clear" or "clearance" refer to reducing or removing by a measurable degree. For example, the clearance of an amyloid deposit as described herein relates to reducing or removing the deposit to a measurable or discernable degree. Clearance may result in 100% removal, but is not required to. Rather, clearance may result in less than 100% removal, such as about 10%, 20%, 30%, 40%, 50%, 60% or more removal.

Conjugate: As used herein, the term "conjugate" refers to the product of coupling or joining of two or more materials, the resulting product having at least two distinct elements, such as at least two domains. The coupled materials may be the same or may be different. Such a coupling may be via one or more linking groups. A "protein conjugate," for example, results from the coupling of two or more amino acid sequences. A conjugate of two proteins, for example, results in a single protein that has a domain corresponding to each of the individually joined proteins.

Antibody refers to single chain, two-chain, and multi-chain proteins and glycoproteins belonging to the classes of polyclonal, monoclonal, chimeric and hetero immunoglobulins (monoclonal antibodies being preferred); it also includes synthetic and genetically engineered variants of these immunoglobulins. An "antibody fragment" includes Fab, Fab', F(ab')2, and Fv fragments, as well as any portion of an antibody having specificity toward a desired target epitope or epitopes. A "monoclonal antibody" is an antibody produced by a single clone of B-lymphocytes. Monoclonal antibodies are produced by methods known to those of skill in the art, for instance by making hybrid antibody-forming cells from a fusion of myeloma cells with immune spleen cells.

An epitope refers to a site on an antigen recognized by an antibody, as determined by the specificity of the antibody amino acid sequence. Epitopes are also called antigenic determinants. For example, the epitope may be portion of a recombinant protein that is recognized by the particular antibody. Further, the epitope may be a conformational epitope and linear epitope.

Chimeric antibody refers to an antibody that includes sequences derived from two different antibodies, which typically are of different species. Most typically, chimeric antibodies include human and murine antibody fragments, generally human constant and murine variable regions.

Humanized antibody refers to an antibody derived from a non-human antibody, typically murine, and a human antibody which retains or substantially retains the antigen-binding properties of the parent antibody but which is less immunogenic in humans.

Complementarity Determining Region or CDR refers to amino acid sequences that together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. By definition, the CDRs of the light chain are bounded by the residues at positions 24 and 34 (L-CDR1), 50 and 56 (L-CDR2), 89 and 97 (L-CDR3); the CDRs of the heavy chain are bounded by the residues at positions 31 and 35b (H-CDR1), 50 and 65 (H-CDR2), 95 and 102 (H-CDR3), using the numbering convention delineated by Kabat et al., (1991) Sequences of Proteins of Immunological Interest, 5th Edition, Department of Health and Human Services, Public Health Service, National Institutes of Health, Bethesda (NIH Publication No. 91-3242).

Framework region refers to amino acid sequences interposed between CDRs. These portions of the antibody serve to hold the CDRs in an appropriate orientation for antigen binding.

Specificity Determining Residue or SDR refers to amino acid residues of an immunoglobulin that are directly involved in antigen contact.

Constant region refers to the portion of the antibody molecule that confers effector functions. In the present invention, the variant antibodies include constant regions derived from human immunoglobulins. The heavy chain constant region can be selected from any of five isotypes: alpha, delta, epsilon, gamma or mu. Heavy chains of various subclasses (such as the IgG subclass of heavy chains) are responsible for different effector functions. Thus, by choosing the desired heavy chain constant region, humanized antibodies with the desired effector function can be produced. The light chain constant region can be of the kappa or lambda type, preferably the kappa type.

Effective amount or Therapeutically effective amount: The amount of agent that is sufficient to prevent, treat (including prophylaxis), reduce and/or ameliorate the symptoms and/or underlying causes of any of a disorder or disease, for example to prevent, inhibit, and/or amyloidosis. In some embodiments, an "effective amount" is sufficient to reduce or eliminate a symptom of a disease. An effective amount can be administered one or more times. For example, an effective amount of a peptide is an amount that is sufficient to bind an amyloid. A peptide may be effective, for example, when parenterally administered in amounts above about 1 µg per kg of body weight to about 30 mg/kg.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et ah, Methods in Enzymology 153:516-544, 1987). For example, when cloning in bacterial systems, inducible promoters such as µL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences. A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Inhibit: To reduce by a measurable degree. Inhibition does not, for example, require complete loss of function or complete cessation of the aspect being measured. For example, inhibiting plaque formation can mean stopping further growth of the plaque, slowing further growth of the plaque, or reducing the size of the plaque.

Inhibiting or treating a disease: Inhibiting the full development of a disease or condition, for example, inhibiting amyloidosis. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

With regard to amyloid deposit formation, "inhibition" refers to the prevention of reduction in the formation of the amyloid deposit, such as when compared to a control. For example, inhibition may result in a reduction of about 10%, 20%, 30%, 40%, 50%, 60% or more of an amyloid deposit as compared to a control.

Label refers to any detectable compound or composition that is conjugated directly or indirectly to another molecule to facilitate detection of that molecule. Specific, non-limiting examples of labels include fluorescent tags, chemiluminescent tags, haptens, enzymatic linkages, and radioactive isotopes. A protein that is "detectably-labeled," for example, means that the presence of the protein can be determined by a label associated with the protein.

Isolated: An "isolated" biological component, such as a peptide (for example one or more of the peptides disclosed herein), cell, nucleic acid, or serum samples has been substantially separated, produced apart from, or purified away from other biological components in the cell of the organism in which the component naturally occurs, for instance, other chromosomal and extrachromosomal DNA and RNA, and proteins. Nucleic acids, peptides and proteins that have been "isolated" thus include nucleic acids and proteins purified by standard purification methods. The term also embraces nucleic acids, peptides and proteins prepared by recombinant expression in a cell as well as chemically synthesized peptide and nucleic acids. The term "isolated" or "purified" does not require absolute purity; rather, it is intended as a relative term. Thus, for example, an isolated peptide preparation is one in which the peptide or protein is more enriched than the peptide or protein is in its natural environment within a cell. Preferably, a preparation is purified such that the protein or peptide represents at least 50% of the total peptide or protein content of the preparation, such as at least 50%, at least 60%, at least 70%, at least 80%, at least 90%, at least 95%, or even at least 99% of the peptide or protein concentration.

Join: As used herein, the term "join," "joined," "link," or "linked" refers to any method known in the art for functionally connecting proteins and/or protein domains. For example, one protein domain may be linked to another protein domain via a covalent bond, such as in a recombinant fusion protein, with or without intervening sequences or domains. Joined also includes, for example, the integration of two sequences together, such as placing two nucleic acid sequences together in the same nucleic acid strand so that the sequences are expressed together.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Nucleotide includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

cDNA refers to a DNA that is complementary or identical to an mRNA, in either single stranded or double stranded form.

Encoding refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (for example, rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

Recombinant nucleic acid refers to a nucleic acid having nucleotide sequences that are not naturally joined together. This includes nucleic acid vectors, such as adenoviral vectors, comprising an amplified or assembled nucleic acid which can be used to transform a suitable host cell. A host cell that comprises the recombinant nucleic acid is referred to as a "recombinant host cell." The gene is then expressed in the recombinant host cell to produce, such as a "recombinant polypeptide." A recombinant nucleic acid may serve a non-coding function (such as a promoter, origin of replication, ribosome-binding site, etc.) as well. A first sequence is an "antisense" with respect to a second sequence if a polynucleotide whose sequence is the first sequence specifically hybridizes with a polynucleotide whose sequence is the second sequence.

Pharmaceutically acceptable carriers: The pharmaceutically acceptable carriers of use are conventional. *Remington's Pharmaceutical Sciences*, by E. W. Martin, Mack Publishing Co., Easton, PA, 19$^{th}$ Edition (1995), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein is intended to encompass any amino acid sequence and include modified sequences such as glycoproteins. The term "polypeptide" is specifically intended to cover naturally occurring proteins, as well as those that are recombinantly or synthetically produced. In some examples, a peptide is one or more of the peptides disclosed herein.

Purified: The term "purified" does not require absolute purity; rather, it is intended as a relative term. Thus, for example, a purified protein preparation is one in which the protein referred to is more pure than the protein in its natural environment within a cell or within a production reaction chamber (as appropriate).

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith & Waterman *Adv. Appl. Math.* 2: 482, 1981; Needleman & Wunsch *J. Mol. Biol.* 48: 443, 1970; Pearson & Lipman *Proc. Natl. Acad. Sci. USA* 85: 2444, 1988; Higgins & Sharp *Gene* 73: 237-244, 1988; Higgins & Sharp *CABIOS* 5: 151-153, 1989; Corpet et al. *Nuc. Acids Res.* 16, 10881-90, 1988; Huang et al. *Computer Appls. In the Biosciences* 8, 155-65, 1992; and Pearson et al. *Meth. Mol. Bio.* 24, 307-31, 1994. Altschul et al. (*J. Mol.*

*Biol.* 215:403-410, 1990), presents a detailed consideration of sequence alignment methods and homology calculations.

The NCBI Basic Local Alignment Search Tool (BLAST) (Altschul et al. *J. Mol. Biol.* 215:403-410, 1990) is available from several sources, including the National Center for Biotechnology Information (NCBI, Bethesda, MD) and on the Internet, for use in connection with the sequence analysis programs blastp, blastn, blastx, tblastn and tblastx.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutical agent: A chemical compound or composition capable of inducing a desired therapeutic or prophylactic effect when properly administered to a subject or a cell.

Vector: A nucleic acid molecule as introduced into a host cell, thereby producing a transformed host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant DNA vectors having at least some nucleic acid sequences derived from one or more viruses. The term vector includes plasmids, linear nucleic acid molecules, and as described throughout adenovirus vectors and adenoviruses.

A subject refers to a vertebrate. The vertebrate may be a mammal, for example, a human. The subject may be a human patient. A subject may be a patient suffering from or suspected of suffering from a disease or condition and may be in need of treatment or diagnosis or may be in need of monitoring for the progression of the disease or condition. The patient may also be in on a treatment therapy that needs to be monitored for efficacy. In some example embodiments, a subject includes a subject suffering from amyloidosis, such as Alzheimer's, Huntington's or prion diseases, or peripheral amyloidosis such as seen in patients with light chain (AL) amyloidosis and type 2 diabetes.

The terms treating or treatment refer to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Preferably, residue positions which are not identical differ by conservative amino acid substitutions. The term "conservative amino acid substitutions" refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. (Bowie et al. *Science* 253:164 (1991). Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. *Nature* 354:105 (1991).

With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of LI, 50-55 of L2, 89-96 of L3, 31-35B of HI, 50-58 of H2, and 95-102 of H3. (See Almagro and Fransson, Front. Biosci. 13: 1619-1633 (2008).)

"Framework" or "FR" refers to variable domain residues other than CDR residues. The FR of a variable domain generally consists of four FR domains: FR1, FR2, FR3, and FR4. Accordingly, the CDR and FR sequences generally appear in the following sequence in VH (or VL): FR1-H1 (L1)-FR2-H2(L2)-FR3-H3(L3)-FR4; or FR1-CDR-H1(L1)-FR2-CDR-H2(L2)-FR3-CDR3-H3(L3)-FR4.

II. Modified Immunoglobulins and Antibody-Peptide Fusion Proteins

A. Modified Immunoglobulins

In certain example embodiments, provided are modified immunoglobulins that target amyloids. Such modified immunoglobulins include, for example, amyloid-reactive peptides that are joined to an immunoglobulin (Ig), such as through extension of the N-terminal of the Ig light chain protein in the fragment, antigen binding (Fab) region or via or the C-terminal of the heavy chain, thereby forming a peptide-Ig fusion. The modified immunoglobulins can be used to treat a subject suffering from amyloidosis, for example, such as by administering the modified immunoglobulins to the subject. In some embodiments, the modified immunoglobulin is a fusion protein comprising an antibody joined to an amyloid reactive peptide.

In some embodiments, the modified immunoglobulin comprises an antibody joined to a peptide. In some embodiments, the modified immunoglobulin comprises antibody that comprises one, two, three, four, five, or six CDRs of antibody 11-1F4. In some embodiments, the antibody comprises the VH and/or the VL of antibody 11-1F4. In some embodiments, the antibody comprises the heavy chain and/or the light chain of antibody 11-1F4, wherein the antibody is joined to a peptide.

In a particular embodiment, the modified immunoglobulin comprises an antibody, wherein the antibody comprises a VH that comprises (a) a CDR-H1 comprising the amino acid sequence of SEQ ID NO:17, (b) a CDR-H2 comprising the amino acid sequence of SEQ ID NO:18, and (c) a CDR-H3 comprising the amino acid sequence LDY, wherein the antibody is joined to a peptide.

In a particular embodiment, the modified immunoglobulin comprises an antibody, wherein the antibody comprises a VL that comprises (a) a CDR-L1 comprising the amino acid sequence of SEQ ID NO:20; (b) a CDR-L2 comprising the amino acid sequence of SEQ ID NO:21; and (c) a CDR-L3 comprising the amino acid sequence of SEQ ID NO:22, wherein the antibody is joined to a peptide.

In one embodiment, the modified immunoglobulin comprises an antibody that comprises a VL comprising the amino acid sequence of SEQ ID NO:16 and a VH comprising the amino acid sequence of SEQ ID NO:15, wherein the antibody is joined to a peptide.

In another aspect, the modified immunoglobulin comprises an antibody, wherein the antibody comprises a VH comprising a CDR-H1 comprising the amino acid sequence of SEQ ID NO: 17, a CDR-H2 comprising the amino acid sequence of SEQ ID NO:18, and a CDR-H3 comprising the amino acid sequence LDY; and a VL comprising a CDR-L1 comprising the amino acid sequence of SEQ ID NO:20, a CDR-L2 comprising the amino acid sequence of SEQ ID NO:21, and a CDR-L3 comprising the amino acid sequence of SEQ ID NO:22, and wherein the antibody is joined to a peptide. In some embodiments, the modified immunoglobulin comprises an antibody joined to an amyloid reactive peptide comprising any of the amino acid sequences listed in Table 1. In some embodiments, the modified immunoglobulin comprises an antibody joined to an amyloid reactive peptide comprising the amino acid sequence of SEQ ID NO:1. In some embodiments, the modified immunoglobulin comprises an antibody joined to an amyloid reactive peptide comprising the amino acid sequence of SEQ ID NO:2.

In another aspect, the modified immunoglobulin comprises an antibody, wherein the antibody comprises a VH CDR1, a VH CDR2, and a VH CDR3 of a VH having the sequence set forth in SEQ ID NO:15 and a VL CDR1, a VL CDR2, and a VL of a VL having the sequence set forth in SEQ ID NO:16; and wherein the antibody is joined to a peptide. In some embodiments, the modified immunoglobulin comprises an antibody joined to an amyloid reactive peptide comprising any of the amino acid sequences listed in Table 1. In some embodiments, the modified immunoglobulin comprises an antibody joined to an amyloid reactive peptide comprising the amino acid sequence of SEQ ID NO:1. In some embodiments, the modified immunoglobulin comprises an antibody joined to an amyloid reactive peptide comprising the amino acid sequence of SEQ ID NO:2.

In some embodiments, the modified immunoglobulin comprises an antibody that comprises a heavy chain comprising a VH comprising the amino acid sequence of SEQ ID NO:15 and a light chain comprising a VL comprising the amino acid sequence of SEQ ID NO:16, wherein the light chain is joined to a peptide. In some embodiments, the modified immunoglobulin comprises a heavy chain comprising a VH comprising the amino acid sequence of SEQ ID NO:15 without the C-terminal lysine residue, and a VL comprising the amino acid sequence of SEQ ID NO:16, wherein the antibody is joined to a peptide.

In another aspect, the modified immunoglobulin comprises an antibody joined to an amyloid reactive peptide. In some embodiments, the modified immunoglobulin comprises an antibody joined to an amyloid reactive peptide comprising any of the amino acid sequences listed in Table 1. In some embodiments, the modified immunoglobulin comprises an antibody joined to an amyloid reactive peptide comprising the amino acid sequence of SEQ ID NO:1. In some embodiments, the modified immunoglobulins comprise an antibody joined to an amyloid reactive peptide comprising the amino acid sequence of SEQ ID NO:2. In some embodiments, the peptide is joined to the N-terminus of the antibody light chain or the C-terminus of the heavy chain. In some embodiments, the antibody also comprises a spacer amino acid sequence between the peptide and the N-terminus of the light chain or the C-terminus of the heavy chain. In some embodiments, the peptide is joined to the N-terminus of the light chain. In some embodiments, the peptide is joined to the N-terminus of the heavy chain.

In some embodiments, the modified immunoglobulin comprises an antibody that comprises a heavy chain comprising a VH comprising the amino acid sequence of SEQ ID NO:15, wherein the heavy chain is joined to a peptide comprising any of the amino acid sequences of Table 1. In some embodiments, the modified immunoglobulins comprise an antibody comprising a heavy chain comprising a VH comprising the amino acid sequence of SEQ ID NO:15, wherein the heavy chain is joined to a peptide comprising the amino acid sequence of SEQ ID NO:1. In some embodiments, the modified immunoglobulin comprises an antibody comprising a heavy chain comprising a VH comprising the amino acid sequence of SEQ ID NO:15, wherein the heavy chain is joined to a peptide comprising the amino acid sequence of SEQ ID NO:2.

In some embodiments, the modified immunoglobulin comprises an antibody that comprises a light chain comprising a VL comprising the amino acid sequence of SEQ ID NO:16, wherein the light chain is joined to a peptide comprising any of the amino acid sequences of Table 1. In some embodiments, the modified immunoglobulin comprises an antibody comprising a light chain comprising a VL comprising the amino acid sequence of SEQ ID NO:16, wherein the light chain is joined to a peptide comprising the amino acid sequence of SEQ ID NO:1. In some embodiments, the modified immunoglobulins comprise an antibody a light chain comprising a VL comprising the amino acid sequence of SEQ ID NO:16, wherein the light chain is joined to a peptide comprising the amino acid sequence of SEQ ID NO:2.

In some embodiments, the modified immunoglobulin comprises an antibody comprising a heavy chain comprising a VH comprising the amino acid sequence of SEQ ID NO:15 and a light chain comprising a VL comprising the amino acid sequence of SEQ ID NO:16, wherein the light chain is joined to a peptide comprising any of the amino acid sequences of Table 1.

In some embodiments, the modified immunoglobulin comprises an antibody comprising heavy chain comprising a VH comprising the amino acid sequence of SEQ ID NO:15 and a light chain comprising a VL comprising the amino acid sequence of SEQ ID NO:16, wherein the light chain is joined to a peptide comprising the amino acid sequence of SEQ ID NO:1. In some embodiments, the peptide is joined to the light chain at the N-terminus.

In some embodiments, the modified immunoglobulin comprises an antibody a heavy chain comprising a VH comprising the amino acid sequence of SEQ ID NO:15 and a light chain comprising a VL comprising the amino acid sequence of SEQ ID NO:16, wherein the light chain is joined to a peptide comprising the amino acid sequence of SEQ ID NO:2. In some embodiments, the peptide is joined to the light chain at the N-terminus.

In some embodiments, the modified immunoglobulins described herein bind to amyloid deposits or fibrils. In some embodiments, the modified immunoglobulin binds to one or more amyloidogenic peptides in amyloids. In some embodiments, amyloids bound by the modified immunoglobulins comprise an amyloidogenic λ6 variable domain protein (Vλ6Wil) or an amyloidogenic immunoglobulin light chain (AL), Aβ(1-40) amyloid-like fibril or an amyloidogenic Aβ precursor protein, or serum amyloid protein A (AA). In other embodiments, the amyloids bound by the modified immunoglobulin comprise amyloidogenic forms of immunoglobulin heavy chain (AH), β$_2$-microglobulin (Aβ$_2$M), transthyretin variants (ATTR), apolipoprotein AI (AApoAI), apolipoprotein AII (AApoAII), gelsolin (AGel), lysozyme (ALys), leukocyte chemotactic factor (ALect2), fibrinogen a variants (AFib), cystatin variants (ACys), calcitonin ((ACal), lactadherin (AMed), islet amyloid polypeptide (AIAPP), prolactin (APro), insulin (AIns), prior protein (APrP); α-synuclein (AαSyn), tau (ATau), atrial natriuretic factor (AANF), or IAAP, ALκ4, Alλ1 other amyloidogenic peptides. The amyloidogenic peptides bound by the modified immunoglobulins can be a protein, a protein fragment, or a protein domain. In some embodiments, the amyloid deposits or amyloid fibrils comprise recombinant amyloidogenic proteins. In some embodiments, the amyloids are part of the pathology of a disease.

As those skilled in the art will appreciate, the fragment antigen binding (or Fab region) is the head of an antibody that naturally interacts with target antigen. Components of the Fab region, for example, allow antibodies to bind to specific ligands and, through that interaction, to further activate the immune system. For IgG, IgA, IgD, IgE, and IgM antibody isotypes, the Ig is composed of two proteins, the heavy chain and light chain that interact in pairs to form an intact Ig comprising 2 heavy chains and 2 light chains. Both the heavy and light chains are further divided into variable domains and constant domains—the light and heavy variable domains comprising the Fab functional region and the heavy chains forming the fragment crystallizable (Fc) domains that interact with cell receptors and complement. The Fc regions of Ig bears a highly conserved N-glycosylation site.

In certain example embodiments, one or more of the peptides shown in Table 1 below can be joined to an Ig antibody or functional fragment thereof through the N-terminal of the light chain protein or the C-terminal of the heavy chain, thereby forming a modified immunoglobulin. That is, any of the sequences identified below in Table 1 can be joined to the heavy or light chain of the Ig antibody or functional fragment thereof independently or simultaneously to form a peptide-Ig conjugate. For example, two of the amyloid reactive peptides can be joined with a single Ig antibody, such by joining the amyloid-reactive peptide amino acid sequences to the N-terminal of the Ig light chain proteins.

TABLE 1

Example Amyloid-Reactive Peptide Sequences

| PEPTIDE | PRIMARY SEQUENCE: | SEQ ID NO |
|---|---|---|
| P5 | KAQKA QAKQA KQAQK AQKAQ AKQAK Q | SEQ ID NO: 1 |
| P5R | RAQRA QARQA ROAQR AQRAQ ARQAR Q | SEQ ID NO: 2 |
| P5G | GAQGA QAGQA GOAQG AQGAQ AGQAG Q | SEQ ID NO: 3 |
| P8 | KAKAK AKAKA KAKAK | SEQ ID NO: 4 |
| P9 | KAQAK AQAKA QAKAQ AKAQA KAQAK AQAK | SEQ ID NO: 5 |
| P19 | KAQQA QAKQA QQAQK AQQAQ AKQAQ Q | SEQ ID NO: 6 |
| P20 | QAQKA QAQQA KQAQQ AQKAQ AQQAK Q | SEQ ID NO: 7 |
| P31 | KAQKA QAKQA KQAQK AQKAQ AKQAK Q | SEQ ID NO: 8 |
| P37 | KTVKT VTKVT KVTVK TVKTV TKVTK V | SEQ ID NO: 9 |
| P42 | VYKVK TKVKT KVKTK VKT | SEQ ID NO: 10 |
| P43 | AQAYS KAQKA QAKQA KQAQK AQKAQ AKAK Q | SEQ ID NO: 11 |
| P44 | AQAYA RAQRA QARQA ROAQR AQRAQ ARQAR Q | SEQ ID NO: 12 |
| P5 + 14 | KAQKA QAKQA KQAQK AQKAQ AKQAK QAQKA QKAQA KQAKQ | SEQ ID NO: 13 |
| P5R + 14 | RAQRA QARQA ROAQR AQRAQ ARQAR QAQRA QRAQA ROARQ | SEQ ID NO: 14 |

Without wishing to be bound by any particular theory, it is believed that the peptide domain of the peptide-Ig conjugate, when administered to a subject, targets the modified immunoglobulin to the amyloid deposits. The Fc domain then triggers an immune response at the site of the amyloid, thereby resulting in removal of the amyloid, such as by opsonization. In addition, the modified immunoglobulin is believed to have a longer half-life than the amyloid-reactive peptides alone. For example, the circulating half-life of an IgG in humans is approximately 21 days whereas the half-life of the amyloid reactive peptide alone in humans is approximatively, 11 hours. Thus, the Ig enhances the half-life of the modified immunoglobulin in circulation. In certain example embodiments, contacting an amyloid deposit with modified immunoglobulin results in a half-life that is increased by about 10%, 20%, 30%, 40%, 50%, 60%, 70%, 80% or more as compared to contacting an amyloid deposit with the amyloid-reactive peptide alone. As such, the modified immunoglobulin, when administered to a subject, can exert its immunostimulatory effects longer at the site of the amyloid deposit, thereby increasing the immune response at the site of the amyloid deposit.

In some embodiments, the amyloid-reactive peptides of the modified immunoglobulin peptides described herein include an amino acid sequence that is at least 80%, 85%, 90% or more identical to the amino acid sequence set forth as any one of SEQ ID NOS: 1-14, such as at least 95%, at least 96%, at least 97%, at least 98%, at least 99%, or 100% identical to the amino acid sequence set forth as any one of SEQ ID NOS: 1-14. In some embodiments, the amyloid-reactive peptides bound to the Ig antibody or functional fragments thereof may comprise or consist of from about 10 to about 55 amino acids. The amyloid-reactive peptides of the present invention may, for example, comprise or consist of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 amino acids. Such peptides are described, for example, in international patent application WO2016032949, which is hereby incorporated herein in its entirety.

The amino acids forming all or a part of the amyloid-reactive peptides bound to the Ig antibody or fragment thereof may be stereoisomers and modifications of naturally occurring amino acids, non-naturally occurring amino acids, post-translationally modified amino acids, enzymatically synthesized amino acids, derivatized amino acids, constructs or structures designed to mimic amino acids, and the like. The amino acids forming the peptides of the present invention may be one or more of the 20 common amino acids found in naturally occurring proteins, or one or more of the modified and unusual amino acids. The modified immunoglobulin may be made by any technique known to those of skill in the art, including chemical synthesis or recombinant means using standard molecular biological techniques.

In certain example embodiments, recombinant DNA technology may be employed wherein a nucleotide sequence that encodes a peptide of the invention is cloned, fused to an Ig light chain, into an expression vector, transformed or transfected into an appropriate host cell, and cultivated under conditions suitable for expression (see Examples). The peptide-Ig light chain fusion is then isolated. Advantageously, and as those skilled in the art will appreciate in view of this disclosure, the methods described herein can be used to join any peptide sequence to the Ig antibody. That is, while amyloid-reactive peptides are used as an example of a peptide joined to the Ig antibody, the method of joining a peptide to an Ig antibody—such as to the N-terminal end of the Ig light chain protein and/or the N and/or C-terminal end of the Ig heavy chain protein—can be used for a variety of different peptides to join the peptide to the Ig antibodies.

In certain example embodiments, multiple of the same or different peptides can be joined to a single Ig antibody or functional fragment thereof. For example, a first expression vector can include a light chain nucleic acid sequence that is integrated with a nucleic acid sequence encoding Peptide A, with the nucleic acid sequence for Peptide A positioned in the vector such that the Peptide A is expressed as joined to the N-terminal of the light chain protein. Further, a second expression vector can include a heavy chain nucleic acid sequence that is integrated with a nucleic acid sequence encoding Peptide B, with the nucleic acid sequence for Peptide B positioned in the vector such that Peptide B is expressed as joined to the N-terminal of the light chain protein.

In such example embodiments, when both expression vectors are expressed within the same cell, the resulting Ig protein can have one Peptide A sequence on the N-terminal of each light chain (for a total of two Peptide As) and a Peptide B on the N-terminal of the heavy chain. In certain example embodiments, the vector may include a Peptide C on the C-terminal end, thereby resulting in an antibody having two Peptide A sequences (one on each light chain), a Peptide B sequence on the N-terminal end of the heavy chain, and a Peptide C sequence joined to the C-terminal end of the heavy chain. As such, and as one skilled in the art will appreciate based on this disclosure, the expression vectors can be tailored to modify the immunoglobulin to have the same or different combinations of proteins. As a specific example using an amyloid-reactive peptide, a modified immunoglobulin may include two p5 proteins sequences (SEQ ID NO: 1), i.e., one on each light chain N-terminal end. In other example embodiments, the peptides joined to the immunoglobulin may have an affinity to a ligand, and hence can be used to detect the ligand.

In certain example embodiments, the modified immunoglobulins may be obtained by isolation or purification. Protein purification techniques involve, at one level, the homogenization and crude fractionation of cells, tissue, or organ to peptide and non-peptide fractions. Other protein purification techniques include, for example, precipitation with ammonium sulfate, polyethylene glycol (PEG), antibodies and the like, or by heat denaturation, followed by: centrifugation; chromatography steps such as ion exchange, gel filtration, reverse phase, hydroxylapatite and affinity chromatography; isoelectric focusing; gel electrophoresis, for example polyacrylamide gel electrophoresis; and combinations of these and other techniques.

Various chromatographic techniques include but are not limited to ion-exchange chromatography, gel exclusion chromatography, affinity chromatography, immuno-affinity chromatography, and reverse phase chromatography. A particularly efficient method of purifying peptides is fast performance liquid chromatography (FPLC) or even high-performance liquid chromatography (HPLC). In certain example embodiments, the Fc domain may be joined to the amyloid-reactive peptide via a GGGYS linker sequence (SEQ ID NO:27).

In certain embodiments, the modified immunoglobulins may include spacer sequences of amino acids between the N-terminal of the light chain or C-terminal of the heavy and the amyloid reactive peptide. In certain embodiments, the peptide-Ig conjugates may include spacer sequences of amino acids between the N-terminal of the peptide and a leader sequence required for secretion of the Ig-peptide from cells expressing the reagent. In some embodiments a spacer peptide may comprise or consist of from about 3 to about 55 amino acids. The spacer peptides of the present invention may comprise or consist of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 amino acids. As used herein, a nucleic acid sequence or amino acid sequence is "adjacent" to another nucleic acid sequence or amino acid sequence if such nucleic acid sequences or amino acid sequences are close to each other in sequence. For example, two nucleic acid sequences can be adjacent to each other as described herein but still include an intervening spacer sequence.

B. Antibody-Peptide Fusion Proteins

Also provided herein are antibody-peptide fusion proteins that target amyloids. Such antibody-peptide fusion proteins include, for example, amyloid-reactive peptides that are joined to an immunoglobulin (Ig), such as through extension of the N-terminal of the Ig light chain protein in the fragment, antigen binding (Fab) region or via or the C-terminal of the heavy chain, thereby forming a peptide-Ig fusion. The antibody-peptide fusion proteins can be used to treat a subject suffering from amyloidosis, for example, such as by administering the antibody-peptide fusion proteins to the subject.

In some embodiments, the antibody-peptide fusion protein comprises an antibody joined to a peptide. In some embodiments, the antibody-peptide fusion protein comprises antibody that comprises one, two, three, four, five, or six CDRs of an antibody as shown in Table 3.

In a particular embodiment, the antibody-peptide fusion protein comprises an antibody, wherein the antibody comprises a VH that comprises (a) a CDR-H1 comprising the amino acid sequence of SEQ ID NO:17, (b) a CDR-H2 comprising the amino acid sequence of SEQ ID NO:18, and (c) a CDR-H3 comprising the amino acid sequence LDY, wherein the antibody is joined to a peptide.

In a particular embodiment, the antibody-peptide fusion protein comprises an antibody, wherein the antibody comprises a VL that comprises (a) a CDR-L1 comprising the amino acid sequence of SEQ ID NO:20; (b) a CDR-L2 comprising the amino acid sequence of SEQ ID NO:21; and (c) a CDR-L3 comprising the amino acid sequence of SEQ ID NO:22, wherein the antibody is joined to a peptide.

In one embodiment, the antibody-peptide fusion protein comprises an antibody that comprises a VL comprising the amino acid sequence of SEQ ID NO:16 and a VH comprising the amino acid sequence of SEQ ID NO:15, wherein the antibody is joined to a peptide.

In another aspect, the antibody-peptide fusion protein comprises an antibody, wherein the antibody comprises a VH comprising a CDR-H1 comprising the amino acid sequence of SEQ ID NO: 17, a CDR-H2 comprising the amino acid sequence of SEQ ID NO:18, and a CDR-H3 comprising the amino acid sequence LDY; and a VL comprising a CDR-L1 comprising the amino acid sequence of SEQ ID NO:20, a CDR-L2 comprising the amino acid sequence of SEQ ID NO:21, and a CDR-L3 comprising the amino acid sequence of SEQ ID NO:22, and wherein the antibody is joined to a peptide. In some embodiments, the antibody-peptide fusion protein comprises an antibody joined to an amyloid reactive peptide comprising any of the amino acid sequences listed in Table 1. In some embodiments, the antibody-peptide fusion protein comprises an antibody joined to an amyloid reactive peptide comprising the amino acid sequence of SEQ ID NO:1. In some embodiments, the antibody-peptide fusion protein comprises an antibody joined to an amyloid reactive peptide comprising the amino acid sequence of SEQ ID NO:2.

In another aspect, the antibody-peptide fusion protein comprises an antibody, wherein the antibody comprises a VH CDR1, a VH CDR2, and a VH CDR3 of a VH having the sequence set forth in SEQ ID NO:15 and a VL CDR1, a VL CDR2, and a VL of a VL having the sequence set forth in SEQ ID NO:16; and wherein the antibody is joined to a peptide. In some embodiments, the antibody-peptide fusion protein comprises an antibody joined to an amyloid reactive peptide comprising any of the amino acid sequences listed in Table 1. In some embodiments, the antibody-peptide fusion protein comprises an antibody joined to an amyloid reactive peptide comprising the amino acid sequence of SEQ ID NO:1. In some embodiments, the antibody-peptide fusion protein comprises an antibody joined to an amyloid reactive peptide comprising the amino acid sequence of SEQ ID NO:2.

In some embodiments, the antibody-peptide fusion protein comprises an antibody that comprises a heavy chain comprising a VH comprising the amino acid sequence of SEQ ID NO:15 and a light chain comprising a VL comprising the amino acid sequence of SEQ ID NO:16, wherein the light chain is joined to a peptide. In some embodiments, the antibody-peptide fusion protein comprises a heavy chain comprising a VH comprising the amino acid sequence of SEQ ID NO:15 without the C-terminal lysine residue, and a VL comprising the amino acid sequence of SEQ ID NO:16, wherein the antibody is joined to a peptide.

In another aspect, the antibody-peptide fusion protein comprises an antibody joined to an amyloid reactive peptide. In some embodiments, the antibody-peptide fusion protein comprises an antibody joined to an amyloid reactive peptide comprising any of the amino acid sequences listed in Table 1. In some embodiments, the antibody-peptide fusion protein comprises an antibody joined to an amyloid reactive peptide comprising the amino acid sequence of SEQ ID NO:1. In some embodiments, the antibody-peptide fusion protein comprises an antibody joined to an amyloid reactive peptide comprising the amino acid sequence of SEQ ID NO:2. In some embodiments, the peptide is joined to the N-terminus of the antibody light chain or the C-terminus of the heavy chain. In some embodiments, the antibody also comprises a spacer amino acid sequence between the peptide and the N-terminus of the light chain or the C-terminus of the heavy chain. In some embodiments, the peptide is joined to the N-terminus of the light chain.

In some embodiments, the antibody-peptide fusion protein comprises an antibody that comprises a heavy chain comprising the a VH comprising the amino acid sequence of SEQ ID NO:15, wherein the heavy chain is joined to a peptide comprising any of the amino acid sequences of Table 1. In some embodiments, the antibody-peptide fusion protein comprise an antibody comprising a heavy chain comprising a VH comprising the amino acid sequence of SEQ ID NO:15, wherein the heavy chain is joined to a peptide comprising the amino acid sequence of SEQ ID NO:1. In some embodiments, the antibody-peptide fusion protein comprises an antibody comprising a heavy chain comprising a VH comprising the amino acid sequence of SEQ ID NO:15, wherein the heavy chain is joined to a peptide comprising the amino acid sequence of SEQ ID NO:2.

In some embodiments, the antibody-peptide fusion protein comprises an antibody that comprises a light chain comprising a VL comprising the amino acid sequence of SEQ ID NO:16, wherein the light chain is joined to a peptide comprising any of the amino acid sequences of Table 1. In some embodiments, the antibody-peptide fusion protein comprises an antibody comprising a light chain comprising a VL comprising the amino acid sequence of SEQ ID NO:16, wherein the light chain is joined to a peptide comprising the amino acid sequence of SEQ ID NO:1. In some embodiments, the antibody-peptide fusion protein comprises an antibody a light chain comprising a VL comprising the amino acid sequence of SEQ ID NO:16, wherein the light chain is joined to a peptide comprising the amino acid sequence of SEQ ID NO:2.

In some embodiments, the antibody-peptide fusion protein comprises an antibody comprising a heavy chain comprising a VH comprising the amino acid sequence of SEQ ID NO:15 and a light chain comprising a VL comprising the amino acid sequence of SEQ ID NO:16, wherein the light chain is joined to a peptide comprising any of the amino acid sequences of Table 1.

In some embodiments, the antibody-peptide fusion protein comprises an antibody comprising heavy chain comprising a VH comprising the amino acid sequence of SEQ ID NO:15 and a light chain comprising a VL comprising the amino acid sequence of SEQ ID NO:16, wherein the light chain is joined to a peptide comprising the amino acid sequence of SEQ ID NO:1. In some embodiments, the peptide is joined to the light chain at the N-terminus.

In some embodiments, the antibody-peptide fusion protein comprises an antibody a heavy chain comprising a VH comprising the amino acid sequence of SEQ ID NO:15 and a light chain comprising a VL comprising the amino acid sequence of SEQ ID NO:16, wherein the light chain is joined to a peptide comprising the amino acid sequence of SEQ ID NO:2. In some embodiments, the peptide is joined to the light chain at the N-terminus.

In some embodiments, the antibody-peptide fusion proteins described herein bind to amyloid deposits or fibrils. In some embodiments, the antibody-peptide fusion protein binds to one or more amyloidogenic peptides in amyloids. In some embodiments, amyloids bound by the antibody-peptide fusion proteins comprise an amyloidogenic λ6 variable domain protein (Vλ6Wil) or an amyloidogenic immunoglobulin light chain (AL), Aβ(1-40) amyloid-like fibril or an amyloidogenic Aβ precursor protein, or serum amyloid protein A (AA). In other embodiments, the amyloids bound by the antibody-peptide fusion protein comprise amyloidogenic forms of immunoglobulin heavy chain (AH), $β_2$-microglobulin (A$β_2$M), transthyretin variants (ATTR), apolipoprotein AI (AApoAI), apolipoprotein AII (AApoAII), gelsolin (AGel), lysozyme (ALys), leukocyte chemotactic factor (ALect2), fibrinogen a variants (AFib), cystatin variants (ACys), calcitonin ((ACal), lactadherin (AMed), islet amyloid polypeptide (AIAPP), prolactin (APro), insulin (AIns), prior protein (APrP); α-synuclein (AαSyn), tau (ATau), atrial natriuretic factor (AANF), or IAAP, ALκ4, Alλ1 other amyloidogenic peptides. The amyloidogenic peptides bound by the antibody-peptide fusion proteins can be a protein, a protein fragment, or a protein domain. In some embodiments, the amyloid deposits or amyloid fibrils comprise recombinant amyloidogenic proteins. In some embodiments, the amyloids are part of the pathology of a disease.

In some embodiments, the antibodies provided herein bind specifically to amyloid light chain fibrils. In some embodiments, the amyloid reactive peptide binds to various amyloid fibrils such as amyloidogenic λ6 variable domain protein (Vλ6Wil) or an amyloidogenic immunoglobulin light chain (AL), Aβ(1-40) amyloid-like fibril or an amyloidogenic Aβ precursor protein, or serum amyloid protein A (AA). In other embodiments, the amyloids bound by the antibody-peptide fusion protein comprise amyloidogenic forms of immunoglobulin heavy chain (AH), $β_2$-microglobulin (A$β_2$M), transthyretin variants (ATTR), apolipoprotein AI (AApoAI), apolipoprotein AII (AApoAII), gelsolin (AGel), lysozyme (ALys), leukocyte chemotactic factor (ALect2), fibrinogen a variants (AFib), cystatin variants (ACys), calcitonin ((ACal), lactadherin (AMed), islet amyloid polypeptide (AIAPP), prolactin (APro), insulin (AIns), prior protein (APrP); α-synuclein (AαSyn), tau (ATau), atrial natriuretic factor (AANF), or IAAP, ALκ4, Alλ1 other amyloidogenic peptides. In some embodiments, the amyloid reactive peptide binds to heparan sulfate glycosaminoglycans.

As those skilled in the art will appreciate, the fragment antigen binding (or Fab region) is the head of an antibody that naturally interacts with target antigen. Components of the Fab region, for example, allow antibodies to bind to specific ligands and, through that interaction, to further activate the immune system. For IgG, IgA, IgD, IgE, and IgM antibody isotypes, the Ig is composed of two proteins, the heavy chain and light chain that interact in pairs to form an intact Ig comprising 2 heavy chains and 2 light chains. Both the heavy and light chains are further divided into variable domains and constant domains—the light and heavy variable domains comprising the Fab functional region and the heavy chains forming the fragment crystallizable (Fc) domains that interact with cell receptors and complement. The Fc regions of Ig bears a highly conserved N-glycosylation site.

In certain example embodiments, one or more of the peptides shown in Table 1 below can be joined to an Ig antibody or functional fragment thereof through the N-terminus of the light chain protein or the C-terminus of the heavy chain, thereby forming an antibody-peptide fusion protein. That is, any of the sequences identified below in Table 1 can be joined to the heavy or light chain of the Ig antibody or functional fragment thereof independently or simultaneously to form a peptide-Ig conjugate. For example, two of the amyloid reactive peptides can be joined with a single Ig antibody, such by joining the amyloid-reactive peptide amino acid sequences to the N-terminal of the Ig light chain proteins.

Without wishing to be bound by any particular theory, it is believed that the peptide domain of the peptide-Ig conjugate, when administered to a subject, targets the antibody-peptide fusion protein to the amyloid deposits. The Fc domain then triggers an immune response at the site of the amyloid, thereby resulting in removal of the amyloid, such as by opsonization. In addition, the antibody-peptide fusion protein is believed to have a longer half-life than the amyloid-reactive peptides alone. For example, the circulating half-life of an IgG in humans is approximately 21 days whereas the half-life of the amyloid reactive peptide alone in humans is approximatively, 11 hours. Thus, the Ig enhances the half-life of the antibody-peptide fusion protein in circulation. In certain example embodiments, contacting an amyloid deposit with antibody-peptide fusion protein results in a half-life that is increased by about 10%, 20%, 30%, 40%, 50%, 60%, 70%, 80% or more as compared to contacting an amyloid deposit with the amyloid-reactive peptide alone. As such, the antibody-peptide fusion protein, when administered to a subject, can exert its immunostimulatory effects longer at the site of the amyloid deposit, thereby increasing the immune response at the site of the amyloid deposit.

In some embodiments, the amyloid-reactive peptides of the antibody-peptide fusion proteins described herein include an amino acid sequence that is at least 80%, 85%, 90% or more identical to the amino acid sequence set forth as any one of SEQ ID NOS: 1-14, such as at least 95%, at least 96%, at least 97%, at least 98%, at least 99%, or 100% identical to the amino acid sequence set forth as any one of SEQ ID NOS: 1-14. In some embodiments, the amyloid-reactive peptides bound to the Ig antibody or functional fragments thereof may comprise or consist of from about 10 to about 55 amino acids. The amyloid-reactive peptides of the present invention may, for example, comprise or consist of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 amino acids. Such peptides are described, for example, in international patent application WO2016032949, which is hereby incorporated herein in its entirety.

The amino acids forming all or a part of the amyloid-reactive peptides bound to the Ig antibody or fragment thereof may be stereoisomers and modifications of naturally occurring amino acids, non-naturally occurring amino acids, post-translationally modified amino acids, enzymatically synthesized amino acids, derivatized amino acids, constructs or structures designed to mimic amino acids, and the like. The amino acids forming the peptides of the present invention may be one or more of the 20 common amino acids found in naturally occurring proteins, or one or more of the modified and unusual amino acids. The antibody-peptide fusion protein may be made by any technique known to those of skill in the art, including chemical synthesis or recombinant means using standard molecular biological techniques.

In certain example embodiments, recombinant DNA technology may be employed wherein a nucleotide sequence that encodes a peptide of the invention is cloned, fused to an Ig light chain, into an expression vector, transformed or transfected into an appropriate host cell, and cultivated under conditions suitable for expression (see Examples). The peptide-Ig light chain fusion is then isolated. Advantageously, and as those skilled in the art will appreciate in view of this disclosure, the methods described herein can be used to join any peptide sequence to the Ig antibody. That is, while amyloid-reactive peptides are used as an example of a peptide joined to the Ig antibody, the method of joining a peptide to an Ig antibody—such as to the N-terminal end of the Ig light chain protein and/or the N and/or C-terminal end of the Ig heavy chain protein—can be used for a variety of different peptides to join the peptide to the Ig antibodies.

In certain example embodiments, multiple of the same or different peptides can be joined to a single Ig antibody or functional fragment thereof. For example, a first expression vector can include a light chain nucleic acid sequence that is integrated with a nucleic acid sequence encoding Peptide A, with the nucleic acid sequence for Peptide A positioned in the vector such that the Peptide A is expressed as joined to the N-terminal of the light chain protein. Further, a second expression vector can include a heavy chain nucleic acid sequence that is integrated with a nucleic acid sequence encoding Peptide B, with the nucleic acid sequence for Peptide B positioned in the vector such that Peptide B is expressed as joined to the N-terminal of the light chain protein.

In such example embodiments, when both expression vectors are expressed within the same cell, the resulting Ig protein can have one Peptide A sequence on the N-terminal of each light chain (for a total of two Peptide As) and a Peptide B on the N-terminal of the heavy chain. In certain example embodiments, the vector may include a Peptide C on the C-terminal end, thereby resulting in an antibody having two Peptide A sequences (one on each light chain), a Peptide B sequence on the N-terminal end of the heavy chain, and a Peptide C sequence joined to the C-terminal end of the heavy chain. As such, and as one skilled in the art will appreciate based on this disclosure, the expression vectors can be tailored to modify the immunoglobulin to have the same or different combinations of proteins. As a specific example using an amyloid-reactive peptide, an antibody-peptide fusion protein may include two p5 proteins sequences (SEQ ID NO: 1), i.e., one on each light chain N-terminal end. In other example embodiments, the peptides joined to the immunoglobulin may have an affinity to a ligand, and hence can be used to detect the ligand.

In certain example embodiments, the antibody-peptide fusion protein may be obtained by isolation or purification. Protein purification techniques involve, at one level, the homogenization and crude fractionation of cells, tissue, or organ to peptide and non-peptide fractions. Other protein purification techniques include, for example, precipitation with ammonium sulfate, polyethylene glycol (PEG), antibodies and the like, or by heat denaturation, followed by: centrifugation; chromatography steps such as ion exchange, gel filtration, reverse phase, hydroxylapatite and affinity chromatography; isoelectric focusing; gel electrophoresis, for example polyacrylamide gel electrophoresis; and combinations of these and other techniques.

Various chromatographic techniques include but are not limited to ion-exchange chromatography, gel exclusion chromatography, affinity chromatography, immuno-affinity chromatography, and reverse phase chromatography. A particularly efficient method of purifying peptides is fast performance liquid chromatography (FPLC) or even high-performance liquid chromatography (HPLC). In certain example embodiments, the Fc domain may be joined to the amyloid-reactive peptide via a GGGYS linker sequence (SEQ ID NO:27).

In certain embodiments, the antibody-peptide fusion protein may include spacer sequences of amino acids between the N-terminal of the light chain or C-terminal of the heavy and the amyloid reactive peptide. In certain embodiments, the peptide-Ig conjugates may include spacer sequences of amino acids between the N-terminal of the peptide and a leader sequence required for secretion of the Ig-peptide from cells expressing the reagent. In some embodiments a spacer peptide may comprise or consist of from about 3 to about 55 amino acids. The spacer peptides of the present invention may comprise or consist of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 amino acids. As used herein, a nucleic acid sequence or amino acid sequence is "adjacent" to another nucleic acid sequence or amino acid sequence if such nucleic acid sequences or amino acid sequences are close to each other in sequence. For example, two nucleic acid sequences can be adjacent to each other as described herein but still include an intervening spacer sequence.

III. Humanized Antibodies that Bind to Human Amyloid Fibrils

Humanized antibodies that bind to human amyloid fibrils are provided herein. In some embodiments, the humanized antibody comprises a light chain variable region (VL) and a heavy chain variable region (VH) comprising one or more CDRs of a murine antibody. In some embodiments, the VH and/or the VL are derived from human VH and/or VL sequences (e.g., "human acceptor sequences"). In some embodiments, the VH and/or the VL comprise amino acid substitutions, e.g., in the framework regions of the VH and/or the VL.

A. Humanized Antibodies

In some embodiments, the humanized antibody comprises a light chain variable region (VL) and a heavy chain variable region (VH), wherein the VL comprises a CDR-L1 comprising the amino acid sequence set forth in SEQ ID NO:20, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in SEQ ID NO:18, and a CDR-H3 comprising the amino acid sequence LDY. In some embodiments, the humanized antibody comprises one, two, three, four, five, or six CDRs of an antibody as shown in Table 3. In some embodiments, the humanized antibody comprises a CDR-H1, a CDR-H2, and a CDR-H3, respectively comprising the amino acid sequences of a CDR-H1, a CDR-H2, and a CDR-H3 of a VH having the sequence set forth in SEQ ID NO:15; and a CDR-L1, a CDR-L2, and a CDR-L3, respectively comprising the amino acid sequences of a CDR-L1, a CDR-L2, and a CDR-L3 of a VL having the sequence set forth in SEQ ID NO:16. In some embodiments, the humanized antibody comprises a light chain variable region (VL) and a heavy chain variable region (VH), wherein the VL comprises a CDR-L1 comprising the amino acid sequence set forth in SEQ ID NO:20 with one or more conservative amino acid substitutions, a CDR-L2 comprising the amino acid sequence set forth in SEQ ID NO:21 with one or more conservative amino acid substitutions, and a CDR-L3 comprising the amino acid sequence set forth in SEQ ID NO:22 with one or more conservative amino acid substitutions, and the VH comprises a CDR-H1 comprising the amino acid sequence set forth in SEQ ID NO:17 with one or more conservative amino acid substitutions, a CDR-H2 comprising the amino acid sequence set forth in SEQ ID NO:18 with one or more conservative amino acid substitutions, and a CDR-H3 comprising the amino acid sequence LDY with one or more conservative amino acid substitutions. In some embodiments, the humanized antibody comprises one, two, three, four, five, or six CDRs of an antibody as shown in Table 3, with one or more conservative amino acid substitutions. In some embodiments, the humanized antibody comprises a CDR-H1, a CDR-H2, and a CDR-H3, respectively comprising the amino acid sequences of a CDR-H1, a CDR-H2, and a CDR-H3 of a VH having the sequence set forth in SEQ ID NO:15 with one or more conservative amino acid substitutions; and a CDR-L1, a CDR-L2, and a CDR-L3, respectively comprising the amino acid sequences of a CDR-L1, a CDR-L2, and a CDR-L3 of a VL having the sequence set forth in SEQ ID NO:16 with one or more conservative amino acid substitutions.

In some embodiments, the humanized antibody that binds to human amyloid fibrils comprises a light chain variable region (VL) and a heavy chain variable region (VH), wherein the VL comprises a framework region (FR), and wherein the VH comprises a framework region (FR). In some embodiments, the framework region is a FR1, FR2, FR3, or FR4. In some embodiments, the VL comprises a FR1, FR2, FR3, and a FR4. In some embodiments, the VL comprises, from N- to C-terminus, a FR1, a CDR-L1, a FR2, a CDR-L2, a FR3, a CDR-L3, and a FR4. In some embodiments, the VH comprises a FR1, FR2, FR3, and FR4. In some embodiments, the VH comprises from N- to C-terminus, a FR1, a CDR-H1, a FR2, a CDR-H2, a FR3, a CDR-H3, and a FR4. In some embodiments, the humanized antibody comprises a VL and/or a VH comprising an amino acid substitution at one or more positions in a framework region (e.g., a FR1, FR2, FR3, or FR4) compared to a human acceptor sequence with grafted CDRs (e.g., SEQ ID NO: 32 or SEQ ID NO: 43).

In some embodiments, the humanized antibody comprises a VL comprising an amino acid substitution in the FR2 compared to a VL comprising an amino acid sequence set forth in SEQ ID NO: 32. In some embodiments, the amino acid substitution in the FR2 is selected from the group consisting of an amino acid substitution at position 36, an amino acid substitution at position 37, and an amino acid substitution at position 46, wherein the amino acid positions are numbered according to the numbering system of Kabat. In some embodiments, the amino acid substitution in the FR2 is selected from the group consisting of Tyr at position 36, Leu at position 37, and Leu at position 46, wherein the amino acid positions are numbered according to the numbering system of Kabat.

In some embodiments, the humanized antibody comprises a VL comprising an amino acid substitution in the FR3 compared to a VL comprising an amino acid sequence set forth in SEQ ID NO: 32. In some embodiments, the amino acid substitution in the FR3 is selected from the group consisting of an amino acid substitution at position 85, and an amino acid substitution at position 87, wherein the amino acid positions are numbered according to the numbering system of Kabat. In some embodiments, the amino acid substitution in the FR3 is selected from the group consisting of Leu at position 85, and Phe at position 87, wherein the amino acid positions are numbered according to the numbering system of Kabat.

In some embodiments, the humanized antibody comprises a VH comprising an amino acid substitution in the FR2 compared to a VH comprising an amino acid sequence set forth in SEQ ID NO: 43. In some embodiments, the amino acid substitution in the FR2 is selected from the group consisting of an amino acid substitution at position 37 and an amino acid substitution at position 48, wherein the amino acid positions are numbered according to the numbering system of Kabat. In some embodiments, the amino acid substitution in the FR2 is selected from the group consisting of Val at position 37 and Leu at position 48, wherein the amino acid positions are numbered according to the numbering system of Kabat.

In some embodiments, the humanized antibody comprises a VH comprising an amino acid substitution in the FR3 compared to a VH comprising an amino acid sequence set forth in SEQ ID NO: 43. In some embodiments, the amino acid substitution in the FR3 is selected from the group consisting of an amino acid substitution at position 67, an amino acid substitution at position 48, an amino acid substitution at position 71, an amino acid substitution at position 76, an amino acid substitution at position 78, an amino acid substitution at position 79, an amino acid substitution at position 80, an amino acid substitution at position 89, an amino acid substitution at position 93, and an amino acid substitution at position 94, wherein the amino acid positions are numbered according to the numbering system of Kabat. In some embodiments, the amino acid substitution in the FR3 is selected from the group consisting of Leu at position 67, Ser at position 48, Lys at position 71, Ser at position 76, Val at position 78, Leu at position 79, Phe at position 80, Thr at position 89, Val at position 93, and Thr at position 94, wherein the amino acid positions are numbered according to the numbering system of Kabat.

In some embodiments, the humanized antibody comprises a VL comprising one or more amino acid substitutions at one or more positions in the VL compared to a VL comprising an amino acid sequence set forth in SEQ ID NO: 32, wherein the amino acid positions are numbered sequentially starting from the N-terminus of SEQ ID NO: 32. In some embodiments, the humanized antibody comprises a VL comprising an amino acid substitution at position 33 compared to a VL comprising an amino acid sequence set forth in SEQ ID NO: 32. In some embodiments, the humanized antibody comprises a VL comprising an amino acid substitution at position 34 compared to a VL comprising an amino acid sequence set forth in SEQ ID NO: 32. In some embodiments, the humanized antibody comprises a VL comprising an amino acid substitution at position 41 compared to a VL comprising an amino acid sequence set forth in SEQ ID NO: 32. In some embodiments, the humanized antibody comprises a VL comprising an amino acid substitution at position 42 compared to a VL comprising an amino acid sequence set forth in SEQ ID NO: 32. In some embodiments, the humanized antibody comprises a VL comprising an amino acid substitution at position 51 compared to a VL comprising an amino acid sequence set forth in SEQ ID NO: 32. In some embodiments, the humanized antibody comprises a VL comprising an amino acid substitution at position 90 compared to a VL comprising an amino acid sequence set forth in SEQ ID NO: 32. In some embodiments, the humanized antibody comprises a VL comprising an amino acid substitution at position 92 compared to a VL comprising an amino acid sequence set forth in SEQ ID NO: 32. In some embodiments, the humanized antibody comprises a VL comprising 1, 2, 3, 4, 5, 6, 7, or 8 amino acid substitutions compared to a VL comprising an amino acid sequence set forth in SEQ ID NO: 32. In some embodiments, the humanized antibody comprises a VL comprising 1, 2, 3, 4, 5, 6, 7, or 8 amino acid substitutions compared to a VL1, as shown in Table 6A.

In some embodiments, the humanized antibody comprises a VL comprising one or more amino acid residues at one or more positions in the VL, wherein the amino acid positions are numbered starting from the N-terminus of the VL according to the numbering of SEQ ID NO:32. In some embodiments, the humanized antibody comprises a VL comprising Ser, Gln, Glu, His, or Ala at position 33. In some embodiments, the humanized antibody comprises a VL comprising Ala or Val at position 34. In some embodiments, the humanized antibody comprises a VL comprising Tyr at position 41. In some embodiments, the humanized antibody comprises a VL comprising Leu at position 42. In some embodiments, the humanized antibody comprises a VL comprising Leu at position 51. In some embodiments, the humanized antibody comprises a VL comprising Leu at position 90. In some embodiments, the humanized antibody comprises a VL comprising Phe at position 92.

In some embodiments, the humanized antibody comprises a VH comprising one or more amino acid residues at one or more positions in the VH, wherein the amino acid positions are numbered starting from the N-terminus of the VH. In some embodiments, the humanized antibody comprises a VH comprising Val at position 37. In some embodiments, the humanized antibody comprises a VH comprising Leu at position 48. In some embodiments, the humanized antibody comprises a VH comprising Leu at position 67. In some embodiments, the humanized antibody comprises a VH comprising Ser at position 68. In some embodiments, the humanized antibody comprises a VH comprising Lys at position 71. In some embodiments, the humanized antibody comprises a VH comprising Ser at position 76. In some embodiments, the humanized antibody comprises a VH comprising Val at position 78. In some embodiments, the humanized antibody comprises a VH comprising Leu at position 79. In some embodiments, the humanized antibody comprises a VH comprising Phe at position 80. In some embodiments, the humanized antibody comprises a VH comprising Thr at position 92. In some embodiments, the humanized antibody comprises a VH comprising Val at position 96. In some embodiments, the humanized antibody comprises a VH comprising Thr position 97.

In some embodiments, the humanized antibody comprises a VL comprising one or more amino acid residues at one or more positions in the VL, wherein the amino acid positions are numbered according to the numbering system of Kabat. In some embodiments, the humanized antibody comprises a VL comprising Tyr at position 36. In some embodiments, the humanized antibody comprises a VL comprising Leu at position 37. In some embodiments, the humanized antibody comprises a VL comprising Leu at position 46. In some embodiments, the humanized antibody comprises a VL comprising Leu at position 85. In some embodiments, the humanized antibody comprises a VL comprising Phe at position 87.

In some embodiments, the humanized antibody comprises a VL comprising one or more amino acid residues at one or more positions in the VL, wherein the amino acid positions are numbered according to the numbering system of Kabat. In some embodiments, the humanized antibody comprises a VL comprising Tyr at position 36 and Leu at position 37. In some embodiments, the humanized antibody comprises a VL comprising Tyr at position 36, Leu at position 37, Leu at position 46, Leu at position 85, and Phe at position 87. In some embodiments, the humanized antibody comprises a VL comprising Leu at position 46 and Phe at position 87.

In some embodiments, the humanized antibody comprises a VH comprising one or more amino acid residues at one or more positions in the VH, wherein the amino acid positions are numbered according to the numbering system of Kabat. In some embodiments, the humanized antibody comprises a VH comprising Val at position 37. In some embodiments, the humanized antibody comprises a VH comprising Leu at position 48. In some embodiments, the humanized antibody comprises a VH comprising Leu at position 67. In some embodiments, the humanized antibody comprises a VH comprising Ser at position 68. In some embodiments, the humanized antibody comprises a VH comprising Lys at position 71. In some embodiments, the humanized antibody comprises a VH comprising Ser at position 76. In some embodiments, the humanized antibody comprises a VH comprising Val at position 78. In some embodiments, the humanized antibody comprises a VH comprising Leu at position 79. In some embodiments, the humanized antibody comprises a VH comprising Phe at position 80. In some embodiments, the humanized antibody comprises a VH comprising Thr at position 89. In some embodiments, the humanized antibody comprises a VH comprising Val at position 93. In some embodiments, the humanized antibody comprises a VH comprising Thr at position 94.

In some embodiments, the humanized antibody comprises a VH comprising one or more amino acid residues at one or more positions in the VH, wherein the amino acid positions are numbered according to the numbering system of Kabat. In some embodiments, the humanized antibody comprises a VH comprising Val at position 37 and Leu at position 48. In some embodiments, the humanized antibody comprises a VH comprising Leu at position 67, Ser at position 68, Thr at position 89, Val at position 93, and Thr at position 94. In some embodiments, the humanized antibody comprises a VH comprising Val at position 37, Leu at position 48, Leu at position 67, and Ser at position 68. In some embodiments, the humanized antibody comprises a VH comprising Val at position 37, Leu at position 48, Val at position 93, and Thr at position 94. In some embodiments, the humanized antibody comprises a VH comprising Val at position 37, Leu at position 48, Leu at position 67, Ser at position 68, Lys at position 71, Thr at position 89, Val at position 93, and Thr at position 94. In some embodiments, the humanized antibody comprises a VH comprising Lys at position 71, Val at position 78, Leu at position 79, Val at position 93, and Thr at position 94. In some embodiments, the humanized antibody comprises a VH comprising Lys at position 71, Ser at position 76, Val at position 93, and Thr at position 94. In some embodiments, the humanized antibody comprises a VH comprising Leu at position 48, Ser at position 96, Val at position 78, Leu at position 79, Phe at position 80, and Thr at position 94. In some embodiments, the humanized antibody comprises a VH comprising Leu at position 48, Leu at position 67, Ser at position 68, Lys at position 71, Ser at position 76, Val at position 78, Leu at position 79, Val at position 93, and Thr at position 94.

In some embodiments, the humanized antibody comprises a VL comprising Tyr at position 36, Leu at position 37, Leu at position 46, Leu at position 85, and Phe at position 87, and a VH comprising Val at position 37, Leu at position 48, Leu at position 67, Ser at position 68, Lys at position 71, Thr at position 89, Val at position 93, and Thr at position 94. In some embodiments, the humanized antibody comprises a VL comprising Leu at position 46 and Phe at position 87, and a VH comprising Leu at position 48, Ser at position 96, Val at position 78, Leu at position 79, Phe at position 80, and Thr at position 94. In some embodiments, the humanized antibody comprises a VL comprising Leu at position 46 and Phe at position 87, and a VH comprising Leu at position 48, Leu at position 67, Ser at position 68, Lys at position 71, Val at position 93, and Thr at position 94. In some embodiments, the humanized antibody comprises a VL comprising Leu at position 46 and Phe at position 87, and a VH comprising Lys at position 71, Ser at position 76, Val at position 93, and Thr at position 94. In some embodiments, the humanized antibody comprises a VL comprising Leu at position 46 and Phe at position 87, and a VH comprising Lys at position 71, Val at position 78, Leu at position 79, Val at position 93, and Thr at position 94.

In some embodiments, the humanized antibody comprises the amino acid sequence of a VL as shown in Table 6A. In some embodiments, the humanized antibody comprises a VL selected from the group consisting of VL2, VL3, VL4, VL4-N33S, VL4-N33Q, VL4-N33E, VL4-N33A, VL4-N33H, VL4-G34A, or VL4-G34V, as shown in Table 6A. In some embodiments, the VL comprises an amino acid sequence set forth in the group consisting of SEQ ID NOs:33-42.

In some embodiments, the humanized antibody comprises the amino acid sequence of a VH as shown in Table 6B. In some embodiments, the humanized antibody comprises a VH selected from the group consisting of VH2, VH3, VH4, VH5, VH6, VH7, VH8, VH9, VH10, VH9-D54S, VH9-D54Q, VH9-D54E, VH9-D54A, VH9-D54H, VH9-G55A, VH9-G55V, VH9-M64V, VH9-M64I, VH9-M64L, or VH9-M64A, as shown in Table 6B. In some embodiments, the VH comprises an amino acid sequence set forth in the group consisting of SEQ ID NOs:44-63.

In some embodiments, the humanized antibody comprises the VL of VL4 as shown in Table 6A, and the VH of VH9 as shown in Table 6B. In some embodiments, the VL comprises an amino acid sequence set forth in SEQ ID NO:35, and the VH comprises an amino acid sequence set forth in SEQ ID NO:51.

In some embodiments, the humanized antibody comprises the VL of VL3 as shown in Table 6A, and the VH of VH6 as shown in Table 6B. In some embodiments, the VL comprises an amino acid sequence set forth in SEQ ID NO:34, and the VH comprises an amino acid sequence set forth in SEQ ID NO:48.

In some embodiments, the humanized antibody comprises the VL of VL4 as shown in Table 6A, and the VH of VH10 as shown in Table 6B. In some embodiments, the VL comprises an amino acid sequence set forth in SEQ ID NO:35, and the VH comprises an amino acid sequence set forth in SEQ ID NO:52. In some embodiments, the humanized antibody comprises the VL of VL4 as shown in Table 6A, and the VH of VH8 as shown in Table 6B. In some embodiments, the VL comprises an amino acid sequence set forth in SEQ ID NO:35, and the VH comprises an amino acid sequence set forth in SEQ ID NO:50. In some embodiments, the humanized antibody comprises the VL of VL4 as shown in Table 6A, and the VH of VH7 as shown in Table 6B. In some embodiments, the VL comprises an amino acid sequence set forth in SEQ ID NO:35, and the VH comprises an amino acid sequence set forth in SEQ ID NO:69.

In some embodiments, the humanized antibody is a full-length antibody, a Fab fragment, or a scFv.

Humanized Antibodies with CDR Substitutions

In some embodiments, the humanized antibody comprises one or more CDR substitutions. In some embodiments, the CDR substitution is in the CDR-L1. In some embodiments, the CDR substitution is in the CDR-H2.

In some embodiments, the humanized antibody comprises a VL comprising a CDR-L1 comprising the amino acid sequence set forth in SEQ ID NO:64-70, a CDR-L2 comprising the amino acid sequence set forth in SEQ ID NO:21, and a CDR-L3 comprising the amino acid sequence set forth in SEQ ID NO:22, and a VH comprising a CDR-H1 comprising the amino acid sequence set forth in SEQ ID NO:17, a CDR-H2 comprising the amino acid sequence set forth in SEQ ID NO:18, and a CDR-H3 comprising the amino acid sequence LDY. In some embodiments, the humanized antibody comprises a VL comprising a CDR-L1 comprising the amino acid sequence set forth in SEQ ID NO: 20; a CDR-L2 comprising the amino acid sequence set forth in SEQ ID NO:21, and a CDR-L3 comprising the amino acid sequence set forth in SEQ ID NO:22, and a VH comprising a CDR-H1 comprising the amino acid sequence set forth in SEQ ID NO:17, a CDR-H2 comprising the amino acid sequence set forth in SEQ ID NO: 71-81; and a CDR-H3 comprising the amino acid sequence LDY. In some embodiments, the humanized antibody comprises a VL comprising one or more amino acid residues selected from the group consisting of Tyr at position 36, Leu at position 37, Leu at position 46, Leu at position 85 and Phe at position 87; wherein the amino acid positions are numbered according to the numbering system of Kabat. In some embodiments, the humanized antibody comprises a VH comprising one or more amino acid residues selected from the group consisting of: Val at position 37, Leu at position 48, Leu at position 67, Ser at position 68, Lys at position 71, Ser at position 76, Val at position 78, Leu at position 79, Phe at position 80, Thr at position 89, Val at position 93, and Thr at position 94; wherein the amino acid positions are numbered according to the numbering system of Kabat.

In some embodiments, the humanized antibody comprises a light chain variable region (VL) and a heavy chain variable region (VH), wherein the VL comprises a CDR-L1 comprising the amino acid sequence set forth in SEQ ID NO:64, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in SEQ ID NO:18, and a CDR-H3 comprising the amino acid sequence LDY. In some embodiments, the humanized antibody comprises a light chain variable region (VL) and a heavy chain variable region (VH), wherein the VL comprises a CDR-L1 comprising the amino acid sequence set forth in SEQ ID NO:65, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in SEQ ID NO:18, and a CDR-H3 comprising the amino acid sequence LDY. In some embodiments, the humanized antibody comprises a light chain variable region (VL) and a heavy chain variable region (VH), wherein the VL comprises a CDR-L1 comprising the amino acid sequence set forth in SEQ ID NO:66, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in SEQ ID NO:18, and a CDR-H3 comprising the amino acid sequence LDY. In some embodiments, the humanized antibody comprises a light chain variable region (VL) and a heavy chain variable region (VH), wherein the VL comprises a CDR-L1 comprising the amino acid sequence set forth in SEQ ID NO:67, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in SEQ ID NO:18, and a CDR-H3 comprising the amino acid sequence LDY. In some embodiments, the humanized antibody comprises a light chain variable region (VL) and a heavy chain variable region (VH), wherein the VL comprises a CDR-L1 comprising the amino acid sequence set forth in SEQ ID NO:68, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in SEQ ID NO:18, and a CDR-H3 comprising the amino acid sequence LDY. In some embodiments, the humanized antibody comprises a light chain variable region (VL) and a heavy chain variable region (VH), wherein the VL comprises a CDR-L1 comprising the amino acid sequence set forth in SEQ ID NO:69, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in SEQ ID NO:18, and a CDR-H3 comprising the amino acid sequence LDY. In some embodiments, the humanized antibody comprises a light chain variable region (VL) and a heavy chain variable region (VH), wherein the VL comprises a CDR-L1 comprising the amino acid sequence set forth in SEQ ID NO:70, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in SEQ ID NO:18, and a CDR-H3 comprising the amino acid sequence LDY.

In some embodiments, the humanized antibody comprises a light chain variable region (VL) and a heavy chain variable region (VH), wherein the VL comprises a CDR-L1 comprising the amino acid sequence set forth in SEQ ID NO:20, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in SEQ ID NO:71, and a CDR-H3 comprising the amino acid sequence LDY. In some embodiments, the humanized antibody comprises a light chain variable region (VL) and a heavy chain variable region (VH), wherein the VL comprises a CDR-L1 comprising the amino acid sequence set forth in SEQ ID NO:20, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in SEQ ID NO:72, and a CDR-H3 comprising the amino acid sequence LDY. In some embodiments, the humanized antibody comprises a light chain variable region (VL) and a heavy chain variable region (VH), wherein the VL comprises a CDR-L1 comprising the amino acid sequence set forth in SEQ ID NO:20, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in SEQ ID NO:73, and a CDR-H3 comprising the amino acid sequence LDY. In some embodiments, the humanized antibody comprises a light chain variable region (VL) and a heavy chain variable region (VH), wherein the VL comprises a CDR-L1 comprising the amino acid sequence set forth in SEQ ID NO:20, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in SEQ ID NO:74, and a CDR-H3 comprising the amino acid sequence LDY. In some embodiments, the humanized antibody comprises a light chain variable region (VL) and a heavy chain variable region (VH), wherein the VL comprises a CDR-L1 comprising the amino acid sequence set forth in SEQ ID NO:20, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in SEQ ID NO:75, and a CDR-H3 comprising the amino acid sequence LDY. In some embodiments, the humanized antibody comprises a light chain variable region (VL) and a heavy chain variable region (VH), wherein the VL comprises a CDR-L1 comprising the amino acid sequence set forth in SEQ ID NO:20, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in SEQ ID NO:76, and a CDR-H3 comprising the amino acid sequence LDY. In some embodiments, the humanized antibody comprises a light chain variable region (VL) and a heavy chain variable region (VH), wherein the VL comprises a CDR-L1 comprising the amino acid sequence set forth in SEQ ID NO:20, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in SEQ ID NO:77, and a CDR-H3 comprising the amino acid sequence LDY. In some embodiments, the humanized antibody comprises a light chain variable region (VL) and a heavy chain variable region (VH), wherein the VL comprises a CDR-L1 comprising the amino acid sequence set forth in SEQ ID NO:20, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in SEQ ID NO:78, and a CDR-H3 comprising the amino acid sequence LDY. In some embodiments, the humanized antibody comprises a light chain variable region (VL) and a heavy chain variable region (VH), wherein the VL comprises a CDR-L1 comprising the amino acid sequence set forth in SEQ ID NO:20, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in SEQ ID NO:79, and a CDR-H3 comprising the amino acid sequence LDY. In some embodiments, the humanized antibody comprises a light chain variable region (VL) and a heavy chain variable region (VH), wherein the VL comprises a CDR-L1 comprising the amino acid sequence set forth in SEQ ID NO:20, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in SEQ ID NO:80, and a CDR-H3 comprising the amino acid sequence LDY. In some embodiments, the humanized antibody comprises a light chain variable region (VL) and a heavy chain variable region (VH), wherein the VL comprises a CDR-L1 comprising the amino acid sequence set forth in SEQ ID NO:20, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in SEQ ID NO:81, and a CDR-H3 comprising the amino acid sequence LDY.

In some embodiments, the humanized antibody comprises one, two, three, four, five, or six CDRs of an antibody as shown in Table 6C and/or Table 6D.

In some embodiments, the humanized antibody comprises a CDR-H1, a CDR-H2, and a CDR-H3, respectively comprising the amino acid sequences of a CDR-H1, a CDR-H2, and a CDR-H3 of a VH having the sequence set forth in SEQ ID NOs: 53-63. In some embodiments, the humanized antibody comprises a CDR-L1, a CDR-L2, and a CDR-L3, respectively comprising the amino acid sequences of a CDR-L1, a CDR-L2, and a CDR-L3 of a VL having the sequence set forth in SEQ ID NO:36-42.

In some embodiments, the humanized antibody comprises a VL comprising an amino acid substitution in the CDR-L1 compared to a VL comprising an amino acid sequence set forth in SEQ ID NO: 35. In some embodiments, the amino acid substitution in the CDR-L1 is selected from the group consisting of an amino acid substitution at position 28 and an amino acid substitution at position 29, wherein the amino acid positions are numbered according to the numbering system of Kabat. In some embodiments, the amino acid substitution in the CDR-L1 is selected from the group consisting of Ser, Gln, Glu, His, or Ala at position 28, wherein the amino acid positions are numbered according to the numbering system of Kabat. In some embodiments, the amino acid substitution in the CDR-L1 is selected from the group consisting of Ala or Val at position 29, wherein the amino acid positions are numbered according to the numbering system of Kabat.

In some embodiments, the humanized antibody comprises a VH comprising an amino acid substitution in the CDR-H2 compared to a VH comprising an amino acid sequence set forth in SEQ ID NO: 51. In some embodiments, the amino acid substitution in the CDR-H2 is selected from the group consisting of an amino acid substitution at position 54, position 55, or position 64, wherein the amino acid positions are numbered according to the numbering system of Kabat. In some embodiments, the amino acid substitution in the CDR-H2 is selected from the group consisting of Ser, Gln, Glu, Ala, or His at position 54, wherein the amino acid positions are numbered according to the numbering system of Kabat. In some embodiments, the amino acid substitution in the CDR-H2 is selected from the group consisting of Ala or Val at position 55, wherein the amino acid positions are numbered according to the numbering system of Kabat. In some embodiments, the amino acid substitution in the CDR-H2 is selected from the group consisting of Val, Ile, Leu, or Ala at position 64, wherein the amino acid positions are numbered according to the numbering system of Kabat.

B. Antibody-Peptide Fusion Proteins Comprising Humanized Antibodies

Also provided herein are antibody-peptide fusion proteins comprising a humanized antibody that binds to human amyloid fibrils fused to an amyloid-reactive peptide. In some embodiments, the antibody-peptide fusion protein comprises a humanized antibody as described herein. In some embodiments, the humanized antibody is any one of the humanized antibodies described above.

In some embodiments, the antibody-peptide fusion protein comprises a humanized antibody comprising a light chain variable region (VL) and a heavy chain variable region (VH), wherein the VL comprises a CDR-L1 comprising the amino acid sequence set forth in SEQ ID NO:20, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO: 17, a CDR-H2 comprising the amino acid sequence set forth in SEQ ID NO:18, and a CDR-H3 comprising the amino acid sequence LDY. In some embodiments, the humanized antibody comprises one, two, three, four, five, or six CDRs of an antibody as shown in Table 3.

In some embodiments, the humanized antibody comprises a CDR-H1, a CDR-H2, and a CDR-H3, respectively comprising the amino acid sequences of a CDR-H1, a CDR-H2, and a CDR-H3 of a VH having the sequence set forth in SEQ ID NO:15; and a CDR-L1, a CDR-L2, and a CDR-L3, respectively comprising the amino acid sequences of a CDR-L1, a CDR-L2, and a CDR-L3 of a VL having the sequence set forth in SEQ ID NO:16. In some embodiments, the humanized antibody comprises a light chain variable region (VL) and a heavy chain variable region (VH), wherein the VL comprises a CDR-L1 comprising the amino acid sequence set forth in SEQ ID NO:20 with one or more conservative amino acid substitutions, a CDR-L2 comprising the amino acid sequence set forth in SEQ ID NO:21 with one or more conservative amino acid substitutions, and a CDR-L3 comprising the amino acid sequence set forth in SEQ ID NO:22 with one or more conservative amino acid substitutions, and the VH comprises a CDR-H1 comprising the amino acid sequence set forth in SEQ ID NO:17 with one or more conservative amino acid substitutions, a CDR-H2 comprising the amino acid sequence set forth in SEQ ID NO:18 with one or more conservative amino acid substitutions, and a CDR-H3 comprising the amino acid sequence LDY with one or more conservative amino acid substitutions. In some embodiments, the humanized antibody comprises one, two, three, four, five, or six CDRs of an antibody as shown in Table 3, with one or more conservative amino acid substitutions. In some embodiments, the humanized antibody comprises a CDR-H1, a CDR-H2, and a CDR-H3, respectively comprising the amino acid sequences of a CDR-H1, a CDR-H2, and a CDR-H3 of a VH having the sequence set forth in SEQ ID NO:15 with one or more conservative amino acid substitutions; and a CDR-L1, a CDR-L2, and a CDR-L3, respectively comprising the amino acid sequences of a CDR-L1, a CDR-L2, and a CDR-L3 of a VL having the sequence set forth in SEQ ID NO:16 with one or more conservative amino acid substitutions.

In some embodiments, the humanized antibody comprises a VL comprising a CDR-L1 comprising the amino acid sequence set forth in SEQ ID NO:64-70, a CDR-L2 comprising the amino acid sequence set forth in SEQ ID NO:21, and a CDR-L3 comprising the amino acid sequence set forth in SEQ ID NO:22, and a VH comprising a CDR-H1 comprising the amino acid sequence set forth in SEQ ID NO:17, a CDR-H2 comprising the amino acid sequence set forth in SEQ ID NO:18, and a CDR-H3 comprising the amino acid sequence LDY. In some embodiments, the antibody-peptide fusion protein comprises a humanized antibody, wherein the humanized antibody comprises a VL comprising a CDR-L1 comprising the amino acid sequence set forth in SEQ ID NO: 20; a CDR-L2 comprising the amino acid sequence set forth in SEQ ID NO:21, and a CDR-L3 comprising the amino acid sequence set forth in SEQ ID NO:22, and a VH comprising a CDR-H1 comprising the amino acid sequence set forth in SEQ ID NO:17, a CDR-H2 comprising the amino acid sequence set forth in SEQ ID NO: 71-81; and a CDR-H3 comprising the amino acid sequence LDY.

In some embodiments, the antibody-peptide fusion protein comprises a humanized antibody, wherein the humanized antibody comprises a VL comprising an amino acid substitution in the FR2 compared to a VL comprising an amino acid sequence set forth in SEQ ID NO: 32. In some embodiments, the amino acid substitution in the FR2 is selected from the group consisting of an amino acid substitution at position 36, an amino acid substitution at position 37, and an amino acid substitution at position 46, wherein the amino acid positions are numbered according to the numbering system of Kabat. In some embodiments, the amino acid substitution in the FR2 is selected from the group consisting of Tyr at position 36, Leu at position 37, and Leu at position 46, wherein the amino acid positions are numbered according to the numbering system of Kabat.

In some embodiments, the antibody-peptide fusion protein comprises a humanized antibody, wherein the humanized antibody comprises a VL comprising an amino acid substitution in the FR3 compared to a VL comprising an amino acid sequence set forth in SEQ ID NO: 32. In some embodiments, the amino acid substitution in the FR3 is selected from the group consisting of an amino acid substitution at position 85, and an amino acid substitution at position 87, wherein the amino acid positions are numbered according to the numbering system of Kabat. In some embodiments, the amino acid substitution in the FR3 is selected from the group consisting of Leu at position 85, and Phe at position 87, wherein the amino acid positions are numbered according to the numbering system of Kabat.

In some embodiments, the antibody-peptide fusion protein comprises a humanized antibody, wherein the humanized antibody comprises a VH comprising an amino acid substitution in the FR2 compared to a VH comprising an amino acid sequence set forth in SEQ ID NO: 43. In some embodiments, the amino acid substitution in the FR2 is selected from the group consisting of an amino acid substitution at position 37 and an amino acid substitution at position 48, wherein the amino acid positions are numbered according to the numbering system of Kabat. In some embodiments, the amino acid substitution in the FR2 is selected from the group consisting of Val at position 37 and Leu at position 48, wherein the amino acid positions are numbered according to the numbering system of Kabat.

In some embodiments, the antibody-peptide fusion protein comprises a humanized antibody, wherein the humanized antibody comprises a VH comprising an amino acid substitution in the FR3 compared to a VH comprising an amino acid sequence set forth in SEQ ID NO: 43. In some embodiments, the amino acid substitution in the FR3 is selected from the group consisting of an amino acid substitution at position 67, an amino acid substitution at position 48, an amino acid substitution at position 71, an amino acid substitution at position 71, an amino acid substitution at position 76, an amino acid substitution at position 78, an amino acid substitution at position 79, an amino acid substitution at position 80, an amino acid substitution at position 89, an amino acid substitution at position 93, and an amino acid substitution at position 94, wherein the amino acid positions are numbered according to the numbering system of Kabat. In some embodiments, the amino acid substitution in the FR3 is selected from the group consisting of Leu at position 67, Ser at position 48, Lys at position 71, Ser at position 76, Val at position 78, Leu at position 79, Phe at position 80, Thr at position 89, Val at position 93, and Thr at position 94, wherein the amino acid positions are numbered according to the numbering system of Kabat.

In some embodiments, the antibody-peptide fusion protein comprises a humanized antibody, wherein the humanized antibody comprises a VL comprising one or more amino acid substitutions at one or more positions in the VL compared to a VL comprising an amino acid sequence set forth in SEQ ID NO: 32, wherein the amino acid positions are numbered starting from the N-terminus of SEQ ID NO: 32. In some embodiments, the antibody-peptide fusion protein comprises a humanized antibody, wherein the humanized antibody comprises a VL comprising an amino acid substitution at position 33 compared to a VL comprising an amino acid sequence set forth in SEQ ID NO: 32. In some embodiments, the antibody-peptide fusion protein comprises a humanized antibody, wherein the humanized antibody comprises a VL comprising an amino acid substitution at position 34 compared to a VL comprising an amino acid sequence set forth in SEQ ID NO: 32. In some embodiments, the antibody-peptide fusion protein comprises a humanized antibody, wherein the humanized antibody comprises a VL comprising an amino acid substitution at position 41 compared to a VL comprising an amino acid sequence set forth in SEQ ID NO: 32. In some embodiments, the antibody-peptide fusion protein comprises a humanized antibody, wherein the humanized antibody comprises a VL comprising an amino acid substitution at position 42 compared to a VL comprising an amino acid sequence set forth in SEQ ID NO: 32. In some embodiments, the antibody-peptide fusion protein comprises a humanized antibody, wherein the humanized antibody comprises a VL comprising an amino acid substitution at position 51 compared to a VL comprising an amino acid sequence set forth in SEQ ID NO: 32. In some embodiments, the antibody-peptide fusion protein comprises a humanized antibody, wherein the humanized antibody comprises a VL comprising an amino acid substitution at position 90 compared to a VL comprising an amino acid sequence set forth in SEQ ID NO: 32. In some embodiments, the antibody-peptide fusion protein comprises a humanized antibody, wherein the humanized antibody comprises a VL comprising an amino acid substitution at position 92 compared to a VL comprising an amino acid sequence set forth in SEQ ID NO: 32. In some embodiments, the antibody-peptide fusion protein comprises a humanized antibody, wherein the humanized antibody comprises a VL comprising 1, 2, 3, 4, 5, 6, 7, or 8 amino acid substitutions compared to a VL comprising an amino acid sequence set forth in SEQ ID NO: 32. In some embodiments, the antibody-peptide fusion protein comprises a humanized antibody, wherein the humanized antibody comprises a VL comprising 1, 2, 3, 4, 5, 6, 7, or 8 amino acid substitutions compared to a VL1, as shown in Table 6A.

In some embodiments, the antibody-peptide fusion protein comprises a humanized antibody, wherein the humanized antibody comprises a VH comprising one or more amino acid substitutions at one or more positions in the VH compared to a VH comprising an amino acid sequence set forth in SEQ ID NO: 43, wherein the amino acid positions are numbered starting from the N-terminus of SEQ ID NO: 43. In some embodiments, the antibody-peptide fusion protein comprises a humanized antibody, wherein the humanized antibody comprises a VH comprising an amino acid substitution at position 37 compared to a VH comprising an amino acid sequence set forth in SEQ ID NO: 43. In some embodiments, the antibody-peptide fusion protein comprises a humanized antibody, wherein the humanized antibody comprises a VH comprising an amino acid substitution at position 48 compared to a VH comprising an amino acid sequence set forth in SEQ ID NO: 43. In some embodiments, the antibody-peptide fusion protein comprises a humanized antibody, wherein the humanized antibody comprises a VH comprising an amino acid substitution at position 67 compared to a VH comprising an amino acid sequence set forth in SEQ ID NO: 43. In some embodiments, the antibody-peptide fusion protein comprises a humanized antibody, wherein the humanized antibody comprises a VH comprising an amino acid substitution at position 68 compared to a VH comprising an amino acid sequence set forth in SEQ ID NO: 43. In some embodiments, the antibody-peptide fusion protein comprises a humanized antibody, wherein the humanized antibody comprises a VH comprising an amino acid substitution at position 71 compared to a VH comprising an amino acid sequence set forth in SEQ ID NO: 43. In some embodiments, the antibody-peptide fusion protein comprises a humanized antibody, wherein the humanized antibody comprises a VH comprising an amino acid substitution at position 76 compared to a VH comprising an amino acid sequence set forth in SEQ ID NO: 43. In some embodiments, the antibody-peptide fusion protein comprises a humanized antibody, wherein the humanized antibody comprises a VH comprising an amino acid substitution at position 78 compared to a VH comprising an amino acid sequence set forth in SEQ ID NO: 43. In some embodiments, the antibody-peptide fusion protein comprises a humanized antibody, wherein the humanized antibody comprises a VH comprising an amino acid substitution at position 79 compared to a VH comprising an amino acid sequence set forth in SEQ ID NO: 43. In some embodiments, the antibody-peptide fusion protein comprises a humanized antibody, wherein the humanized antibody comprises a VH comprising an amino acid substitution at position 80 compared to a VH comprising an amino acid sequence set forth in SEQ ID NO: 43. In some embodiments, the antibody-peptide fusion protein comprises a humanized antibody, wherein the humanized antibody comprises a VH comprising an amino acid substitution at position 92 compared to a VH comprising an amino acid sequence set forth in SEQ ID NO: 43. In some embodiments, the antibody-peptide fusion protein comprises a humanized antibody, wherein the humanized antibody comprises a VH comprising an amino acid substitution at position 96 compared to a VH comprising an amino acid sequence set forth in SEQ ID NO: 43. In some embodiments, the antibody-peptide fusion protein comprises a humanized antibody, wherein the humanized antibody comprises a VH comprising an amino acid substitution at position 97 compared to a VH comprising an amino acid sequence set forth in SEQ ID NO: 43. In some embodiments, the antibody-peptide fusion protein comprises a humanized antibody, wherein the humanized antibody comprises a VH comprising 1, 2, 3, 4, 5, 6, 7, 8, 9 or 10 amino acid substitutions compared to a VH comprising an amino acid sequence set forth in SEQ ID NO: 43. In some embodiments, the antibody-peptide fusion protein comprises a humanized antibody, wherein the humanized antibody comprises a VH comprising 1, 2, 3, 4, 5, 6, 7, 8, 9 or 10 amino acid substitutions compared to VH1, as shown in Table 6B.

In some embodiments, the antibody-peptide fusion comprises a humanized antibody, wherein the humanized antibody comprises a VL comprising one or more amino acid residues at one or more positions in the VL, wherein the amino acid positions are numbered starting from the N-terminus of the VL. In some embodiments, the antibody-peptide fusion comprises a humanized antibody, wherein the humanized antibody comprises a VL comprising Ser, Gln, Glu, His, or Ala at position 33. In some embodiments, the antibody-peptide fusion comprises a humanized antibody, wherein the humanized antibody comprises a VL comprising Ala or Val at position 34. In some embodiments, the antibody-peptide fusion comprises a humanized antibody, wherein the humanized antibody comprises a VL comprising Tyr at position 41. In some embodiments, the antibody-peptide fusion comprises a humanized antibody, wherein the humanized antibody comprises a VL comprising Leu at position 42. In some embodiments, the antibody-peptide fusion comprises a humanized antibody, wherein the humanized antibody comprises a VL comprising Leu at position 51. In some embodiments, the antibody-peptide fusion comprises a humanized antibody, wherein the humanized antibody comprises a VL comprising Leu at position 90. In some embodiments, the antibody-peptide fusion comprises a humanized antibody, wherein the humanized antibody comprises a VL comprising Phe at position 92.

In some embodiments, the antibody-peptide fusion comprises a humanized antibody, wherein the humanized antibody comprises a VH comprising one or more amino acid residues at one or more positions in the VH, wherein the amino acid positions are numbered starting from the N-terminus of the VH. In some embodiments, the antibody-peptide fusion comprises a humanized antibody, wherein the humanized antibody comprises a VH comprising Val at position 37. In some embodiments, the antibody-peptide fusion comprises a humanized antibody, wherein the humanized antibody comprises a VH comprising Leu at position 48. In some embodiments, the antibody-peptide fusion comprises a humanized antibody, wherein the humanized antibody comprises a VH comprising Leu at position 67. In some embodiments, the antibody-peptide fusion comprises a humanized antibody, wherein the humanized antibody comprises a VH comprising Ser at position 68. In some embodiments, the antibody-peptide fusion comprises a humanized antibody, wherein the humanized antibody comprises a VH comprising Lys at position 71. In some embodiments, the antibody-peptide fusion comprises a humanized antibody, wherein the humanized antibody comprises a VH comprising Ser at position 76. In some embodiments, the antibody-peptide fusion comprises a humanized antibody, wherein the humanized antibody comprises a VH comprising Val at position 78. In some embodiments, the antibody-peptide fusion comprises a humanized antibody, wherein the humanized antibody comprises a VH comprising Leu at position 79. In some embodiments, the antibody-peptide fusion comprises a humanized antibody, wherein the humanized antibody comprises a VH comprising Phe at position 80. In some embodiments, the antibody-peptide fusion comprises a humanized antibody, wherein the humanized antibody comprises a VH comprising Thr at position 92. In some embodiments, the antibody-peptide fusion comprises a humanized antibody, wherein the humanized antibody comprises a VH comprising Val at position 96. In some embodiments, the antibody-peptide fusion comprises a humanized antibody, wherein the humanized antibody comprises a VH comprising Thr position 97.

In some embodiments, the antibody-peptide fusion protein comprises a humanized antibody, wherein the humanized antibody comprises a VL comprising one or more amino acid substitutions at one or more positions in the VL, wherein the amino acid positions are numbered according to the numbering system of Kabat. In some embodiments, the antibody-peptide fusion protein comprises a humanized antibody, wherein the humanized antibody comprises a VL comprising Tyr at position 36. In some embodiments, the antibody-peptide fusion protein comprises a humanized antibody, wherein the humanized antibody comprises a VL comprising Leu at position 37. In some embodiments, the antibody-peptide fusion protein comprises a humanized antibody, wherein the humanized antibody comprises a VL comprising Leu at position 46. In some embodiments, the antibody-peptide fusion protein comprises a humanized antibody, wherein the humanized antibody comprises a VL comprising Leu at position 85. In some embodiments, the antibody-peptide fusion protein comprises a humanized antibody, wherein the humanized antibody comprises a VL comprising Phe at position 87.

In some embodiments, the antibody-peptide fusion protein comprises a humanized antibody, wherein the humanized antibody comprises a VL comprising one or more amino acid residues at one or more positions in the VL, wherein the amino acid positions are numbered according to the numbering system of Kabat. In some embodiments, the antibody-peptide fusion protein comprises a humanized antibody, wherein the humanized antibody comprises a VL comprising Tyr at position 36 and Leu at position 37. In some embodiments, the antibody-peptide fusion protein comprises a humanized antibody, wherein the humanized antibody comprises a VL comprising Tyr at position 36, Leu at position 37, Leu at position 46, Leu at position 85, and Phe at position 87. In some embodiments, the antibody-peptide fusion protein comprises a humanized antibody, wherein the humanized antibody comprises a VL comprising Leu at position 46 and Phe at position 87.

In some embodiments, the antibody-peptide fusion protein comprises a humanized antibody, wherein the humanized antibody comprises a VH comprising one or more amino acid residues at one or more positions in the VH, wherein the amino acid positions are numbered according to the numbering system of Kabat. In some embodiments, the antibody-peptide fusion protein comprises a humanized antibody, wherein the humanized antibody comprises a VH comprising Val at position 37. In some embodiments, the antibody-peptide fusion protein comprises a humanized antibody, wherein the humanized antibody comprises a VH comprising Leu at position 48. In some embodiments, the antibody-peptide fusion protein comprises a humanized antibody, wherein the humanized antibody comprises a VH comprising Leu at position 67. In some embodiments, the antibody-peptide fusion protein comprises a humanized antibody, wherein the humanized antibody comprises a VH comprising Ser at position 68. In some embodiments, the antibody-peptide fusion protein comprises a humanized antibody, wherein the humanized antibody comprises a VH comprising Lys at position 71. In some embodiments, the antibody-peptide fusion comprises a humanized antibody, wherein the humanized antibody comprises a VH comprising Ser at position 76. In some embodiments, the antibody-peptide fusion comprises a humanized antibody, wherein the humanized antibody comprises a VH comprising Val at position 78. In some embodiments, the antibody-peptide fusion comprises a humanized antibody, wherein the humanized antibody comprises a VH comprising Leu at position 79. In some embodiments, the antibody-peptide fusion comprises a humanized antibody, wherein the humanized antibody comprises a VH comprising Phe at position 80. In some embodiments, the antibody-peptide fusion protein comprises a humanized antibody, wherein the humanized antibody comprises a VH comprising Thr at position 89. In some embodiments, the antibody-peptide fusion protein comprises a humanized antibody, wherein the humanized antibody comprises a VH comprising Val at position 93. In some embodiments, the antibody-peptide fusion protein comprises a humanized antibody, wherein the humanized antibody comprises a VH comprising Thr at position 94.

In some embodiments, the antibody-peptide fusion protein comprises a humanized antibody, wherein the humanized antibody comprises a VH comprising one or more amino acid residues at one or more positions in the VH, wherein the amino acid positions are numbered according to the numbering system of Kabat. In some embodiments, the antibody-peptide fusion protein comprises a humanized antibody, wherein the humanized antibody comprises a VH comprising Val at position 37 and Leu at position 48. In some embodiments, the antibody-peptide fusion protein comprises a humanized antibody, wherein the humanized antibody comprises a VH comprising Leu at position 67, Ser at position 68, Thr at position 89, Val at position 93, and Thr at position 94. In some embodiments, the antibody-peptide fusion protein comprises a humanized antibody, wherein the humanized antibody comprises a VH comprising Val at position 37, Leu at position 48, Leu at position 67, and Ser at position 68. In some embodiments, the antibody-peptide fusion protein comprises a humanized antibody, wherein the humanized antibody comprises a VH comprising Val at position 37, Leu at position 48, Val at position 93, and Thr at position 94. In some embodiments, the antibody-peptide fusion protein comprises a humanized antibody, wherein the humanized antibody comprises a VH comprising Val at position 37, Leu at position 48, Leu at position 67, Ser at position 68, Lys at position 71, Thr at position 89, Val at position 93, and Thr at position 94. In some embodiments, the antibody-peptide fusion protein comprises a humanized antibody, wherein the humanized antibody comprises a VH comprising Lys at position 71, Val at position 78, Leu at position 79, Val at position 93, and Thr at position 94. In some embodiments, the antibody-peptide fusion protein comprises a humanized antibody, wherein the humanized antibody comprises a VH comprising Lys at position 71, Ser at position 76, Val at position 93, and Thr at position 94. In some embodiments, the antibody-peptide fusion protein comprises a humanized antibody, wherein the humanized antibody comprises a VH comprising Leu at position 48, Ser at position 96, Val at position 78, Leu at position 79, Phe at position 80, and Thr at position 94. In some embodiments, the antibody-peptide fusion protein comprises a humanized antibody, wherein the humanized antibody comprises a VH comprising Leu at position 48, Leu at position 67, Ser at position 68, Lys at position 71, Ser at position 76, Val at position 78, Leu at position 79, Val at position 93, and Thr at position 94.

In some embodiments, the antibody-peptide fusion protein comprises a humanized antibody, wherein the humanized antibody comprises a VL comprising Tyr at position 36, Leu at position 37, Leu at position 46, Leu at position 85, and Phe at position 87, and a VH comprising Val at position 37, Leu at position 48, Leu at position 67, Ser at position 68, Lys at position 71, Thr at position 89, Val at position 93, and Thr at position 94. In some embodiments, the antibody-peptide fusion protein comprises a humanized antibody, wherein the humanized antibody comprises a VL comprising Leu at position 46 and Phe at position 87, and a VH comprising Leu at position 48, Ser at position 96, Val at position 78, Leu at position 79, Phe at position 80, and Thr at position 94. In some embodiments, the antibody-peptide fusion protein comprises a humanized antibody, wherein the humanized antibody comprises a VL comprising Leu at position 46 and Phe at position 87, and a VH comprising Leu at position 48, Leu at position 67, Ser at position 68, Lys at position 71, Ser at position 76, Val at position 78, Leu at position 79, Val at position 93, and Thr at position 94. In some embodiments, the antibody-peptide fusion protein comprises a humanized antibody, wherein the humanized antibody comprises a VL comprising Leu at position 46 and Phe at position 87, and a VH comprising Lys at position 71, Ser at position 76, Val at position 93, and Thr at position 94. In some embodiments, the antibody-peptide fusion protein comprises a humanized antibody, wherein the humanized antibody comprises a VL comprising Leu at position 46 and Phe at position 87, and a VH comprising Lys at position 71, Val at position 78, Leu at position 79, Val at position 93, and Thr at position 94.

In some embodiments, the antibody-peptide fusion protein comprises a humanized antibody comprising the amino acid sequence of a VL as shown in Table 6A. In some embodiments, the antibody-peptide fusion protein comprises a humanized antibody, wherein the humanized antibody comprises a VL selected from the group consisting of VL2, VL3, VL4, VL4-N33S, VL4-N33Q, VL4-N33E, VL4-N33A, VL4-N33H, VL4-G34A, or VL4-G34V, as shown in Table 6A. In some embodiments, the VL comprises an amino acid sequence set forth in the group consisting of SEQ ID NOs:33-42.

In some embodiments, the antibody-peptide fusion protein comprises a humanized antibody comprising the amino acid sequence of a VH as shown in Table 6B. In some embodiments, the antibody-peptide fusion protein comprises a humanized antibody, wherein the humanized antibody comprises a VH selected from the group consisting of VH2, VH3, VH4, VH5, VH6, VH7, VH8, VH9, VH10, VH9-D54S, VH9-D54Q, VH9-D54E, VH9-D54A, VH9-D54H, VH9-G55A, VH9-G55V, VH9-M64V, VH9-M64I, VH9-M64L, or VH9-M64A, as shown in Table 6B. In some embodiments, the VH comprises an amino acid sequence set forth in the group consisting of SEQ ID NOs:44-63.

In some embodiments, the antibody-peptide fusion protein comprises a humanized antibody comprising the VL of VL4 as shown in Table 6A, and the VH of VH9 as shown in Table 6B. In some embodiments, the antibody-peptide fusion protein comprises a humanized antibody comprising a VL comprising an amino acid sequence set forth in SEQ ID NO:35, and a VH comprising an amino acid sequence set forth in SEQ ID NO:51.

In some embodiments, the antibody-peptide fusion protein comprises a humanized antibody comprising the VL of VL3 as shown in Table 6A, and the VH of VH6 as shown in Table 6B. In some embodiments, the antibody-peptide fusion protein comprises a humanized antibody comprising a VL comprising an amino acid sequence set forth in SEQ ID NO:34, and a VH comprising an amino acid sequence set forth in SEQ ID NO:48.

In some embodiments, the antibody-peptide fusion protein comprises a humanized antibody comprising the VL of VL4 as shown in Table 6A, and the VH of VH10 as shown in Table 6B. In some embodiments, the antibody-peptide fusion protein comprises a humanized antibody comprising a VL comprising an amino acid sequence set forth in SEQ ID NO:35, and a VH comprising an amino acid sequence set forth in SEQ ID NO:52. In some embodiments, the antibody-peptide fusion protein comprises a humanized antibody comprising the VL of VL4 as shown in Table 6A, and the VH of VH8 as shown in Table 6B. In some embodiments, the antibody-peptide fusion protein comprises a humanized antibody comprising a VL comprising an amino acid sequence set forth in SEQ ID NO:35, and a VH comprising an amino acid sequence set forth in SEQ ID NO:50. In some embodiments, the antibody-peptide fusion protein comprises a humanized antibody comprising the VL of VL4 as shown in Table 6A, and the VH of VH7 as shown in Table 6B. In some embodiments, the antibody-peptide fusion protein comprises a humanized antibody comprising a VL comprising an amino acid sequence set forth in SEQ ID NO:35, and a VH comprising an amino acid sequence set forth in SEQ ID NO:69.

In some embodiments, the antibody-peptide fusion protein comprises an amyloid-reactive peptide. In some embodiments, the amyloid-reactive peptide comprises one or more of the peptides shown in Table 1. In certain some embodiments, the amyloid-reactive peptide comprises an amino acid sequence selected from the group consisting of SEQ ID NOs:1-14. In some embodiments, the amyloid-reactive peptide comprises the amino acid sequence set forth in SEQ ID NO:1. In some embodiments, the amyloid-reactive peptide comprises the amino acid sequence set forth in SEQ ID NO:2. In some embodiments, the amyloid-reactive peptide is positively charged.

In some embodiments, the antibody-peptide fusion protein comprises a humanized antibody, wherein the humanized antibody comprises a light chain. In some embodiments, the amyloid reactive peptide is fused to the N-terminus of the light chain. In some embodiments, the antibody-peptide fusion protein comprises a humanized antibody, wherein the humanized antibody comprises a light chain, wherein the amyloid reactive peptide is fused to the N-terminus of the light chain by a linker. In some embodiments, the linker is a peptide linker. In some embodiments, the linker comprises the amino acid sequence GGGYS (SEQ ID NO:27). In some embodiments, the linker comprises the amino acid sequence set forth in SEQ ID NO:27. In some embodiments, the linker is uncharged.

In some embodiments, one or more of the peptides shown in Table 1 below can be joined to a humanized antibody or functional fragment thereof through the N-terminus of the light chain protein or the C-terminus of the heavy chain, thereby forming an antibody-peptide fusion protein comprising a humanized antibody. That is, any of the sequences identified below in Table 1 can be joined to the heavy or light chain of the humanized antibody or functional fragment thereof independently or simultaneously to form an antibody-peptide fusion protein. For example, two of the amyloid reactive peptides can be joined with a single Ig antibody, such by joining the amyloid-reactive peptide amino acid sequences to the N-terminal of a humanized antibody light chain.

In some embodiments, the antibody-peptide fusion protein comprises a light chain comprising, from N- to C-terminus, an amyloid reactive peptide and a light chain. In some embodiments, the light chain comprises, from N- to C-terminus, a VL and a CL1. In some embodiments, the VL is any one of the VLs described herein. In some embodiments, the antibody-peptide fusion protein comprises a heavy chain comprising, from N- to C-terminus, a VH, a CH1, a CH2, and a CH3. In some embodiments, the VH is any one of the VHs described herein.

In some embodiments, the antibody-peptide fusion protein comprises a light chain comprising, from N- to C-terminus, an amyloid reactive peptide, a spacer peptide, and a light chain. In some embodiments, the spacer peptide comprises the amino acid sequence of SEQ ID NO: 23. In some embodiments, the spacer peptide comprises the amino acid sequence of SEQ ID NO: 27. In some embodiments, the light chain comprises, from N- to C-terminus, a VL and a CL1. In some embodiments, the VL is any one of the VLs described herein. In some embodiments, the antibody-peptide fusion protein comprises a heavy chain comprising, from N- to C-terminus, a VH, a CH1, a CH2, and a CH3.

Figures 11A, 11B:
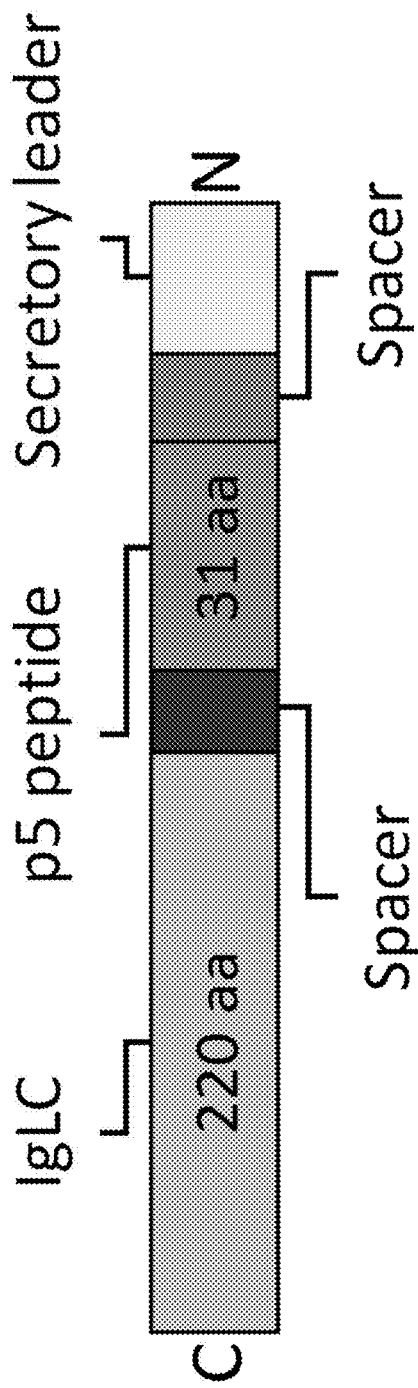
FIG. 11A shows a schematic diagram of mIgG-p5. From left to right, regions from the C- to N-terminus of mIgG-p5 are diagrammed, including the Ig light chain sequence ("IgLC," 220 amino acids), a spacer sequence, peptide p5 (31 amino acids), a spacer sequence, and the N-terminal secretory leader sequence.
FIG. 11B shows the amino acid sequence of regions of mIgG-p5 including, from left to right, the N-terminus of the Ig light chain (beginning with amino acid residues DVVMTQTP (SEQ ID NO: 82)), the spacer sequence at the C-terminal of the p5 peptide (amino acid residues VTPTV (SEQ ID NO: 24)), peptide p5 (amino acid residues KAQKAQAKQAKQAQKAQKAQAKQAKQ (SEQ ID NO: 1)), and the spacer sequence at the N-terminal (amino acid residues AQAGQAGQAQGGYS (SEQ ID NO: 23)).
Figure 11D:
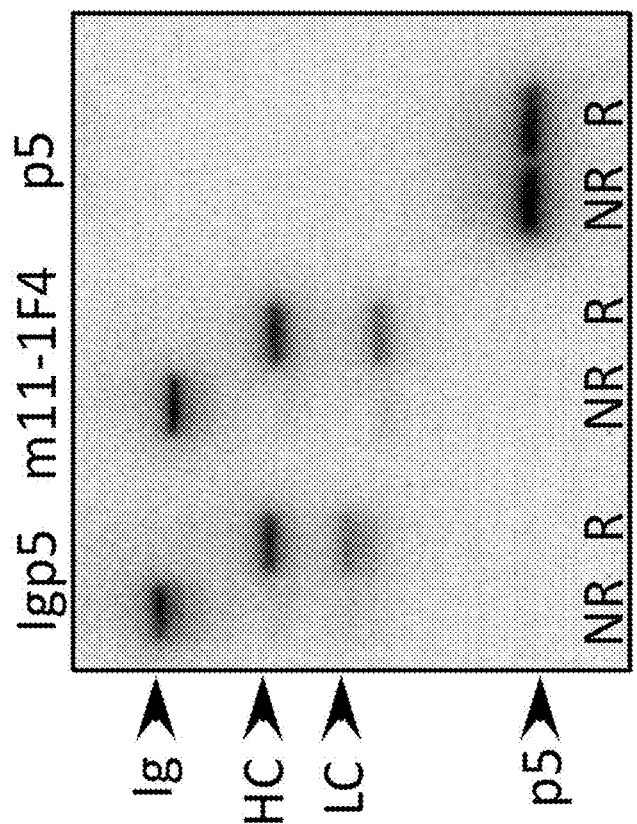
FIG. 11D shows an autoradiograph of $^{125}$I-labeled mIgG-p5, $^{125}$I-ml 1-1F4, and $^{125}$I-p5 following SDS-PAGE gel electrophoresis. Each protein is shown under non-reducing ("NR") or reducing ("R") conditions, and the relative positions of the full-length antibody ("Ig"), heavy chain ("HC"), light chain ("LC"), and peptide p5 are indicated.
Figure 11C:
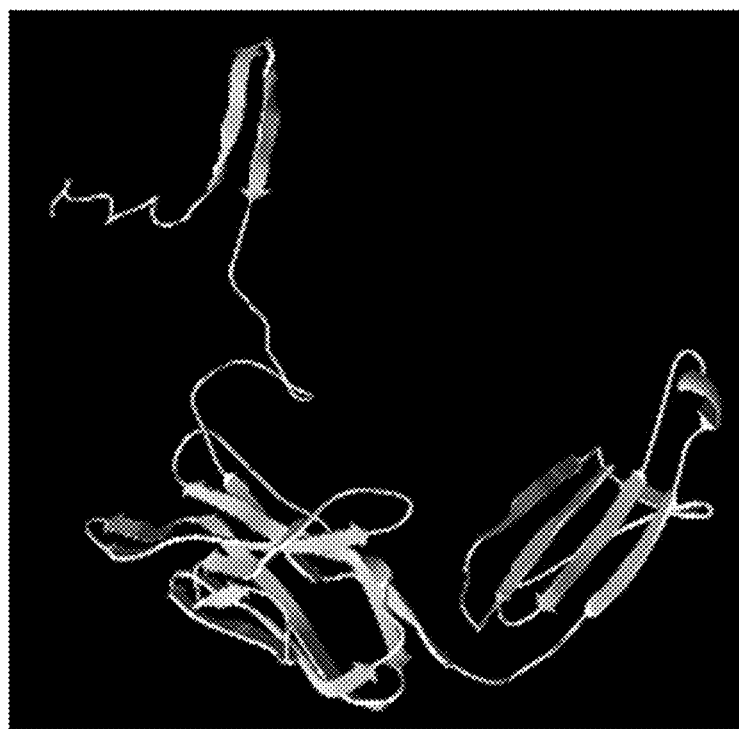
FIG. 11C shows a proposed structural model of peptide p5 fused to the N-terminus of the Ig light chain.
Figure 11E:
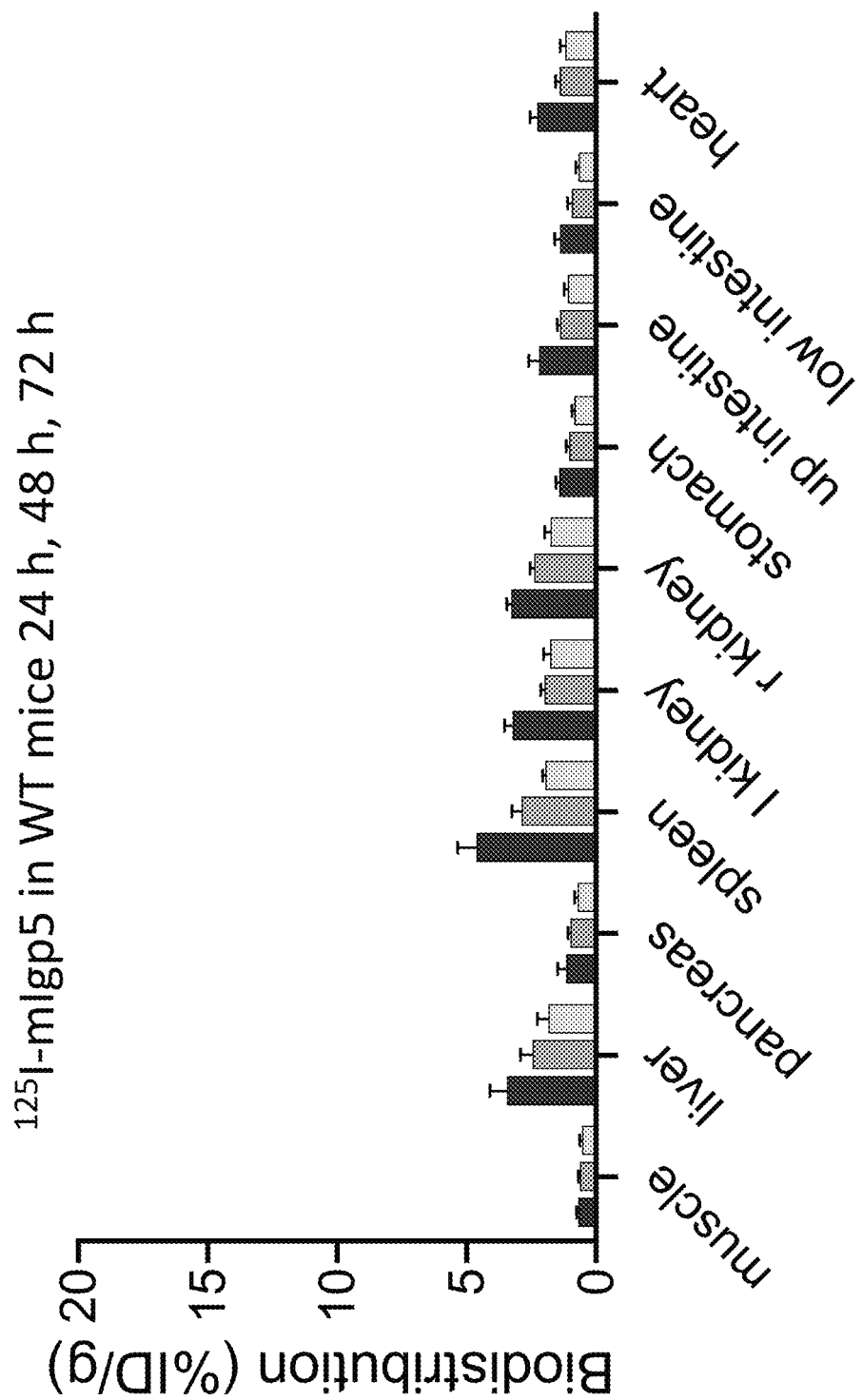
FIG. 11E shows the biodistribution of $^{125}$I-labeled mIgG-p5 in wild-type, amyloid-free, mice at 24, 48, or 72 hours post-injection with $^{125}$I-mIgG-p5.
Figure 11F:
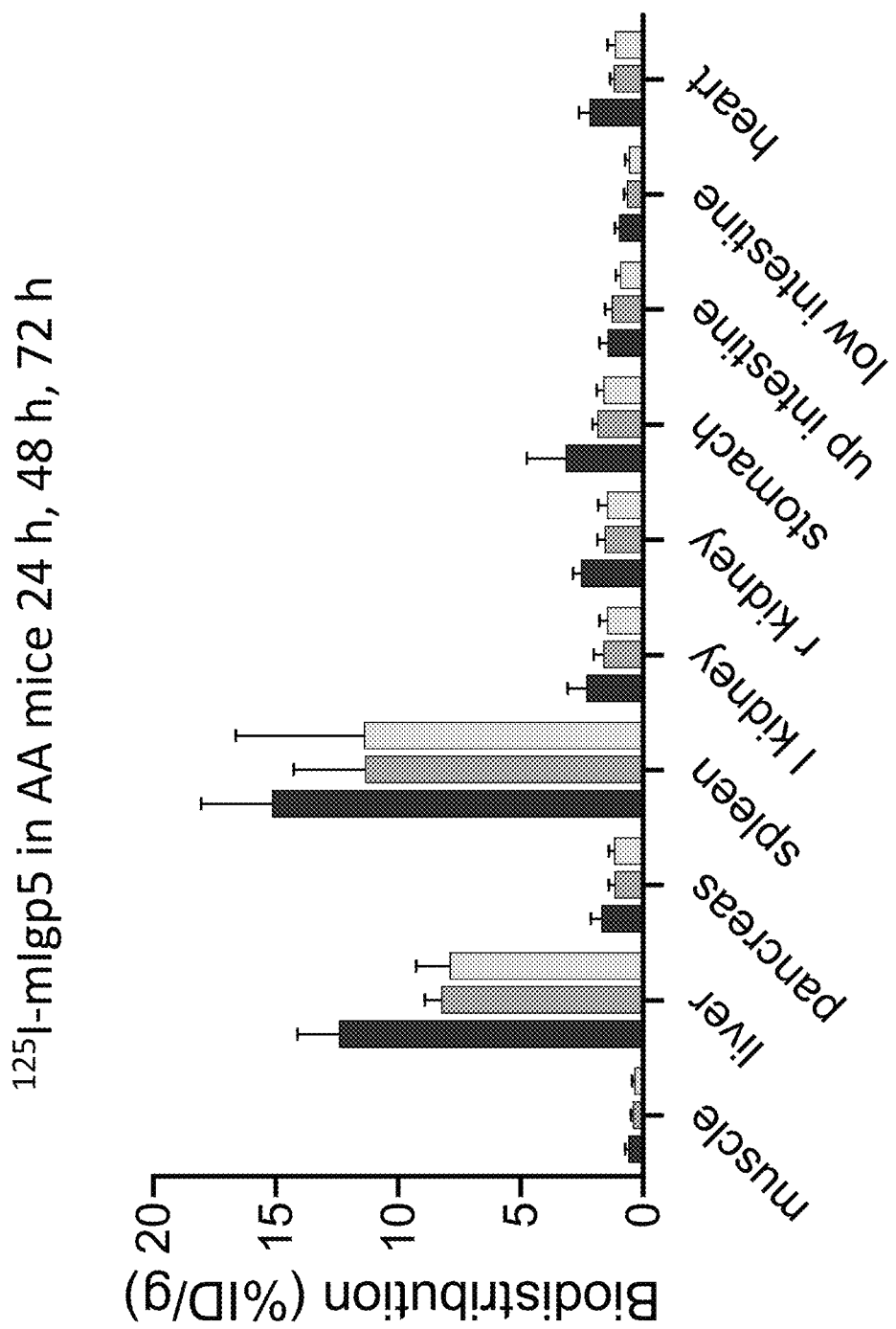
FIG. 11F shows the biodistribution of $^{125}$I-labeled mIgG-p5 in mice with AA amyloidosis (predominantly in the liver and spleen) at 24, 48, or 72 hours post-injection with $^{125}$I-mIgG-p5. In each of FIGS. 11E and 11F, the y-axis shows the level of biodistribution as a percentage of the injected dose per gram of tissue, and the type of tissue is indicated on the x-axis.
Figure 11G:
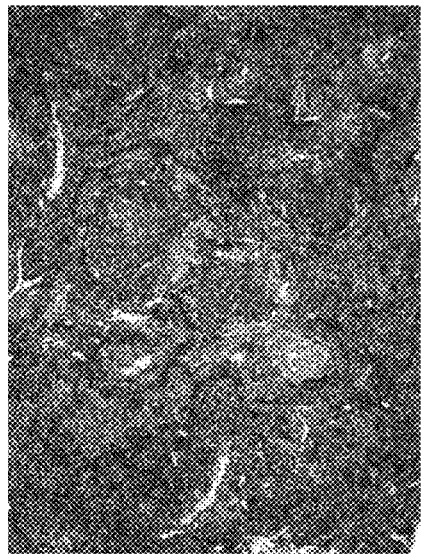
FIG. 11G shows microautoradiography images showing $^{125}$I-labeled mIg-p5 in mice with AA amyloidosis at 24 hours post-injection. 24 h is shown in black; 48 hours is shown in dark gray, and 72 hours is shown in light grey.
Figure 11G:
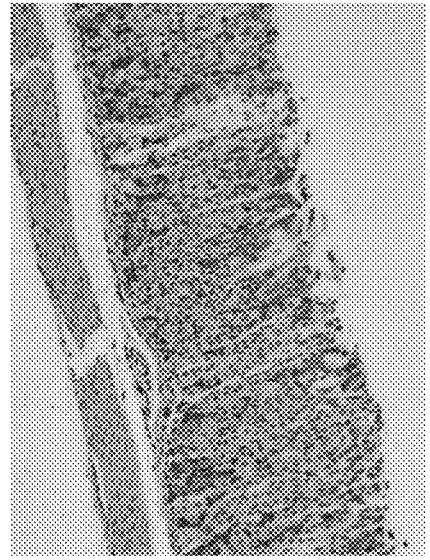
Figure 11G:
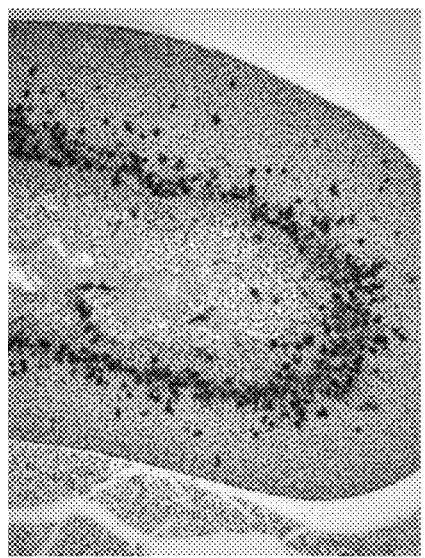
Figure 11G:
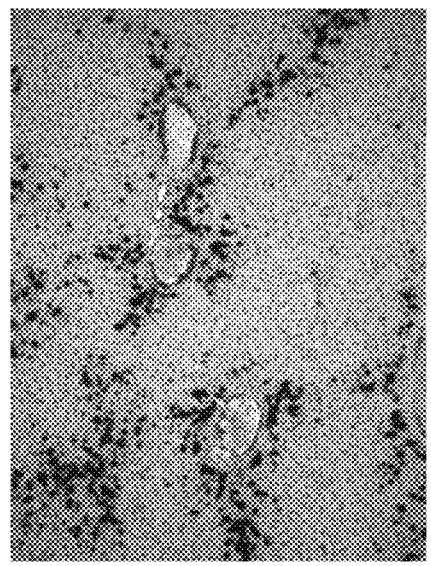

In some embodiments, the antibody-peptide fusion protein comprises, from N- to C-terminus, a secretory leader peptide, a first spacer peptide, an amyloid reactive peptide, a second spacer peptide, and a light chain. In some embodiments, the first spacer peptide comprises the amino acid sequence of SEQ ID NO: 23. In some embodiments, the first spacer peptide comprises the amino acid sequence of SEQ ID NO: 27. In some embodiments, the second spacer peptide comprises the amino acid sequence of SEQ ID NO: 24. In some embodiments, the light chain comprises, from N- to C-terminus, a VL and a CL1. In some embodiments, the VL is any one of the VLs described herein. In some embodiments, the antibody-peptide fusion protein comprises a heavy chain comprising, from N- to C-terminus, a VH, a CH1, a CH2, and a CH3. In some embodiments, the VH is any one of the VHs described herein. In some embodiments, the VH is any one of the VHs described herein. In some embodiments, the antibody-peptide fusion protein comprises a structure as diagrammed in FIG. 11A or FIG. 11B.

In some embodiments, the antibody-peptide fusion protein comprises a spacer sequence of amino acids between the N-terminus of the light chain and the amyloid reactive peptide. In some embodiments, the antibody-peptide fusion protein comprises a spacer sequence of amino acids between the N-terminus of the peptide and a leader sequence required for secretion of the antibody-peptide fusion protein from cells expressing the antibody-peptide fusion protein. In some embodiments, the spacer peptide is a flexible spacer peptide. In some embodiments, the spacer peptide is uncharged. In some embodiments, the spacer peptide is a glycine serine linker. In some embodiments, the spacer peptide comprises a glycine serine linker. In some embodiments the spacer peptide comprises or consist of from about 3 to about 55 amino acids. The spacer peptides of the present invention may comprise or consist of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 amino acids. In some embodiments, the spacer peptide is about 3, 4, 5, 6, 7, 8, 9, 10, 11, 12, 13, 14, 15, 16, 17, 18, 19, 20, 21, 22, 23, 24, 25, 50, 100, or 155 amino acids in length, including any value or range between these values. In some embodiments, the spacer peptide comprises 15 amino acids. In some embodiments, the spacer peptide comprises the amino acid sequence of SEQ ID NO: 23. In some embodiments, the spacer peptide comprises the amino acid sequence of SEQ ID NO: 24. In some embodiments, the spacer peptide comprises the amino acid sequence of SEQ ID NO: 27. In some embodiments, the antibody-peptide fusion protein does not comprise a spacer between the amyloid reactive peptide and the antibody.

In some embodiments, the antibody-peptide fusion protein comprises a humanized antibody that comprises a heavy chain comprising a VH comprising an amino acid sequence set forth in the group consisting of SEQ ID NOs:44-63, and a light chain comprising a VL comprising an amino acid set forth in the group consisting of SEQ ID NOs:33-42, wherein the light chain is joined to a peptide. In some embodiments, the antibody-peptide fusion protein comprises a heavy chain comprising a VH comprising an amino acid sequence set forth in the group consisting of SEQ ID NOs:44-63 without the C-terminal lysine residue, and a VL comprising an amino acid sequence set forth in the group consisting of SEQ ID NOs:33-42, wherein the antibody is joined to a peptide. In some embodiments, the antibody-peptide fusion protein comprises a humanized antibody that comprises a heavy chain comprising a VH comprising the amino acid sequence of SEQ ID NO: 51, and a light chain comprising a VL comprising the amino acid of SEQ ID NO: 35, wherein the light chain is joined to a peptide. In some embodiments, the antibody-peptide fusion protein comprises a humanized antibody that comprises a heavy chain comprising a VH comprising the amino acid sequence of SEQ ID NO: 51 without the C-terminal lysine residue, and a VL comprising the amino acid of SEQ ID NO: 35, wherein the antibody is joined to a peptide. In some embodiments, the antibody-peptide fusion protein comprises a humanized antibody that comprises a heavy chain comprising a VH comprising the amino acid sequence of SEQ ID NO: 48, and a light chain comprising a VL comprising the amino acid of SEQ ID NO: 34, wherein the light chain is joined to a peptide. In some embodiments, the antibody-peptide fusion protein comprises a humanized antibody that comprises a heavy chain comprising a VH comprising the amino acid sequence of SEQ ID NO: 48 without the C-terminal lysine residue, and a VL comprising the amino acid of SEQ ID NO: 34, wherein the antibody is joined to a peptide.

In some embodiments, the antibody-peptide fusion protein comprises a humanized antibody that comprises a heavy chain comprising a VH comprising an amino acid sequence set forth in the group consisting of SEQ ID NOs:44-63, wherein the heavy chain is joined to a peptide comprising any of the amino acid sequences of Table 1. In some embodiments, the antibody-peptide fusion protein comprises a humanized antibody comprising a heavy chain comprising a VH comprising an amino acid sequence set forth in the group consisting of SEQ ID NOs:44-63, wherein the heavy chain is joined to a peptide comprising the amino acid sequence of SEQ ID NO:1. In some embodiments, the antibody-peptide fusion protein comprises a humanized antibody comprising a heavy chain comprising a VH comprising an amino acid sequence set forth in the group consisting of SEQ ID NOs:44-63, wherein the heavy chain is joined to a peptide comprising the amino acid sequence of SEQ ID NO:2. In some embodiments, the antibody-peptide fusion protein comprises a humanized antibody that comprises a heavy chain comprising the VH comprising the amino acid sequence of SEQ ID NO: 51, wherein the heavy chain is joined to a peptide comprising any of the amino acid sequences of Table 1. In some embodiments, the antibody-peptide fusion protein comprises a humanized antibody comprising a heavy chain comprising a VH comprising the amino acid sequence of SEQ ID NO: 51, wherein the heavy chain is joined to a peptide comprising the amino acid sequence of SEQ ID NO:1. In some embodiments, the antibody-peptide fusion protein comprises a humanized antibody comprising a heavy chain comprising a VH comprising the amino acid sequence of SEQ ID NO: 51, wherein the heavy chain is joined to a peptide comprising the amino acid sequence of SEQ ID NO:2. In some embodiments, the antibody-peptide fusion protein comprises a humanized antibody that comprises a heavy chain comprising the a VH comprising the amino acid sequence of SEQ ID NO:48, wherein the heavy chain is joined to a peptide comprising any of the amino acid sequences of Table 1. In some embodiments, the antibody-peptide fusion protein comprises a humanized antibody comprising a heavy chain comprising a VH comprising the amino acid sequence of SEQ ID NO: 48, wherein the heavy chain is joined to a peptide comprising the amino acid sequence of SEQ ID NO:1. In some embodiments, the antibody-peptide fusion protein comprises a humanized antibody comprising a heavy chain comprising a VH comprising the amino acid sequence of SEQ ID NO: 48, wherein the heavy chain is joined to a peptide comprising the amino acid sequence of SEQ ID NO:2.

In some embodiments, the antibody-peptide fusion protein comprises a humanized antibody that comprises a light chain comprising a VL comprising an amino acid sequence set forth in the group consisting of SEQ ID NOs:33-42, wherein the light chain is joined to a peptide comprising any of the amino acid sequences of Table 1. In some embodiments, the antibody-peptide fusion protein comprises a humanized antibody comprising a light chain comprising a VL comprising an amino acid sequence set forth in the group consisting of SEQ ID NOs:33-42, wherein the light chain is joined to a peptide comprising the amino acid sequence of SEQ ID NO:1. In some embodiments, the antibody-peptide fusion protein comprises a humanized antibody comprising a light chain comprising a VL comprising an amino acid sequence set forth in the group consisting of SEQ ID NOs:33-42, wherein the light chain is joined to a peptide comprising the amino acid sequence of SEQ ID NO:2. In some embodiments, the antibody-peptide fusion protein comprises a humanized antibody that comprises a light chain comprising a VL comprising the amino acid sequence of SEQ ID NO: 35, wherein the light chain is joined to a peptide comprising any of the amino acid sequences of Table 1. In some embodiments, the antibody-peptide fusion protein comprises a humanized antibody comprising a light chain comprising a VL comprising the amino acid sequence of SEQ ID NO: 35, wherein the light chain is joined to a peptide comprising the amino acid sequence of SEQ ID NO:1. In some embodiments, the antibody-peptide fusion protein comprises a humanized antibody comprising a light chain comprising a VL comprising the amino acid sequence of SEQ ID NO: 35, wherein the light chain is joined to a peptide comprising the amino acid sequence of SEQ ID NO:2. In some embodiments, the antibody-peptide fusion protein comprises a humanized antibody that comprises a light chain comprising a VL comprising the amino acid sequence of SEQ ID NO: 34, wherein the light chain is joined to a peptide comprising any of the amino acid sequences of Table 1. In some embodiments, the antibody-peptide fusion protein comprises a humanized antibody comprising a light chain comprising a VL comprising the amino acid sequence of SEQ ID NO: 34, wherein the light chain is joined to a peptide comprising the amino acid sequence of SEQ ID NO:1. In some embodiments, the antibody-peptide fusion protein comprises a humanized antibody comprising a light chain comprising a VL comprising the amino acid sequence of SEQ ID NO: 34, wherein the light chain is joined to a peptide comprising the amino acid sequence of SEQ ID NO:2.

In some embodiments, the antibody-peptide fusion protein comprises a humanized antibody comprising a heavy chain comprising a VH comprising the amino acid sequence of SEQ ID NO:51 and a light chain comprising a VL comprising the amino acid sequence of SEQ ID NO:35, wherein the light chain is joined to a peptide comprising any of the amino acid sequences of Table 1.

In some embodiments, the antibody-peptide fusion protein comprises a humanized antibody comprising heavy chain comprising a VH comprising the amino acid sequence of SEQ ID NO:51 and a light chain comprising a VL comprising the amino acid sequence of SEQ ID NO:35, wherein the light chain is joined to a peptide comprising the amino acid sequence of SEQ ID NO:1. In some embodiments, the peptide is joined to the light chain at the N-terminus.

In some embodiments, the antibody-peptide fusion protein comprises a humanized antibody a heavy chain comprising a VH comprising the amino acid sequence of SEQ ID NO:51 and a light chain comprising a VL comprising the amino acid sequence of SEQ ID NO:35, wherein the light chain is joined to a peptide comprising the amino acid sequence of SEQ ID NO:2. In some embodiments, the peptide is joined to the light chain at the N-terminus.

In some embodiments, the antibody-peptide fusion protein comprises a humanized antibody comprising a heavy chain comprising a VH comprising the amino acid sequence of SEQ ID NO:48 and a light chain comprising a VL comprising the amino acid sequence of SEQ ID NO:34, wherein the light chain is joined to a peptide comprising any of the amino acid sequences of Table 1.

In some embodiments, the antibody-peptide fusion protein comprises a humanized antibody comprising heavy chain comprising a VH comprising the amino acid sequence of SEQ ID NO:48 and a light chain comprising a VL comprising the amino acid sequence of SEQ ID NO:34, wherein the light chain is joined to a peptide comprising the amino acid sequence of SEQ ID NO:1. In some embodiments, the peptide is joined to the light chain at the N-terminus.

In some embodiments, the antibody-peptide fusion protein comprises a humanized antibody a heavy chain comprising a VH comprising the amino acid sequence of SEQ ID NO:48 and a light chain comprising a VL comprising the amino acid sequence of SEQ ID NO:34, wherein the light chain is joined to a peptide comprising the amino acid sequence of SEQ ID NO:2. In some embodiments, the peptide is joined to the light chain at the N-terminus.

C. Humanized Antibodies and Antibody-Peptide Fusion Proteins Comprising Humanized Antibodies In some embodiments, the humanized antibody or antibody-peptide fusion protein comprising a humanized antibody of the present disclosure comprises an Fc region. In some embodiments, the Fc is of an IgG1, IgG2, IgG3, or IgG4 isotype. In some embodiments, the humanized antibody or antibody-peptide fusion protein comprising a humanized antibody promotes an Fc-mediated antibody effector function. In some embodiments, the humanized antibody or antibody-peptide fusion protein comprising a humanized antibody promotes antibody-dependent cellular phagocytosis.

In some embodiments, the humanized antibody or antibody-peptide fusion protein binds to human amyloid fibrils with a dissociation constant (Kd) that is less than about 100, 10, 1, 0.1, 0.01 µM. In some embodiments, the humanized antibody or antibody-peptide fusion protein binds to human amyloid fibrils with a dissociation constant (Kd) that is about 0.01, 0.05, 0.1, 0.2, 0.3, 0.4, 0.5, 0.6, 0.7, 0.8, 0.9, 1, 2, 3, 4, 5, 6, 7, 8, 9, 10, 15, 20, 25, 50, 75, or 100 µM including any value or range between these values. In some embodiments, the humanized antibody or antibody-peptide fusion protein binds to human amyloid fibrils with a dissociation constant (Kd) that is less than 500, 100, 10, or 1 nM. In some embodiments, the humanized antibody or antibody-peptide fusion protein binds to human amyloid fibrils with a dissociation constant (Kd) that is less than about 5, 10, 20, 30, 40, 50, 60, 70, 80, 90, 100, 250, 500, 750, 1000, 2000, or 2200 nM. In some embodiments, the humanized antibody or antibody-peptide fusion protein binds to human amyloid fibrils with a dissociation constant (Kd) that is about 5, 10, 20, 30, 40, 50, 60, 70, 80, 90, 100, 250, 500, 750, 1000, 2000, or 2200 nM, including any value or range between these values. In some embodiments, the humanized antibody or antibody-peptide fusion protein binds to human amyloid fibrils with a dissociation constant (Kd) that is about 40-50 nM. In some embodiments, the humanized antibody or antibody-peptide fusion protein binds to human amyloid fibrils with a dissociation constant (Kd) that is 40-50 nM. In some embodiments, the humanized antibody or antibody-peptide fusion protein binds to human amyloid fibrils with a dissociation constant (Kd) that is less than 50 nM. In some embodiments, the humanized antibody or antibody-peptide fusion protein binds to human amyloid fibrils with a dissociation constant (Kd) that is less than the Kd of c11-1F4 binding to human amyloid fibrils.

In some embodiments, the humanized antibody or antibody-peptide fusion protein binds to human amyloid fibrils with half-maximal binding at a concentration of antibody ($EC_{50}$) that is less than about 0.01, 0.1, or 1 µM. In some embodiments, the humanized antibody or antibody-peptide fusion protein binds to human amyloid fibrils with half-maximal binding at a concentration of antibody ($EC_{50}$) that is about 0.01, 0.05, 0.1, 0.2, 0.3, 0.4, 0.5, 0.6, 0.7, 0.8, 0.9, 1, 2, 3, 4, 5, 6, 7, 8, 9, or 10 µM, including any value or range between these values. In some embodiments, the humanized antibody or antibody-peptide fusion protein binds to human amyloid fibrils with half-maximal binding at a concentration of antibody ($EC_{50}$) that is less than about 1, 10, 100, or 1000 nM. In some embodiments, the humanized antibody or antibody-peptide fusion protein binds to human amyloid fibrils with half-maximal binding at a concentration of antibody ($EC_{50}$) that is about 1, 5, 10, 15, 20, 25, 30, 35, 40, 45, 50, 55, 60, 65, 70, 75, 80, 85, 90, 95, 100, 100, 250, 500, 750, or 1000 nM, including any value or range between these values. In some embodiments, the humanized antibody or antibody-peptide fusion protein binds to human amyloid fibrils with half-maximal binding at a concentration of antibody ($EC_{50}$) that is about 17 nM, 7 nM, 16 nM, 75 nM, or 95 nM. In some embodiments, the humanized antibody or antibody-peptide fusion protein binds to human amyloid fibrils with half-maximal binding at a concentration of antibody ($EC_{50}$) that is less than about 10 nM, 20 nM, 80 nM, or 100 nM. In some embodiments, the humanized antibody or antibody-peptide fusion protein binds to human amyloid fibrils with half-maximal binding at a concentration of antibody ($EC_{50}$) that is less than the $EC_{50}$ of c11-1F4 binding to human amyloid fibrils.

Methods for calculating dissociation constants and $EC_{50}$s are known in the art, and include, for example, surface plasmon resonance and EuLISAs (see, e.g., the Examples, Table 7, and FIGS. 13A-13G). In some embodiments, the dissociation constant is determined by measuring binding to a Len(1-22) monomer peptide, for example, using surface plasmon resonance. In some embodiments, the $EC_{50}$ is determined using a EuLISA. In some embodiments, the $EC_{50}$ is determined using a EuLISA to measure the level of binding to rVλ6Wil fibrils, Per125 wtATTR extract, Ken ATTR extract, SHI AL liver extract, or TAL ALκ liver extract.

In some embodiments, the humanized antibody or antibody-peptide fusion protein is conjugated to a detectable label. In some embodiments, the detectable label is selected from the group consisting of radionuclides (e.g., $I^{-125}$, $I^{-123}$, $I^{-131}$, $Zr^{-89}$, $Tc^{-99m}$, $Cu^{-64}$, $Br^{-76}$, $F^{-18}$); enzymes (horse radish peroxidase); biotin; and fluorophores, etc. Any means known in the art for detectably labeling a protein can be used and/or adapted for use with the methods described herein. For example, the humanized antibodies or antibody-peptide fusion proteins, can be radiolabeled with a radioisotope, or labeled with a fluorescent tag or a chemiluminescent tag. Example radioisotopes include, for example, $^{18}F$, $^{111}In$, $^{99m}Tc$, and $^{123}I$, and $^{125}I$. These and other radioisotopes can be attached to the humanized antibody or antibody-peptide fusion protein using well known chemistry that may or not involve the use of a chelating agent, such as DTPA or DOTA covalently linked to the light chain protein of the humanized antibody or antibody-peptide fusion protein, for example. Example fluorescent or chemiluminescent tags include fluorescein, Texas red, rhodamine, Alexa dyes, and luciferase that can be conjugated to the humanized antibody or antibody-peptide fusion protein by reaction with lysine, cysteine, glutamic acid, and aspartic acid side chains. In one example embodiment, the label is detected using a fluorescent microplate reader, or fluorimeter, using the excitation and emission wavelengths appropriate for the tag that is used. Radioactive labels can be detected, for example, using a gamma or scintillation counter depending on the type of radioactive emission and by using energy windows suitable for the accurate detection of the specific radionuclide. However, any other suitable technique for detection of radioisotopes can also be used to detect the label. In some embodiments, the detectable label is $^{125}I$.

In some embodiments, the humanized antibody or the antibody-peptide fusion protein binds to rVλ6Wil fibrils, Per125 wtATTR extract, KEN hATTR extract, SHI ALλ liver extract, and/or TAL ALκ liver extract. In some embodiments, the humanized antibodies or antibody-peptide fusion proteins described herein bind to amyloid deposits or fibrils. In some embodiments, the humanized antibody or the antibody-peptide fusion protein binds to one or more amyloidogenic peptides in amyloids. In some embodiments, amyloids bound by the humanized antibody or the antibody-peptide fusion protein comprise an amyloidogenic λ6 variable domain protein (Vλ6Wil) or an amyloidogenic immunoglobulin light chain (AL), Aβ(1-40) amyloid-like fibril or an amyloidogenic Aβ precursor protein, or serum amyloid protein A (AA). In other embodiments, the amyloids bound by the humanized antibody or the antibody-peptide fusion protein comprise amyloidogenic forms of immunoglobulin heavy chain (AH), $β_2$-microglobulin ($Aβ_2M$), transthyretin variants (ATTR), apolipoprotein AI (AApoAI), apolipoprotein AII (AApoAII), gelsolin (Agel), lysozyme (Alys), leukocyte chemotactic factor (Alect2), fibrinogen a variants (Afib), cystatin variants (Acys), calcitonin ((Acal), lactadherin (Amed), islet amyloid polypeptide (AIAPP), prolactin (Apro), insulin (Ains), prior protein (AprP); α-synuclein (AαSyn), tau (Atau), atrial natriuretic factor (AANF), or IAAP, ALκ4, Alλ1 other amyloidogenic peptides. The amyloidogenic peptides bound by the humanized antibody or the antibody-peptide fusion protein can be a protein, a protein fragment, or a protein domain. In some embodiments, the amyloid deposits or amyloid fibrils comprise recombinant amyloidogenic proteins. In some embodiments, the amyloids are part of the pathology of a disease.

In some embodiments, binding of the humanized antibody or antibody-peptide fusion protein to human amyloid promotes the phagocytosis of human amyloid fibrils. In some embodiments, the humanized antibody or antibody-peptide fusion protein opsonizes human amyloid fibrils. In some embodiments, the humanized antibody or antibody-peptide fusion protein opsonizes rVλ6Wil fibrils. In some embodiments, contacting human amyloid fibrils with a humanized antibody or antibody-peptide fusion protein of the present disclosure in the presence of macrophages promotes the uptake of the human amyloid fibrils by the macrophages. In some embodiments, contacting human amyloid fibrils with a humanized antibody or antibody-peptide fusion protein of the present disclosure in the presence of macrophages promotes the opsonization of the human amyloid fibrils. In some embodiments, binding of the humanized antibody or antibody-peptide fusion protein to human amyloid promotes the phagocytosis of human amyloid fibrils to an equal or greater extent than a control antibody (e.g., mIgp5 and/or c11-1F4). In some embodiments, the humanized antibody or antibody-peptide fusion protein comprising a humanized antibody promotes antibody-dependent cellular phagocytosis.

Also provided herein are pharmaceutical compositions comprising any of the modified immunoglobulins, humanized antibodies, or antibody-peptide fusion proteins described herein. In some embodiments, the pharmaceutical composition further comprises a pharmaceutically acceptable carrier.

IV. Diagnostic and Detection Methods

In certain example embodiments, the modified immunoglobulins, humanized antibodies, and antibody-peptide fusion proteins can be labeled with various agents to allow their detection in vivo and in in vitro assays, such as after the fusion peptides are purified. Without being limited this may include radionuclides (e.g., $I^{-125}$, $I^{-123}$, $I^{-131}$, $Zr^{-89}$, $Tc^{-99m}$, $Cu^{-64}$, $Br^{-76}$, $F^{-18}$); enzymes (horse radish peroxidase); biotin; fluorophores, etc. Any means known in the art for detectably labeling a protein can be used and/or adapted for use with the methods described herein. For example, the Ig antibodies or fragments thereof, and/or the amyloid reactive peptides, can be radiolabeled with a radioisotope, or labeled with a fluorescent tag or a chemiluminescent tag. Example radioisotopes include, for example, $^{18}F$, $^{111}In$, $^{99m}Tc$, and $^{123}I$, and $^{125}I$. These and other radioisotopes can be attached to the isolated immunoglobulin light chain using well known chemistry that may or may not involve the use of a chelating agent, such as DTPA or DOTA covalently linked to the light chain protein of the Ig antibody, for example. Example fluorescent or chemiluminescent tags include fluorescein, Texas red, rhodamine, Alexa dyes, and luciferase that can be conjugated to the protein by reaction with lysine, cysteine, glutamic acid, and aspartic acid side chains. In one example embodiment, the label is detected using a fluorescent microplate reader, or fluorimeter, using the excitation and emission wavelengths appropriate for the tag that is used. Radioactive labels can be detected, for example, using a gamma or scintillation counter depending on the type of radioactive emission and by using energy windows suitable for the accurate detection of the specific radionuclide. However, any other suitable technique for detection of radioisotopes can also be used to detect the label.

With regard to amyloidosis, such labeling, for example, can be used to diagnose the presence of amyloid, to determine the amyloid protein load, to monitor the ability of the modified immunoglobulin, humanized antibodies, or antibody-peptide fusion proteins to bind amyloid in a particular subject, to monitor the progression of amyloidosis, and/or to monitor a subject's response to an amyloid treatment (including treatments associated with the administration of the modified immunoglobulins, humanized antibodies, or antibody-peptide fusion proteins to the subject). For example, modified immunoglobulins including an amyloid reactive peptide, humanized antibodies, or antibody-peptide fusion proteins are labeled with a detectable label as described herein and thereafter administered to a subject that is suffering from, or suspected to be suffering from, an amyloid-based disease (e.g., amyloidosis, monoclonal gammopathy of unknown significance (MGUS), multiple myeloma (MM), or related plasma cell diseases). Thereafter, the subject can be imaged, for example, to detect the presence of the detectably-labeled immunoglobulins, humanized antibodies, or antibody-peptide fusion proteins.

In certain example embodiments, the signals from the detectably-labeled modified immunoglobulins, humanized antibodies, or antibody-peptide fusion proteins can be quantified, thereby providing an indication of the level of amyloid deposit in the subject. For example, the signal intensity may be compared to a standard signal threshold, above which amyloidosis is present but below which amyloidosis is absent or at a low level. The subject can be diagnosed as having amyloid, in which case a treatment can be administered, such as such as chemotherapy, corticosteroid medicines (lenalidomide or thalidomide) and/or bortezomib (Velcade). Additionally or alternatively, the modified immunoglobulins, humanized antibodies, or antibody-peptide fusion proteins described herein can be administered to the subject in an effort to treat the subject as described herein. In certain example embodiments, the subject may be stratified into one or more groups, such as a low amyloid load, medium amyloid load, or high amyloid load, and then treated accordingly. To monitor treatment progress, the subject may be re-administered the detectably-labeled modified immunoglobulins, humanized antibodies, or antibody-peptide fusion proteins, and hence reassessed for their amyloid load.

V. Methods of Treatment

A. Methods Using Modified Immunoglobulins

In certain example embodiments, provided herein are methods of treating a subject having amyloidosis. For example, an effective amount of a modified immunoglobulin as described herein is administered to a subject, thereby treating the subject or allowing imaging of the amyloid deposits. In certain example aspects, provided is a method for clearing amyloid deposits in a subject. The method includes, for example, selecting a subject with amyloidosis and administering to the subject an effective amount of a modified immunoglobulins as described herein. The modified immunoglobulins include, for example, an amyloid-reactive peptide that binds to amyloid deposits that is joined with an Ig antibody or fragment thereof through the N-terminal of the light chain protein or the C-terminal of the heavy chain of the Ig antibody or fragment thereof. Administration of the amyloid-reactive Ig-fusion peptide thereby results in clearance of the amyloid and hence treatment of the subject.

In some embodiments, the modified immunoglobulins are binding amyloids in an individual. In some embodiments, the amyloid deposits may contribute to the pathology of a disease. In other embodiments, the amyloid deposits may be indicative of amyloidosis or an amyloid-related disease in an individual. In some embodiments, the modified immunoglobulins bind to amyloids in an individual with an amyloidosis. In some embodiments, the amyloidosis is localized to a specific tissue or organ system, such as the liver, the heart, or the central nervous system. In other embodiments, the amyloidosis is a systemic amyloidosis. In some embodiments, the amyloidosis is a familial amyloidosis. In other embodiments, the amyloidosis is a sporadic amyloidosis. In some embodiments, the amyloidosis or amyloid-related disease is AA amyloidosis, AL amyloidosis, AH amyloidosis, Aβ amyloidosis, ATTR amyloidosis, Alect2 amyloidosis, and IAPP amyloidosis of type II diabetes, Alzheimer's disease, Down's syndrome, hereditary cerebral hemorrhage with amyloidosis of the Dutch type, cerebral beta-amyloid angiopathy, spongiform encelohalopathy, thyroid tumors, Parkinson's disease, dementia with Lewis bodies, a tauopathy, Huntington's disease, senile systemic amyloidosis, familial hemodialysis, senile systemic aging, aging pituitary disorder, iatrogenic syndrome, spongiform encephalopathies, reactive chronic inflammation, thyroid tumors, myeloma or other forms of cancer. In some embodiments, the modified immunoglobulins bind to amyloids associated with normal aging. In other embodiments, the modified immunoglobulins are used in the diagnosis, treatment, or prognosis of an amyloidosis or amyloid-related disease in a subject.

In certain example embodiments, provided is a method for both diagnosing and treating a subject suffering from amyloidosis. Such method includes administering to the subject a detectably-labeled, modified immunoglobulin comprising an amyloid-reactive peptide and, based on administering the labeled modified immunoglobulin, determining that the subject is suffering from an amyloidosis. An effective amount of an amyloid treatment can then be administered to the subject. For example, an effective amount of one or more modified immunoglobulin including the amyloid reactive peptides can be administered.

In some embodiments, the subject is a mammal such as primate, bovine, rodent, or pig. In some embodiments, the subject is a human.

B. Methods Using Humanized Antibodies or Antibody-Peptide Fusion Proteins

Also provided herein are methods of treating a subject having an amyloid related disorder, comprising administering to the subject an effective amount of a humanized antibody or antibody-peptide fusion protein of the present disclosure.

In some embodiments, the amyloid-related disorder is selected from the group consisting of AL, AH, Aβ2M, ATTR, transthyretin, AA, AapoAI, AApoAII, Agel, Alys, ALEct2, Afib, Acys, Acal, Amed, AIAPP, Apro, Ains, AprP, alpha-synuclein, au, or Aβ amyloidosis. In some embodiments, the amyloidosis or amyloid-related disease is AA amyloidosis, AL amyloidosis, AH amyloidosis, Aβ amyloidosis, ATTR amyloidosis, Alect2 amyloidosis, and IAPP amyloidosis of type II diabetes, Alzheimer's disease, Down's syndrome, hereditary cerebral hemorrhage with amyloidosis of the Dutch type, cerebral beta-amyloid angiopathy, spongiform encelohalopathy, thyroid tumors, Parkinson's disease, dementia with Lewis bodies, a tauopathy, Huntington's disease, senile systemic amyloidosis, familial hemodialysis, senile systemic aging, aging pituitary disorder, iatrogenic syndrome, spongiform encephalopathies, reactive chronic inflammation, thyroid tumors, myeloma or other forms of cancer. In some embodiments, the amyloid-related disorder is systemic amyloidosis. In some embodiments, the humanized antibody or antibody-peptide fusion protein binds to amyloids associated with normal aging. In other embodiments, the humanized antibody or antibody-peptide fusion protein are used in the diagnosis, treatment, or prognosis of an amyloidosis or amyloid-related disease in a subject.

Also provided herein are methods of targeting an amyloid deposit for clearance. In some embodiments, the method comprises contacting an amyloid deposit with a humanized antibody or an antibody-peptide fusion protein of the present disclosure. In some embodiments, the amyloid deposit is removed. In some embodiments, the amyloid deposit is cleared. In some embodiments, the amyloid deposit is opsonized by the humanized antibody or the antibody-peptide fusion protein. In some embodiments, binding of the humanized antibody or antibody-peptide fusion protein to human amyloid fibrils promotes the phagocytosis of the human amyloid fibrils and the removal of the amyloid deposit. In some embodiments, the humanized antibody or antibody-peptide fusion protein opsonizes human amyloid fibrils, thereby removing of the amyloid deposit. In some embodiments, the humanized antibody or antibody-peptide fusion protein opsonizes rVλ6Wil fibrils. In some embodiments, binding of the humanized antibody or antibody-peptide fusion protein to human amyloid fibrils promotes the phagocytosis and/or opsonization of human amyloid fibrils to an equal or greater extent than a control antibody (e.g., mIgp5 and/or c11-1F4).

In some embodiments, provided herein is a method of treating an amyloid-related disorder comprising a administering a modified immunoglobulin or an antibody-peptide fusion protein conjugated to a detectable label, detecting the label, and administering to the subject an amyloidosis treatment if the signal is detected. In some embodiments, the detectable label is a radio label. In some embodiments the detectable label is an $I^{125}$, $Tc^{99}$ label. In some embodiments, the detectable label is a fluorescent label. In some embodiments the detectable label is an enzymatic label. In some embodiments, the label is horseradish peroxidase or alkaline phosphatase. Labels further include chemical moieties such as biotin, which may be detected via binding to a specific cognate detectable moiety, e.g., labeled avidin. In some embodiments, the amyloid deposit is identified in the liver, spleen, or blood of the subject. In some embodiments, the amyloidosis treatment comprises a modified immunoglobulin or an antibody-peptide fusion protein provided herein.

Also provided herein is a method of identifying an amyloid deposit in a subject comprising administering a modified immunoglobulin or antibody-peptide fusion protein, wherein the modified immunoglobulin or antibody-peptide fusion protein is conjugated to a detectable label. In some embodiments, the method comprises detecting a signal from the modified immunoglobulin or antibody-peptide fusion protein. In some embodiments, the detectable label is a radio label. In some embodiments the detectable label is an $I^{125}$, $Tc^{99}$ label. In some embodiments, the detectable label is a fluorescent label. In some embodiments the detectable label is an enzymatic label. In some embodiments, the label is horseradish peroxidase or alkaline phosphatase. Labels further include chemical moieties such as biotin, which may be detected via binding to a specific cognate detectable moiety, e.g., labeled avidin. In some embodiments, the amyloid deposit is identified in the liver, spleen, or blood of the subject.

In some embodiments, provided herein is a method of detecting a ligand comprising contacting the ligand with a modified immunoglobulin or an antibody-peptide fusion conjugated to a detectable label, and determining a signal from the detectable label. In some embodiments, the detectable label is a radio label. In some embodiments the detectable label is an $I^{125}$, $Tc^{99}$ label. In some embodiments, the detectable label is a fluorescent label. In some embodiments the detectable label is an enzymatic label. In some embodiments, the label is horseradish peroxidase or alkaline phosphatase. Labels further include chemical moieties such as biotin, which may be detected via binding to a specific cognate detectable moiety, e.g., labeled avidin. In some embodiments, the detection is in vitro. In some embodiments, the detection is in vivo.

VI. Nucleic Acids, Vectors, Host Cells, and Methods of Making Antibodies

A. Nucleic Acids Encoding a Modified Immunoglobulin or an Antibody-Peptide Fusion Protein Also provided herein is nucleic acid encoding a modified immunoglobulin. In some embodiments, the nucleic acid encodes any of the modified immunoglobulins described herein.

In some embodiments, the nucleic acid encodes a modified immunoglobulin comprising an antibody comprising the VH and/or the VL of antibody 11-1F4, wherein the antibody is joined to a peptide. In some embodiments, the nucleic acids encode an antibody comprising the heavy chain and/or the light chain of antibody 11-1F4, wherein the antibody is joined to a peptide.

In a particular embodiment, the nucleic acid encodes a modified immunoglobulin comprising an antibody comprising a VH that comprises (a) a CDR-H1 comprising the amino acid sequence of SEQ ID NO:17, (b) a CDR-H2 comprising the amino acid sequence of SEQ ID NO:18, and (c) a CDR-H3 comprising the amino acid sequence LDY, wherein the antibody is joined to a peptide.

In a particular embodiment, the nucleic acid encodes a modified immunoglobulin comprising an antibody comprising a VL that comprises (a) a CDR-L1 comprising the amino acid sequence of SEQ ID NO:20; (b) a CDR-L2 comprising the amino acid sequence of SEQ ID NO:21; and (c) a CDR-L3 comprising the amino acid sequence of SEQ ID NO:22, wherein the antibody is joined to a peptide.

In one embodiment, the nucleic acid encodes a modified immunoglobulin an antibody comprising a VL comprising the amino acid sequence of SEQ ID NO:16 and a VH comprising the amino acid sequence of SEQ ID NO:15, wherein the antibody is joined to a peptide.

In another aspect, the nucleic acid encodes a modified immunoglobulin comprising an antibody comprising a VH comprising a CDR-H1 comprising the amino acid sequence of SEQ ID NO:17, a CDR-H2 comprising the amino acid sequence of SEQ ID NO:18, and a CDR-H3 comprising the amino acid sequence LDY; and a VL comprising a CDR-L1 comprising the amino acid sequence of SEQ ID NO:20, a CDR-L2 comprising the amino acid sequence of SEQ ID NO:21, and a CDR-L3 comprising the amino acid sequence of SEQ ID NO:22, wherein the antibody is joined to a peptide. In some embodiments, the modified immunoglobulin comprises an antibody joined to an amyloid reactive peptide comprising any of the amino acid sequences listed in Table 1. In some embodiments, the modified immunoglobulin comprises an antibody joined to an amyloid reactive peptide comprising the amino acid sequence of SEQ ID NO:1. In some embodiments, the modified immunoglobulin comprises an antibody joined to an amyloid reactive peptide comprising the amino acid sequence of SEQ ID NO:2.

In another aspect, the nucleic acid encodes a modified immunoglobulin comprising an antibody comprising a VH CDR1, a VH CDR2, and a VH CDR3, of a VH having the sequence set forth in SEQ ID NO:15; and a VL CDR1, a VL CDR2, and a VL CDR3 of a VL having the sequence set forth in SEQ ID NO:16, wherein the antibody is joined to a peptide. In some embodiments, the modified immunoglobulin comprises an antibody joined to an amyloid reactive peptide comprising any of the amino acid sequences listed in Table 1. In some embodiments, the modified immunoglobulin comprises an antibody joined to an amyloid reactive peptide comprising the amino acid sequence of SEQ ID NO:1. In some embodiments, the modified immunoglobulin comprises an antibody joined to an amyloid reactive peptide comprising the amino acid sequence of SEQ ID NO:2.

In some embodiments, the nucleic acid encodes a modified immunoglobulin comprising an antibody comprising an antibody heavy chain comprising a VH comprising the amino acid sequence of SEQ ID NO:15 and antibody a light chain comprising a VL comprising the amino acid sequence of SEQ ID NO:16, wherein the light chain is joined to a peptide. In some embodiments, the modified immunoglobulin comprises an antibody comprising a heavy chain comprising the amino acid sequence of SEQ ID NO:15 without the C-terminal lysine residue, and a light chain comprising the amino acid sequence of SEQ ID NO:16, wherein the antibody is joined to a peptide.

In another aspect, the nucleic acid encodes a modified immunoglobulin comprising an antibody comprising a VH as in any of the embodiments provided above, and a VL as in any of the embodiments provided above, and wherein the antibody is joined to a peptide.

In some embodiments, the nucleic acid encodes an antibody joined to an amyloid reactive peptide. In some embodiments, the nucleic acid encodes an antibody joined to an amyloid reactive peptide comprising any of the amino acid sequences listed in Table 1. In some embodiments, the nucleic acid encodes an antibody joined to an amyloid reactive peptide comprising the amino acid sequence of SEQ ID NO:1. In some embodiments, the nucleic acid encodes an antibody comprising a light chain joined to an amyloid reactive peptide comprising the amino acid sequence of SEQ ID NO:2. In some embodiments, the peptide is joined to the N-terminus of the antibody light chain or the C-terminus of the heavy chain. In some embodiments, the nucleic acid encodes an antibody that also comprises is a spacer amino acid sequence between the peptide and the N-terminus of the antibody light chain or the C-terminus of the heavy chain. In some embodiments, the peptide is joined to the N-terminus of the antibody light chain.

In some embodiments, the nucleic acid encodes a modified immunoglobulin comprising an antibody that comprises a heavy chain comprising a VH comprising the amino acid sequence of SEQ ID NO:15 joined to a peptide comprising any of the amino acid sequences of Table 1. In some embodiments, the nucleic acid encodes an antibody comprising a heavy chain comprising a VH comprising the amino acid sequence of SEQ ID NO:15 joined to a peptide comprising the amino acid sequence of SEQ ID NO:1. In some embodiments, the nucleic acid encodes an antibody comprising a heavy chain comprising a VH comprising the amino acid sequence of SEQ ID NO:15 joined to a peptide comprising the amino acid sequence of SEQ ID NO:2.

In some embodiments, the nucleic acid encodes a modified immunoglobulin comprising an antibody that comprises a light chain comprising a VL comprising the amino acid sequence of SEQ ID NO:16 joined to a peptide comprising any of the amino acid sequences of Table 1. In some embodiments, the nucleic acid encodes an antibody comprising a light chain comprising a VL comprising the amino acid sequence of SEQ ID NO:16 joined to a peptide comprising the amino acid sequence of SEQ ID NO:1. In some embodiments, the nucleic acid encodes an antibody a light chain comprising a VL comprising the amino acid sequence of SEQ ID NO:16 joined to a peptide comprising the amino acid sequence of SEQ ID NO:2.

In some embodiments, the nucleic acid encodes a modified immunoglobulin comprising an antibody comprising a heavy chain comprising a VH comprising the amino acid sequence of SEQ ID NO:15 and a light chain comprising a VL comprising the amino acid sequence of SEQ ID NO:16, wherein the light chain is joined to a peptide comprising any of the amino acid sequences of Table 1.

In some embodiments, the nucleic acid encodes a modified immunoglobulin comprising an antibody comprising a heavy chain comprising a VH comprising the amino acid sequence of SEQ ID NO:15 and a light chain comprising a VL comprising the amino acid sequence of SEQ ID NO:16, wherein the light chain is joined to a peptide comprising the amino acid sequence of SEQ ID NO:1.

In some embodiments, the nucleic acid encodes a modified immunoglobulin comprising an antibody comprising a heavy chain comprising a VH comprising the amino acid sequence of SEQ ID NO:15 and a light chain comprising a VL comprising the amino acid sequence of SEQ ID NO:16, wherein the light chain is joined to a peptide comprising the amino acid sequence of SEQ ID NO:2.

Also provided herein are nucleic acid(s) encoding an antibody-peptide fusion protein. In some embodiments, the nucleic acid encodes any of the antibody-peptide fusion proteins described herein.

In a particular embodiment, the nucleic acid encodes an antibody-peptide fusion protein comprising an antibody, wherein the antibody comprises a VH that comprises (a) a CDR-H1 comprising the amino acid sequence of SEQ ID NO:17, (b) a CDR-H2 comprising the amino acid sequence of SEQ ID NO:18, and (c) a CDR-H3 comprising the amino acid sequence LDY, wherein the antibody is joined to a peptide.

In a particular embodiment, the nucleic acid encodes an antibody-peptide fusion protein comprising an antibody, wherein the antibody comprises a VL that comprises (a) a CDR-L1 comprising the amino acid sequence of SEQ ID NO:20; (b) a CDR-L2 comprising the amino acid sequence of SEQ ID NO:21; and (c) a CDR-L3 comprising the amino acid sequence of SEQ ID NO:22, wherein the antibody is joined to a peptide.

In one embodiment, the nucleic acid encodes an antibody-peptide fusion protein comprising an antibody that comprises a VL comprising the amino acid sequence of SEQ ID NO:16 and a VH comprising the amino acid sequence of SEQ ID NO:15, wherein the antibody is joined to a peptide.

In another aspect, the nucleic acid encodes an antibody-peptide fusion protein comprising an antibody, wherein the antibody comprises a VH comprising a CDR-H1 comprising the amino acid sequence of SEQ ID NO: 17, a CDR-H2 comprising the amino acid sequence of SEQ ID NO:18, and a CDR-H3 comprising the amino acid sequence LDY; and a VL comprising a CDR-L1 comprising the amino acid sequence of SEQ ID NO:20, a CDR-L2 comprising the amino acid sequence of SEQ ID NO:21, and a CDR-L3 comprising the amino acid sequence of SEQ ID NO:22, and wherein the antibody is joined to a peptide. In some embodiments, the nucleic acid encodes an antibody-peptide fusion protein comprising an antibody joined to an amyloid reactive peptide comprising any of the amino acid sequences listed in Table 1. In some embodiments, the nucleic acid encodes an antibody-peptide fusion protein comprising an antibody joined to an amyloid reactive peptide comprising the amino acid sequence of SEQ ID NO:1. In some embodiments, the nucleic acid encodes an antibody-peptide fusion protein comprising an antibody joined to an amyloid reactive peptide comprising the amino acid sequence of SEQ ID NO:2.

In another aspect, the nucleic acid encodes an antibody-peptide fusion protein comprising an antibody, wherein the antibody comprises a VH CDR1, a VH CDR2, and a VH CDR3 of a VH having the sequence set forth in SEQ ID NO:15 and a VL CDR1, a VL CDR2, and a VL of a VL having the sequence set forth in SEQ ID NO:16; and wherein the antibody is joined to a peptide. In some embodiments, the nucleic acid encodes an antibody-peptide fusion protein comprising an antibody joined to an amyloid reactive peptide comprising any of the amino acid sequences listed in Table 1. In some embodiments, the nucleic acid encodes an antibody-peptide fusion protein comprising an antibody joined to an amyloid reactive peptide comprising the amino acid sequence of SEQ ID NO:1. In some embodiments, the nucleic acid encodes an antibody-peptide fusion protein comprising an antibody joined to an amyloid reactive peptide comprising the amino acid sequence of SEQ ID NO:2.

In some embodiments, the nucleic acid encodes an antibody-peptide fusion protein comprising an antibody that comprises a heavy chain comprising a VH comprising the amino acid sequence of SEQ ID NO:15 and a light chain comprising a VL comprising the amino acid sequence of SEQ ID NO:16, wherein the light chain is joined to a peptide. In some embodiments, the nucleic acid encodes an antibody-peptide fusion protein comprising a heavy chain comprising a VH comprising the amino acid sequence of SEQ ID NO:15 without the C-terminal lysine residue, and a VL comprising the amino acid sequence of SEQ ID NO:16, wherein the antibody is joined to a peptide.

In another aspect, the nucleic acid encodes an antibody-peptide fusion protein comprising an antibody joined to an amyloid reactive peptide. In some embodiments, the nucleic acid encodes an antibody-peptide fusion protein comprising an antibody joined to an amyloid reactive peptide comprising any of the amino acid sequences listed in Table 1. In some embodiments, the nucleic acid encodes an antibody-peptide fusion protein comprising an antibody joined to an amyloid reactive peptide comprising the amino acid sequence of SEQ ID NO:1. In some embodiments, the nucleic acid encodes an antibody-peptide fusion protein comprising an antibody joined to an amyloid reactive peptide comprising the amino acid sequence of SEQ ID NO:2. In some embodiments, the peptide is joined to the N-terminus of the antibody light chain or the C-terminus of the heavy chain. In some embodiments, the antibody also comprises a spacer amino acid sequence between the peptide and the N-terminus of the light chain or the C-terminus of the heavy chain.

In some embodiments, the nucleic acid encodes an antibody-peptide fusion protein comprising an antibody that comprises a heavy chain comprising the a VH comprising the amino acid sequence of SEQ ID NO:15, wherein the heavy chain is joined to a peptide comprising any of the amino acid sequences of Table 1. In some embodiments, the nucleic acid encodes an antibody-peptide fusion protein comprising an antibody comprising a heavy chain comprising a VH comprising the amino acid sequence of SEQ ID NO:15, wherein the heavy chain is joined to a peptide comprising the amino acid sequence of SEQ ID NO:1. In some embodiments, the nucleic acid encodes an antibody-peptide fusion protein comprising an antibody comprising a heavy chain comprising a VH comprising the amino acid sequence of SEQ ID NO:15, wherein the heavy chain is joined to a peptide comprising the amino acid sequence of SEQ ID NO:2.

In some embodiments, the nucleic acid encodes an antibody-peptide fusion protein comprising an antibody that comprises a light chain comprising a VL comprising the amino acid sequence of SEQ ID NO:16, wherein the light chain is joined to a peptide comprising any of the amino acid sequences of Table 1. In some embodiments, the nucleic acid encodes an antibody-peptide fusion protein comprising an antibody comprising a light chain comprising a VL comprising the amino acid sequence of SEQ ID NO:16, wherein the light chain is joined to a peptide comprising the amino acid sequence of SEQ ID NO:1. In some embodiments, the nucleic acid encodes an antibody-peptide fusion protein comprising an antibody a light chain comprising a VL comprising the amino acid sequence of SEQ ID NO:16, wherein the light chain is joined to a peptide comprising the amino acid sequence of SEQ ID NO:2.

In some embodiments, the nucleic acid encodes an antibody-peptide fusion protein comprising an antibody comprising a heavy chain comprising a VH comprising the amino acid sequence of SEQ ID NO:15 and a light chain comprising a VL comprising the amino acid sequence of SEQ ID NO:16, wherein the light chain is joined to a peptide comprising any of the amino acid sequences of Table 1.

In some embodiments, the nucleic acid encodes an antibody-peptide fusion protein comprising an antibody comprising heavy chain comprising a VH comprising the amino acid sequence of SEQ ID NO:15 and a light chain comprising a VL comprising the amino acid sequence of SEQ ID NO:16, wherein the light chain is joined to a peptide comprising the amino acid sequence of SEQ ID NO:1.

In some embodiments, the nucleic acid encodes an antibody-peptide fusion protein comprising an antibody a heavy chain comprising a VH comprising the amino acid sequence of SEQ ID NO:15 and a light chain comprising a VL comprising the amino acid sequence of SEQ ID NO:16, wherein the light chain is joined to a peptide comprising the amino acid sequence of SEQ ID NO:2.

B. Nucleic Acids Encoding a Humanized Antibody or Antibody-Peptide Fusion Protein Comprising a Humanized Antibody Also provided herein are nucleic acid(s) encoding a humanized antibody or antibody-peptide fusion protein of the present disclosure. The humanized antibody or antibody-peptide fusion protein may be any of the humanized antibodies or antibody-peptide fusion proteins described herein.

In some embodiments, the nucleic acid encodes a humanized antibody comprising a light chain variable region (VL) and a heavy chain variable region (VH), wherein the VL comprises a CDR-L1 comprising the amino acid sequence set forth in SEQ ID NO:20, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in SEQ ID NO:18, and a CDR-H3 comprising the amino acid sequence LDY. In some embodiments, the nucleic acid encodes a humanized antibody comprising one, two, three, four, five, or six CDRs of an antibody as shown in Table 3. In some embodiments, the nucleic acid encodes a humanized antibody comprising a CDR-H1, a CDR-H2, and a CDR-H3, respectively comprising the amino acid sequences of a CDR-H1, a CDR-H2, and a CDR-H3 of a VH having the sequence set forth in SEQ ID NO:15; and a CDR-L1, a CDR-L2, and a CDR-L3, respectively comprising the amino acid sequences of a CDR-L1, a CDR-L2, and a CDR-L3 of a VL having the sequence set forth in SEQ ID NO:16.

In some embodiments, the nucleic acid encodes a humanized antibody, wherein the humanized antibody comprises one or more CDR substitutions. In some embodiments, the humanized antibody comprises a VL comprising a CDR-L1 comprising the amino acid sequence set forth in SEQ ID NO:64-70, a CDR-L2 comprising the amino acid sequence set forth in SEQ ID NO:21, and a CDR-L3 comprising the amino acid sequence set forth in SEQ ID NO:22, and a VH comprising a CDR-H1 comprising the amino acid sequence set forth in SEQ ID NO:17, a CDR-H2 comprising the amino acid sequence set forth in SEQ ID NO:18, and a CDR-H3 comprising the amino acid sequence LDY. In some embodiments, the nucleic acid encodes a humanized antibody, wherein the humanized antibody comprises a VL comprising a CDR-L1 comprising the amino acid sequence set forth in SEQ ID NO: 20; a CDR-L2 comprising the amino acid sequence set forth in SEQ ID NO:21, and a CDR-L3 comprising the amino acid sequence set forth in SEQ ID NO:22, and a VH comprising a CDR-H1 comprising the amino acid sequence set forth in SEQ ID NO:17, a CDR-H2 comprising the amino acid sequence set forth in SEQ ID NO: 71-81; and a CDR-H3 comprising the amino acid sequence LDY.

In some embodiments, the nucleic acid encodes a humanized antibody comprising a VL comprising one or more amino acid substitutions at one or more positions in the VL compared to a VL comprising an amino acid sequence set forth in SEQ ID NO: 32, wherein the amino acid positions are numbered starting from the N-terminus of SEQ ID NO: 32. In some embodiments, the nucleic acid encodes a humanized antibody comprising a VL comprising an amino acid substitution at position 33 compared to a VL comprising an amino acid sequence set forth in SEQ ID NO: 32. In some embodiments, the nucleic acid encodes a humanized antibody comprising a VL comprising an amino acid substitution at position 34 compared to a VL comprising an amino acid sequence set forth in SEQ ID NO: 32. In some embodiments, the nucleic acid encodes a humanized antibody comprising a VL comprising an amino acid substitution at position 41 compared to a VL comprising an amino acid sequence set forth in SEQ ID NO: 32. In some embodiments, the nucleic acid encodes a humanized antibody comprising a VL comprising an amino acid substitution at position 42 compared to a VL comprising an amino acid sequence set forth in SEQ ID NO: 32. In some embodiments, the nucleic acid encodes a humanized antibody comprising a VL comprising an amino acid substitution at position 51 compared to a VL comprising an amino acid sequence set forth in SEQ ID NO: 32. In some embodiments, the nucleic acid encodes a humanized antibody comprising a VL comprising an amino acid substitution at position 90 compared to a VL comprising an amino acid sequence set forth in SEQ ID NO: 32. In some embodiments, the nucleic acid encodes a humanized antibody comprising a VL comprising an amino acid substitution at position 92 compared to a VL comprising an amino acid sequence set forth in SEQ ID NO: 32. In some embodiments, the nucleic acid encodes a humanized antibody comprising a VL comprising 1, 2, 3, 4, 5, 6, 7, or 8 amino acid substitutions compared to a VL comprising an amino acid sequence set forth in SEQ ID NO: 32. In some embodiments, the nucleic acid encodes a humanized antibody comprising a VL comprising 1, 2, 3, 4, 5, 6, 7, or 8 amino acid substitutions compared to a VL1, as shown in Table 6A.

In some embodiments, the nucleic acid encodes a humanized antibody comprising comprises a VH comprising one or more amino acid substitutions at one or more positions in the VH compared to a VH comprising an amino acid sequence set forth in SEQ ID NO: 43, wherein the amino acid positions are numbered starting from the N-terminus of SEQ ID NO: 43. In some embodiments, the nucleic acid encodes a humanized antibody comprising a VH comprising an amino acid substitution at position 37 compared to a VH comprising an amino acid sequence set forth in SEQ ID NO: 43. In some embodiments, the nucleic acid encodes a humanized antibody comprising a VH comprising an amino acid substitution at position 48 compared to a VH comprising an amino acid sequence set forth in SEQ ID NO: 43. In some embodiments, the nucleic acid encodes a humanized antibody comprising a VH comprising an amino acid substitution at position 67 compared to a VH comprising an amino acid sequence set forth in SEQ ID NO: 43. In some embodiments, the nucleic acid encodes a humanized antibody comprising a VH comprising an amino acid substitution at position 68 compared to a VH comprising an amino acid sequence set forth in SEQ ID NO: 43. In some embodiments, the nucleic acid encodes a humanized antibody comprising a VH comprising an amino acid substitution at position 71 compared to a VH comprising an amino acid sequence set forth in SEQ ID NO: 43. In some embodiments, the nucleic acid encodes a humanized antibody comprising a VH comprising an amino acid substitution at position 76 compared to a VH comprising an amino acid sequence set forth in SEQ ID NO: 43. In some embodiments, the nucleic acid encodes a humanized antibody comprising a VH comprising an amino acid substitution at position 78 compared to a VH comprising an amino acid sequence set forth in SEQ ID NO: 43. In some embodiments, the nucleic acid encodes a humanized antibody comprising a VH comprising an amino acid substitution at position 79 compared to a VH comprising an amino acid sequence set forth in SEQ ID NO: 43. In some embodiments, the nucleic acid encodes a humanized antibody comprising a VH comprising an amino acid substitution at position 80 compared to a VH comprising an amino acid sequence set forth in SEQ ID NO: 43. In some embodiments, the nucleic acid encodes a humanized antibody comprising a VH comprising an amino acid substitution at position 92 compared to a VH comprising an amino acid sequence set forth in SEQ ID NO: 43. In some embodiments, the nucleic acid encodes a humanized antibody comprising a VH comprising an amino acid substitution at position 96 compared to a VH comprising an amino acid sequence set forth in SEQ ID NO: 43. In some embodiments, the nucleic acid encodes a humanized antibody comprising a VH comprising an amino acid substitution at position 97 compared to a VH comprising an amino acid sequence set forth in SEQ ID NO: 43. In some embodiments, the nucleic acid encodes a humanized antibody comprising a VH comprising 1, 2, 3, 4, 5, 6, 7, 8, 9 or 10 amino acid substitutions compared to a VH comprising an amino acid sequence set forth in SEQ ID NO: 43. In some embodiments, the nucleic acid encodes a humanized antibody comprising a VH comprising 1, 2, 3, 4, 5, 6, 7, 8, 9 or 10 amino acid substitutions compared to VH1, as shown in Table 6B.

In some embodiments, the nucleic acid encodes a humanized antibody comprising a VL comprising one or more amino acid residues at one or more positions in the VL, wherein the amino acid positions are numbered starting from the N-terminus of the VL. In some embodiments, the nucleic acid encodes a humanized antibody comprising a VL comprising Ser, Gln, Glu, His, or Ala at position 33. In some embodiments, the nucleic acid encodes a humanized antibody comprising a VL comprising Ala or Val at position 34. In some embodiments, the nucleic acid encodes a humanized antibody comprising a VL comprising Tyr at position 41. In some embodiments, the nucleic acid encodes a humanized antibody comprising a VL comprising Leu at position 42. In some embodiments, the nucleic acid encodes a humanized antibody comprising a VL comprising Leu at position 51. In some embodiments, the nucleic acid encodes a humanized antibody comprising a VL comprising Leu at position 90. In some embodiments, the nucleic acid encodes a humanized antibody comprising a VL comprising Phe at position 92.

In some embodiments, the nucleic acid encodes a humanized antibody comprising a VH comprising one or more amino acid residues at one or more positions in the VH, wherein the amino acid positions are numbered starting from the N-terminus of the VH. In some embodiments, the nucleic acid encodes a humanized antibody comprising a VH comprising Val at position 37. In some embodiments, the nucleic acid encodes a humanized antibody comprising a VH comprising Leu at position 48. In some embodiments, the nucleic acid encodes a humanized antibody comprising a VH comprising Leu at position 67. In some embodiments, the nucleic acid encodes a humanized antibody comprising a VH comprising Ser at position 68. In some embodiments, the nucleic acid encodes a humanized antibody comprising a VH comprising Lys at position 71. In some embodiments, the nucleic acid encodes a humanized antibody comprising a VH comprising Ser at position 76. In some embodiments, the nucleic acid encodes a humanized antibody comprising a VH comprising Val at position 78. In some embodiments, the nucleic acid encodes a humanized antibody comprising a VH comprising Leu at position 79. In some embodiments, the nucleic acid encodes a humanized antibody comprising a VH comprising Phe at position 80. In some embodiments, the nucleic acid encodes a humanized antibody comprising a VH comprising Thr at position 92. In some embodiments, the nucleic acid encodes a humanized antibody comprising a VH comprising Val at position 96. In some embodiments, the nucleic acid encodes a humanized antibody comprising a VH comprising Thr position 97.

In some embodiments, the nucleic acid encodes a humanized antibody comprising a VL comprising one or more amino acid residues at one or more positions in the VL, wherein the amino acid positions are numbered according to the numbering system of Kabat. In some embodiments, the nucleic acid encodes a humanized antibody comprising a VL comprising Tyr at position 36. In some embodiments, the nucleic acid encodes a humanized antibody comprising a VL comprising Leu at position 37. In some embodiments, the nucleic acid encodes a humanized antibody comprising a VL comprising Leu at position 46. In some embodiments, the nucleic acid encodes a humanized antibody comprising a VL comprising Leu at position 85. In some embodiments, the nucleic acid encodes a humanized antibody comprising a VL comprising Phe at position 87.

In some embodiments, the nucleic acid encodes a humanized antibody comprising a VL comprising one or more amino acid residues at one or more positions in the VL, wherein the amino acid positions are numbered according to the numbering system of Kabat. In some embodiments, the nucleic acid encodes a humanized antibody comprising a VL comprising Tyr at position 36 and Leu at position 37. In some embodiments, the nucleic acid encodes a humanized antibody comprising a VL comprising Tyr at position 36, Leu at position 37, Leu at position 46, Leu at position 85, and Phe at position 87. In some embodiments, the nucleic acid encodes a humanized antibody comprising a VL comprising Leu at position 46 and Phe at position 87.

In some embodiments, the nucleic acid encodes a humanized antibody comprising a VH comprising one or more amino acid residues at one or more positions in the VH, wherein the amino acid positions are numbered according to the numbering system of Kabat. In some embodiments, the nucleic acid encodes a humanized antibody comprising a VH comprising Val at position 37. In some embodiments, the nucleic acid encodes a humanized antibody comprising a VH comprising Leu at position 48. In some embodiments, the nucleic acid encodes a humanized antibody comprising a VH comprising Leu at position 67. In some embodiments, the nucleic acid encodes a humanized antibody comprising a VH comprising Ser at position 68. In some embodiments, the nucleic acid encodes a humanized antibody comprising a VH comprising Lys at position 71. In some embodiments, the nucleic acid encodes a humanized antibody comprising a VH comprising Ser at position 76. In some embodiments, the nucleic acid encodes a humanized antibody comprising a VH comprising Val at position 78. In some embodiments, the nucleic acid encodes a humanized antibody comprising a VH comprising Leu at position 79. In some embodiments, the nucleic acid encodes a humanized antibody comprising a VH comprising Phe at position 80. In some embodiments, the nucleic acid encodes a humanized antibody comprising a VH comprising Thr at position 89. In some embodiments, the nucleic acid encodes a humanized antibody comprising a VH comprising Val at position 93. In some embodiments, the nucleic acid encodes a humanized antibody comprising a VH comprising Thr at position 94.

In some embodiments, the nucleic acid encodes a humanized antibody comprising a VH comprising one or more amino acid residues at one or more positions in the VH, wherein the amino acid positions are numbered according to the numbering system of Kabat. In some embodiments, the nucleic acid encodes a humanized antibody comprising a VH comprising Val at position 37 and Leu at position 48. In some embodiments, the nucleic acid encodes a humanized antibody comprising a VH comprising Leu at position 67, Ser at position 68, Thr at position 89, Val at position 93, and Thr at position 94. In some embodiments, the nucleic acid encodes a humanized antibody comprising a VH comprising Val at position 37, Leu at position 48, Leu at position 67, and Ser at position 68. In some embodiments, the nucleic acid encodes a humanized antibody comprising a VH comprising Val at position 37, Leu at position 48, Val at position 93, and Thr at position 94. In some embodiments, the nucleic acid encodes a humanized antibody comprising a VH comprising Val at position 37, Leu at position 48, Leu at position 67, Ser at position 68, Lys at position 71, Thr at position 89, Val at position 93, and Thr at position 94. In some embodiments, the nucleic acid encodes a humanized antibody comprising a VH comprising Lys at position 71, Val at position 78, Leu at position 79, Val at position 93, and Thr at position 94. In some embodiments, the nucleic acid encodes a humanized antibody comprising a VH comprising Lys at position 71, Ser at position 76, Val at position 93, and Thr at position 94. In some embodiments, the nucleic acid encodes a humanized antibody comprising a VH comprising Leu at position 48, Ser at position 96, Val at position 78, Leu at position 79, Phe at position 80, and Thr at position 94. In some embodiments, the nucleic acid encodes a humanized antibody comprising a VH comprising Leu at position 48, Leu at position 67, Ser at position 68, Lys at position 71, Ser at position 76, Val at position 78, Leu at position 79, Val at position 93, and Thr at position 94.

In some embodiments, the nucleic acid encodes a humanized antibody comprising a VL comprising Tyr at position 36, Leu at position 37, Leu at position 46, Leu at position 85, and Phe at position 87, and a VH comprising Val at position 37, Leu at position 48, Leu at position 67, Ser at position 68, Lys at position 71, Thr at position 89, Val at position 93, and Thr at position 94. In some embodiments, the nucleic acid encodes a humanized antibody comprising a VL comprising Leu at position 46 and Phe at position 87, and a VH comprising Leu at position 48, Ser at position 96, Val at position 78, Leu at position 79, Phe at position 80, and Thr at position 94. In some embodiments, the nucleic acid encodes a humanized antibody comprising a VL comprising Leu at position 46 and Phe at position 87, and a VH comprising Leu at position 48, Leu at position 67, Ser at position 68, Lys at position 71, Ser at position 76, Val at position 78, Leu at position 79, Val at position 93, and Thr at position 94. In some embodiments, the nucleic acid encodes a humanized antibody comprising a VL comprising Leu at position 46 and Phe at position 87, and a VH comprising Lys at position 71, Ser at position 76, Val at position 93, and Thr at position 94. In some embodiments, the nucleic acid encodes a humanized antibody comprising a VL comprising Leu at position 46 and Phe at position 87, and a VH comprising Lys at position 71, Val at position 78, Leu at position 79, Val at position 93, and Thr at position 94.

In some embodiments, the nucleic acid encodes a humanized antibody comprising the amino acid sequence of a VL as shown in Table 6A. In some embodiments, the nucleic acid encodes a humanized antibody comprising a VL selected from the group consisting of VL2, VL3, VL4, VL4-N33S, VL4-N33Q, VL4-N33E, VL4-N33A, VL4-N33H, VL4-G34A, or VL4-G34V, as shown in Table 6A. In some embodiments, the nucleic acid encodes a humanized antibody comprising a VL comprising an amino acid sequence set forth in the group consisting of SEQ ID NOs:33-42.

In some embodiments, the nucleic acid encodes a humanized antibody comprising the amino acid sequence of a VH as shown in Table 6B. In some embodiments, the nucleic acid encodes a humanized antibody comprising a VH selected from the group consisting of VH2, VH3, VH4, VH5, VH6, VH7, VH8, VH9, VH10, VH9-D54S, VH9-D54Q, VH9-D54E, VH9-D54A, VH9-D54H, VH9-G55A, VH9-G55V, VH9-M64V, VH9-M64I, VH9-M64L, or VH9-M64A, as shown in Table 6B. In some embodiments, the nucleic acid encodes a humanized antibody comprising a VH comprising an amino acid sequence set forth in the group consisting of SEQ ID NOs:44-63.

In some embodiments, the nucleic acid encodes a humanized antibody comprising the VL of VL4 as shown in Table 6A, and the VH of VH9 as shown in Table 6B. In some embodiments, the nucleic acid encodes a humanized antibody comprising a VL comprising an amino acid sequence set forth in SEQ ID NO:35, and a VH comprising an amino acid sequence set forth in SEQ ID NO:51.

In some embodiments, the nucleic acid encodes a humanized antibody comprising the VL of VL3 as shown in Table 6A, and the VH of VH6 as shown in Table 6B. In some embodiments, the nucleic acid encodes a humanized antibody comprising a VL comprising an amino acid sequence set forth in SEQ ID NO:34, and a VH comprising an amino acid sequence set forth in SEQ ID NO:48.

In some embodiments, the nucleic acid encodes a humanized antibody comprising the VL of VL4 as shown in Table 6A, and the VH of VH10 as shown in Table 6B. In some embodiments, the nucleic acid encodes a humanized antibody comprising a VL comprising an amino acid sequence set forth in SEQ ID NO:35, and a VH comprising an amino acid sequence set forth in SEQ ID NO:52. In some embodiments, the nucleic acid encodes a humanized antibody comprising the VL of VL4 as shown in Table 6A, and the VH of VH8 as shown in Table 6B. In some embodiments, the nucleic acid encodes a humanized antibody comprising a VL comprising an amino acid sequence set forth in SEQ ID NO:35, and a VH comprising an amino acid sequence set forth in SEQ ID NO:50. In some embodiments, the nucleic acid encodes a humanized antibody comprising the VL of VL4 as shown in Table 6A, and the VH of VH7 as shown in Table 6B. In some embodiments, the VL comprises an amino acid sequence set forth in SEQ ID NO:35, and the VH comprises an amino acid sequence set forth in SEQ ID NO:69.

Also provided herein are nucleic acid(s) encoding an antibody-peptide fusion protein comprising a humanized antibody of the present disclosure. In some embodiments, the nucleic acid encodes an antibody-peptide fusion protein comprising any one of the humanized antibodies of the present disclosure.

In some embodiments, the nucleic acid encodes an antibody-peptide fusion protein comprising a humanized antibody that comprises a heavy chain comprising a VH comprising an amino acid sequence set forth in the group consisting of SEQ ID NOs:44-63, and a light chain comprising a VL comprising an amino acid set forth in the group consisting of SEQ ID NOs:33-42, wherein the light chain is joined to a peptide. In some embodiments, the nucleic acid encodes an antibody-peptide fusion protein comprising a heavy chain comprising a VH comprising an amino acid sequence set forth in the group consisting of SEQ ID NOs:44-63 without the C-terminal lysine residue, and a VL comprising an amino acid sequence set forth in the group consisting of SEQ ID NOs:33-42, wherein the antibody is joined to a peptide. In some embodiments, the nucleic acid encodes an antibody-peptide fusion protein comprising a humanized antibody that comprises a heavy chain comprising a VH comprising the amino acid sequence of SEQ ID NO: 51, and a light chain comprising a VL comprising the amino acid of SEQ ID NO: 35, wherein the light chain is joined to a peptide. In some embodiments, the nucleic acid encodes an antibody-peptide fusion protein comprising a humanized antibody that comprises a heavy chain comprising a VH comprising the amino acid sequence of SEQ ID NO: 51 without the C-terminal lysine residue, and a VL comprising the amino acid of SEQ ID NO: 35, wherein the antibody is joined to a peptide. In some embodiments, the nucleic acid encodes an antibody-peptide fusion protein comprising a humanized antibody that comprises a heavy chain comprising a VH comprising the amino acid sequence of SEQ ID NO: 48, and a light chain comprising a VL comprising the amino acid of SEQ ID NO: 34, wherein the light chain is joined to a peptide. In some embodiments, the nucleic acid encodes an antibody-peptide fusion protein comprising a humanized antibody that comprises a heavy chain comprising a VH comprising the amino acid sequence of SEQ ID NO: 48 without the C-terminal lysine residue, and a VL comprising the amino acid of SEQ ID NO: 34, wherein the antibody is joined to a peptide.

In some embodiments, the nucleic acid encodes an antibody-peptide fusion protein comprising a humanized antibody that comprises a heavy chain comprising a VH comprising an amino acid sequence set forth in the group consisting of SEQ ID NOs:44-63, wherein the heavy chain is joined to a peptide comprising any of the amino acid sequences of Table 1. In some embodiments, the nucleic acid encodes an antibody-peptide fusion protein comprising a humanized antibody comprising a heavy chain comprising a VH comprising an amino acid sequence set forth in the group consisting of SEQ ID NOs:44-63, wherein the heavy chain is joined to a peptide comprising the amino acid sequence of SEQ ID NO:1. In some embodiments, the nucleic acid encodes an antibody-peptide fusion protein comprising a humanized antibody comprising a heavy chain comprising a VH comprising an amino acid sequence set forth in the group consisting of SEQ ID NOs:44-63, wherein the heavy chain is joined to a peptide comprising the amino acid sequence of SEQ ID NO:2. In some embodiments, the nucleic acid encodes an antibody-peptide fusion protein comprising a humanized antibody that comprises a heavy chain comprising the VH comprising the amino acid sequence of SEQ ID NO: 51, wherein the heavy chain is joined to a peptide comprising any of the amino acid sequences of Table 1. In some embodiments, the nucleic acid encodes an antibody-peptide fusion protein comprising a humanized antibody comprising a heavy chain comprising a VH comprising the amino acid sequence of SEQ ID NO: 51, wherein the heavy chain is joined to a peptide comprising the amino acid sequence of SEQ ID NO:1. In some embodiments, the nucleic acid encodes an antibody-peptide fusion protein comprising a humanized antibody comprising a heavy chain comprising a VH comprising the amino acid sequence of SEQ ID NO: 51, wherein the heavy chain is joined to a peptide comprising the amino acid sequence of SEQ ID NO:2. In some embodiments, the nucleic acid encodes an antibody-peptide fusion protein comprising a humanized antibody that comprises a heavy chain comprising the a VH comprising the amino acid sequence of SEQ ID NO:48, wherein the heavy chain is joined to a peptide comprising any of the amino acid sequences of Table 1. In some embodiments, the nucleic acid encodes an antibody-peptide fusion protein comprising a humanized antibody comprising a heavy chain comprising a VH comprising the amino acid sequence of SEQ ID NO: 48, wherein the heavy chain is joined to a peptide comprising the amino acid sequence of SEQ ID NO:1. In some embodiments, the nucleic acid encodes an antibody-peptide fusion protein comprising a humanized antibody comprising a heavy chain comprising a VH comprising the amino acid sequence of SEQ ID NO: 48, wherein the heavy chain is joined to a peptide comprising the amino acid sequence of SEQ ID NO:2.

In some embodiments, the nucleic acid encodes an antibody-peptide fusion protein comprising a humanized antibody that comprises a light chain comprising a VL comprising an amino acid sequence set forth in the group consisting of SEQ ID NOs:33-42, wherein the light chain is joined to a peptide comprising any of the amino acid sequences of Table 1. In some embodiments, the nucleic acid encodes an antibody-peptide fusion protein comprising a humanized antibody comprising a light chain comprising a VL comprising an amino acid sequence set forth in the group consisting of SEQ ID NOs:33-42, wherein the light chain is joined to a peptide comprising the amino acid sequence of SEQ ID NO:1. In some embodiments, the nucleic acid encodes an antibody-peptide fusion protein comprising a humanized antibody comprising a light chain comprising a VL comprising an amino acid sequence set forth in the group consisting of SEQ ID NOs:33-42, wherein the light chain is joined to a peptide comprising the amino acid sequence of SEQ ID NO:2. In some embodiments, the nucleic acid encodes an antibody-peptide fusion protein comprising a humanized antibody that comprises a light chain comprising a VL comprising the amino acid sequence of SEQ ID NO:

35, wherein the light chain is joined to a peptide comprising any of the amino acid sequences of Table 1. In some embodiments, the nucleic acid encodes an antibody-peptide fusion protein comprising a humanized antibody comprising a light chain comprising a VL comprising the amino acid sequence of SEQ ID NO: 35, wherein the light chain is joined to a peptide comprising the amino acid sequence of SEQ ID NO:1. In some embodiments, the nucleic acid encodes an antibody-peptide fusion protein comprising a humanized antibody comprising a light chain comprising a VL comprising the amino acid sequence of SEQ ID NO: 35, wherein the light chain is joined to a peptide comprising the amino acid sequence of SEQ ID NO:2. In some embodiments, the nucleic acid encodes an antibody-peptide fusion protein comprising a humanized antibody that comprises a light chain comprising a VL comprising the amino acid sequence of SEQ ID NO: 34, wherein the light chain is joined to a peptide comprising any of the amino acid sequences of Table 1. In some embodiments, the nucleic acid encodes an antibody-peptide fusion protein comprising a humanized antibody comprising a light chain comprising a VL comprising the amino acid sequence of SEQ ID NO: 34, wherein the light chain is joined to a peptide comprising the amino acid sequence of SEQ ID NO:1. In some embodiments, the nucleic acid encodes an antibody-peptide fusion protein comprising a humanized antibody comprising a light chain comprising a VL comprising the amino acid sequence of SEQ ID NO: 34, wherein the light chain is joined to a peptide comprising the amino acid sequence of SEQ ID NO:2.

In some embodiments, the nucleic acid encodes an antibody-peptide fusion protein comprising a humanized antibody comprising a heavy chain comprising a VH comprising the amino acid sequence of SEQ ID NO:51 and a light chain comprising a VL comprising the amino acid sequence of SEQ ID NO:35, wherein the light chain is joined to a peptide comprising any of the amino acid sequences of Table 1.

In some embodiments, the nucleic acid encodes an antibody-peptide fusion protein comprising a humanized antibody comprising heavy chain comprising a VH comprising the amino acid sequence of SEQ ID NO:51 and a light chain comprising a VL comprising the amino acid sequence of SEQ ID NO:35, wherein the light chain is joined to a peptide comprising the amino acid sequence of SEQ ID NO:1.

In some embodiments, the nucleic acid encodes an antibody-peptide fusion protein comprising a humanized antibody a heavy chain comprising a VH comprising the amino acid sequence of SEQ ID NO:51 and a light chain comprising a VL comprising the amino acid sequence of SEQ ID NO:35, wherein the light chain is joined to a peptide comprising the amino acid sequence of SEQ ID NO:2.

In some embodiments, the nucleic acid encodes an antibody-peptide fusion protein comprising a humanized antibody comprising a heavy chain comprising a VH comprising the amino acid sequence of SEQ ID NO:48 and a light chain comprising a VL comprising the amino acid sequence of SEQ ID NO:34, wherein the light chain is joined to a peptide comprising any of the amino acid sequences of Table 1.

In some embodiments, the nucleic acid encodes an antibody-peptide fusion protein comprising a humanized antibody comprising heavy chain comprising a VH comprising the amino acid sequence of SEQ ID NO:48 and a light chain comprising a VL comprising the amino acid sequence of SEQ ID NO:34, wherein the light chain is joined to a peptide comprising the amino acid sequence of SEQ ID NO:1.

In some embodiments, the nucleic acid encodes an antibody-peptide fusion protein comprising a humanized antibody a heavy chain comprising a VH comprising the amino acid sequence of SEQ ID NO:48 and a light chain comprising a VL comprising the amino acid sequence of SEQ ID NO:34, wherein the light chain is joined to a peptide comprising the amino acid sequence of SEQ ID NO:2.

C. Vectors, Host Cells

In some embodiments, the nucleic acid provided herein are in one or more vectors. For example, in some embodiments, provided herein is a vector comprising a heavy chain and light chain of a modified immunoglobulin, wherein the light chain is joined to a peptide. In some embodiments, the heavy chain and the light chain joined to a peptide are in different vectors.

In some embodiments, the vector comprises the nucleic acid(s) encoding a humanized antibody or antibody-peptide fusion protein of the present disclosure.

For antibody production, the heavy chain and light chain joined to a peptide expression vectors may be introduced into appropriate production cell lines know in the art. Introduction of the expression vectors may be accomplished by co-transfection via electroporation or any other suitable transformation technology available in the art. Antibody producing cell lines can then be selected and expanded and antibodies purified. The purified antibodies can then be analyzed by standard techniques such as SDS-PAGE.

Also provided is a host cell comprising a nucleic acid encoding any of the modified immunoglobulins described herein. Suitable host cells for cloning or expression of antibody-encoding vectors include prokaryotic or eukaryotic cells described herein. For example, the modified immunoglobulin may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N J, 2003), pp. 245-254, describing expression of antibody fragments in *E. coli*.) After expression, the antibody joined to a peptide may be isolated from the bacterial cell paste in a soluble fraction and can be further purified.

In some embodiments, the host cell comprising a vector comprising a nucleic acid(s) encoding a humanized antibody or antibody-peptide fusion protein of the present disclosure.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse Sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR-CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, NJ), pp. 255-268 (2003).

D. Methods of Making Antibodies or Antibody-Peptide Fusion Proteins

Also provided herein are methods of making a modified immunoglobulin, humanized antibody, or antibody-peptide fusion protein of the present disclosure. In some embodiments, the method comprises culturing a host cell of the present disclosure under conditions suitable for expression of the vector encoding the modified immunoglobulin, humanized antibody, or antibody-peptide fusion protein and recovering the modified immunoglobulin, humanized antibody, or antibody-peptide fusion protein.

VII. Method of Humanizing a Mouse Antibody

Provided herein are methods of humanizing a mouse antibody. In some embodiments, the mouse antibody comprises a light chain variable region (VL) and a heavy chain variable region (VH), wherein the VL comprises a CDR-L1, a CDR-L2, and a CDR-L3, and the VH comprises a CDR-H1, a CDR-H2, and a CDR-H3, wherein the VH and the VL comprise one or more framework residues. In some embodiments, the CDR-L1 of the mouse antibody comprises the amino acid sequence set forth in SEQ ID NO:20, the CDR-L2 of the mouse antibody comprises the amino acid sequence set forth in SEQ ID NO:21, and the CDR-L3 of the mouse antibody comprises the amino acid sequence set forth in SEQ ID NO:22, and the CDR-H1 of the mouse antibody comprises the amino acid sequence set forth in SEQ ID NO:17, the CDR-H2 of the mouse antibody comprises comprising the amino acid sequence set forth in SEQ ID NO:18, and the CDR-H3 of the mouse antibody comprises the amino acid sequence LDY. In some embodiments, the mouse antibody comprises one, two, three, four, five, or six CDRs of antibody 11-1F4 as shown in Table 3. In some embodiments, the mouse antibody comprises a CDR-H1, a CDR-H2, and a CDR-H3, respectively comprising the amino acid sequences of a CDR-H1, a CDR-H2, and a CDR-H3 of a VH having the sequence set forth in SEQ ID NO:15; and a CDR-L1, a CDR-L2, and a CDR-L3, respectively comprising the amino acid sequences of a CDR-L1, a CDR-L2, and a CDR-L3 of a VL having the sequence set forth in SEQ ID NO:16.

In some embodiments, the method of humanizing a mouse antibody comprises: i. performing homology modeling to obtain a modeled structure of the mouse antibody; ii. Calculating the solvent accessible surface area of the framework residues in the modeled structure of the mouse antibody; iii. Determining whether the framework residues are buried residues, wherein a buried residue is a residue with a solvent accessible surface area of less than about 15%; iv. Providing a human VH and VL; v. introducing the CDR-L1, CDR-L2, CDR-L3, CDR-H1, CDR-H2, CDR-H3 of the mouse antibody into the human VH and VL, respectively, thereby generating a grafted antibody; and vi. Introducing a back-mutation into a position in the grafted antibody, wherein the position for back-mutation is a buried residue.

In some embodiments, wherein step vi is repeated. In some embodiments, step vi is performed 1, 2, 3, 4, 5, 6, 7, 8, 9, or 10 times.

In some embodiments, the position for back-mutation is in close proximity to a CDR. In some embodiments, the position for back-mutation is separated from a CDR by no more than 1, 2, 3, 4, 5, 6, 7, 8, 9, or 10 amino acid residues. In some embodiments, the position for back-mutation is separated from a CDR by no more than 0.5, 1, 2, 3, 4, 5, 6, 7, 8, 9, or 10 Angstroms, including any range or value in between.

In some embodiments, the back-mutation is introduced in the human VL, wherein the amino acid positions are numbered according to the numbering system of Kabat. In some embodiments, the back-mutation is introduced in the human VL, wherein the back-mutation comprises Tyr at position 36. In some embodiments, the back-mutation is introduced in the human VL, wherein the back-mutation comprises Leu at position 37. In some embodiments, the back-mutation is introduced in the human VL, wherein the back-mutation comprises Leu at position 46. In some embodiments, the back-mutation is introduced in the human VL, wherein the back-mutation comprises Leu at position 85. In some embodiments, the back-mutation is introduced in the human VL, wherein the back-mutation comprises Phe at position 87.

In some embodiments, the back-mutation is introduced in the human VH, wherein the amino acid positions are numbered according to the numbering system of Kabat. In some embodiments, the back-mutation is introduced in the human VH, wherein the back-mutation comprises Val at position 37. In some embodiments, the back-mutation is introduced in the human VH, wherein the back-mutation comprises Leu at position 48. In some embodiments, the back-mutation is introduced in the human VH, wherein the back-mutation comprises Leu at position 67. In some embodiments, the back-mutation is introduced in the human VH, wherein the back-mutation comprises Ser at position 68. In some embodiments, the back-mutation is introduced in the human VH, wherein the back-mutation comprises Lys at position 71. In some embodiments, the back-mutation is introduced in the human VH, wherein the back-mutation comprises Ser at position 76. In some embodiments, the back-mutation is introduced in the human VH, wherein the back-mutation comprises Val at position 78. In some embodiments, the back-mutation is introduced in the human VH, wherein the back-mutation comprises Leu at position 79. In some embodiments, the back-mutation is introduced in the human VH, wherein the back-mutation comprises Phe at position 80. In some embodiments, the back-mutation is introduced in the human VH, wherein the back-mutation comprises Thr at position 89. In some embodiments, the back-mutation is introduced in the human VH, wherein the back-mutation comprises Val at position 93. In some embodiments, the back-mutation is introduced in the human VH, wherein the back-mutation comprises Thr at position 94.

In some embodiments, the method further comprises introducing one or more amino acid substitutions in the CDRs of the grafted antibody. In some embodiments, the humanized antibody comprises a VL comprising an amino acid substitution in the CDR-L1 compared to the VL of the grafted antibody. In some embodiments, the amino acid substitution in the CDR-L1 is selected from the group consisting of an amino acid substitution at position 28 and an amino acid substitution at position 29, wherein the amino acid positions are numbered according to the numbering system of Kabat. In some embodiments, the amino acid substitution in the CDR-L1 is selected from the group consisting of Ser, Gln, Glu, His, or Ala at position 28, wherein the amino acid positions are numbered according to the numbering system of Kabat. In some embodiments, the amino acid substitution in the CDR-L1 is selected from the group consisting of Ala or Val at position 29, wherein the amino acid positions are numbered according to the numbering system of Kabat. In some embodiments, the humanized antibody comprises a VH comprising an amino acid substitution in the CDR-H2 compared to the VH of the grafted antibody. In some embodiments, the amino acid substitution in the CDR-H2 is selected from the group consisting of an amino acid substitution at position 54, position 55, or position 64, wherein the amino acid positions are numbered according to the numbering system of Kabat. In some embodiments, the amino acid substitution in the CDR-H2 is selected from the group consisting of Ser, Gln, Glu, Ala, or His at position 54, wherein the amino acid positions are numbered according to the numbering system of Kabat. In some embodiments, the amino acid substitution in the CDR-H2 is selected from the group consisting of Ala or Val at position 55, wherein the amino acid positions are numbered according to the numbering system of Kabat. In some embodiments, the amino acid substitution in the CDR-H2 is selected from the group consisting of Val, Ile, Leu, or Ala at position 64, wherein the amino acid positions are numbered according to the numbering system of Kabat.

EMBODIMENTS

Embodiment 1. A modified immunoglobulin, comprising an amyloid-reactive peptide, wherein the amyloid reactive peptide comprises an amino acid sequence having at least 85% sequence identity to any one of the amino acid sequences set forth as SEQ ID NOS:1-14; and
an Ig antibody or functional fragment thereof.
Embodiment 2. The modified immunoglobulin of embodiment 1, wherein the amyloid-reactive peptide and the Ig antibody or functional fragment thereof are joined together at the N-terminal end of the Ig light chain protein or the C-terminal end of the Ig heavy chain protein.
Embodiment 3. The modified immunoglobulin of embodiments 1 or 2, wherein the modified immunoglobulin comprises a spacer sequence between the amyloid-reactive peptide and the Ig antibody or functional fragment thereof.
Embodiment 4. The modified immunoglobulin any of embodiments 1-3, wherein the modified immunoglobulin comprises at least two amyloid-reactive peptides and wherein the amyloid-reactive peptides are the same peptide or different peptides.
Embodiment 5. A method of treating a subject suffering from amyloidosis, comprising administering to the subject an effective amount of the modified immunoglobulin set forth as any one of embodiments 1-4.
Embodiment 6. A method of targeting an amyloid deposit for clearance, comprising contacting an amyloid deposit with a modified immunoglobulin set forth as any one of embodiments 1-4.
Embodiment 7. The method of embodiment 6, wherein targeting the amyloid deposit for clearance results in clearance of the amyloid deposit.
Embodiment 8. The method of embodiments 6 or 7, wherein clearance results from opsonization of the amyloid deposit.
Embodiment 9. The method any of embodiments 1-8, wherein the amyloid-reactive peptide joined to the Ig antibody or functional fragment thereof binds to one or more amyloid deposit types comprising AA, AL, AH, ATTR, Aβ2M, Alect2, Wild type, TTR, AapoAI, AApoAII, Agel, Alys, Alect2, Afib, Acys, Acal, Amedin, AIAPP, Apro, Ains, AprP, or Aβ.
Embodiment 10. The method of any of embodiments 6-8, wherein contacting the amyloid deposit with the amyloid-reactive peptide joined to the Ig antibody or functional fragment thereof increases the half-life of the amyloid-reactive Igp5 conjugate by about 10%, 20%, 30%, 40%, 50%, 60%, 70%, 80% or more as compared to the amyloid-reactive peptide alone.
Embodiment 11. A modified immunoglobulin, comprising:
a peptide; and
an Ig antibody or functional fragment thereof, wherein the peptide and the Ig antibody or functional fragment thereof are joined together at the N-terminal end of the Ig light chain protein and/or the N- and/or C-terminal end of the Ig heavy chain protein.
Embodiment 12. The modified immunoglobulin of embodiment 11, wherein the modified immunoglobulin comprises a spacer sequence between the peptide and the Ig antibody or functional fragment thereof.
Embodiment 13. The modified immunoglobulin any of embodiments 1-3, wherein the modified immunoglobulin comprises at least two peptides, wherein peptides are the same peptide or different peptides.
Embodiment 14. A method for generating a modified immunoglobulin, comprising:
providing a first expression vector and a second expression vector,
wherein the first expression vector comprises a first nucleic acid sequence encoding an Ig antibody light chain or functional fragment thereof;
wherein the second expression vector comprises a second nucleic acid sequence encoding an Ig antibody heavy chain or functional fragment thereof; and
wherein the first expression vector and/or the second expression vector comprise a third nucleic acid sequence that encodes a first peptide, the third nucleic acid sequence being located adjacent to the first nucleic acid sequence and/or the second nucleic acid sequence; and
inserting the first and second expression vectors into a cell, wherein expression of the first and second expression vectors in the cell results in an immunoglobulin that is joined to the first peptide.
Embodiment 15. The method of embodiment 14, wherein the first expression vector and/or the second expression vector comprise a fourth nucleic acid sequence that encodes a second peptide, the fourth nucleic acid sequence being located adjacent to the first nucleic acid sequence and/or the second nucleic acid sequence.
Embodiment 16. The method of embodiment 15, wherein expression of the first and second expression vectors in the cell results in an immunoglobulin that is joined to the first peptide and the second peptide.
Embodiment 17. The method of embodiment 14, wherein a spacer nucleic acid sequence is located between the third nucleic acid sequence and the first nucleic acid sequence and/or the second first nucleic acid sequence.
Embodiment 18. The method of embodiment 14, wherein the first peptide is comprises an amino acid sequence having at least 85% sequence identity to any one of the amino acids set forth as SEQ ID NOS: 1-14.

Embodiment 19. A modified immunoglobulin produced by the method of any of embodiments 14-19.

Embodiment 20. A method of treating a subject suffering from, or suspected to be suffering from, an amyloid-based disease, comprising:
determining whether the subject has an amyloid deposit by:
detectably labeling the modified immunoglobulin of any of embodiments 1-4,
administering the modified immunoglobulin to the subject,
determining whether a signal associated with the detectable label can be detected from the subject; and,
if the signal is detected, administering to the subject an amyloidosis treatment.

Embodiment 21. The method of embodiment 20, wherein, if a signal is not detected, monitoring the subject for a later development of an amyloid deposit.

Embodiment 22. The method of embodiment 21, further comprising determining the intensity of the signal and comparing the signal to a threshold value, above which the subject is determined to possess an amyloid deposit.

Embodiment 23. The method of any of embodiments 20-22, wherein the amyloidosis treatment comprises administering the modified immunoglobulin of any of claims 1-4 to the subject.

Embodiment 24. The method of embodiment 23, wherein administration of the modified immunoglobulin results in clearance of the amyloid deposit in the subject.

Embodiment 25. A method of identifying an amyloid deposit in a subject, comprising detectably labeling the modified immunoglobulin of any of embodiments 1-4, administering the modified immunoglobulin to the subject, and detecting a signal from the modified immunoglobulin.

Embodiment 26. The method of any of embodiments 20-25, wherein the subject is determined to be amyloid free or suffering from monoclonal gammopathy of unknown significance (MGUS), multiple myeloma (MM), or one or more related plasma cell diseases.

Embodiment 27. A method of detecting a ligand, comprising:
detectably labeling the modified immunoglobulin of any of embodiments 11-13, wherein the peptide of the modified immunoglobulin has binding affinity to the ligand;
contacting the ligand with the modified immunoglobulin; and,
determining a signal from the detectable label, thereby detecting the ligand.

Embodiment 28. A modified immunoglobulin, comprising an amyloid-reactive peptide, wherein the amyloid reactive peptide comprises any one of the amino acid sequences set forth as SEQ ID NOS:1-14; and
an antibody or immunologically active fragment thereof, wherein the antibody comprises a heavy chain variable domain comprising a CDRH1 set forth in SEQ ID NO: 17, a CDRH2 set forth in SEQ ID NO: 18, a CDRH3 set forth in the amino acid sequence LDY;
and a light chain variable domain comprising a CDRL1 set forth in SEQ ID NO:20, A CDRL2 set forth in SEQ ID NO: 21, and a CDRL3 set forth in SEQ ID NO: 22.

Embodiment 29. The modified immunoglobulin of claim 28, wherein the amyloid reactive peptide comprises SEQ ID NO: 1 or SEQ ID NO: 2.

Embodiment 30. The modified immunoglobulin of embodiments 28 or 29, wherein the amyloid reactive peptide is joined to the N terminus of the light chain of the antibody or immunologically active fragment thereof.

Embodiment 31. The modified immunoglobulin of any one of embodiments 28-30, wherein the amyloid reactive peptide is joined to the N-terminus of the light chain of the antibody or immunologically active fragment thereof by a linker.

Embodiment 32. The modified immunoglobulin of any one of embodiments 28-31, wherein the antibody or immunologically active fragment thereof comprises an Fc region.

Embodiment 33. The modified immunoglobulin of any one of embodiments 28-32, wherein the antibody is chimeric or humanized.

Embodiment 34. The modified immunoglobulin of any one of embodiments 28-32, wherein the antibody comprises human framework sequences.

Embodiment 35. A method of treating amyloidosis in a subject comprising administering the modified immunoglobulin of any one of embodiments 28-34 to a subject in need thereof.

Embodiment 36. A method of producing the modified immunoglobulin of any one of embodiments 28-34 comprising transforming a host cell with one or more nucleic acids encoding the modified immunoglobulin and culturing the cell under conditions to produce the modified immunoglobulin.

Embodiment 37. The modified immunoglobulin of any one of embodiments 1-4, 11-13, or 28-34 wherein the modified immunoglobulin binds to rVλ6Wil, Aβ, Aβ(1-40), IAAP, ALκ4, Alλ1, or ATTR fibrils.

Embodiment 38. Nucleic acid encoding the modified immunoglobulin of any one of embodiments 1-4, 11-13, or 28-34.

Embodiment 39. A host cell comprising the nucleic acid of embodiment 38.

Embodiment 40. The host cell of claim 39, wherein the host cell is a CHO cell.

EXAMPLES

The following examples further illustrate the invention but should not be construed as in any way limiting its scope. In light of the present disclosure and the general level of skill in the art, those of skill will appreciate that the following Examples are intended to be exemplary only and that numerous changes, modifications, and alterations can be employed without departing from the scope of the presently disclosed subject matter. The attached figures are meant to be considered as integral parts of the specification and description of the disclosure.

As used herein, the following abbreviations apply: eq (equivalents); M (Molar); μM (micromolar); N (Normal); mol (moles); mmol (millimoles); μmol (micromoles); nmol (nanomoles); g (grams); mg (milligrams); kg (kilograms); μg (micrograms); L (liters); ml (milliliters); μl (microliters); cm (centimeters); mm (millimeters); μm (micrometers); nm (nanometers); ° C. (degrees Centigrade); h (hours); min (minutes); sec (seconds); msec (milliseconds).

Figure 2:
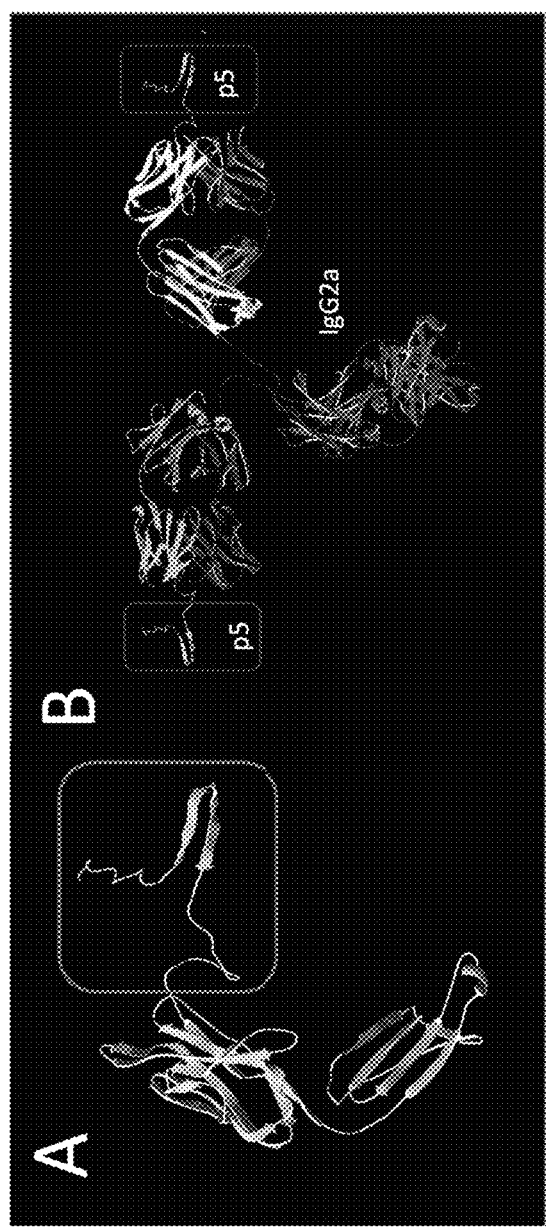
FIG. 2 is a schematic representation of an Ig-peptide fusion. Panel A shows a schematic of peptide p5 (SEQ ID NO:1) fused to Ig light chain at the N-terminal. Panel B depicts an Ig-peptide fusion showing Ig structure with two Ig light chains fused to peptide p5 (SEQ ID NO:1).

Example 1. Generation and Use Immunoglobulin Fused to Amyloidophilic Peptides for Targeting and Removal of Amyloid Deposits INTRODUCTION: Immunoglobulin-peptide fusion constructs are synthetic biomolecules composed of an Ig that incorporates another protein or peptide. The Ig endows two major benefits to the peptide of interest; principally, enhancement of the plasma half-life of the amyloid-reactive peptide due to the interaction of the Ig with the neonatal Fc-receptor and, secondly, the ability to engage and activate effector immune cells via interactions through membrane-bound Fc-receptors and binding of complement. To generate fusion peptide antibodies for targeting and removal (e.g., clearing) of amyloid deposits we have synthesized a murine Ig-peptide fusion construct that incorporates the synthetic amyloidopihilic peptide p5 (SEQ IN NO:1) with a murine IgG2a by joining the peptide amino acid sequence and spacer elements to the N-terminal of the Ig light chain protein (FIG. 2).

Figure 3:
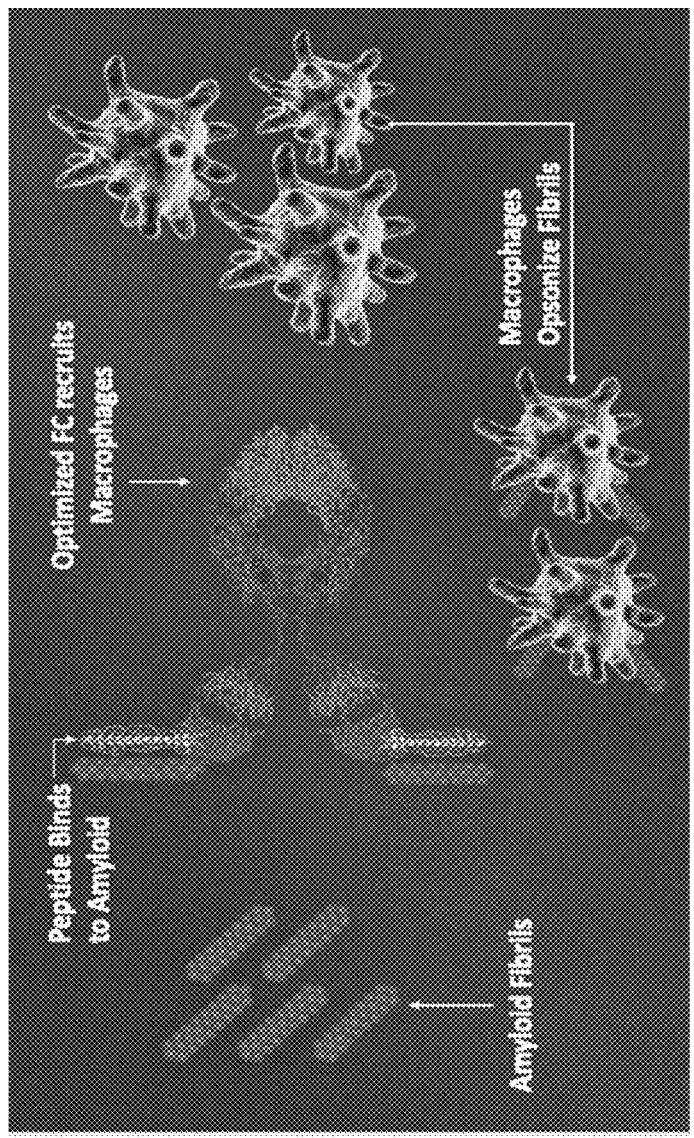
FIG. 3 shows a schematic representation of proposed mode of action for Ig-peptide fusion for clearing amyloid deposits (not to scale). The Ig-peptide binds amyloid through peptide interactions with amyloid fibrils (or heparan sulfate glycosaminoglycans) which recruits macrophages that then engulf (phagocytose) the amyloid for destruction.

As those skilled in the art will appreciate based on this disclosure, this construct could include any number of amyloid-reactive peptides that we have developed or proposed and any number of spacer sequences, as described herein (including those in Table 1; see also WO2016032949). The murine Igp5 fusion was generated in HEK 293T/17 cells and used to generate proof of principle data using a panel of in vitro binding and phagocytosis assays and, using a mouse models of amyloidosis, has been shown to localize with systemic amyloid deposits. Taken together, these data demonstrate that the Ig-peptide fusion is capable of: (1) binding multiple forms of amyloid deposits, (2) specifically binding amyloid in vivo, and; (3) opsonizing amyloid extracts and synthetic fibrils, in vitro, using a cultured macrophage assay system. We anticipate the mode of action to be that the Ig-peptide fusion binds to the hypersulfated heparan sulfate proteoglycans and/or protein fibrils found in all amyloid deposits, via the amyloid-reactive peptide. The Fc region can then, fix compliment and engage macrophages and other cells expressing Fc receptors that can then remove the amyloid. FIG. 3 shows a schematic of this process.

MATERIALS & METHODS: For the Igp5 heavy chain construct the pFUSE-mIgG2A-Fc vector coding for the CH2 (constant heavy domain 2) and CH3 (constant heavy domain 3) domains of the murine IgG2a heavy chain, was purchased from InvivoGen (San Diego, CA). The cDNA for the murine heavy chain VH (variable heavy) and CH1 (constant heavy domain 1) domains derived from the sequence of the murine 11-1F4 Ig was synthesized (Genscript, Piscataway, NJ) and cloned into the vector in frame with the 5' secretory leader and CH2/CH3 domains of the Fc region. For the Igp5 light chain construct, the cDNA for peptide p5 (SEQ ID NO: 1), with a 5' secretory leader, a 15 amino acid 5' spacer (SEQ ID NO:23) and a 5 amino acid 3' spacer (SEQ ID NO:24) followed by sequences encoding the murine 11-1F4 VL (variable light) and CL (constant light) regions was synthesized (Genscript) and cloned into the pcDNA3.1-Hygro(+) vector. The amino acid sequence of the Igp5 light chain construct is provided in SEQ ID NO:25. The vectors were transiently transfected into HEK293T/17 cell line cultured in medium with Ig-depleted serum. Secreted Igp5 was purified from the medium using a protein A-conjugated matrix. Binding of the purified Igp5 with synthetic amyloid fibrils was demonstrated by using a pulldown assay. Reactivity with murine AA amyloid in vivo was assessed by microautoradiography, tissue biodistribution measurements and small animal SPECT/CT imaging using iodine-125 ($^{125}$I)-labeled Igp5. Igp5-mediated phagocytosis of a synthetic fibrils was measured in vitro using THP-1 human macrophage cells in a quantitative pHrodo-red fluorescence assay.

Figure 4:
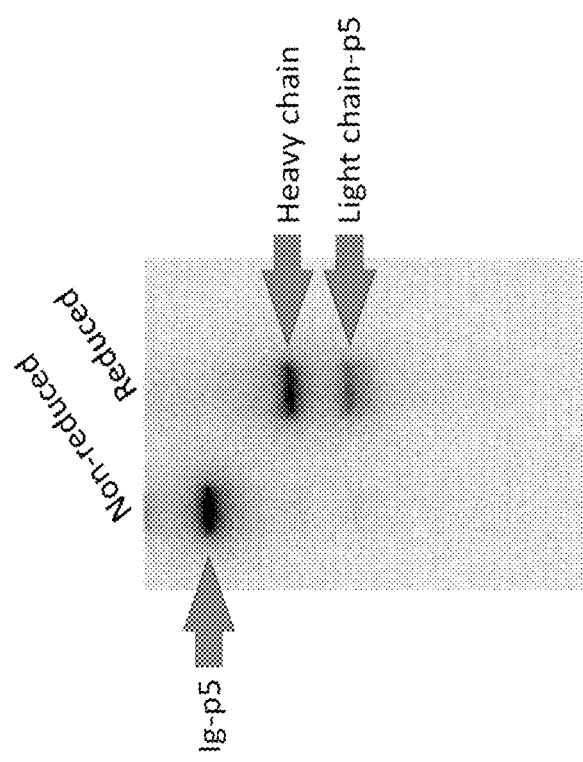
FIG. 4 shows an autoradiograph of $^{125}$I-Igp5 following SDS-PAGE gel electrophoresis. Under non-reducing conditions the protein ran as a single Ig, which when reduced was shown to comprise a heavy and light chain-p5, consistent with an intact Ig molecule.

RESULTS: Fcp5 fusion was expressed in both HEK cell lines at ~1-4 µg/mL of culture medium. For the pulldown assay, Igp5 was labeled with 125I. Gel electrophoresis using reducing and non-reducing conditions was used to show the presence of both heavy and light chain in the Igp5 construct (FIG. 4).

Using a pulldown assay the $^{125}$I-Igp5 was shown to bind synthetic fibrils composed of recombinant amyloidogenic λ6 variable domain protein (rVλ6Wil; Table 2). The reactivity was >70% as evidenced by the presence of radiolabeled material in the fibril pellet.

TABLE 2

| Binding of $^{125}$I-Igp5 to synthetic light chain (rVλ6Wil) amyloid fibrils. | |
|---|---|
| Sample | $^{125}$I-Igp5 bound to fibril pellet (% added material) |
| rVλ6Wil | 73 |

Figure 5:
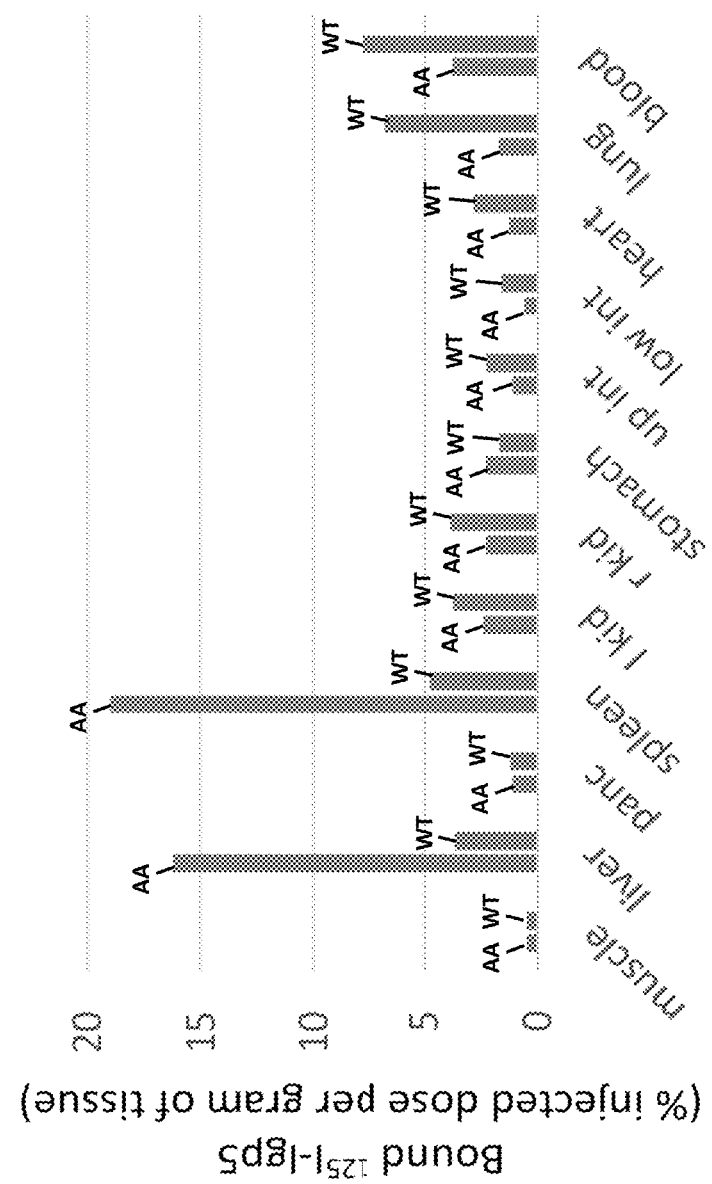
FIG. 5 shows the biodistribution of $^{125}$I-Igp5 in AA amyloid mice (AA) and healthy amyloid-free mice (WT) at 20 h post injection.
Figure 6:
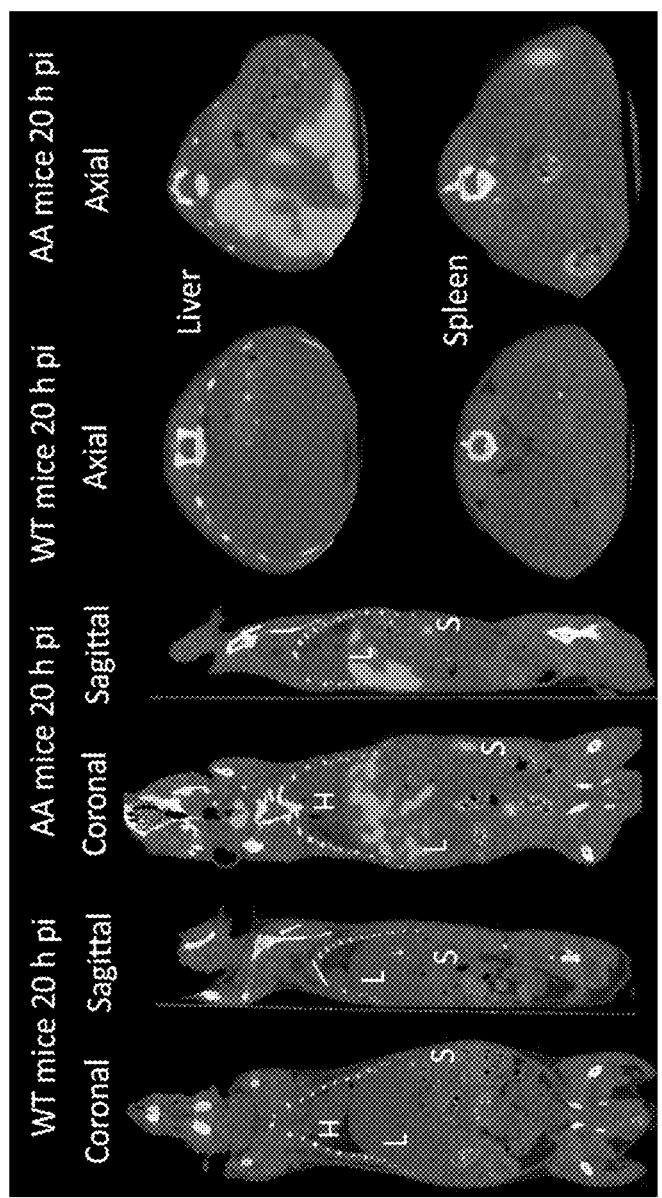
FIG. 6 shows SPECT/CT images of $^{125}$I-Igp5 in an AA mouse and a healthy wild type control, at 20 h post injection of Igp5, showing uptake in the amyloid-laden liver and spleen of AA mice and the long blood pool half-life of the reagent in WT animals. H, heart; L, liver; S, spleen. Red/yellow indicates presence of $^{125}$I-Igp5.

In mice with AA amyloid, $^{125}$I-Igp5 specifically bound the amyloid deposits in the liver and spleen (sites of greatest amyloid deposition in these mice) as evidenced by tissue biodistribution measurements (FIG. 5). Notably, there was no retention of $^{125}$Igp5 in these organs in healthy amyloid-free mice (FIG. 5). Microautoradiography revealed uptake in the lesser amyloid deposits all organs and tissues (not shown). SPECT/CT imaging of AA mice and healthy amyloid-free controls, at 20 h post iV injection confirmed that the $^{125}$I-Igp5 was taken up in the liver and spleen of the AA mice; however, in WT mice, only blood pool as evidenced (FIG. 6).

Figure 7:
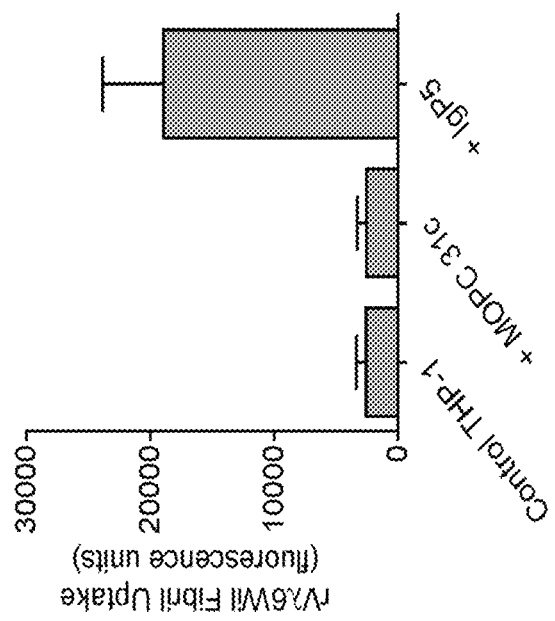
FIG. 7 shows the in vitro phagocytosis of pHrodo red-labeled rVλ6Wil fibrils in the presence of human THP1 monocyte/macrophages. The increase in fluorescence intensity indicates the presence of labeled amyloid substrate in the low pH environment of the phagolysosome of the macrophage. MOPC 31c is a mouse monoclonal antibody control with no reactivity with fibrils.

Finally, Igp5 effectively mediated the phagocytosis of pHrodo green-labeled synthetic light chain amyloid fibrils in vitro (FIG. 7).

DISCUSSION: Based on these data we have demonstrated that it is possible to generate functional Ig molecules with enhanced ligand binding properties by fusing functional peptides at the N-terminal of the Ig light chain. Furthermore, our data indicate that by fusing amyloid-reactive peptides to an Ig light chain, an Ig-peptide fusion can be generated that specifically binds amyloid in vitro and in vivo and that can serve as an opsonizing reagent and enhance amyloid uptake by macrophages. The Igp5 fusion, or a similar constructs employing other amyloidophilic peptides, may provide a novel reagent for targeting an immunologically active biomolecule (Ig) to amyloid deposits and thereby expedite clearance of the amyloid in patients by cells of the immune system (macrophages and neutrophils). These reagents could provide pan-amyloid reactivity and benefit to patients with many, if not all, forms of amyloid disease. Furthermore, these reagents, when labeled with appropriate radionuclides could also be used for detecting amyloid deposits in patients by SPECT to PET imaging and be used for monitoring response to therapy, or stratification of patients prior to therapy using unlabeled Ig-peptide fusion reagents.

Example 2. Binding of Ig-Peptide Fusion to Amyloid Fibrils

This example shows binding of Igp5 to diverse amyloid-related substrates. This example also shows of a peptide-Ig fusion in mouse tissues.

Materials and Methods

The peptide-Ig fusion comprising an IgκLC sequence fused to peptide p5 was expressed in a vector. The IgHC sequence comprising IgG1 variable, IgG1 CH1, and IgG2a CH2 and CH3 domains was expressed in a second vector system. The vectors were co-transfected into HEK 293T/17 cells and the Ig product isolated using Protein A-conjugated beads. Igp5 and Ig control were radiolabeled with $^{125}$I and analyzed by gel electrophoresis. Binding of $^{125}$I-Igp5 and Ig control with synthetic amyloid fibrils and amyloid extracts was assessed using pulldown assays. For assessing tissue retention, $^{125}$I-Igp5 was intravenously injected into healthy (WT) mice and those with severe systemic serum albumin protein A (AA) amyloidosis (H2/IL-6 transgenic). Tissue localization of $^{125}$I-Igp5 was then assessed by microautoradiography (ARG).

Results

Figure 8:
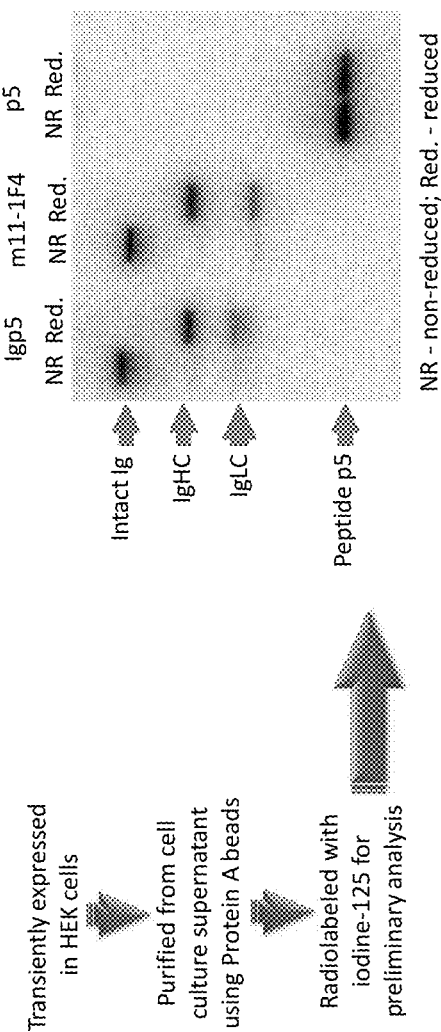
FIG. 8 shows an autoradiograph of $^{125}$I-Igp5 following SDS-PAGE gel electrophoresis. Igp5 was purified from tissue culture supernatant, radiolabeled with $^{125}$I and the product characterized by SDS-PAGE using the murine 11-1F4 (IgG1κ) as a control. The protein was analyzed under both reducing (Red.) and non-reducing conditions (NR).

Igp5 was transiently expressed in HEK cells, purified from the cell culture supernatant using Protein A beads, and radiolabeled with $^{125}$I for preliminary analysis. $^{125}$I-labelled Igp5 was analyzed by SDS-PAGE under both reducing and non-reducing conditions. The murine 11-1F4 (IgG1κ) was used as an Ig control. P5 peptide alone was also analyzed as a comparison. FIG. 8 shows the results of the SDS-PAGE analysis of purified $^{125}$I-Igp5. Purified Igp5 appeared as an intact Ig with both heavy and light chains following gel electrophoresis.

Figure 9:
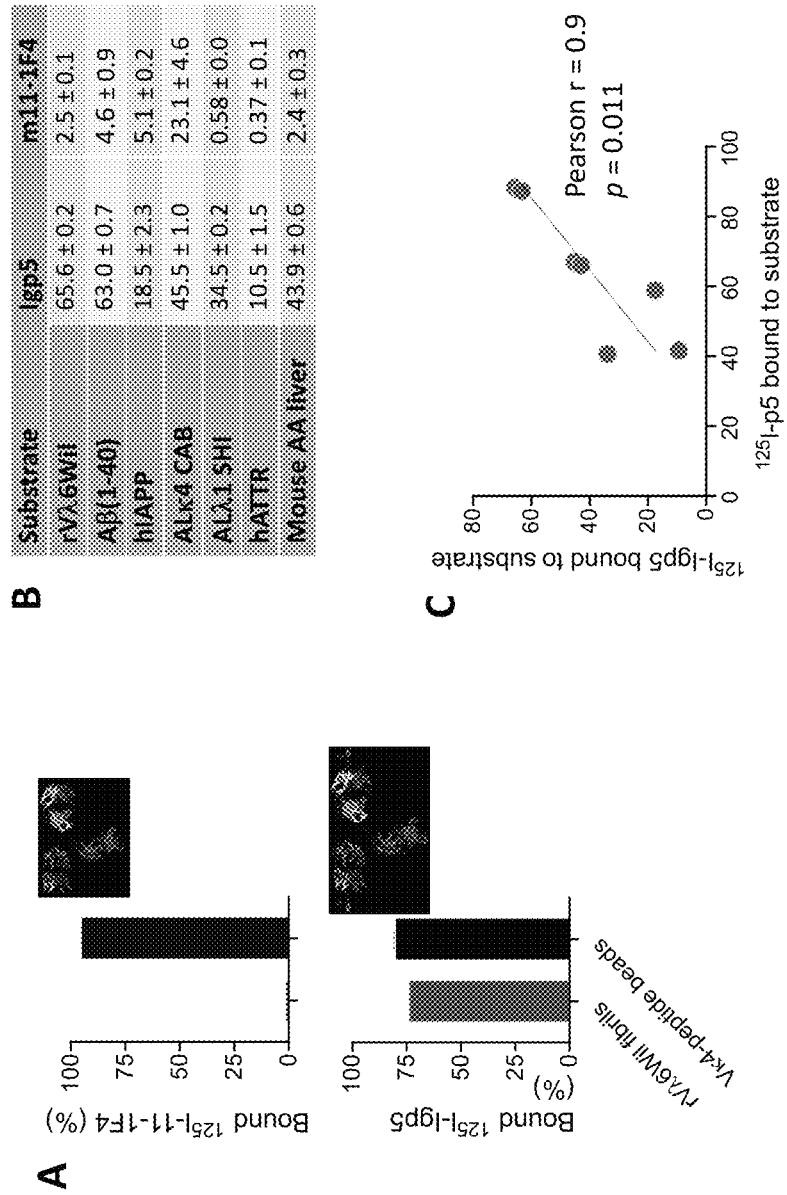
FIG. 9 depicts the binding of $^{125}$I-Igp5 to diverse amyloid-related substrates. Panel A shows the binding of $^{125}$I-m11-1F4 and $^{125}$I-Igp5 to κ4-peptide-coated beads or rVλ6Wil fibrils. $^{125}$I-m11-1F4 binds κ4-peptide-coated beads but not rVλ6Wil fibrils, whereas $^{125}$I-Igp5 binds both substrates. Panel B shows the quantification of binding of $^{125}$I-Igp5 and m11-1F4 to diverse synthetic amyloid fibrils and amyloid extracts. Panel C shows the correlation between $^{125}$I-Igp5 and $^{125}$I-p5 binding to substrate. Binding of $^{125}$I-Igp5 to diverse synthetic amyloid fibrils and amyloid extracts is greatly enhanced relative to m11-1F4, where the reactivity correlates with that of the p5 peptide alone, indicating that binding is driven by the peptide.

The binding of $^{125}$I-Igp5 and Ig control to synthetic amyloid fibrils and amyloid extracts was assessed using pulldown assays. As shown in FIG. 9, $^{125}$I-Igp5 binds diverse amyloid-related substrates. $^{125}$I-m11-1F4 bound κ4-peptide-coated beads but not rVλ6Wil fibrils, whereas $^{125}$I-Igp5 bound both substrates. $^{125}$I-Igp5 bound rVλ6Wil and Aβ(1-40) amyloid-like fibrils at ~64% (21 fold higher than the control Ig, murine 11-1F4). Binding to amyloid extracts was also 10-30 fold higher and correlated positively with that of $^{125}$I-p5 (r=0.9, p=0.01). The binding of $^{125}$I-Igp5 to diverse synthetic amyloid fibrils and amyloid extracts is greatly enhanced relative to m11-1F4, where the reactivity correlates with that of p5 peptide alone, indicating binding is driven by the peptide.

Figure 10:
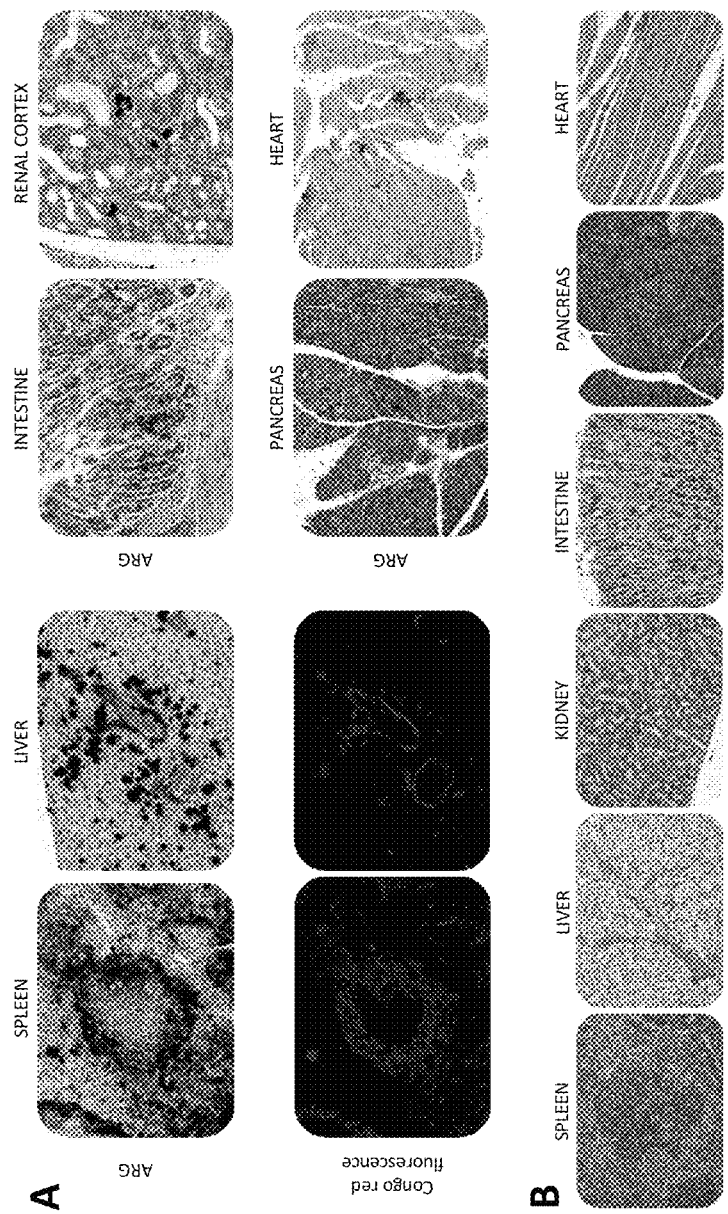
FIG. 10 shows microautoradiography (ARG) analysis and Congo red staining of various tissues. Panel A shows the retention of $^{125}$I-Igp5 in hepatosplenic AA amyloid in the mouse, as well as amyloid binding in other tissues. ARG and Congo red staining demonstrate specific retention of $^{125}$I-Igp5 in hepatosplenic AA amyloid in the mouse, as well as amyloid binding in other tissues. Panel B shows the results of ARG analysis of amyloid-free tissues. No specific reactivity with amyloid-free tissues was observed in healthy (WT) mice, where blood pool was the only identified source of $^{125}$I-Igp5.

To assess for retention of IgP5 in in vivo, $^{125}$I-Igp5 was intravenously injected into healthy (WT) mice and those with severe systemic serum albumin protein A (AA) amyloidosis (H2/IL-6 transgenic). Localization of $^{125}$I-Igp5 across various tissues was assessed by microautoradiography (ARG). Congo red staining was used to stain for amyloid deposits. As shown in panel A of FIG. 10, ARG and Congo red staining demonstrate specific retention of $^{125}$I-Igp5 in hepatosplenic AA amyloid in the mouse, as well as amyloid binding in other tissues. No specific reactivity with amyloid-free tissues was observed in WT mice, where blood pool was the only identified source of $^{125}$I-Igp5, as shown in panel B of FIG. 10.

These results show that Igp5 binds many forms of amyloid and specifically targets amyloid in vivo.

Example 3. Humanization of Anti-Amyloid Antibodies

The following example describes the generation of humanized anti-amyloid antibodies.

Materials and Methods

Parental Antibody and Peptide Amino Acid Sequences

The murine antibody m11-1F4 was used as a parental antibody to generate humanized antibodies. The parental murine antibody with peptide p5 fused at the N-terminal of the light chain was termed "mIgG-p5." From N-terminus to C-terminus, mIgG-p5 light chain included a secretory leader sequence that was fused to an amino acid spacer sequence, the p5 peptide sequence, another amino acid spacer sequence, and the antibody light chain (see FIG. 11A and FIG. 11B).

The amino acid sequence of p5 is set forth in SEQ ID NO:1 (see Table 1).

Antibody Humanization

Humanized antibodies were generated as follows. First, variable domain sequences of m11-1F4 were analyzed. The complementarity-determining regions (CDRs), hypervariable loops, and framework regions (FRs) were identified. The amino acid sequences of the complementarity-determining regions of m11-1F4 are set forth in Table 3, below. The amino acid sequences of the CDRs, FRs, and residues at the VH-VL interface are also shown in FIG. 12.

TABLE 3

Amino acid sequences of m11-1F4 CDRs

| 11-1F4 CDR | Amino Acid Sequence | SEQ ID NO |
|---|---|---|
| CDR-L1 | RSSQSLVHRNGNTYLH | 20 |
| CDR-L2 | KVSNRFS | 21 |
| CDR-L3 | FQTTYVPNT | 22 |
| CDR-H1 | GFSLSSYGVS | 17 |
| CDR-H2 | VIWGDGSTNYHPNLMS | 18 |
| CDR-H3 | LDY | |

Next, homology modeling was performed to obtain the modeled structure of the mouse antibody. Homology models were built using a customized Build Homology Models protocol. Disulfide bridges were specified and linked. Loops were optimized using the Discrete Optimized Protein Energy (DOPE) method.

The solvent accessible surface area of the framework residues was calculated. Based on this result, the framework residues that were buried were identified. Residues that had a solvent accessible surface area of <15% were considered to be buried residues.

Next, one human acceptor for each of the VH and VL sequences that shared the highest sequence identities to the mouse counterparts was selected (see Tables 4A-41B). The CDRs of the mouse antibody were directly grafted to the human acceptor frameworks to obtain the sequence of the grafted antibody without any back-mutations. These sequences are termed "VH1" and "VL1" (see Tables 6A-6B, below).

TABLE 4A

Parental and human VL sequences used to generate humanized antibodies

| IgG | Description | VL Amino Acid Sequence | SEQ ID NO |
|---|---|---|---|
| 11-1F4 VL | Parental murine antibody | DVVMTQTPLSLPVSLGDQASISCRSSQSLVHRNGN TYLHWYLQKPGQSPKLLIYKVSNRFSGVPDRFSGS GSGTDFTLKISRVEAEDLGLYFCFQTTYVPNTFGG GTKLEIK | 16 |
| IGKV2-30*02 | Human germline sequence | DVVMTQSPLSLPVTLGQPASISCRSSQSLVHSDGN TYLNWFQQRPGQSPRRLIYKVSNRDSGVPDRFSGS GSGTDFTLKISRVEAEDVGVYYCMQGTHWPP | 28 |
| VL acceptor | Human acceptor sequence | DVVMTQSPLSLPVTLGQPASISCRSSQSLVHSDGN TYLNWFQQRPGQSPRRLIYKVSNRDSGVPDRFSGS GSGTDFTLKISRVEAEDVGVYYCFQTTYVPNTFGG GTKLEIK | 29 |

TABLE 4B

Parental and human VH sequences used to generate humanized antibodies

| IgG | Description | VH Amino Acid Sequence | SEQ ID NO |
|---|---|---|---|
| 11-1F4 VH | Parental murine antibody | QVQLKESGPGLVAPSQSLSITCTVSGFSLSSYGVS WVRQPPGKGLEWLGVIWGDGSTNYHPNLMSRLSIS KDISKSQVLFKLNSLQTDDTATYYCVTLDYWGQGT SVTVSS | 15 |
| IGHV4-4*08 | Human germline sequence | QVQLQESGPGLVKPSETLSLTCTVSGGSISSYYWS WIRQPPGKGLEWIGYIYTSGSTNYNPSLKSRVTIS VDTSKNQFSLKLSSVTAADTAVYYCAR | 30 |
| VH acceptor | Human acceptor sequence | QVQLQESGPGLVKPSETLSLTCTVSGGSISSYYWS WIRQPPGKGLEWIGYIYTSGSTNYNPSLKSRVTIS VDTSKNQFSLKLSSVTAADTAVYYCARLDYWGQGT SVTVSS | 31 |

Next, the critical residues identified in step 5 were compared in the sequences of the grafted VH1 and VL1 and the mouse VH and VL. All critical residues that were different in the grafted and mouse antibody framework sequences (i.e. putative back-mutation sites) were identified.

Next, one or more back mutations were incorporated into the grafted antibody sequence in a stepwise fashion according to the following guidelines: (1) buried residues which were less likely to elicit an immune response were selected for back-mutation; (2) buried residues that were also in the proximity of CDRs were selected for higher priority back-mutation; and (3) the other buried FR residues were selected for lower priority back-mutation.

Finally, additional mutations were introduced into the CDRs of the humanized heavy chain variable region VH9 at residues D54, G55, or M64, and into CDRs of the humanized light chain variable region VL4 at residues N33 or G34, as counted from the N-terminus of the VH or VL. These mutations were designed to remove sites of post-translational modifications, and are listed in Tables 6A-6B, below.
Surface Plasmon Resonance (SPR)

The affinity of humanized anti-amyloid antibodies binding to VκLen(1-22) ("Len(1-22) monomer") monomer peptide—the natural ligand for the m11-1F4 antibody—was measured using a Biacore 8K surface plasmon resonance (SPR) system. Parental antibody m11-1F4 binds to an epitope present at the N-terminal of denatured kappa 4 light chain proteins. The Len (1-22) monomer is a peptide comprising this epitope, as described in International Application No. PCT/US2017/015905. Binding affinities of anti-amyloid antibodies incorporating the humanized heavy chain region VH9 and the humanized light chain VL4 were tested, including versions of VH9 and VL4 with additional mutations (Table 5).

All SPR data were processed using the Biacore 8K Evaluation software version 1.1. Flow cell 1 and blank injections of buffer in each cycle were used as double reference for Response Units subtraction. Additional experimental conditions for the SPR experiments are provided in Table 3, below.

TABLE 5

Anti-amyloid antibody Len(1-22) monomer binding SPR experimental conditions

| Immobilization | |
|---|---|
| Ligand | Antibodies |
| Immobilization level (Ru) | ~7000 |
| Association & Dissociation | |
| Association contact time(s) | 120 |
| Dissociation contact time(s) | 360 |

TABLE 5-continued

Anti-amyloid antibody Len(1-22) monomer
binding SPR experimental conditions

| | |
|---|---|
| Flow rate(μl/min) | 30 |
| Sample concentrations(nM) | 6.25, 12.5, 25, 50, 100, 200, 400 |
| Surface regeneration | |
| Regeneration buffer | 10 mM Glycine-HCl |
| Contact time(s) | 30 |
| Flow rate(μl/min) | 30 |

Results

Antibodies with humanized VH and VL sequences were derived from m11-1F4. The humanized VL sequences were designated VL1-VL4, and the humanized VH sequences were designated VH1-VH10. The amino acid sequences of the humanized VH and VL regions are provided below in Tables 6A-6B. In Tables 6A-6B, the CDR sequences are underlined, and the back mutated residues and further mutations that were introduced into VL4 and VH9 are bolded, and italicized. Further mutations that were introduced into VL4 and VH9 are listed in the IgG column of Tables 6A and 61B; these mutations are numbered relative to the N-terminus of the VL or VH. Variants of VL4 and VH9 were generated with modified CDRs, and these CDR sequences are presented in Tables 6C and 6D, compared to VL4 and VH9.

TABLE 6A

Amino acid sequences of humanized light chain variable region sequences

| IgG | VL Amino Acid Sequence | SEQ ID NO |
|---|---|---|
| VL1 | DVVMTQSPLSLPVTLGQPASISCRSSQSLVHRNGNTYLHWFQQRPGQSPRRLIYKVSNRFSGVPDRFSGSGSGTDFTLKISRVEAEDVGVYYCFQTTYVPNTFGGGTKLEIK | 32 |
| VL2 | DVVMTQSPLSLPVTLGQPASISCRSSQSLVHRNGNTYLHW*YL*QRPGQSPRRLIYKVSNRFSGVPDRFSGSGSGTDFTLKISRVEAEDVGVYYCFQTTYVPNTFGGGTKLEIK | 33 |
| VL3 | DVVMTQSPLSLPVTLGQPASISCRSSQSLVHRNGNTYLHW*YL*QRPGQSPR*L*LIYKVSNRFSGVPDRFSGSGSGTDFTLKISRVEAEDVG*LYF*CFQTTYVPNTFGGGTKLEIK | 34 |
| VL4 | DVVMTQSPLSLPVTLGQPASISCRSSQSLVHRNGNTYLHWFQQRPGQSPR*L*LIYKVSNRFSGVPDRFSGSGSGTDFTLKISRVEAEDVGVY*F*CFQTTYVPNTFGGGTKLEIK | 35 |
| VL4-N33S | DVVMTQSPLSLPVTLGQPASISCRSSQSLVHR*S*GNTYLHWFQQRPGQSPR*L*LIYKVSNRFSGVPDRFSGSGSGTDFTLKISRVEAEDVGVYFCFQTTYVPNTFGGGTKLEIK | 36 |
| VL4-N33Q | DVVMTQSPLSLPVTLGQPASISCRSSQSLVHR*Q*GNTYLHWFQQRPGQSPR*L*LIYKVSNRFSGVPDRFSGSGSGTDFTLKISRVEAEDVGVYFCFQTTYVPNTFGGGTKLEIK | 37 |
| VL4-N33E | DVVMTQSPLSLPVTLGQPASISCRSSQSLVHR*E*GNTYLHWFQQRPGQSPR*L*LIYKVSNRFSGVPDRFSGSGSGTDFTLKISRVEAEDVGVYFCFQTTYVPNTFGGGTKLEIK | 38 |
| VL4-N33A | DVVMTQSPLSLPVTLGQPASISCRSSQSLVHR*A*GNTYLHWFQQRPGQSPR*L*LIYKVSNRFSGVPDRFSGSGSGTDFTLKISRVEAEDVGVYFCFQTTYVPNTFGGGTKLEIK | 39 |
| VL4-N33H | DVVMTQSPLSLPVTLGQPASISCRSSQSLVHR*H*GNTYLHWFQQRPGQSPR*L*LIYKVSNRFSGVPDRFSGSGSGTDFTLKISRVEAEDVGVYFCFQTTYVPNTFGGGTKLEIK | 40 |
| VL4-G34A | DVVMTQSPLSLPVTLGQPASISCRSSQSLVHR*A*GNTYLHWFQQRPGQSPR*L*LIYKVSNRFSGVPDRFSGSGSGTDFTLKISRVEAEDVGVYFCFQTTYVPNTFGGGTKLEIK | 41 |
| VL4-G34V | DVVMTQSPLSLPVTLGQPASISCRSSQSLVHR*V*GNTYLHWFQQRPGQSPR*L*LIYKVSNRFSGVPDRFSGSGSGTDFTLKISRVEAEDVGVYFCFQTTYVPNTFGGGTKLEIK | 42 |

TABLE 6B

Amino acid sequences of humanized heavy chain variable region sequences

| IgG | VH Amino Acid Sequence | SEQ ID NO |
|---|---|---|
| VH1 | QVQLQESGPGLVKPSETLSLTCTVSGFSLSSYGVSWIRQPPGKGLEWIGVIWGDGSTNYHPNLMSRVTISVDTSKNQFSLKLSSVTAADTAVYYCARLDYWGQGTSVTVSS | 43 |
| VH2 | QVQLQESGPGLVKPSETLSLTCTVSGFSLSSYGVSWVRQPPGKGLEWLGVIWGDGSTNYHPNLMSRVTISVDTSKNQFSLKLSSVTAADTAVYYCARLDYWGQGTSVTVSS | 44 |
| VH3 | QVQLQESGPGLVKPSETLSLTCTVSGFSLSSYGVSWIRQPPGKGLEWIGVIWGDGSTNYHPNLMSRLSISVDTSKNQFSLKLSSVTAADTATYYCVTLDYWGQGTSVTVSS | 45 |
| VH4 | QVQLQESGPGLVKPSETLSLTCTVSGFSLSSYGVSWVRQPPGKGLEWLGVIWGDGSTNYHPNLMSRLSISVDTSKNQFSLKLSSVTAADTAVYYCARLDYWGQGTSVTVSS | 46 |
| VH5 | QVQLQESGPGLVKPSETLSLTCTVSGFSLSSYGVSWVRQPPGKGLEWLGVIWGDGSTNYHPNLMSRLSISVDTSKNQFSLKLSSVTAADTAVYYCVTLDYWGQGTSVTVSS | 47 |
| VH6 | QVQLQESGPGLVKPSETLSLTCTVSGFSLSSYGVSWVRQPPGKGLEWLLGVIWGDGSTNYHPNLMSRLSISKDTSKNQFSLKLSSVTAADTATYYCVTLDYWGQGTSVTVSS | 48 |
| VH7 | QVQLQESGPGLVKPSETLSLTCTVSGFSLSSYGVSWIRQPPGKGLEWIGVIWGDGSTNYHPNLMSRVTISKDTSKNQVLLKLSSVTAADTAVYYCVTLDYWGQGTSVTVSS | 49 |
| VH8 | QVQLQESGPGLVKPSETLSLTCTVSGFSLSSYGVSWIRQPPGKGLEWIGVIWGDGSTNYHPNLMSRVTISKDTSKSQFSLKLSSVTAADTAVYYCVTLDYWGQGTSVTVSS | 50 |
| VH9 | QVQLQESGPGLVKPSETLSLTCTVSGFSLSSYGVSWIRQPPGKGLEWLGVIWGDGSTNYHPNLMSRVTISVDTSKSQVLFKLSSVTAADTAVYYCATLDYWGQGTSVTVSS | 51 |
| VH10 | QVQLQESGPGLVKPSETLSLTCTVSGFSLSSYGVSWIRQPPGKGLEWLGVIWGDGSTNYHPNLMSRLSISKDTSKSQVLLKLSSVTAADTAVYYCVTLDYWGQGTSVTVSS | 52 |
| VH9-D54S | QVQLQESGPGLVKPSETLSLTCTVSGFSLSSYGVSWIRQPPGKGLEWLGVIWGSGSTNYHPNLMSRVTISVDTSKSQVLFKLSSVTAADTAVYYCATLDYWGQGTSVTVSS | 53 |
| VH9-D54Q | QVQLQESGPGLVKPSETLSLTCTVSGFSLSSYGVSWIRQPPGKGLEWLGVIWGQGSTNYHPNLMSRVTISVDTSKSQVLFKLSSVTAADTAVYYCATLDYWGQGTSVTVSS | 54 |
| VH9-D54E | QVQLQESGPGLVKPSETLSLTCTVSGFSLSSYGVSWIRQPPGKGLEWLGVIWGEGSTNYHPNLMSRVTISVDTSKSQVLFKLSSVTAADTAVYYCATLDYWGQGTSVTVSS | 55 |
| VH9-D54A | QVQLQESGPGLVKPSETLSLTCTVSGFSLSSYGVSWIRQPPGKGLEWLGVIWGAGSTNYHPNLMSRVTISVDTSKSQVLFKLSSVTAADTAVYYCATLDYWGQGTSVTVSS | 56 |
| VH9-D54H | QVQLQESGPGLVKPSETLSLTCTVSGFSLSSYGVSWIRQPPGKGLEWLGVIWGHGSTNYHPNLMSRVTISVDTSKSQVLFKLSSVTAADTAVYYCATLDYWGQGTSVTVSS | 57 |
| VH9-G55A | QVQLQESGPGLVKPSETLSLTCTVSGFSLSSYGVSWIRQPPGKGLEWLGVIWGDASTNYHPNLMSRVTISVDTSKSQVLFKLSSVTAADTAVYYCATLDYWGQGTSVTVSS | 58 |
| VH9-G55V | QVQLQESGPGLVKPSETLSLTCTVSGFSLSSYGVSWIRQPPGKGLEWLGVIWGDVSTNYHPNLMSRVTISVDTSKSQVLFKLSSVTAADTAVYYCATLDYWGQGTSVTVSS | 59 |
| VH9-M64V | QVQLQESGPGLVKPSETLSLTCTVSGFSLSSYGVSWIRQPPGKGLEWLGVIWGDGSTNYHPNLVSRVTISVDTSKSQVLFKLSSVTAADTAVYYCATLDYWGQGTSVTVSS | 60 |
| VH9-M64I | QVQLQESGPGLVKPSETLSLTCTVSGFSLSSYGVSWIRQPPGKGLEWLGVIWGDGSTNYHPNLISRVTISVDTSKSQVLFKLSSVTAADTAVYYCA | 61 |

TABLE 6B-continued

Amino acid sequences of humanized heavy chain variable region sequences

| IgG | VH Amino Acid Sequence | SEQ ID NO |
|---|---|---|
|  | TLDYWGQGTSVTVSS |  |
| VH9-M64L | QVQLQESGPGLVKPSETLSLTCTVSGFSLSSYGVSWIRQPPGKGLEWLGVIWGDGSTNYHPNLLSRVTISVDTSKSQVLFKLSSVTAADTAVYYCATLDYWGQGTSVTVSS | 62 |
| VH9-M64A | QVQLQESGPGLVKPSETLSLTCTVSGFSLSSYGVSWIRQPPGKGLEWLGVIWGDGSTNYHPNLASRVTISVDTSKSQVLFKLSSVTAADTAVYYCATLDYWGQGTSVTVSS | 63 |

TABLE 6C

Amino acid sequences of VL4 CDRs

| IgG | CDR-L1 Amino Acid Sequence | SEQ ID NO | CDR-L2 Amino Acid Sequence | SEQ ID NO | CDR-L3 Amino Acid Sequence | SEQ ID NO |
|---|---|---|---|---|---|---|
| VL4 | RSSQSLVHRNGNTYLH | 20 | KVSNRFS | 21 | FQTTYVPNT | 22 |
| VL4-N33S | RSSQSLVHRSGNTYLH | 64 | KVSNRFS | 21 | FQTTYVPNT | 22 |
| VL4-N33Q | RSSQSLVHRQGNTYLH | 65 | KVSNRFS | 21 | FQTTYVPNT | 22 |
| VL4-N33E | RSSQSLVHREGNTYLH | 66 | KVSNRFS | 21 | FQTTYVPNT | 22 |
| VL4-N33A | RSSQSLVHRAGNTYLH | 67 | KVSNRFS | 21 | FQTTYVPNT | 22 |
| VL4-N33H | RSSQSLVHRHGNTYLH | 68 | KVSNRFS | 21 | FQTTYVPNT | 22 |
| VL4-G34A | RSSQSLVHRAGNTYLH | 69 | KVSNRFS | 21 | FQTTYVPNT | 22 |
| VL4-G34V | RSSQSLVHRVGNTYLH | 70 | KVSNRFS | 21 | FQTTYVPNT | 22 |

TABLE 6D

Amino acid sequences of VH9 CDRs

| IgG | CDR-H1 Amino Acid Sequence | SEQ ID NO | CDR-H2 Amino Acid Sequence | SEQ ID NO | CDR-H3 Amino Acid Sequence | SEQ ID NO |
|---|---|---|---|---|---|---|
| VH9 | GFSLSSYGVS | 17 | VIWGDGSTNYHPNLMS | 18 | LDY |  |
| VH9-D54S | GFSLSSYGVS | 17 | VIWGSGSTNYHPNLMS | 71 | LDY |  |
| VH9-D54Q | GFSLSSYGVS | 17 | VIWGQGSTNYHPNLMS | 72 | LDY |  |
| VH9-D54E | GFSLSSYGVS | 17 | VIWGEGSTNYHPNLMS | 73 | LDY |  |

TABLE 6D-continued

Amino acid sequences of VH9 CDRs

| | CDR-H1 | | CDR-H2 | | CDR-H3 | |
|---|---|---|---|---|---|---|
| IgG | Amino Acid Sequence | SEQ ID NO | Amino Acid Sequence | SEQ ID NO | Amino Acid Sequence | SEQ ID NO |
| VH9-D54A | GFSLSSYGVS | 17 | VIWGAGSTNYHPNLMS | 74 | LDY | |
| VH9-D54H | GFSLSSYGVS | 17 | VIWGHGSTNYHPNLMS | 75 | LDY | |
| VH9-G55A | GFSLSSYGVS | 17 | VIWGDASTNYHPNLMS | 76 | LDY | |
| VH9-G55V | GFSLSSYGVS | 17 | VIWGDVSTNYHPNLMS | 77 | LDY | |
| VH9-M64V | GFSLSSYGVS | 17 | VIWGDGSTNYHPNLVS | 78 | LDY | |
| VH9-M64I | GFSLSSYGVS | 17 | VIWGDGSTNYHPNLIS | 79 | LDY | |
| VH9-M64L | GFSLSSYGVS | 17 | VIWGDGSTNYHPNLLS | 80 | LDY | |
| VH9-M64A | GFSLSSYGVS | 17 | VIWGDGSTNYHPNLAS | 81 | LDY | |

The amino acid sequence identities of the humanized and parental VL sequences were compared by sequence alignment. Of the 112 residue VL sequence, VL4 had a 91.1% identity to m11-1F4, VL had a 93.8% identity to m11-1F4, and VL3 had a 98.1% identity to VL4.

Binding Affinities of Humanized Anti-Amyloid Antibodies

Table 7 provides the results of SPR assays measuring the binding of the humanized anti-amyloid antibodies to a Len(1-22) Monomer peptide. Specifically, the humanized VH9 and VL4 sequences were tested with or without additional amino acid substitutions, as indicated in the "Ligand" column of Table 7.

TABLE 7

SPR analysis of binding to Len(1-22) monomer peptide

| Ligand | Analyte | Chi$^2$ (RU$^2$) | $k_a$ (1/Ms) | $k_d$ (1/s) | $K_D$ (M) | $R_{max}$ (RU) |
|---|---|---|---|---|---|---|
| VH9 − D54S + VL4 | Len 1-22 Monomer peptide | 2.29E−02 | 2.30E+03 | 1.39E−04 | 6.05E−08 | 9.8 |
| VH9 − D54Q + VL4 | Len 1-22 Monomer peptide | 5.00E−03 | 3.90E+03 | 9.97E−04 | 2.56E−07 | 21.8 |
| VH9 − D54E + VL4 | Len 1-22 Monomer peptide | 1.04E−02 | 8.28E+03 | 1.35E−03 | 1.63E−07 | 26.8 |
| VH9 − D54A + VL4 | Len 1-22 Monomer peptide | 3.06E−02 | 3.56E+02 | 7.78E−04 | 2.18E−06 | 10.7 |
| VH9 − D54H + VL4 | Len 1-22 Monomer peptide | 1.97E−02 | 5.93E+03 | 1.39E−03 | 2.35E−07 | 15.1 |
| VH9 − G55A + VL4 | Len 1-22 Monomer peptide | 7.41E−02 | 2.82E+04 | 4.84E−04 | 1.72E−08 | 21.3 |
| VH9 − G55V + VL4 | Len 1-22 Monomer peptide | 8.29E−02 | 3.38E+03 | 1.63E−03 | 4.83E−07 | 9.8 |
| VH9 − M64V + VL4 | Len 1-22 Monomer peptide | 6.24E−02 | 2.38E+04 | 5.20E−04 | 2.18E−08 | 12.8 |
| VH9 − M64I + VL4 | Len 1-22 Monomer peptide | 1.07E−01 | 9.29E+04 | 1.92E−03 | 2.07E−08 | 6.5 |
| VH9 − M64L + VL4 | Len 1-22 Monomer peptide | 1.16E−01 | 9.30E+04 | 2.08E−03 | 2.24E−08 | 7.8 |
| VH9 − M64A + VL4 | Len 1-22 Monomer peptide | 1.50E−01 | 7.79E+04 | 1.04E−03 | 1.33E−08 | 10.5 |
| VH9 + VL4 − N33S | Len 1-22 Monomer peptide | 1.10E−01 | 1.43E+04 | 9.54E−04 | 6.69E−08 | 23.8 |
| VH9 + VL4 − N33Q | Len 1-22 Monomer peptide | 6.49E−02 | 1.33E+04 | 1.04E−03 | 7.84E−08 | 21.7 |
| VH9 + VL4 − N33E | Len 1-22 Monomer peptide | 5.27E−02 | 1.23E+04 | 1.31E−03 | 1.06E−07 | 15.4 |

TABLE 7-continued

SPR analysis of binding to Len(1-22) monomer peptide

| Ligand | Analyte | Chi$^2$ (RU$^2$) | $k_a$ (1/Ms) | $k_d$ (1/s) | $K_D$ (M) | $R_{max}$ (RU) |
|---|---|---|---|---|---|---|
| VH9 + VL4 – N33A | Len 1-22 Monomer peptide | 5.56E−02 | 1.13E+04 | 1.00E−03 | 8.85E−08 | 17.4 |
| VH9 + VL4 – N33H | Len 1-22 Monomer peptide | 7.20E−02 | 1.31E+04 | 7.43E−04 | 5.66E−08 | 17.6 |
| VH9 + VL4 – G34A | Len 1-22 Monomer peptide | 9.04E−01 | 5.95E+04 | 1.81E−03 | 3.04E−08 | 24.9 |
| VH9 + VL4 – G34V | Len 1-22 Monomer peptide | 5.83E−01 | 4.18E+04 | 1.46E−03 | 3.50E−08 | 29.7 |
| VH9 + VL4 | Len 1-22 Monomer peptide | 1.88E+00 | 6.04E+04 | 2.60E−03 | 4.30E−08 | 47.2 |

Example 4. Binding of Anti-Amyloid Antibodies Fused to Peptide p5 to Amyloid Fibrils and Cell Extracts The following example describes enzyme-linked immunosorbent assays and pulldown experiments testing the ability of humanized anti-amyloid antibodies to bind amyloid fibrils and human AL and ATTR amyloid extracts.

Materials and Methods

Anti-Amyloid Antibodies Tested

Humanized anti-amyloid antibodies were used, as described in Example 3. In addition, variants of peptide p5 with lysine ("p5") or arginine ("p5R") residues were fused to the N-terminal of the light chain and VH6/VL3-p5, VH6/VL3-p5R, VH9/VL4-p5, and VH9/VL4-p5R were generated. The amino acid sequence of p5R is set forth in SEQ ID NO:2 (see Table 1).

Europium-Linked Immunosorbent Assays (EuLISAs)

To perform europium-linked immunosorbent assays (EuLISAs), suspensions of rVλ6Wil fibrils (sonicated) were prepared at 0.83 µM in phosphate buffered saline (PBS). The fibrils were coated onto the wells of a 96-well microplate by adding 50 µL to each well. The plates dried at 37° C. overnight. The wells of the microplate were blocked by addition of Superblock (Thermofisher) (SB) using 200 µL/well, and left at 37° C. for 1 hour. The primary (test) antibody (i.e., the humanized antibody) were added, prepared in SB+0.05% tween 20 (SBT) in a 1:2 dilution series starting at 1 µM using 100 µL/well. Plates were then incubated for 1 hour at 37° C. After a wash step (plates were washed three times using PBS+0.05% tween 20), secondary antibody was added as a 1:3000 dilution of biotinylated goat anti-human IgG (Sigma) in SBT at 100 µL/well. The plates were incubated for 1 hour at 37° C. After another wash step, 100 µL/well of a 1:1000 dilution of europium/streptavidin (Perkin Elmer) in SBT was added. The plates were incubated for 1 hour at 37° C. After a final wash step, 100 µL/well of europium enhancement solution (Perkin Elmer) was added. Time-resolved fluorescence emission was detected using a microplate reader (Wallac).

Pulldown Binding Assay

To prepare synthetic amyloid fibrils from rVλ6Wil, a 1 mL-volume containing 1 mg/mL of monomer in phosphate-buffered saline (PBS), 0.01% w/v NaN3, pH7.5, was filtered through 0.2 mm pore-sized filter, added to a 15 mL conical polypropylene tube (BD BioSciences, Bedford, MA) and shaken at a 45° angle at 225 rpm for 3-5 days at 37° C. until the reaction mixture became opaque.

Purified human amyloid tissue extracts were prepared using autopsy-derived tissues from patients with light chain- (AL) or transthyretin-associated (ATTR) amyloidosis using the water flotation method as described by Pras et al. (Pras, M. et al. *J Clin Invest.* 1968 April; 47(4): 924-933) without modification. Purified amyloid material isolated in the water wash, and amyloid rich pellet, was collected and stored lyophilized at RT until used.

For the pulldown assay twenty-five microliters of 1 mg/mL AL extract, or synthetic rVλ6Wil variable domain fibrils (Wall, J. et al. *Biochemistry* 38 (1999) 14101-14108) were centrifuged in a 0.5 mL microfuge tube at 21,000×g for 5 minutes. The supernatant was discarded and pellet resuspended in 200 µL of PBS with 0.05% tween-20 (PBST). Ten microliters of a 1:100 dilution of $^{125}$I-p5+14 (~100,000 counts per minute (CPM); ~5 ng peptide) stock was added to the suspension. The mixture was rotated at RT for 1 hour. Samples were then centrifuged twice at 15,000×g for 10 minutes. Supernatants and pellets were separated after each step and the radioactivity in each was measured using a Cobra II gamma counter (Perkin Elmer) with a 1 minute acquisition. The percentage of $^{125}$I-p5+14 bound to pellet was determined as follows:

Pellet *CPM*/(Pellet *CPM*+Supernatant *CPM*)×100

Results
EuLISA

Figure 13A:
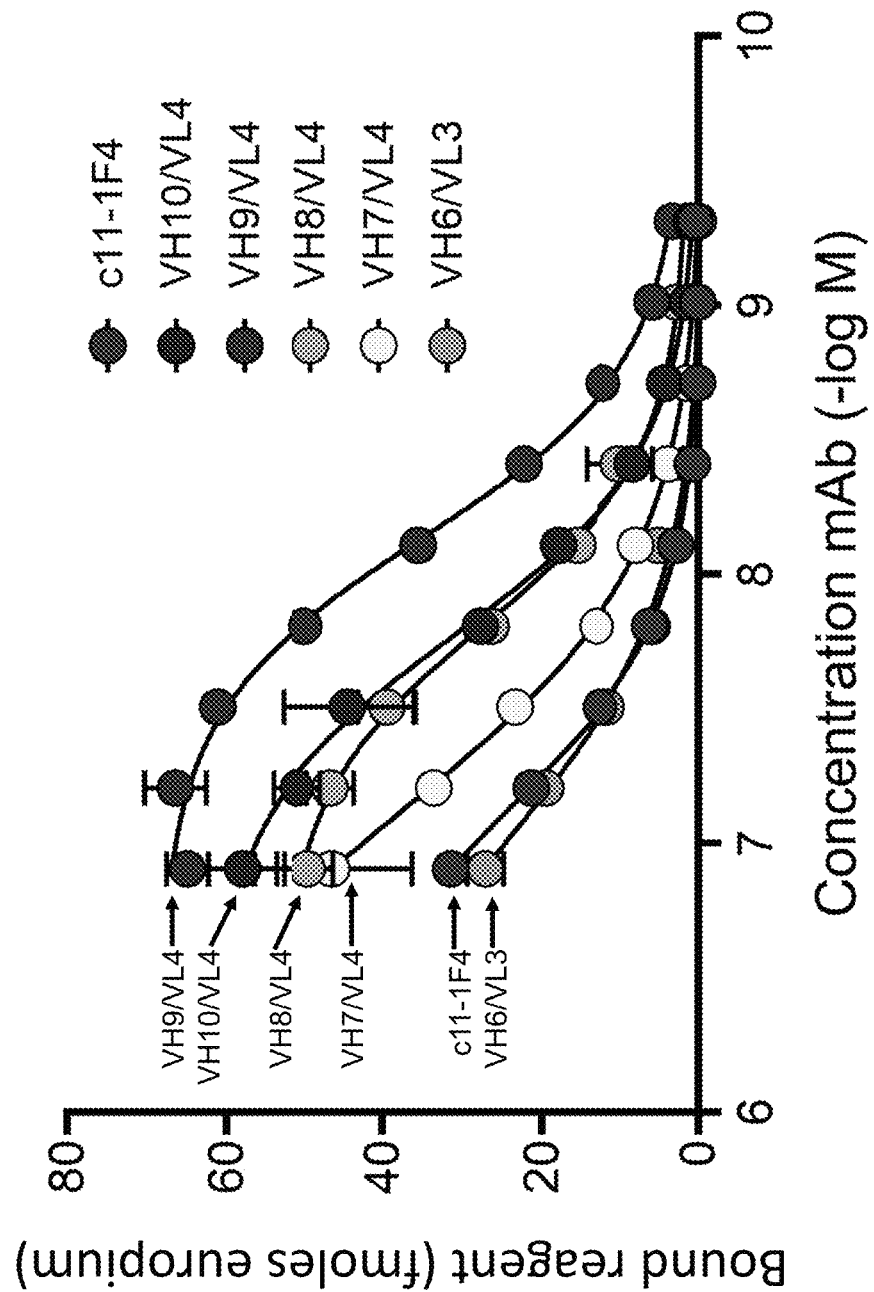
FIG. 13A shows data from an euripoium-linked immunosorbent assay (EuLISA) measuring binding of chimeric (c) 11-1F4, and humanized variants, VH10/VL4, VH9/VL4, VH8/VL4, VH7/VL4, or VH6/VL3 to synthetic rVλ6Wil light chain amyloid-like fibrils.

The ability of humanized anti-amyloid antibodies to bind rVλ6Wil fibrils was tested by EuLISA (FIG. 13A). Based on that data presented in FIG. 13A, c11-1F4 bound with an EC$_{50}$ value of ~72 nM, VH10/VL4 bound with an EC$_{50}$ value of 17 nM, VH9/VL4 bound with an EC$_{50}$ value of 7 nM, VH8/VL4 bound with an EC$_{50}$ value of 16 nM, VH7/VL4 bound with an EC$_{50}$ value of 75 nM and VH6/VL3 bound with an EC$_{50}$ value of 95 nM. VH9/VL4 exhibited increased binding relative to c11-1F4 (FIG. 13A). The VH9/VL4 antibody bound amyloid fibrils to a greater extent than VH6/VL3 did (FIG. 13A). VH9/VL4 and VH6/VL3 were chosen for additional development.

Figure 13B:
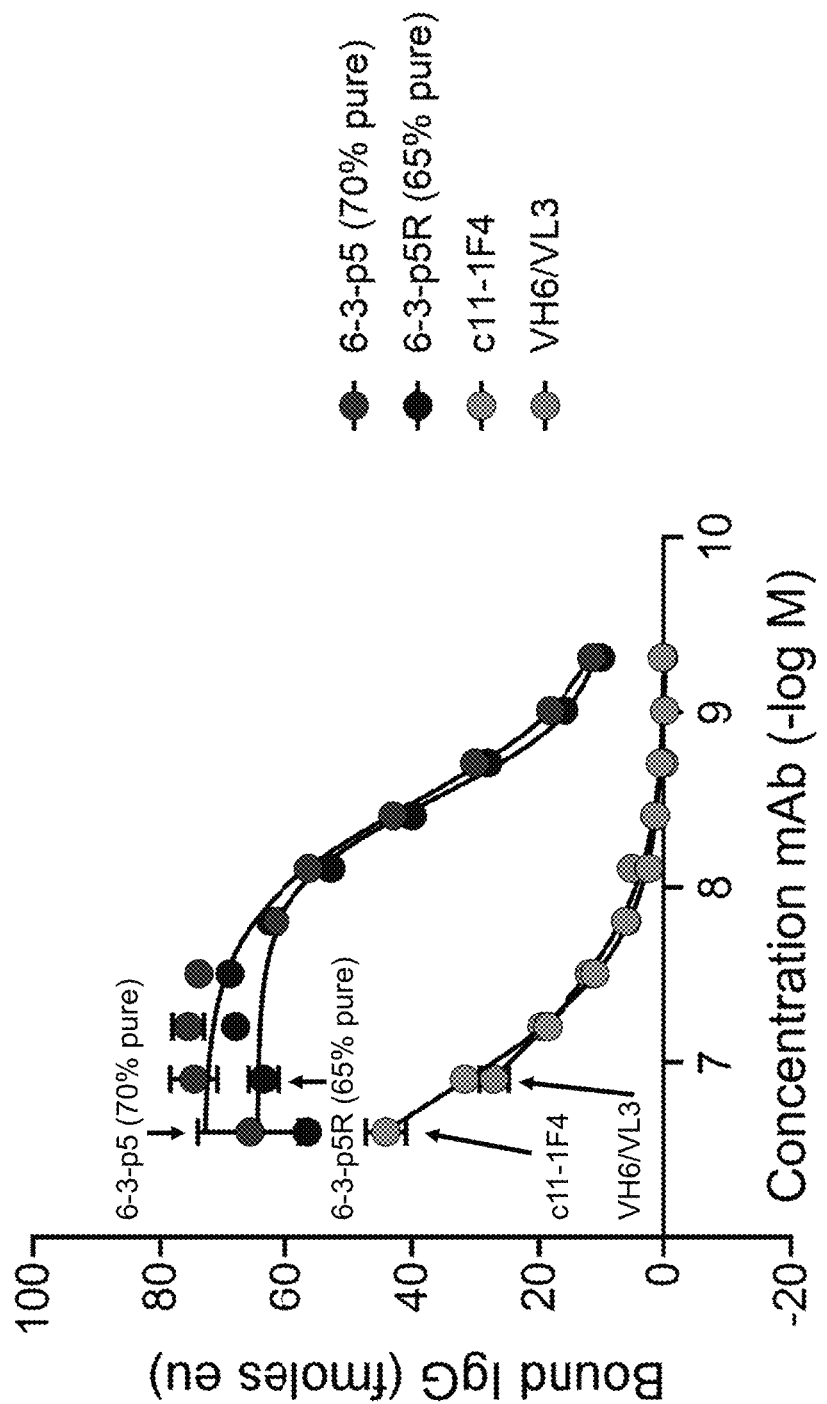
FIG. 13B shows data from an EuLISA measuring binding of 70% pure VH6/VL3-p5 (6-3-p5), 65% pure VH6/VL3-p5R (6-3-p5R), c11-1F4, or VH6/VL3 to rVλ6Wil fibrils.

As shown in FIG. 13B, addition of peptides p5 and p5R to the N-terminal of the light chain of VH6/VL3 enhanced the binding to rVλ6Wil fibrils by ~30-fold (based on EC$_{50}$). Based on that data presented in FIG. 13B, VH6/VL3-p5 bound with an EC$_{50}$ value of 3 nM, VH6/VL3-p5R bound with an EC$_{50}$ value of 3 nM, c11-1F4 bound with an EC$_{50}$ value of ~100 nM, and VH6/VL3 bound with an EC$_{50}$ value of 95 nM.

Figure 13C:
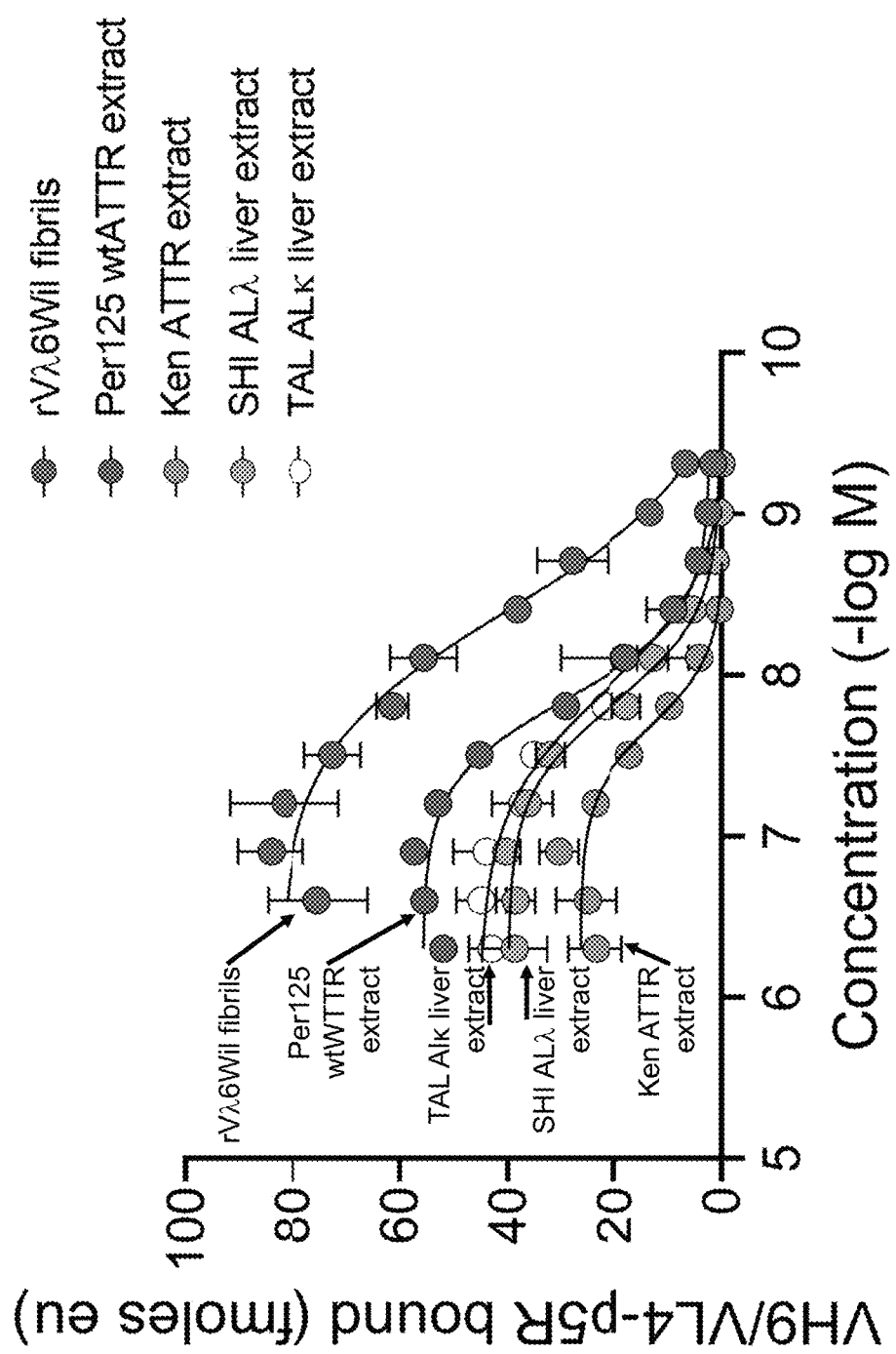
FIG. 13C shows data from an EuLISA measuring binding of VH9/VL/4-p5R to rVλ6Wil fibrils, Per125 wtATTR extract, Ken ATTR extract, SHI AL liver extract, or TAL ALκ liver extract.
Figure 13D:
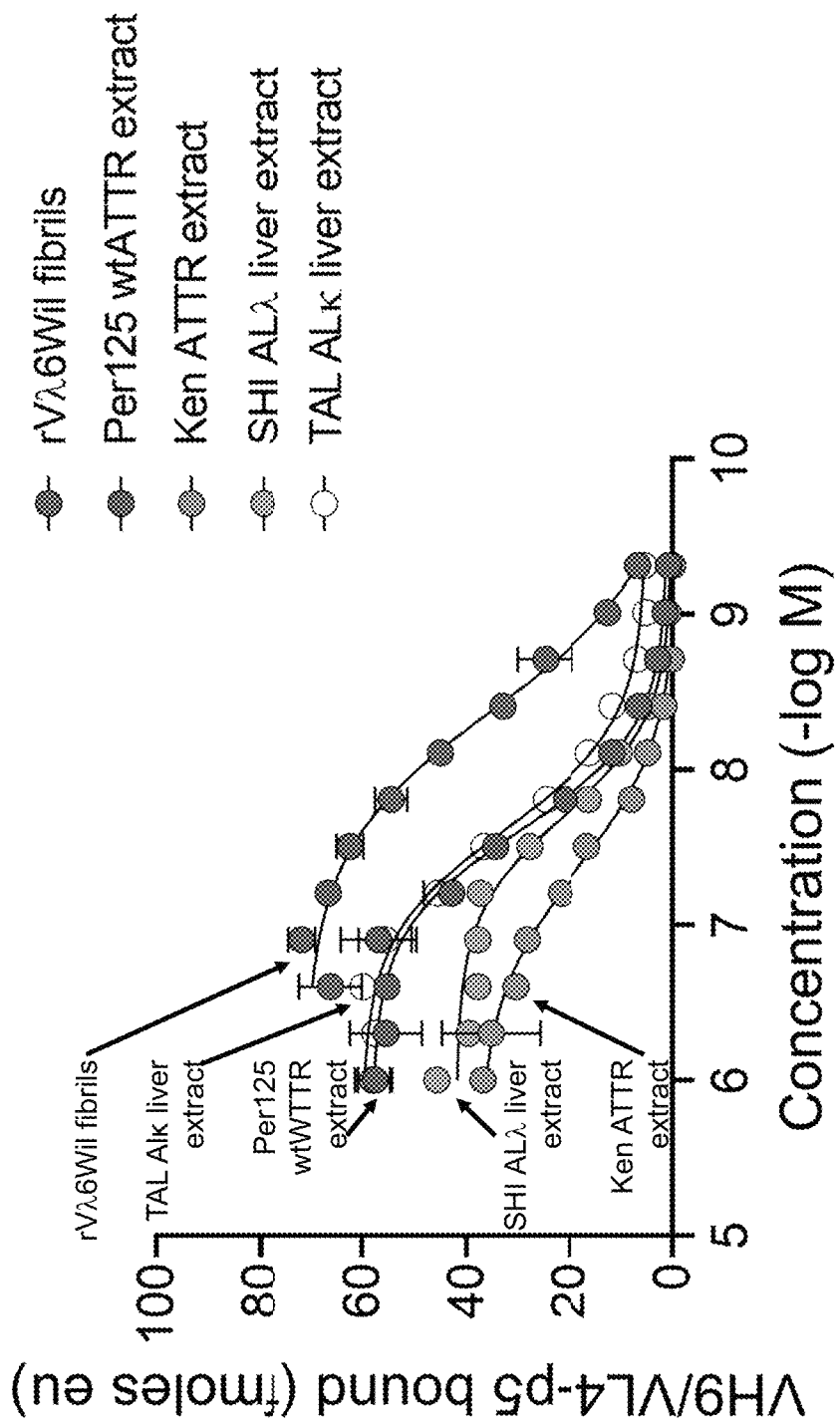
FIG. 13D shows data from an EuLISA measuring binding of VH9/VL/4-p5 to rVλ6Wil fibrils, Per125 wtATTR extract, Ken ATTR extract, SHI AL liver extract, or TAL ALκ liver extract.

In general, variants with the arginine variant of p5 (p5R) were superior to the p5 variants (FIG. 13C and FIG. 13D).

This result was consistent with previous studies of the peptides alone (Wall, J. S. et al. *PLoS One*. 2013 Jun. 4; 8(6):e66181).

Figure 13E:
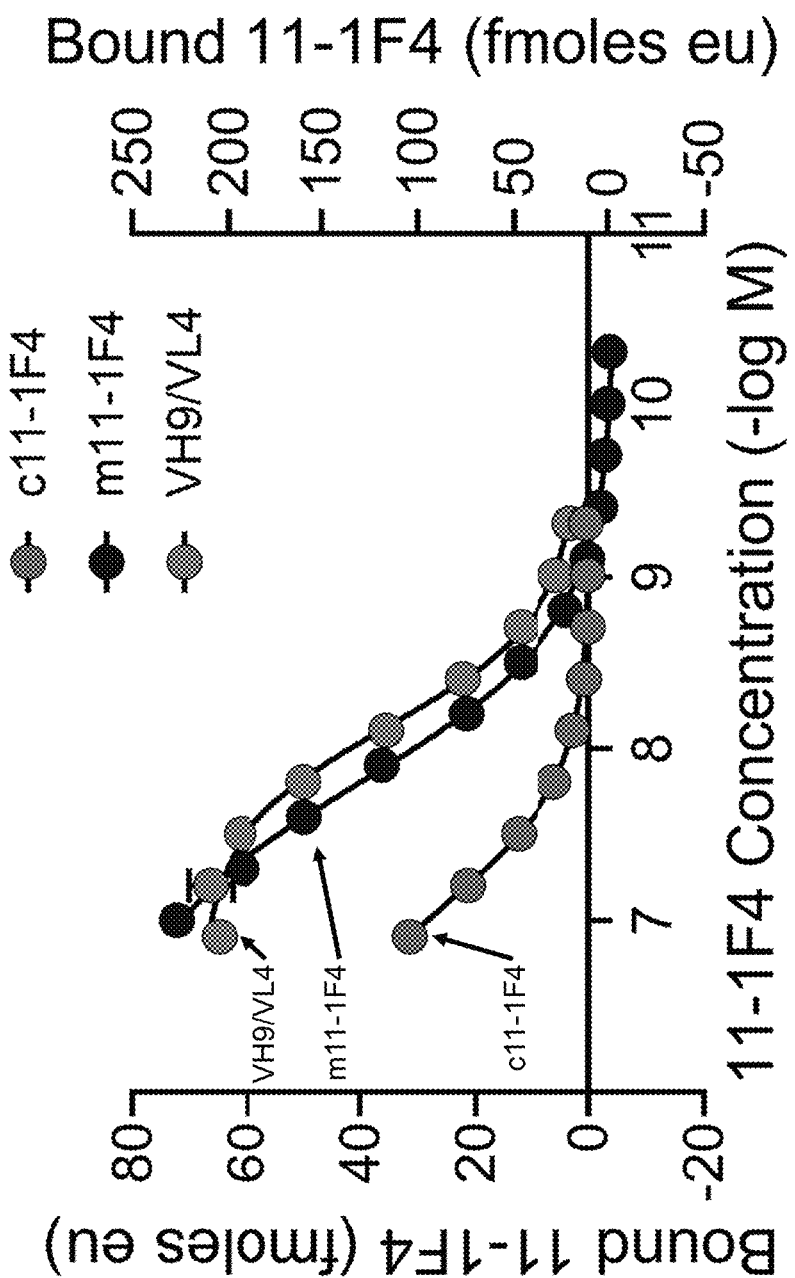
FIG. 13E shows data from an EuLISA measuring binding of c11-1F4, m11-1F4, or VH9/VL4 to rVλ6Wil fibrils.
Figure 13G:
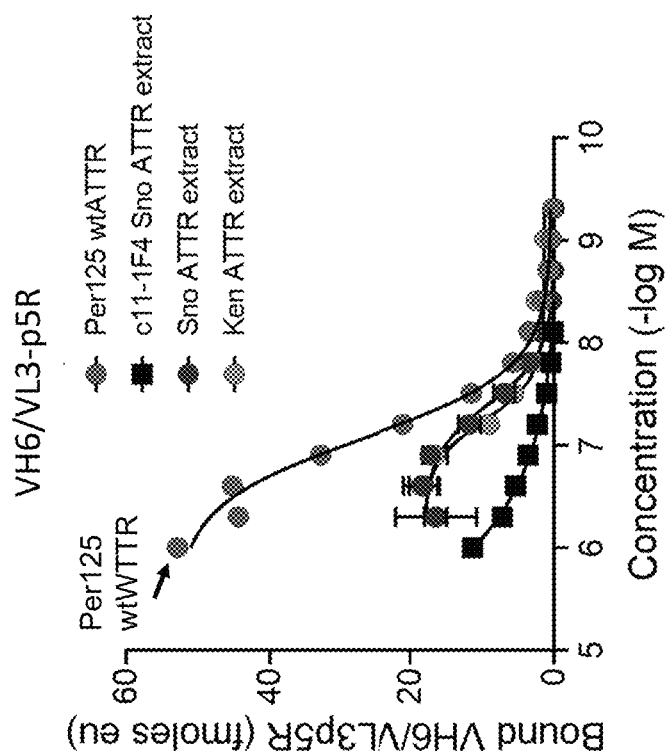

As shown in FIG. 13E, VH9/VL4 had the same reactivity to rVλ6Wil fibrils as the murine parent.

Figure 13F:
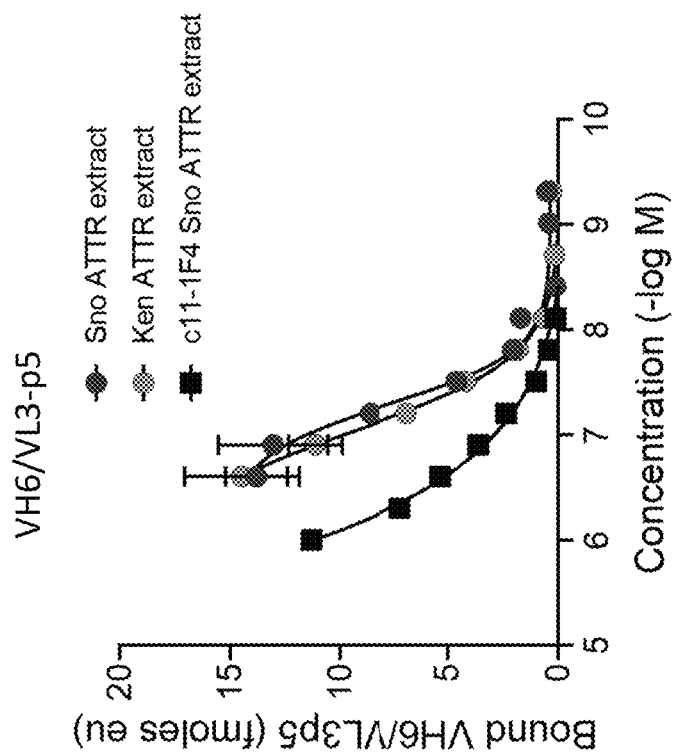
FIG. 13F shows data from an EuLISA measuring binding of VH6/VL3-p5 to Sno ATTR extract (dark gray circles) or Ken ATTR extract (light gray circles), and c11-1F4 binding to Sno ATTR extract (black squares).

As shown in FIG. 13E and FIG. 13F, both VH6/VL3-p5 and VH6/VL3-p5R exhibited binding to hATTR amyloid extracts. Based on the data in FIG. 13E and FIG. 13F, VH6/VL3-p5 bound to Sno hATTR extract with an $EC_{50}$ value of 50 nM, and to Ken ATTR extract with an $EC_{50}$ value of 90 nM, and VH6/VL3-p5R bound to Sno ATTR extract with an $EC_{50}$ value of 47 nM, Ken ATTR extract with an $EC_{50}$ value of 70 nM, and Per125 wtATTR with an $EC_{50}$ value of 85 nM.

Table 8, below, provides the results of the ELISAs measuring the ability of mIgp5, hIgG1, c11-1F4, m1 1-1F4, VH6/VL3-p5, VH9/VL4-p5, and VH9/VL4-p5R to bind rVλ6Wil fibrils, Per125 wtATTR extract, KEN hATTR extract, SHI ALλ liver extract, and TAL ALκ liver extract. For each combination of antibody and substrate, the Log-transformed $EC_{50}$, $EC_{50}$, and maximal level of binding in the assay is shown. Conditions labeled "na" were not tested.

As shown in Table 8, the humanized anti-amyloid antibodies fused to p5 or p5R were able to bind various amyloid fibrils and amyloid extracts. VH6/VL3-p5, VH9/VL4-p5, and VH9/VL4-p5R bound all fibrils and extracts tested with higher affinity (based on $EC_{50}$ measurements) than m11-1F4 and all other control antibodies. VH9/VL4-p5R generally exhibited lower $EC_{50}$s than VH9/VL4-p5 did, and VH9/VL4-p5 generally exhibited lower $EC_{50}$s than VH6/VL3-p5.

TABLE 8

EuLISA data

| Substrate | LogEC$_{50}$ | EC$_{50}$ | Max |
|---|---|---|---|
| mIgp5 | | | |
| rVλ6Wil | 8.541 | 2.88E−09 | 58.5 |
| Per125 wtATTR | 8.205 | 6.24E−09 | 31.7 |
| KEN hATTR | 8.448 | 3.56E−09 | 19.9 |
| SHI ALλ liver | 8.532 | 2.94E−09 | 24.0 |
| TAL ALκ liver | 8.472 | 3.37E−09 | 24.6 |
| hIgG1 | | | |
| rVλ6Wil | 5.894 | 1.28E−06 | 39.3 |
| Per125 wtATTR | ~7.917 | na | ~8.378 |
| KEN hATTR | ~9.061 | na | −0.8 |
| SHI ALλ liver | ~7.878 | na | 2.5 |
| TAL ALκ liver | ~3.001 | na | ~2217 |
| c11-1F4 | | | |
| rVλ6Wil | 6.536 | 2.91E−07 | 63.9 |
| Per125 wtATTR | 6.419 | 3.81E−07 | 71.12 |
| KEN hATTR | ~−1.360 | na | ~19728 |
| SHI ALλ liver | 6.592 | 2.56E−07 | 51.31 |
| TAL ALκ liver | ~0.5994 | na | ~17788 |
| m11-1F4 | | | |
| rVλ6Wil | 6.265 | 5.43E−07 | 183.6 |
| Per125 wtATTR | 5.725 | 1.88E−06 | 208.8 |
| KEN hATTR | ~2.386 | na | ~294290 |
| SHI ALλ liver | ~4.447 | na | ~1506 |
| TAL ALκ liver | ~3.028 | na | ~35143 |
| VH6/VL3-p5 | | | |
| rVλ6Wil | 8.457 | 3.49E−09 | 65.3 |
| Per125 wtATTR | 7.404 | 3.94E−08 | 33.9 |
| KEN hATTR | 7.18 | 6.61E−08 | 16.9 |
| SHI ALλ liver | 7.303 | 4.98E−08 | 29.8 |
| TAL ALκ liver | 7.314 | 4.85E−08 | 29.5 |

TABLE 8-continued

EuLISA data

| Substrate | LogEC$_{50}$ | EC$_{50}$ | Max |
|---|---|---|---|
| VH9/VL4-p5 | | | |
| rVλ6Wil | 8.393 | 4.05E−09 | 71.02 |
| Per125 wtATTR | 7.611 | 2.45E−08 | 58.06 |
| KEN hATTR | 7.357 | 4.40E−08 | 37.79 |
| SHI ALλ liver | 7.709 | 1.95E−08 | 41.93 |
| TAL ALκ liver | 7.613 | 2.44E−08 | 60.05 |
| VH9/VL4-p5R | | | |
| rVλ6Wil | 8.408 | 3.91E−09 | 82.68 |
| Per125 wtATTR | 7.855 | 1.40E−08 | 55.74 |
| KEN hATTR | 7.683 | 2.07E−08 | 26.64 |
| SHI ALλ liver | 7.823 | 1.50E−08 | 40 |
| TAL ALκ liver | 7.901 | 1.26E−08 | 45.28 |

Pulldown Experiments

The ability of anti-amyloid antibodies to immunoprecipitate substrates was examined. mIgG-p5 yielded excellent binding to Wil fibrils and amyloid extracts in the pulldown assay (FIG. 14).

The VH9/VL4 parent and variants ability to pulldown substrates was significantly decreased relative to mIgp5 as shown in Table 9, below. In Table 9, the values shown are the percent bound, and cells without data represent antibody/substrate combinations that were not tested.

TABLE 9

Summary of pulldown experiments

| Substrate | mIgp5 | VH9/VL4-p5 | VH9/VL4-p5R | VH9/VL4 | VH6/VL3-p5 |
|---|---|---|---|---|---|
| rVλ6Wil synthetic fibrils | 71 | 24.73 | 22.62 | 10.45 | 22.53 |
| Aβ(1-40) fibrils | | | | 7.38 | 20.57 |
| hIAPP fibril | | | | 2.46 | 4.82 |
| Vκ4(LEN(1-22) beads | | 54.44 | 50.17 | 57.44 | 54.87 |
| HIG ALκ1 | 10 | | | 0.19 | 0.51 |
| TAL ALκ | 37 | | | 0.72 | 0.94 |
| SHI ALλ | 34 | 1.97 | 1.22 | 0.68 | 0.60 |
| TYL ALλ | 21 | | | 0.56 | 0.69 |
| CAB ALκ4 | | | | 2.43 | 2.80 |
| SNO hATTR | 12 | | | 0.41 | 0.49 |
| KEN hATTR | 15 | | | 0.61 | 0.79 |
| wtATTR - PER125 | 31 | 1.33 | 1.12 | 1.36 | 1.00 |
| wtATTR - PER253 | 17 | | | 0.80 | 1.58 |

Example 5. Anti-Amyloid Antibodies Fused to Peptide p5 and Ex Vivo Phagocytosis

The following example describes experiments testing the ability of humanized anti-amyloid antibodies to act as opsonins. Specifically, the level of ex vivo phagocytosis of amyloid fibrils in the presence of anti-amyloid antibodies was measured.

Materials and Methods

Ex Vivo Phagocytosis

For assays of solid phase Wil fibril uptake 24 well tissue culture plates are coated with Type I rat collagen (75 μg/ml in 20 mM acetic acid, 0.4 ml) for 2 hours at room temperature, washed with 0.5 ml PBS, and coated with 20 μg/well of pHrodo Red-labeled rVλ6 fibrils (30% labeled fraction) overnight in 0.5 ml of PBS at 4° C. The wells are washed with 0.5 ml PBS, and 0.5 ml serum-free phenol red-free RPMI 1640 is added. Antibody opsonins are added at 5 µg/well, followed by immediate addition of RAW 264.7 or uninduced THP-1 cells in serum-free, phenol red-free RPMI 1640 (1.2×10$^6$ in 0.5 ml) for 4 hour incubation at 37° C. For uptake measurement cells from each well are transferred to triplicate wells of a black plastic/clear bottom 96 well microplate (Corning) for fluorescence measurement in a BioTek SynergyHT-1 microplate reader at 530/25 nm excitation and 645/40 nm emission in well-scanning mode. Background readings from wells incubated in 1 ml of medium alone are subtracted to give relative fluorescence units.

Results

The ability of humanized anti-amyloid antibodies to act as opsonins for amyloid fibrils (i.e., promote the phagocytosis of amyloid fibrils) was tested.

VH9/VL4-p5 and VH9/VL4-p5R promoted rVλ6Wil fibril uptake better than VH6/VL3-p5 and VH6/VL3-p5R did, which was consistent with the difference in ELISA binding data described above (see FIG. 15A and FIG. 15B). VH9/VL4 without peptide was approximately as good as VH6/VL3 with p5 or p5R attached and many fold better than VH6/Vl3 without peptide, as shown in FIG. 15C.

VH9/VL4 alone was a better opsonin than c11-1F4 (FIG. 15B).

VH6/VL3-p5 and VH6/VL3-p5R promoted equivalent levels of fibril uptake to the mIgp5, and performed better than c11-1F4 (FIG. 15A). VH9/VL4-p5 and VH9/VL4-p5R also promoted equivalent levels of fibril uptake to mIgp5, and performed better than c11-1F4 (FIG. 15B).

Surprisingly, the humanized anti-amyloid antibodies conjugated to the p5 or p5R peptides provided significantly better opsonization than c11-1F4.

Example 6. Pharmacokinetics Measurement of VH9/VL4 in Wild-Type Mice

The following example describes an assessment of the pharmacokinetics of VH9/VL4 administered to wild-type mice.

Materials and Methods

VH9/VL4 Administration

VH9/VL4 was labeled with $^{125}$I and administered to wild-type mice.

Results $^{125}$I-labeled VH9/VL4 was administered to wild-type mice, and the level of $^{125}$I-labeled VH9/VL4 present over time was measured (FIG. 16).

By fitting the linear elimination component (larger points in FIG. 16) to a curve, the half-life was calculated as (−0.693/-slope): $t_{1/2}$=173.5 h (7 days).

By fitting the entire curve (smaller points with dotted line in FIG. 16) to a double exponential decay, the half-life was calculated as (−0.693/-k$_2$): $t_{1/2}$=86.6 h (3.6 days).

Example 7. VH9/VL4 Biodistribution in Wild-Type Mice

The following example describes an assessment of the biodistribution of VH9/VL4 conjugated to p5 or p5R administered to wild-type mice.

Materials and Methods

VH9/VL4-p5 or VH9/VL4-p5R were administered to wild-type mice, and the level of antibody present in muscle, liver, pancreas, spleen, left and right kidneys, stomach, upper intestine, lower intestine, heart, lung, and blood were measured at 48 hours post injection (FIG. 17A and FIG. 17B).

Results

There was no evidence of specific accumulation of VH9/VL4-p5 (FIG. 17A) or VH9/VL4-p5R (FIG. 17B) in wild-type mice. The high blood pool at 48 hours was consistent with pharmacokinetic estimates for the parent IgG. The high level of lung activity was due to blood infiltration during euthanasia.

Example 8. Verification of Peptide Integrity and Plasma Stability

The following example describes SDS-PAGE and peptide capture ELISA experiments to assess the integrity and plasma stability of humanized anti-amyloid antibodies conjugated to p5 and p5R.

Materials and Methods

Peptide Capture ELISA

A peptide capture ELISA was performed to measure the stability of VH6/VL3-p5 in mice plasma. 100 nm of VH6/VL3-p5 was added to either PBS at 4° C., PBS at 37° C., EDTA plasma at 37° C., or heparin plasma at 37° C. (FIG. 18), and the amount of intact VH6/VL3-p5 present was measured over the course of 72 hours. The VH6/VL3-p5 was captured using an anti-human Fc-reactive antibody and detected using a biotinylated anti-peptide p5 mAb The signal was detected using streptavidin-conjugated HRPO and the quantified suing a plate reader.

Results

In addition, binding of anti-peptide p5 monoclonal antibodies and heparin-binding studies indicated that the peptide was present on the IgGs (data not shown).

In the moues plasma stability assay, the level of VH6/VL3-p5 did not change over 72 hours in fresh mouse plasma (FIG. 18).

Sequences

All polynucleotide sequences are depicted in the 5'→3 direction. All polypeptide sequences are depicted in the N-terminal to C-terminal direction.

11-1F4 VH sequence (SEQ ID NO: 15)
QVQLKESGPGLVAPSQSLSITCTVSGFSLSSYGVSWVRQPPGKGLEWLGVIWGDGS

TNYHPNLMSRLSISKDISKSQVLFKLNSLQTDDTATYYCVTLDYWGQGTSVTVSS 11-1F4 VL sequence (SEQ ID NO: 16)
DVVMTQTPLSLPVSLGDQASISCRSSQSLVHRNGNTYLHWYLQKPGQSPKLLIYKV

SNRFSGVPDRFSGSGSGTDFTLKISRVEAEDLGLYFCFQTTYVPNTFGGGTKLEIK

-continued

```
11-1F4 CDR-H1 sequence
                                           (SEQ ID NO: 17)
GFSLSSYGVS 11-1F4 CDR-H2 sequence
                                           (SEQ ID NO: 18)
VIWGDGSTNYHPNLMS 11-1F4 CDR-H3 sequence
                                           (SEQ ID NO: 19)
LDY 11-1F4 CDR-L1 sequence
                                           (SEQ ID NO: 20)
RSSQSLVHRNGNTYLH 11-1F4 CDR-L2 sequence
                                           (SEQ ID NO: 21)
KVSNRFS 11-1F4 CDR-L3 sequence
                                           (SEQ ID NO: 22)
FQTTYVPNT 5' spacer sequence
                                           (SEQ ID NO: 23)
AQAGQAGQAQGGGYS 3' spacer sequence
                                           (SEQ ID NO: 24)
VTPTV Igp5 light chain construct
                                           (SEQ ID NO: 25)
AQAGQAGQAQGGGYSKAQKAQAKQAKQAQKAQKAQAKQAKQVTPTVDVVMTQ

TPLSLPVSLGDQASISCRSSQSLVHRNGNTYLHWYLQKPGQSPKLLIYKVSNRFSGVP

DRFSGSGSGTDFTLKISRVEAEDLGLYFCFQTTYVPNTFGGGTKLEIK p5-3'spacer-11-1F4 VL sequence
                                           (SEQ ID NO: 26)
KAQKAQAKQAKQAQKAQKAQAKQAKQVTPTVDVVMTQTPLSLPVSLGDQASISCR

SSQSLVHRNGNTYLHWYLQKPGQSPKLLIYKVSNRFSGVPDRFSGSGSGTDFTLKISR

VEAEDLGLYFCFQTTYVPNTFGGGTKLEIK

Linker sequence
                                           (SEQ ID NO: 27)
GGGYS IGKV2-30*02- Human germline sequence
                                           (SEQ ID NO: 28)
DVVMTQSPLSLPVTLGQPASISCRSSQSLVHSDGNTYLNWFQQRPGQSPRRLIYKVSN

RDSGVPDRFSGSGSGTDFTLKISRVEAEDVGVYYCMQGTHWPP

Human VL acceptor sequence
                                           (SEQ ID NO: 29)
DVVMTQSPLSLPVTLGQPASISCRSSQSLVHSDGNTYLNWFQQRPGQSPRRLIYKVSN

RDSGVPDRFSGSGSGTDFTLKISRVEAEDVGVYYCFQTTYVPNTFGGGTKLEIK

IGHV4-4*08- Human germline sequence
                                           (SEQ ID NO: 30)
QVQLQESGPGLVKPSETLSLTCTVSGGSISSYYWSWIRQPPGKGLEWIGYIYTSGSTN

YNPSLKSRVTISVDTSKNQFSLKLSSVTAADTAVYYCAR

Human VL acceptor sequence
                                           (SEQ ID NO: 31)
QVQLQESGPGLVKPSETLSLTCTVSGGSISSYYWSWIRQPPGKGLEWIGYIYTSGSTN

YNPSLKSRVTISVDTSKNQFSLKLSSVTAADTAVYYCARLDYWGQGTSVTVSS

VL1
                                           (SEQ ID NO: 32)
DVVMTQSPLSLPVTLGQPASISCRSSQSLVHRNGNTYLHWFQQRPGQSPRRLIYKVS

NRFSGVPDRFSGSGSGTDFTLKISRVEAEDVGVYYCFQTTYVPNTFGGGTKLEIK
```

-continued

VL2

(SEQ ID NO: 33)
DVVMTQSPLSLPVTLGQPASISCRSSQSLVHRNGNTYLHWYLQRPGQSPRRLIYKVS

NRFSGVPDRFSGSGSGTDFTLKISRVEAEDVGVYYCFQTTYVPNTFGGGTKLEIK

VL3

(SEQ ID NO: 34)
DVVMTQSPLSLPVTLGQPASISCRSSQSLVHRNGNTYLHWYLQRPGQSPRLLIYKVS

NRFSGVPDRFSGSGSGTDFTLKISRVEAEDVGLYFCFQTTYVPNTFGGGTKLEIK

VL4

(SEQ ID NO: 35)
DVVMTQSPLSLPVTLGQPASISCRSSQSLVHRNGNTYLHWFQQRPGQSPRLLIYKVS

NRFSGVPDRFSGSGSGTDFTLKISRVEAEDVGVYFCFQTTYVPNTFGGGTKLEIK

VL4-N33S (SEQ ID NO: 36)
DVVMTQSPLSLPVTLGQPASISCRSSQSLVHRSGNTYLHWFQQRPGQSPRLLIYKVSN

RFSGVPDRFSGSGSGTDFTLKISRVEAEDVGVYFCFQTTYVPNTFGGGTKLEIK

VL4-N33Q (SEQ ID NO: 37)
DVVMTQSPLSLPVTLGQPASISCRSSQSLVHRQGNTYLHWFQQRPGQSPRLLIYKVS

NRFSGVPDRFSGSGSGTDFTLKISRVEAEDVGVYFCFQTTYVPNTFGGGTKLEIK

VL4-N33E (SEQ ID NO: 38)
DVVMTQSPLSLPVTLGQPASISCRSSQSLVHREGNTYLHWFQQRPGQSPRLLIYKVSN

RFSGVPDRFSGSGSGTDFTLKISRVEAEDVGVYFCFQTTYVPNTFGGGTKLEIK

VL4-N33A (SEQ ID NO: 39)
DVVMTQSPLSLPVTLGQPASISCRSSQSLVHRAGNTYLHWFQQRPGQSPRLLIYKVS

NRFSGVPDRFSGSGSGTDFTLKISRVEAEDVGVYFCFQTTYVPNTFGGGTKLEIK

VL4-N33H (SEQ ID NO: 40)
DVVMTQSPLSLPVTLGQPASISCRSSQSLVHRHGNTYLHWFQQRPGQSPRLLIYKVS

NRFSGVPDRFSGSGSGTDFTLKISRVEAEDVGVYFCFQTTYVPNTFGGGTKLEIK

VL4-G34A (SEQ ID NO: 41)
DVVMTQSPLSLPVTLGQPASISCRSSQSLVHRAGNTYLHWFQQRPGQSPRLLIYKVS

NRFSGVPDRFSGSGSGTDFTLKISRVEAEDVGVYFCFQTTYVPNTFGGGTKLEIK

VL4-G34V (SEQ ID NO: 42)
DVVMTQSPLSLPVTLGQPASISCRSSQSLVHRVGNTYLHWFQQRPGQSPRLLIYKVS

NRFSGVPDRFSGSGSGTDFTLKISRVEAEDVGVYFCFQTTYVPNTFGGGTKLEIK

VH1

(SEQ ID NO: 43)
QVQLQESGPGLVKPSETLSLTCTVSGFSLSSYGVSWIRQPPGKGLEWIGVIWGDSTN

YHPNLMSRVTISVDTSKNQFSLKLSSVTAADTAVYYCARLDYWGQGTSVTVSS

VH2

(SEQ ID NO: 44)
QVQLQESGPGLVKPSETLSLTCTVSGFSLSSYGVSWVRQPPGKGLEWLGVIWGDGST

NYHPNLMSRVTISVDTSKNQFSLKLSSVTAADTAVYYCARLDYWGQGTSVTVSS

VH3

(SEQ ID NO: 45)
QVQLQESGPGLVKPSETLSLTCTVSGFSLSSYGVSWIRQPPGKGLEWIGVIWGDSTN

YHPNLMSRLSISVDTSKNQFSLKLSSVTAADTATYYCVTLDYWGQGTSVTVSS

-continued

VH4
(SEQ ID NO: 46)
QVQLQESGPGLVKPSETLSLTCTVSGFSLSSYGVSWVRQPPGKGLEWLGVIWGDST

NYHPNLMSRLSISVDTSKNQFSLKLSSVTAADTAVYYCARLDYWGQGTSVTVSS

VH5
(SEQ ID NO: 47)
QVQLQESGPGLVKPSETLSLTCTVSGFSLSSYGVSWVRQPPGKGLEWLGVIWGDST

NYHPNLMSRLSISVDTSKNQFSLKLSSVTAADTAVYYCVTLDYWGQGTSVTVSS

VH6
(SEQ ID NO: 48)
QVQLQESGPGLVKPSETLSLTCTVSGFSLSSYGVSWVRQPPGKGLEWLGVIWGDST

NYHPNLMSRLSISKDTSKNQFSLKLSSVTAADTATYYCVTLDYWGQGTSVTVSS

VH7
(SEQ ID NO: 49)
QVQLQESGPGLVKPSETLSLTCTVSGFSLSSYGVSWIRQPPGKGLEWIGVIWGDSTN

YHPNLMSRVTISKDTSKNQVLLKLSSVTAADTAVYYCVTLDYWGQGTSVTVSS

VH8
(SEQ ID NO: 50)
QVQLQESGPGLVKPSETLSLTCTVSGFSLSSYGVSWIRQPPGKGLEWIGVIWGDSTN

YHPNLMSRVTISKDTSKQFSLKLSSVTAADTAVYYCVTLDYWGQGTSVTVSS

VH9
(SEQ ID NO: 51)
QVQLQESGPGLVKPSETLSLTCTVSGFSLSSYGVSWIRQPPGKGLEWLGVIWGDST

NYHPNLMSRVTISVDTSKSQVLFKLSSVTAADTAVYYCATLDYWGQGTSVTVSS

VH10
(SEQ ID NO: 52)
QVQLQESGPGLVKPSETLSLTCTVSGFSLSSYGVSWIRQPPGKGLEWLGVIWGDST

NYHPNLMSRLSISKDTSKSQVLLKLSSVTAADTAVYYCVTLDYWGQGTSVTVSS

VH9-D54S
(SEQ ID NO: 53)
QVQLQESGPGLVKPSETLSLTCTVSGFSLSSYGVSWIRQPPGKGLEWLGVIWGSGST

NYHPNLMSRVTISVDTSKSQVLFKLSSVTAADTAVYYCATLDYWGQGTSVTVSS

VH9-D54Q
(SEQ ID NO: 54)
QVQLQESGPGLVKPSETLSLTCTVSGFSLSSYGVSWIRQPPGKGLEWLGVIWGQGST

NYHPNLMSRVTISVDTSKSQVLFKLSSVTAADTAVYYCATLDYWGQGTSVTVSS

VH9-D54E
(SEQ ID NO: 55)
QVQLQESGPGLVKPSETLSLTCTVSGFSLSSYGVSWIRQPPGKGLEWLGVIWGEGST

NYHPNLMSRVTISVDTSKSQVLFKLSSVTAADTAVYYCATLDYWGQGTSVTVSS

VH9-D54A
(SEQ ID NO: 56)
QVQLQESGPGLVKPSETLSLTCTVSGFSLSSYGVSWIRQPPGKGLEWLGVIWGAGST

NYHPNLMSRVTISVDTSKSQVLFKLSSVTAADTAVYYCATLDYWGQGTSVTVSS

VH9-D54H
(SEQ ID NO: 57)
QVQLQESGPGLVKPSETLSLTCTVSGFSLSSYGVSWIRQPPGKGLEWLGVIWGHGST

NYHPNLMSRVTISVDTSKSQVLFKLSSVTAADTAVYYCATLDYWGQGTSVTVSS

VH9-G55A
(SEQ ID NO: 58)
QVQLQESGPGLVKPSETLSLTCTVSGFSLSSYGVSWIRQPPGKGLEWLGVIWGDAST

NYHPNLMSRVTISVDTSKSQVLFKLSSVTAADTAVYYCATLDYWGQGTSVTVSS

-continued

VH9-G55V
(SEQ ID NO: 59)
QVQLQESGPGLVKPSETLSLTCTVSGFSLSSYGVSWIRQPPGKGLEWLGVIWGDVST
NYHPNLMSRVTISVDTSKSQVLFKLSSVTAADTAVYYCATLDYWGQGTSVTVSS

VH9-M64V
(SEQ ID NO: 60)
QVQLQESGPGLVKPSETLSLTCTVSGFSLSSYGVSWIRQPPGKGLEWLGVIWGDGST
NYHPNLVSRVTISVDTSKSQVLFKLSSVTAADTAVYYCATLDYWGQGTSVTVSS

VH9-M64I
(SEQ ID NO: 61)
QVQLQESGPGLVKPSETLSLTCTVSGFSLSSYGVSWIRQPPGKGLEWLGVIWGDGST
NYHPNLISRVTISVDTSKSQVLFKLSSVTAADTAVYYCATLDYWGQGTSVTVSS

VH9-M64L
(SEQ ID NO: 62)
QVQLQESGPGLVKPSETLSLTCTVSGFSLSSYGVSWIRQPPGKGLEWLGVIWGDGST
NYHPNLLSRVTISVDTSKSQVLFKLSSVTAADTAVYYCATLDYWGQGTSVTVSS

VH9-M64A
(SEQ ID NO: 63)
QVQLQESGPGLVKPSETLSLTCTVSGFSLSSYGVSWIRQPPGKGLEWLGVIWGDGST
NYHPNLASRVTISVDTSKSQVLFKLSSVTAADTAVYYCATLDYWGQGTSVTVSS

VL4-N33S CDR-L1
(SEQ ID NO: 64)
RSSQSLVHRSGNTYLH

VL4-N33Q CDR-L1
(SEQ ID NO: 65)
RSSQSLVHRQGNTYLH

VL4-N33E CDR-L1
(SEQ ID NO: 66)
RSSQSLVHREGNTYLH

VL4-N33A CDR-L1
(SEQ ID NO: 67)
RSSQSLVHRAGNTYLH

VL4-N33H CDR-L1
(SEQ ID NO: 68)
RSSQSLVHRHGNTYLH

VL4-G34A CDR-L1
(SEQ ID NO: 69)
RSSQSLVHRAGNTYLH

VL4-G34V CDR-L1
(SEQ ID NO: 70)
RSSQSLVHRVGNTYLH

VH9-D54S CDR-H2
(SEQ ID NO: 71)
VIWGSGSTNYHPNLMS

VH9-D54Q CDR-H2
(SEQ ID NO: 72)
VIWGQGSTNYHPNLMS

VH9-D54E CDR-H2
(SEQ ID NO: 73)
VIWGEGSTNYHPNLMS

VH9-D54A CDR-H2
(SEQ ID NO: 74)
VIWGAGSTNYHPNLMS

VH9-D54H CDR-H2
(SEQ ID NO: 75)
VIWGHGSTNYHPNLMS

VH9-G55A CDR-H2
(SEQ ID NO: 76)
VIWGDASTNYHPNLMS

-continued

```
VH9-G55V CDR-H2
                                                          (SEQ ID NO: 77)
VIWGDVSTNYHPNLMS

VH9-M64V CDR-H2
                                                          (SEQ ID NO: 78)
VIWGDGSTNYHPNLVS

VH9-M64I CDR-H2
                                                          (SEQ ID NO: 79)
VIWGDGSTNYHPNLIS

VH9-M64L CDR-H2
                                                          (SEQ ID NO: 80)
VIWGDGSTNYHPNLLS

VH9-M64A CDR-H2
                                                          (SEQ ID NO: 81)
VIWGDGSTNYHPNLAS

N-terminus of Ig light chain
                                                          (SEQ ID NO: 82)
DVVMTQTP
```

---

We claim:

1. A method of treating a subject having systemic amyloidosis, comprising administering to the subject an effective amount of a modified immunoglobulin, comprising:
   (i) an amyloid-reactive peptide comprising an amino acid sequence selected from the group consisting of SEQ ID NOs: 1-14; and
   (ii) an Ig antibody or functional fragment thereof that binds to human amyloid fibrils, wherein the Ig antibody or functional fragment thereof comprises a light chain comprising a light chain variable region (VL) and a heavy chain comprising a heavy chain variable region (VH), wherein:
   a) the VL comprises a CDR-L1 comprising the amino acid sequence set forth in any one of SEQ ID NOs: 64-70, a CDR-L2 comprising the amino acid sequence set forth in SEQ ID NO: 21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in SEQ ID NO:18, and a CDR-H3 comprising the amino acid sequence LDY;
   b) the VL comprises a CDR-L1 comprising the amino acid sequence set forth in SEQ ID NO: 20; a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in any one of SEQ ID NOs: 71-81; and a CDR-H3 comprising the amino acid sequence LDY; or
   c) the VL comprises a CDR-L1 comprising the amino acid sequence set forth in any one of SEQ ID NOs: 64-70, a CDR-L2 comprising the amino acid sequence set forth in SEQ ID NO: 21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in any one of SEQ ID NOs: 71-81; and a CDR-H3 comprising the amino acid sequence LDY; and
   wherein the modified immunoglobulin is a fusion protein comprising the Ig antibody or functional fragment thereof joined to the amyloid-reactive peptide.

2. The method of claim 1, wherein the amyloid-reactive peptide comprises an amino acid sequence set forth in SEQ ID NO:1 or SEQ ID NO:2.

3. The method of claim 1, wherein the Ig antibody or functional fragment thereof comprises human framework sequences.

4. The method of claim 1, wherein the Ig antibody or functional fragment thereof comprises a human Fc region.

5. The method of claim 1, wherein the Ig antibody is humanized.

6. The method of claim 1, wherein the VL comprises one or more amino acid residues selected from the group consisting of:
   a. Tyr at position 36;
   b. Leu at position 37;
   c. Leu at position 46;
   d. Leu at position 85; and
   e. Phe at position 87,
   wherein the amino acid positions are numbered according to the numbering system of Kabat.

7. The method of claim 1, wherein the systemic amyloidosis is selected from the group consisting of AL, AH, Aβ2M, ATTR, transthyretin, AA, AApoAI, AApoAII, AGel, ALys, ALEct2, AFib, or ACys.

8. The method of claim 1, wherein the subject is a human.

9. The method of claim 1,
   wherein the VH comprises one or more amino acid residues selected from the group consisting of:
   a. Val at position 37;
   b. Leu at position 48;
   c. Leu at position 67;
   d. Ser at position 68;
   e. Lys at position 71;
   f. Ser at position 76;
   g. Val at position 78;
   h. Leu at position 79;

i. Phe at position 80;
j. Thr at position 89;
k. Val at position 93; and
l. Thr at position 94,
   wherein the amino acid positions are numbered according to the numbering system of Kabat.

10. The method of claim 9, wherein the VL comprises Leu at position 46 and Phe at position 87, and the VH comprises Leu at position 48, Ser at position 76, Val at position 78, Leu at position 79, Phe at position 80, and Thr at position 94.

11. The method of claim 10, wherein the VL comprises the amino acid sequence set forth in SEQ ID NO:36 and the VH comprises the amino acid sequence set forth in SEQ ID NO:55.

12. The method of claim 11, wherein the amyloid-reactive peptide comprises the amino acid sequence set forth in SEQ ID NO:2.

13. A method of identifying an amyloid deposit of a systemic amyloidosis in a subject, comprising:
   administering a modified immunoglobulin to the subject, wherein the modified immunoglobulin comprises:
   (i) an amyloid-reactive peptide comprising an amino acid sequence selected from the group consisting of SEQ ID NOs: 1-14; and
   (ii) an Ig antibody or functional fragment thereof that binds to human amyloid fibrils, wherein the Ig antibody or functional fragment thereof comprises a light chain comprising a light chain variable region (VL) and a heavy chain comprising a heavy chain variable region (VH), wherein:
   a) the VL comprises a CDR-L1 comprising the amino acid sequence set forth in any one of SEQ ID NOs: 64-70, a CDR-L2 comprising the amino acid sequence set forth in SEQ ID NO: 21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in SEQ ID NO:18, and a CDR-H3 comprising the amino acid sequence LDY;
   b) the VL comprises a CDR-L1 comprising the amino acid sequence set forth in SEQ ID NO: 20; a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in any one of SEQ ID NOs: 71-81; and a CDR-H3 comprising the amino acid sequence LDY; or
   c) the VL comprises a CDR-L1 comprising the amino acid sequence set forth in any one of SEQ ID NOs: 64-70, a CDR-L2 comprising the amino acid sequence set forth in SEQ ID NO: 21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in any one of SEQ ID NOs: 71-81; and a CDR-H3 comprising the amino acid sequence LDY; and
   wherein the modified immunoglobulin is a fusion protein comprising the Ig antibody or functional fragment thereof joined to the amyloid-reactive peptide, and
   wherein the modified immunoglobulin comprises a detectable label; and
   detecting a signal from the modified immunoglobulin.

14. The method of claim 13, wherein the VL comprises a CDR-L1 comprising the amino acid sequence set forth in SEQ ID NO:64, a CDR-L2 comprising the amino acid sequence set forth in SEQ ID NO:21, and a CDR-L3 comprising the amino acid sequence set forth in SEQ ID NO:22, and the VH comprises a CDR-H1 comprising the amino acid sequence set forth in SEQ ID NO:17, a CDR-H2 comprising the amino acid sequence set forth in SEQ ID NO:73, and a CDR-H3 comprising the amino acid sequence LDY.

15. The method of claim 13, wherein the amyloid-reactive peptide comprises the amino acid sequence set forth in SEQ ID NO:2.

16. The method of claim 13, wherein the Ig antibody or functional fragment thereof comprises human framework sequences.

17. The method of claim 13, wherein the Ig antibody or functional fragment thereof comprises a human Fc region.

18. The method of claim 13, wherein the VL comprises the amino acid sequence set forth in SEQ ID NO:36 and the VH comprises the amino acid sequence set forth in SEQ ID NO:55.

19. The method of claim 13, wherein the systemic amyloidosis is selected from the group consisting of AL, AH, Aβ2M, ATTR, transthyretin, AA, AApoAI, AApoAII, AGel, ALys, ALEct2, AFib, or ACys.

20. The method of claim 13, wherein the subject is a human.

21. The method of claim 13, wherein the VH comprises one or more amino acid residues selected from the group consisting of:
   a. Val at position 37;
   b. Leu at position 48;
   c. Leu at position 67;
   d. Ser at position 68;
   e. Lys at position 71;
   f. Ser at position 76;
   g. Val at position 78;
   h. Leu at position 79;
   i. Phe at position 80;
   j. Thr at position 89;
   k. Val at position 93; and
   l. Thr at position 94,
   wherein the amino acid positions are numbered according to the numbering system of Kabat.

22. The method of claim 21, wherein the VL comprises Leu at position 46 and Phe at position 87, and the VH comprises Leu at position 48, Ser at position 76, Val at position 78, Leu at position 79, Phe at position 80, and Thr at position 94.

23. The method of claim 12, wherein the systemic amyloidosis is AL.

24. The method of claim 12, wherein the systemic amyloidosis is ATTR.

* * * * *

```
                        SEQUENCE LISTING

Sequence total quantity: 83
SEQ ID NO: 1            moltype = AA  length = 26
FEATURE                 Location/Qualifiers
REGION                  1..26
                        note = Synthetic Construct
source                  1..26
                        mol_type = protein
                        organism = synthetic construct
SEQUENCE: 1
KAQKAQAKQA KQAQKAQKAQ AKQAKQ                                         26

SEQ ID NO: 2            moltype = AA  length = 26
FEATURE                 Location/Qualifiers
REGION                  1..26
                        note = Synthetic Construct
source                  1..26
                        mol_type = protein
                        organism = synthetic construct
SEQUENCE: 2
RAQRAQARQA RQAQRAQRAQ ARQARQ                                         26

SEQ ID NO: 3            moltype = AA  length = 26
FEATURE                 Location/Qualifiers
REGION                  1..26
                        note = Synthetic Construct
source                  1..26
                        mol_type = protein
                        organism = synthetic construct
SEQUENCE: 3
GAQGAQAGQA GQAQGAQGAQ AGQAGQ                                         26

SEQ ID NO: 4            moltype = AA  length = 15
FEATURE                 Location/Qualifiers
REGION                  1..15
                        note = Synthetic Construct
source                  1..15
                        mol_type = protein
                        organism = synthetic construct
SEQUENCE: 4
KAKAKAKAKA KAKAK                                                     15

SEQ ID NO: 5            moltype = AA  length = 29
FEATURE                 Location/Qualifiers
REGION                  1..29
                        note = Synthetic Construct
source                  1..29
                        mol_type = protein
                        organism = synthetic construct
SEQUENCE: 5
KAQAKAQAKA QAKAQAKAQA KAQAKAQAK                                      29
```

```
SEQ ID NO: 6              moltype = AA   length = 26
FEATURE                   Location/Qualifiers
REGION                    1..26
                          note = Synthetic Construct
source                    1..26
                          mol_type = protein
                          organism = synthetic construct
SEQUENCE: 6
KAQQAQAKQA QQAQKAQQAQ AKQAQQ                                        26

SEQ ID NO: 7              moltype = AA   length = 26
FEATURE                   Location/Qualifiers
REGION                    1..26
                          note = Synthetic Construct
source                    1..26
                          mol_type = protein
                          organism = synthetic construct
SEQUENCE: 7
QAQKAQAQQA KQAQQAQKAQ AQQAKQ                                        26

SEQ ID NO: 8              moltype = AA   length = 26
FEATURE                   Location/Qualifiers
REGION                    1..26
                          note = Synthetic Construct
source                    1..26
                          mol_type = protein
                          organism = synthetic construct
SEQUENCE: 8
KAQKAQAKQA KQAQKAQKAQ AKQAKQ                                        26

SEQ ID NO: 9              moltype = AA   length = 26
FEATURE                   Location/Qualifiers
REGION                    1..26
                          note = Synthetic Construct
source                    1..26
                          mol_type = protein
                          organism = synthetic construct
SEQUENCE: 9
KTVKTVTKVT KVTVKTVKTV TKVTKV                                        26

SEQ ID NO: 10             moltype = AA   length = 18
FEATURE                   Location/Qualifiers
REGION                    1..18
                          note = Synthetic Construct
source                    1..18
                          mol_type = protein
                          organism = synthetic construct
SEQUENCE: 10
VYKVKTKVKT KVKTKVKT                                                 18

SEQ ID NO: 11             moltype = AA   length = 30
FEATURE                   Location/Qualifiers
REGION                    1..30
                          note = Synthetic Construct
source                    1..30
                          mol_type = protein
                          organism = synthetic construct
SEQUENCE: 11
AQAYSKAQKA QAKQAKQAQK AQKAQAKAKQ                                    30

SEQ ID NO: 12             moltype = AA   length = 31
FEATURE                   Location/Qualifiers
REGION                    1..31
                          note = Synthetic Construct
source                    1..31
                          mol_type = protein
                          organism = synthetic construct
SEQUENCE: 12
AQAYARAQRA QARQARQAQR AQRAQARQAR Q                                  31

SEQ ID NO: 13             moltype = AA   length = 40
FEATURE                   Location/Qualifiers
REGION                    1..40
                          note = Synthetic Construct
source                    1..40
                          mol_type = protein
                          organism = synthetic construct
SEQUENCE: 13
```

```
KAQKAQAKQA KQAQKAQKAQ AKQAKQAQKA QKAQAKQAKQ                          40

SEQ ID NO: 14           moltype = AA   length = 40
FEATURE                 Location/Qualifiers
REGION                  1..40
                        note = Synthetic Construct
source                  1..40
                        mol_type = protein
                        organism = synthetic construct
SEQUENCE: 14
RAQRAQARQA RQAQRAQRAQ ARQARQAQRA QRAQARQARQ                          40

SEQ ID NO: 15           moltype = AA   length = 111
FEATURE                 Location/Qualifiers
REGION                  1..111
                        note = Synthetic Construct
source                  1..111
                        mol_type = protein
                        organism = synthetic construct
SEQUENCE: 15
QVQLKESGPG LVAPSQSLSI TCTVSGFSLS SYGVSWVRQP PGKGLEWLGV IWGDGSTNYH    60
PNLMSRLSIS KDISKSQVLF KLNSLQTDDT ATYYCVTLDY WGQGTSVTVS S            111

SEQ ID NO: 16           moltype = AA   length = 112
FEATURE                 Location/Qualifiers
REGION                  1..112
                        note = Synthetic Construct
source                  1..112
                        mol_type = protein
                        organism = synthetic construct
SEQUENCE: 16
DVVMTQTPLS LPVSLGDQAS ISCRSSQSLV HRNGNTYLHW YLQKPGQSPK LLIYKVSNRF    60
SGVPDRFSGS GSGTDFTLKI SRVEAEDLGL YFCFQTTYVP NTFGGGTKLE IK           112

SEQ ID NO: 17           moltype = AA   length = 10
FEATURE                 Location/Qualifiers
REGION                  1..10
                        note = Synthetic Construct
source                  1..10
                        mol_type = protein
                        organism = synthetic construct
SEQUENCE: 17
GFSLSSYGVS                                                           10

SEQ ID NO: 18           moltype = AA   length = 16
FEATURE                 Location/Qualifiers
REGION                  1..16
                        note = Synthetic Construct
source                  1..16
                        mol_type = protein
                        organism = synthetic construct
SEQUENCE: 18
VIWGDGSTNY HPNLMS                                                    16

SEQ ID NO: 19           moltype =      length =
SEQUENCE: 19
000

SEQ ID NO: 20           moltype = AA   length = 16
FEATURE                 Location/Qualifiers
REGION                  1..16
                        note = Synthetic Construct
source                  1..16
                        mol_type = protein
                        organism = synthetic construct
SEQUENCE: 20
RSSQSLVHRN GNTYLH                                                    16

SEQ ID NO: 21           moltype = AA   length = 7
FEATURE                 Location/Qualifiers
REGION                  1..7
                        note = Synthetic Construct
source                  1..7
                        mol_type = protein
                        organism = synthetic construct
SEQUENCE: 21
KVSNRFS                                                               7

SEQ ID NO: 22           moltype = AA   length = 9
```

```
FEATURE                 Location/Qualifiers
REGION                  1..9
                        note = Synthetic Construct
source                  1..9
                        mol_type = protein
                        organism = synthetic construct
SEQUENCE: 22
FQTTYVPNT                                                                  9

SEQ ID NO: 23           moltype = AA  length = 15
FEATURE                 Location/Qualifiers
REGION                  1..15
                        note = Synthetic Construct
source                  1..15
                        mol_type = protein
                        organism = synthetic construct
SEQUENCE: 23
AQAGQAGQAQ GGGYS                                                          15

SEQ ID NO: 24           moltype = AA  length = 5
FEATURE                 Location/Qualifiers
REGION                  1..5
                        note = Synthetic Construct
source                  1..5
                        mol_type = protein
                        organism = synthetic construct
SEQUENCE: 24
VTPTV                                                                      5

SEQ ID NO: 25           moltype = AA  length = 158
FEATURE                 Location/Qualifiers
REGION                  1..158
                        note = Synthetic Construct
source                  1..158
                        mol_type = protein
                        organism = synthetic construct
SEQUENCE: 25
AQAGQAGQAQ GGGYSKAQKA QAKQAKQAQK AQKAQAKQAK QVTPTVDVVM TQTPLSLPVS          60
LGDQASISCR SSQSLVHRNG NTYLHWYLQK PGQSPKLLIY KVSNRFSGVP DRFSGSGSGT         120
DFTLKISRVE AEDLGLYFCF QTTYVPNTFG GGTKLEIK                                 158

SEQ ID NO: 26           moltype = AA  length = 143
FEATURE                 Location/Qualifiers
REGION                  1..143
                        note = Synthetic Construct
source                  1..143
                        mol_type = protein
                        organism = synthetic construct
SEQUENCE: 26
KAQKAQAKQA KQAQKAQKAQ AKQAKQVTPT VDVVMTQTPL SLPVSLGDQA SISCRSSQSL          60
VHRNGNTYLH WYLQKPGQSP KLLIYKVSNR FSGVPDRFSG SGSGTDFTLK ISRVEAEDLG         120
LYFCFQTTYV PNTFGGGTKL EIK                                                 143

SEQ ID NO: 27           moltype = AA  length = 5
FEATURE                 Location/Qualifiers
REGION                  1..5
                        note = Synthetic Construct
source                  1..5
                        mol_type = protein
                        organism = synthetic construct
SEQUENCE: 27
GGGYS                                                                      5

SEQ ID NO: 28           moltype = AA  length = 101
FEATURE                 Location/Qualifiers
REGION                  1..101
                        note = Synthetic Construct
source                  1..101
                        mol_type = protein
                        organism = synthetic construct
SEQUENCE: 28
DVVMTQSPLS LPVTLGQPAS ISCRSSQSLV HSDGNTYLNW FQQRPGQSPR RLIYKVSNRD          60
SGVPDRFSGS GSGTDFTLKI SRVEAEDVGV YYCMQGTHWP P                             101

SEQ ID NO: 29           moltype = AA  length = 112
FEATURE                 Location/Qualifiers
REGION                  1..112
                        note = Synthetic Construct
source                  1..112
```

```
                            mol_type = protein
                            organism = synthetic construct
SEQUENCE: 29
DVVMTQSPLS LPVTLGQPAS ISCRSSQSLV HSDGNTYLNW FQQRPGQSPR RLIYKVSNRD    60
SGVPDRFSGS GSGTDFTLKI SRVEAEDVGV YYCFQTTYVP NTFGGGTKLE IK           112

SEQ ID NO: 30               moltype = AA   length = 97
FEATURE                     Location/Qualifiers
REGION                      1..97
                            note = Synthetic Construct
source                      1..97
                            mol_type = protein
                            organism = synthetic construct
SEQUENCE: 30
QVQLQESGPG LVKPSETLSL TCTVSGGSIS SYYWSWIRQP PGKGLEWIGY IYTSGSTNYN    60
PSLKSRVTIS VDTSKNQFSL KLSSVTAADT AVYYCAR                            97

SEQ ID NO: 31               moltype = AA   length = 111
FEATURE                     Location/Qualifiers
REGION                      1..111
                            note = Synthetic Construct
source                      1..111
                            mol_type = protein
                            organism = synthetic construct
SEQUENCE: 31
QVQLQESGPG LVKPSETLSL TCTVSGGSIS SYYWSWIRQP PGKGLEWIGY IYTSGSTNYN    60
PSLKSRVTIS VDTSKNQFSL KLSSVTAADT AVYYCARLDY WGQGTSVTVS S            111

SEQ ID NO: 32               moltype = AA   length = 112
FEATURE                     Location/Qualifiers
REGION                      1..112
                            note = Synthetic Construct
source                      1..112
                            mol_type = protein
                            organism = synthetic construct
SEQUENCE: 32
DVVMTQSPLS LPVTLGQPAS ISCRSSQSLV HRNGNTYLHW FQQRPGQSPR RLIYKVSNRF    60
SGVPDRFSGS GSGTDFTLKI SRVEAEDVGV YYCFQTTYVP NTFGGGTKLE IK           112

SEQ ID NO: 33               moltype = AA   length = 112
FEATURE                     Location/Qualifiers
REGION                      1..112
                            note = Synthetic Construct
source                      1..112
                            mol_type = protein
                            organism = synthetic construct
SEQUENCE: 33
DVVMTQSPLS LPVTLGQPAS ISCRSSQSLV HRNGNTYLHW YLQRPGQSPR RLIYKVSNRF    60
SGVPDRFSGS GSGTDFTLKI SRVEAEDVGV YYCFQTTYVP NTFGGGTKLE IK           112

SEQ ID NO: 34               moltype = AA   length = 112
FEATURE                     Location/Qualifiers
REGION                      1..112
                            note = Synthetic Construct
source                      1..112
                            mol_type = protein
                            organism = synthetic construct
SEQUENCE: 34
DVVMTQSPLS LPVTLGQPAS ISCRSSQSLV HRNGNTYLHW YLQRPGQSPR LLIYKVSNRF    60
SGVPDRFSGS GSGTDFTLKI SRVEAEDVGL YFCFQTTYVP NTFGGGTKLE IK           112

SEQ ID NO: 35               moltype = AA   length = 112
FEATURE                     Location/Qualifiers
REGION                      1..112
                            note = Synthetic Construct
source                      1..112
                            mol_type = protein
                            organism = synthetic construct
SEQUENCE: 35
DVVMTQSPLS LPVTLGQPAS ISCRSSQSLV HRNGNTYLHW FQQRPGQSPR LLIYKVSNRF    60
SGVPDRFSGS GSGTDFTLKI SRVEAEDVGV YFCFQTTYVP NTFGGGTKLE IK           112

SEQ ID NO: 36               moltype = AA   length = 112
FEATURE                     Location/Qualifiers
REGION                      1..112
                            note = Synthetic Construct
source                      1..112
                            mol_type = protein
                            organism = synthetic construct
```

-continued

```
SEQUENCE: 36
DVVMTQSPLS LPVTLGQPAS ISCRSSQSLV HRSGNTYLHW FQQRPGQSPR LLIYKVSNRF    60
SGVPDRFSGS GSGTDFTLKI SRVEAEDVGV YFCFQTTYVP NTFGGGTKLE IK           112

SEQ ID NO: 37           moltype = AA   length = 112
FEATURE                 Location/Qualifiers
REGION                  1..112
                        note = Synthetic Construct
source                  1..112
                        mol_type = protein
                        organism = synthetic construct
SEQUENCE: 37
DVVMTQSPLS LPVTLGQPAS ISCRSSQSLV HRQGNTYLHW FQQRPGQSPR LLIYKVSNRF    60
SGVPDRFSGS GSGTDFTLKI SRVEAEDVGV YFCFQTTYVP NTFGGGTKLE IK           112

SEQ ID NO: 38           moltype = AA   length = 112
FEATURE                 Location/Qualifiers
REGION                  1..112
                        note = Synthetic Construct
source                  1..112
                        mol_type = protein
                        organism = synthetic construct
SEQUENCE: 38
DVVMTQSPLS LPVTLGQPAS ISCRSSQSLV HREGNTYLHW FQQRPGQSPR LLIYKVSNRF    60
SGVPDRFSGS GSGTDFTLKI SRVEAEDVGV YFCFQTTYVP NTFGGGTKLE IK           112

SEQ ID NO: 39           moltype = AA   length = 112
FEATURE                 Location/Qualifiers
REGION                  1..112
                        note = Synthetic Construct
source                  1..112
                        mol_type = protein
                        organism = synthetic construct
SEQUENCE: 39
DVVMTQSPLS LPVTLGQPAS ISCRSSQSLV HRAGNTYLHW FQQRPGQSPR LLIYKVSNRF    60
SGVPDRFSGS GSGTDFTLKI SRVEAEDVGV YFCFQTTYVP NTFGGGTKLE IK           112

SEQ ID NO: 40           moltype = AA   length = 112
FEATURE                 Location/Qualifiers
REGION                  1..112
                        note = Synthetic Construct
source                  1..112
                        mol_type = protein
                        organism = synthetic construct
SEQUENCE: 40
DVVMTQSPLS LPVTLGQPAS ISCRSSQSLV HRHGNTYLHW FQQRPGQSPR LLIYKVSNRF    60
SGVPDRFSGS GSGTDFTLKI SRVEAEDVGV YFCFQTTYVP NTFGGGTKLE IK           112

SEQ ID NO: 41           moltype = AA   length = 112
FEATURE                 Location/Qualifiers
REGION                  1..112
                        note = Synthetic Construct
source                  1..112
                        mol_type = protein
                        organism = synthetic construct
SEQUENCE: 41
DVVMTQSPLS LPVTLGQPAS ISCRSSQSLV HRAGNTYLHW FQQRPGQSPR LLIYKVSNRF    60
SGVPDRFSGS GSGTDFTLKI SRVEAEDVGV YFCFQTTYVP NTFGGGTKLE IK           112

SEQ ID NO: 42           moltype = AA   length = 112
FEATURE                 Location/Qualifiers
REGION                  1..112
                        note = Synthetic Construct
source                  1..112
                        mol_type = protein
                        organism = synthetic construct
SEQUENCE: 42
DVVMTQSPLS LPVTLGQPAS ISCRSSQSLV HRVGNTYLHW FQQRPGQSPR LLIYKVSNRF    60
SGVPDRFSGS GSGTDFTLKI SRVEAEDVGV YFCFQTTYVP NTFGGGTKLE IK           112

SEQ ID NO: 43           moltype = AA   length = 111
FEATURE                 Location/Qualifiers
REGION                  1..111
                        note = Synthetic Construct
source                  1..111
                        mol_type = protein
                        organism = synthetic construct
SEQUENCE: 43
QVQLQESGPG LVKPSETLSL TCTVSGFSLS SYGVSWIRQP PGKGLEWIGV IWGDGSTNYH    60
```

```
PNLMSRVTIS VDTSKNQFSL KLSSVTAADT AVYYCARLDY WGQGTSVTVS S            111

SEQ ID NO: 44           moltype = AA   length = 111
FEATURE                 Location/Qualifiers
REGION                  1..111
                        note = Synthetic Construct
source                  1..111
                        mol_type = protein
                        organism = synthetic construct
SEQUENCE: 44
QVQLQESGPG LVKPSETLSL TCTVSGFSLS SYGVSWVRQP PGKGLEWLGV IWGDGSTNYH   60
PNLMSRVTIS VDTSKNQFSL KLSSVTAADT AVYYCARLDY WGQGTSVTVS S            111

SEQ ID NO: 45           moltype = AA   length = 111
FEATURE                 Location/Qualifiers
REGION                  1..111
                        note = Synthetic Construct
source                  1..111
                        mol_type = protein
                        organism = synthetic construct
SEQUENCE: 45
QVQLQESGPG LVKPSETLSL TCTVSGFSLS SYGVSWIRQP PGKGLEWIGV IWGDGSTNYH   60
PNLMSRLSIS VDTSKNQFSL KLSSVTAADT ATYYCVTLDY WGQGTSVTVS S            111

SEQ ID NO: 46           moltype = AA   length = 111
FEATURE                 Location/Qualifiers
REGION                  1..111
                        note = Synthetic Construct
source                  1..111
                        mol_type = protein
                        organism = synthetic construct
SEQUENCE: 46
QVQLQESGPG LVKPSETLSL TCTVSGFSLS SYGVSWVRQP PGKGLEWLGV IWGDGSTNYH   60
PNLMSRLSIS VDTSKNQFSL KLSSVTAADT AVYYCARLDY WGQGTSVTVS S            111

SEQ ID NO: 47           moltype = AA   length = 111
FEATURE                 Location/Qualifiers
REGION                  1..111
                        note = Synthetic Construct
source                  1..111
                        mol_type = protein
                        organism = synthetic construct
SEQUENCE: 47
QVQLQESGPG LVKPSETLSL TCTVSGFSLS SYGVSWVRQP PGKGLEWLGV IWGDGSTNYH   60
PNLMSRLSIS VDTSKNQFSL KLSSVTAADT AVYYCVTLDY WGQGTSVTVS S            111

SEQ ID NO: 48           moltype = AA   length = 111
FEATURE                 Location/Qualifiers
REGION                  1..111
                        note = Synthetic Construct
source                  1..111
                        mol_type = protein
                        organism = synthetic construct
SEQUENCE: 48
QVQLQESGPG LVKPSETLSL TCTVSGFSLS SYGVSWVRQP PGKGLEWLGV IWGDGSTNYH   60
PNLMSRLSIS KDTSKNQFSL KLSSVTAADT ATYYCVTLDY WGQGTSVTVS S            111

SEQ ID NO: 49           moltype = AA   length = 111
FEATURE                 Location/Qualifiers
REGION                  1..111
                        note = Synthetic Construct
source                  1..111
                        mol_type = protein
                        organism = synthetic construct
SEQUENCE: 49
QVQLQESGPG LVKPSETLSL TCTVSGFSLS SYGVSWIRQP PGKGLEWIGV IWGDGSTNYH   60
PNLMSRVTIS KDTSKNQVLL KLSSVTAADT AVYYCVTLDY WGQGTSVTVS S            111

SEQ ID NO: 50           moltype = AA   length = 111
FEATURE                 Location/Qualifiers
REGION                  1..111
                        note = Synthetic Construct
source                  1..111
                        mol_type = protein
                        organism = synthetic construct
SEQUENCE: 50
QVQLQESGPG LVKPSETLSL TCTVSGFSLS SYGVSWIRQP PGKGLEWIGV IWGDGSTNYH   60
PNLMSRVTIS KDTSKSQFSL KLSSVTAADT AVYYCVTLDY WGQGTSVTVS S            111
```

```
SEQ ID NO: 51              moltype = AA   length = 111
FEATURE                    Location/Qualifiers
REGION                     1..111
                           note = Synthetic Construct
source                     1..111
                           mol_type = protein
                           organism = synthetic construct
SEQUENCE: 51
QVQLQESGPG LVKPSETLSL TCTVSGFSLS SYGVSWIRQP PGKGLEWLGV IWGDGSTNYH    60
PNLMSRVTIS VDTSKSQVLF KLSSVTAADT AVYYCATLDY WGQGTSVTVS S            111

SEQ ID NO: 52              moltype = AA   length = 111
FEATURE                    Location/Qualifiers
REGION                     1..111
                           note = Synthetic Construct
source                     1..111
                           mol_type = protein
                           organism = synthetic construct
SEQUENCE: 52
QVQLQESGPG LVKPSETLSL TCTVSGFSLS SYGVSWIRQP PGKGLEWLGV IWGDGSTNYH    60
PNLMSRLSIS KDTSKSQVLL KLSSVTAADT AVYYCVTLDY WGQGTSVTVS S            111

SEQ ID NO: 53              moltype = AA   length = 111
FEATURE                    Location/Qualifiers
REGION                     1..111
                           note = Synthetic Construct
source                     1..111
                           mol_type = protein
                           organism = synthetic construct
SEQUENCE: 53
QVQLQESGPG LVKPSETLSL TCTVSGFSLS SYGVSWIRQP PGKGLEWLGV IWGSGSTNYH    60
PNLMSRVTIS VDTSKSQVLF KLSSVTAADT AVYYCATLDY WGQGTSVTVS S            111

SEQ ID NO: 54              moltype = AA   length = 111
FEATURE                    Location/Qualifiers
REGION                     1..111
                           note = Synthetic Construct
source                     1..111
                           mol_type = protein
                           organism = synthetic construct
SEQUENCE: 54
QVQLQESGPG LVKPSETLSL TCTVSGFSLS SYGVSWIRQP PGKGLEWLGV IWGQGSTNYH    60
PNLMSRVTIS VDTSKSQVLF KLSSVTAADT AVYYCATLDY WGQGTSVTVS S            111

SEQ ID NO: 55              moltype = AA   length = 111
FEATURE                    Location/Qualifiers
REGION                     1..111
                           note = Synthetic Construct
source                     1..111
                           mol_type = protein
                           organism = synthetic construct
SEQUENCE: 55
QVQLQESGPG LVKPSETLSL TCTVSGFSLS SYGVSWIRQP PGKGLEWLGV IWGEGSTNYH    60
PNLMSRVTIS VDTSKSQVLF KLSSVTAADT AVYYCATLDY WGQGTSVTVS S            111

SEQ ID NO: 56              moltype = AA   length = 111
FEATURE                    Location/Qualifiers
REGION                     1..111
                           note = Synthetic Construct
source                     1..111
                           mol_type = protein
                           organism = synthetic construct
SEQUENCE: 56
QVQLQESGPG LVKPSETLSL TCTVSGFSLS SYGVSWIRQP PGKGLEWLGV IWGAGSTNYH    60
PNLMSRVTIS VDTSKSQVLF KLSSVTAADT AVYYCATLDY WGQGTSVTVS S            111

SEQ ID NO: 57              moltype = AA   length = 111
FEATURE                    Location/Qualifiers
REGION                     1..111
                           note = Synthetic Construct
source                     1..111
                           mol_type = protein
                           organism = synthetic construct
SEQUENCE: 57
QVQLQESGPG LVKPSETLSL TCTVSGFSLS SYGVSWIRQP PGKGLEWLGV IWGHGSTNYH    60
PNLMSRVTIS VDTSKSQVLF KLSSVTAADT AVYYCATLDY WGQGTSVTVS S            111

SEQ ID NO: 58              moltype = AA   length = 111
FEATURE                    Location/Qualifiers
```

```
REGION                       1..111
                             note = Synthetic Construct
source                       1..111
                             mol_type = protein
                             organism = synthetic construct
SEQUENCE: 58
QVQLQESGPG LVKPSETLSL TCTVSGFSLS SYGVSWIRQP PGKGLEWLGV IWGDASTNYH     60
PNLMSRVTIS VDTSKSQVLF KLSSVTAADT AVYYCATLDY WGQGTSVTVS S             111

SEQ ID NO: 59                moltype = AA   length = 111
FEATURE                      Location/Qualifiers
REGION                       1..111
                             note = Synthetic Construct
source                       1..111
                             mol_type = protein
                             organism = synthetic construct
SEQUENCE: 59
QVQLQESGPG LVKPSETLSL TCTVSGFSLS SYGVSWIRQP PGKGLEWLGV IWGDVSTNYH     60
PNLMSRVTIS VDTSKSQVLF KLSSVTAADT AVYYCATLDY WGQGTSVTVS S             111

SEQ ID NO: 60                moltype = AA   length = 111
FEATURE                      Location/Qualifiers
REGION                       1..111
                             note = Synthetic Construct
source                       1..111
                             mol_type = protein
                             organism = synthetic construct
SEQUENCE: 60
QVQLQESGPG LVKPSETLSL TCTVSGFSLS SYGVSWIRQP PGKGLEWLGV IWGDGSTNYH     60
PNLVSRVTIS VDTSKSQVLF KLSSVTAADT AVYYCATLDY WGQGTSVTVS S             111

SEQ ID NO: 61                moltype = AA   length = 111
FEATURE                      Location/Qualifiers
REGION                       1..111
                             note = Synthetic Construct
source                       1..111
                             mol_type = protein
                             organism = synthetic construct
SEQUENCE: 61
QVQLQESGPG LVKPSETLSL TCTVSGFSLS SYGVSWIRQP PGKGLEWLGV IWGDGSTNYH     60
PNLISRVTIS VDTSKSQVLF KLSSVTAADT AVYYCATLDY WGQGTSVTVS S             111

SEQ ID NO: 62                moltype = AA   length = 111
FEATURE                      Location/Qualifiers
REGION                       1..111
                             note = Synthetic Construct
source                       1..111
                             mol_type = protein
                             organism = synthetic construct
SEQUENCE: 62
QVQLQESGPG LVKPSETLSL TCTVSGFSLS SYGVSWIRQP PGKGLEWLGV IWGDGSTNYH     60
PNLLSRVTIS VDTSKSQVLF KLSSVTAADT AVYYCATLDY WGQGTSVTVS S             111

SEQ ID NO: 63                moltype = AA   length = 111
FEATURE                      Location/Qualifiers
REGION                       1..111
                             note = Synthetic Construct
source                       1..111
                             mol_type = protein
                             organism = synthetic construct
SEQUENCE: 63
QVQLQESGPG LVKPSETLSL TCTVSGFSLS SYGVSWIRQP PGKGLEWLGV IWGDGSTNYH     60
PNLASRVTIS VDTSKSQVLF KLSSVTAADT AVYYCATLDY WGQGTSVTVS S             111

SEQ ID NO: 64                moltype = AA   length = 16
FEATURE                      Location/Qualifiers
REGION                       1..16
                             note = Synthetic Construct
source                       1..16
                             mol_type = protein
                             organism = synthetic construct
SEQUENCE: 64
RSSQSLVHRS GNTYLH                                                     16

SEQ ID NO: 65                moltype = AA   length = 16
FEATURE                      Location/Qualifiers
REGION                       1..16
                             note = Synthetic Construct
source                       1..16
```

```
                        mol_type = protein
                        organism = synthetic construct
SEQUENCE: 65
RSSQSLVHRQ GNTYLH                                                    16

SEQ ID NO: 66           moltype = AA   length = 16
FEATURE                 Location/Qualifiers
REGION                  1..16
                        note = Synthetic Construct
source                  1..16
                        mol_type = protein
                        organism = synthetic construct
SEQUENCE: 66
RSSQSLVHRE GNTYLH                                                    16

SEQ ID NO: 67           moltype = AA   length = 16
FEATURE                 Location/Qualifiers
REGION                  1..16
                        note = Synthetic Construct
source                  1..16
                        mol_type = protein
                        organism = synthetic construct
SEQUENCE: 67
RSSQSLVHRA GNTYLH                                                    16

SEQ ID NO: 68           moltype = AA   length = 16
FEATURE                 Location/Qualifiers
REGION                  1..16
                        note = Synthetic Construct
source                  1..16
                        mol_type = protein
                        organism = synthetic construct
SEQUENCE: 68
RSSQSLVHRH GNTYLH                                                    16

SEQ ID NO: 69           moltype = AA   length = 16
FEATURE                 Location/Qualifiers
REGION                  1..16
                        note = Synthetic Construct
source                  1..16
                        mol_type = protein
                        organism = synthetic construct
SEQUENCE: 69
RSSQSLVHRA GNTYLH                                                    16

SEQ ID NO: 70           moltype = AA   length = 16
FEATURE                 Location/Qualifiers
REGION                  1..16
                        note = Synthetic Construct
source                  1..16
                        mol_type = protein
                        organism = synthetic construct
SEQUENCE: 70
RSSQSLVHRV GNTYLH                                                    16

SEQ ID NO: 71           moltype = AA   length = 16
FEATURE                 Location/Qualifiers
REGION                  1..16
                        note = Synthetic Construct
source                  1..16
                        mol_type = protein
                        organism = synthetic construct
SEQUENCE: 71
VIWGSGSTNY HPNLMS                                                    16

SEQ ID NO: 72           moltype = AA   length = 16
FEATURE                 Location/Qualifiers
REGION                  1..16
                        note = Synthetic Construct
source                  1..16
                        mol_type = protein
                        organism = synthetic construct
SEQUENCE: 72
VIWGQGSTNY HPNLMS                                                    16

SEQ ID NO: 73           moltype = AA   length = 16
FEATURE                 Location/Qualifiers
REGION                  1..16
                        note = Synthetic Construct
```

```
source                   1..16
                         mol_type = protein
                         organism = synthetic construct
SEQUENCE: 73
VIWGEGSTNY HPNLMS                                                          16

SEQ ID NO: 74            moltype = AA  length = 16
FEATURE                  Location/Qualifiers
REGION                   1..16
                         note = Synthetic Construct
source                   1..16
                         mol_type = protein
                         organism = synthetic construct
SEQUENCE: 74
VIWGAGSTNY HPNLMS                                                          16

SEQ ID NO: 75            moltype = AA  length = 16
FEATURE                  Location/Qualifiers
REGION                   1..16
                         note = Synthetic Construct
source                   1..16
                         mol_type = protein
                         organism = synthetic construct
SEQUENCE: 75
VIWGHGSTNY HPNLMS                                                          16

SEQ ID NO: 76            moltype = AA  length = 16
FEATURE                  Location/Qualifiers
REGION                   1..16
                         note = Synthetic Construct
source                   1..16
                         mol_type = protein
                         organism = synthetic construct
SEQUENCE: 76
VIWGDASTNY HPNLMS                                                          16

SEQ ID NO: 77            moltype = AA  length = 16
FEATURE                  Location/Qualifiers
REGION                   1..16
                         note = Synthetic Construct
source                   1..16
                         mol_type = protein
                         organism = synthetic construct
SEQUENCE: 77
VIWGDVSTNY HPNLMS                                                          16

SEQ ID NO: 78            moltype = AA  length = 16
FEATURE                  Location/Qualifiers
REGION                   1..16
                         note = Synthetic Construct
source                   1..16
                         mol_type = protein
                         organism = synthetic construct
SEQUENCE: 78
VIWGDGSTNY HPNLVS                                                          16

SEQ ID NO: 79            moltype = AA  length = 16
FEATURE                  Location/Qualifiers
REGION                   1..16
                         note = Synthetic Construct
source                   1..16
                         mol_type = protein
                         organism = synthetic construct
SEQUENCE: 79
VIWGDGSTNY HPNLIS                                                          16

SEQ ID NO: 80            moltype = AA  length = 16
FEATURE                  Location/Qualifiers
REGION                   1..16
                         note = Synthetic Construct
source                   1..16
                         mol_type = protein
                         organism = synthetic construct
SEQUENCE: 80
VIWGDGSTNY HPNLLS                                                          16

SEQ ID NO: 81            moltype = AA  length = 16
FEATURE                  Location/Qualifiers
REGION                   1..16
```

```
                        note = Synthetic Construct
source                  1..16
                        mol_type = protein
                        organism = synthetic construct
SEQUENCE: 81
VIWGDGSTNY HPNLAS                                                    16

SEQ ID NO: 82           moltype = AA  length = 8
FEATURE                 Location/Qualifiers
REGION                  1..8
                        note = Synthetic Construct
source                  1..8
                        mol_type = protein
                        organism = synthetic construct
SEQUENCE: 82
PTQTMVVD                                                             8

SEQ ID NO: 83           moltype = AA  length = 55
FEATURE                 Location/Qualifiers
REGION                  1..55
                        note = Synthetic Construct
source                  1..55
                        mol_type = protein
                        organism = synthetic construct
SEQUENCE: 83
AQAGQAGAQA QGGGYSKAQK AQAKQAKQAQ KAQKAQAKQA KQVTPTVDVV MTQTP          55
```